US011951009B2

(12) United States Patent
Mahfouz

(10) Patent No.: US 11,951,009 B2
(45) Date of Patent: Apr. 9, 2024

(54) METHODS AND DEVICES FOR BONE SURGERIES

(71) Applicant: Mohamed R. Mahfouz, Knoxville, TN (US)

(72) Inventor: Mohamed R. Mahfouz, Knoxville, TN (US)

(73) Assignee: Mohamed R. Mahfouz, Knoxville, TN (US)

( * ) Notice: Subject to any disclaimer, the term of this patent is extended or adjusted under 35 U.S.C. 154(b) by 30 days.

(21) Appl. No.: 17/903,727

(22) Filed: Sep. 6, 2022

(65) Prior Publication Data

US 2023/0157829 A1    May 25, 2023

Related U.S. Application Data

(63) Continuation of application No. 17/130,015, filed on Dec. 22, 2020, now Pat. No. 11,813,165, which is a
(Continued)

(51) Int. Cl.
*A61F 2/30*    (2006.01)
*A61F 2/28*    (2006.01)
(Continued)

(52) U.S. Cl.
CPC ............ *A61F 2/30942* (2013.01); *A61F 2/28* (2013.01); *A61F 2/2875* (2013.01); *A61F 2/34* (2013.01);
(Continued)

(58) Field of Classification Search
CPC ...... A61F 2/30942; A61F 2/28; A61F 2/2875; A61F 2/34; A61F 2/36; A61F 2002/2825;
(Continued)

(56) References Cited

U.S. PATENT DOCUMENTS 9,504,538 B2 * 11/2016 Sachdeva ................. A61C 5/77
9,956,047 B2 *  5/2018 Bojarski ................. A61F 2/389
(Continued)

FOREIGN PATENT DOCUMENTS

EP    2514373      10/2012
JP    H10201779    8/1998
(Continued)

OTHER PUBLICATIONS

Japan Patent Office, Notice of Reasons for Rejection in JP 2021-124449, dated Aug. 29, 2022.

*Primary Examiner* — Ramesh B Patel
(74) *Attorney, Agent, or Firm* — Dorton & Willis LLP; Ryan Willis

(57) ABSTRACT

A method of constructing a patient-specific orthopedic implant comprising: (a) comparing a patient-specific abnormal bone model, derived from an actual anatomy of a patient's abnormal bone, with a reconstructed patient-specific bone model, also derived from the anatomy of the patient's bone, where the reconstructed patient-specific bone model reflects a normalized anatomy of the patient's bone, and where the patient-specific abnormal bone model reflects an actual anatomy of the patient's bone including at least one of a partial bone, a deformed bone, and a shattered bone, wherein the patient-specific abnormal bone model comprises at least one of a patient-specific abnormal point cloud and a patient-specific abnormal bone surface model, and wherein the reconstructed patient-specific bone model comprises at least one of a reconstructed patient-specific point cloud and a reconstructed patient-specific bone surface model; (b) optimizing one or more parameters for a patient-specific orthopedic implant to be mounted to the patient's abnormal bone using data output from comparing the patient-specific abnormal bone model to the reconstructed patient-specific bone model; and, (c) generating an elec-
(Continued)

tronic design file for the patient-specific orthopedic implant taking into account the one or more parameters.

42 Claims, 93 Drawing Sheets

Related U.S. Application Data continuation of application No. 14/515,483, filed on Oct. 15, 2014, now Pat. No. 11,426,281.

(60) Provisional application No. 61/891,047, filed on Oct. 15, 2013.

(51) Int. Cl.
*A61F 2/34* (2006.01)
*A61F 2/36* (2006.01)
*G05B 19/4099* (2006.01)
*G06F 30/00* (2020.01)

(52) U.S. Cl.
CPC ............ *A61F 2/36* (2013.01); *G05B 19/4099* (2013.01); *G06F 30/00* (2020.01); *A61F 2002/2825* (2013.01); *A61F 2002/30943* (2013.01); *A61F 2002/30948* (2013.01)

(58) Field of Classification Search
CPC .. A61F 2002/30943; A61F 2002/30948; A61F 2002/30952; G05B 19/4099; G06F 30/00; A61B 5/055
See application file for complete search history.

(56) References Cited

U.S. PATENT DOCUMENTS

| | | | | |
|---|---|---|---|---|
| 10,004,565 B2 * | 6/2018 | Kang | .................... | A61B 34/10 |
| 10,441,298 B2 * | 10/2019 | Eash | .................. | A61B 17/1778 |
| 10,456,263 B2 * | 10/2019 | Bojarski | ................ | A61F 2/4202 |
| 10,922,448 B2 * | 2/2021 | McKinnon | ............. | A61B 34/10 |
| 10,973,535 B2 * | 4/2021 | Iannotti | .................. | A61B 34/10 |
| 11,007,012 B2 * | 5/2021 | Netravali | ................. | G16B 5/00 |
| 11,229,519 B2 * | 1/2022 | Radermacher | ......... | A61B 17/15 |
| 11,253,323 B2 * | 2/2022 | Hughes | .................. | A61B 34/20 |
| 11,488,721 B2 * | 11/2022 | Otto | ....................... | G16H 30/20 |
| 11,717,349 B2 * | 8/2023 | Rueber | ................... | G06F 30/00 703/1 |
| 2006/0094951 A1 * | 5/2006 | Dean | ....................... | G06T 17/10 600/407 |
| 2008/0269906 A1 * | 10/2008 | Iannotti | ................... | G16H 50/50 703/11 |
| 2009/0222102 A1 * | 9/2009 | Deffrennes | ........... | A61F 2/3099 700/118 |
| 2011/0184419 A1 * | 7/2011 | Meridew | .............. | A61B 17/152 606/91 |
| 2012/0116203 A1 * | 5/2012 | Vancraen | ............ | A61F 2/30942 600/407 |
| 2012/0230556 A1 * | 9/2012 | Wollenweber | ........ | G06T 11/008 382/128 |
| 2012/0303035 A1 * | 11/2012 | Geebelen | .............. | A61F 2/4609 606/91 |
| 2013/0035766 A1 * | 2/2013 | Meridew | ................... | A61F 2/34 623/22.21 |
| 2013/0197687 A1 * | 8/2013 | Pavlovskaia | .......... | G06T 7/0012 700/118 |
| 2018/0033338 A1 * | 2/2018 | Iannotti | .............. | A61B 17/1739 |
| 2018/0360609 A1 * | 12/2018 | Steines | ............... | A61F 2/30942 |
| 2020/0155323 A1 * | 5/2020 | Lang | .................... | A61F 2/3662 |
| 2021/0161608 A1 * | 6/2021 | Borus | ................... | A61B 34/20 |

FOREIGN PATENT DOCUMENTS

| | | |
|---|---|---|
| JP | 2009529933 | 8/2009 |
| JP | 2010534500 | 11/2010 |
| JP | 2011506040 | 3/2011 |
| JP | 2011517996 | 6/2011 |
| JP | 2011519605 | 7/2011 |
| JP | 2013534843 | 9/2013 |
| JP | 2014529314 | 11/2014 |
| JP | 2019-188196 | 10/2019 |
| WO | 2010099359 | 9/2010 |

* cited by examiner

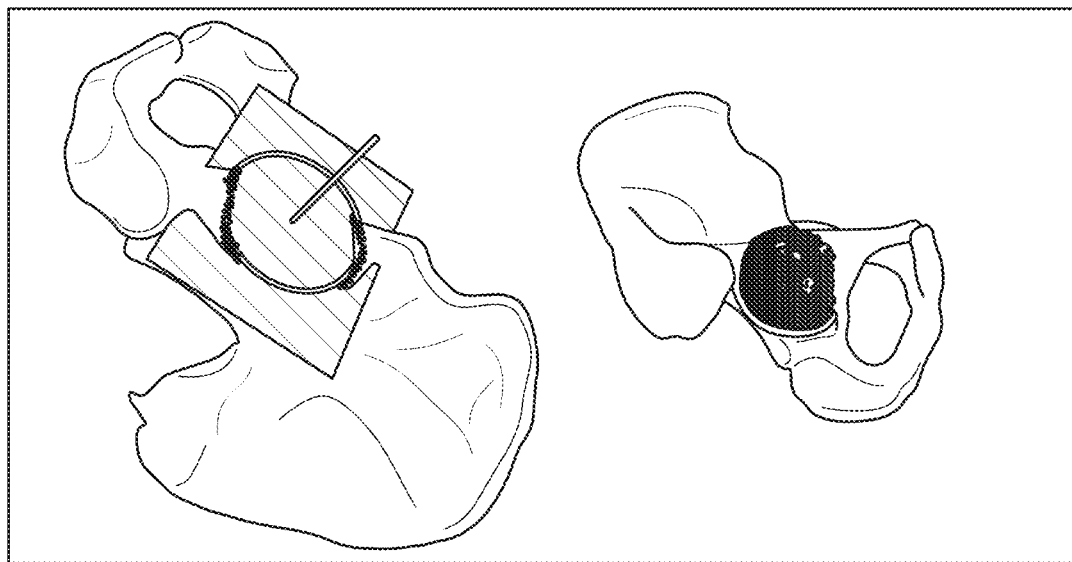
FIG. 70
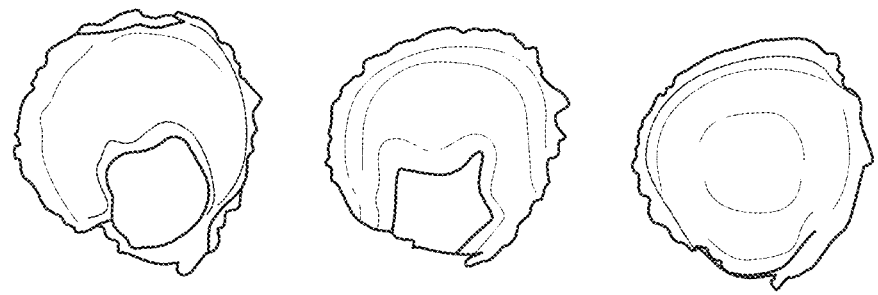
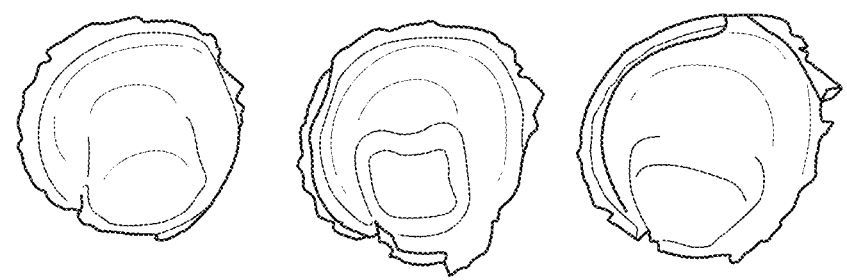
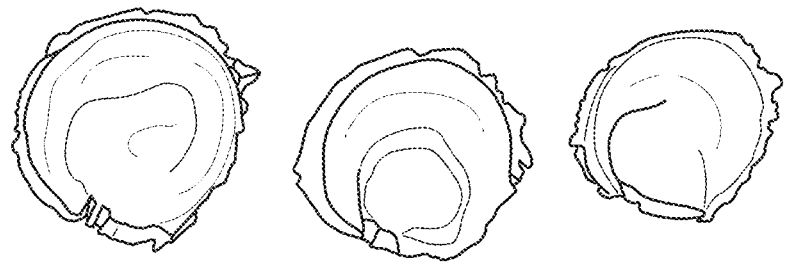
FIG. 71

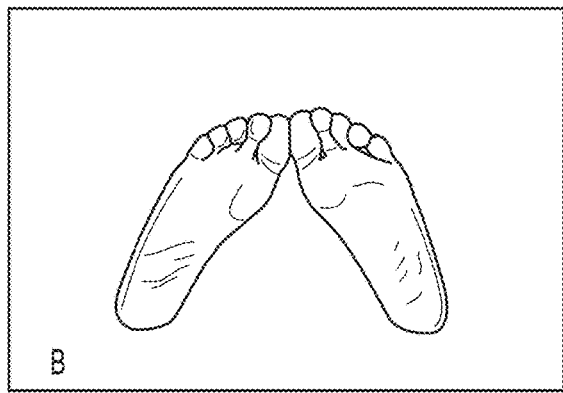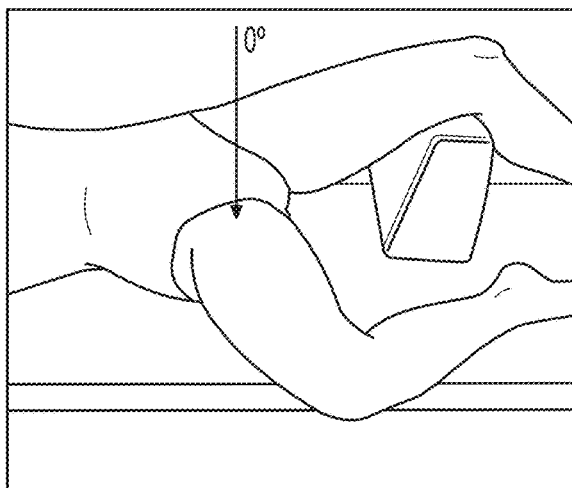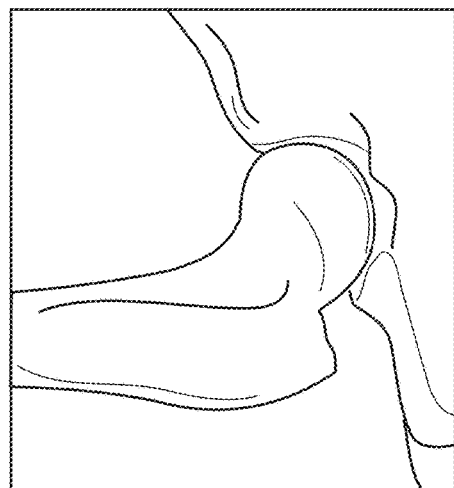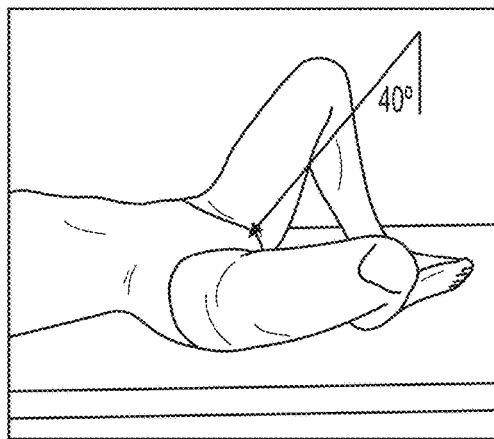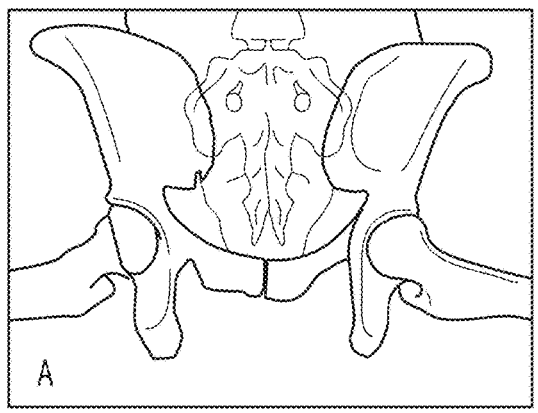
FIG. 81

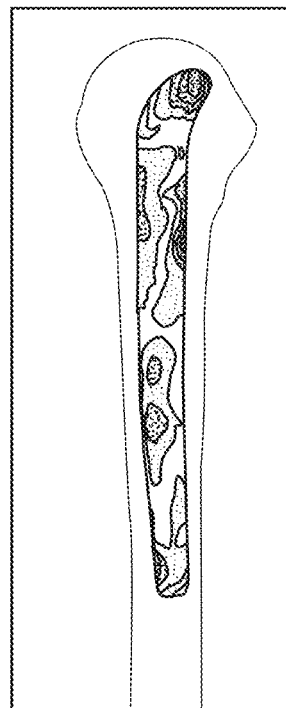
FIG. 107
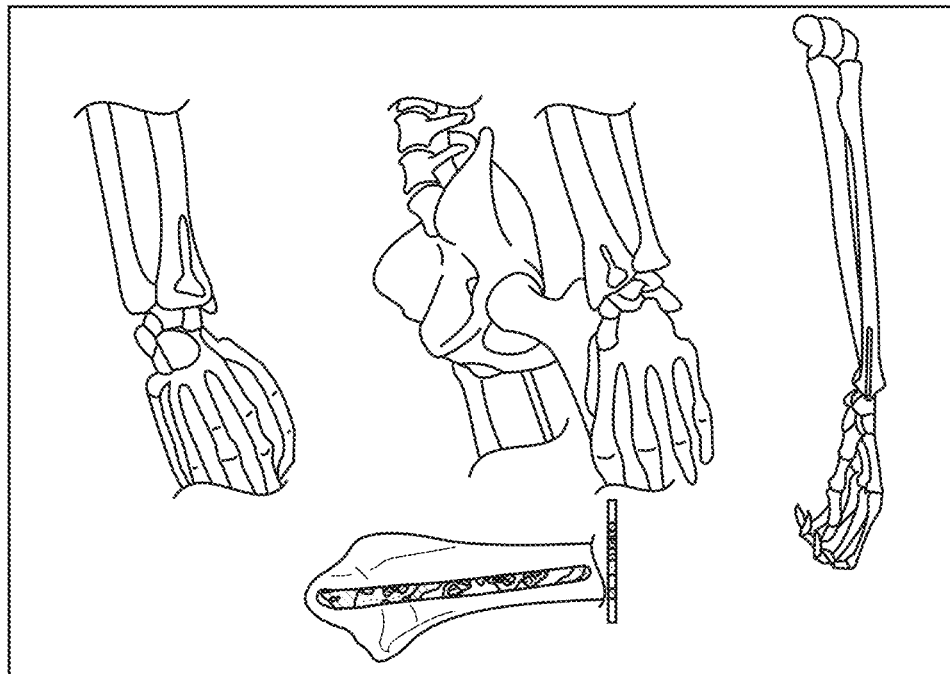
FIG. 108

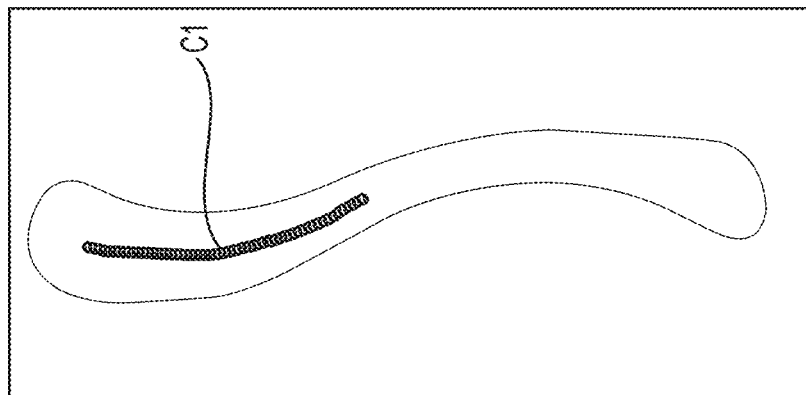
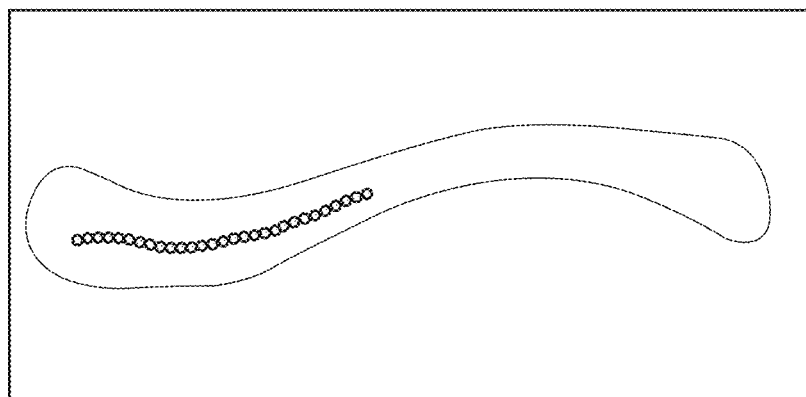
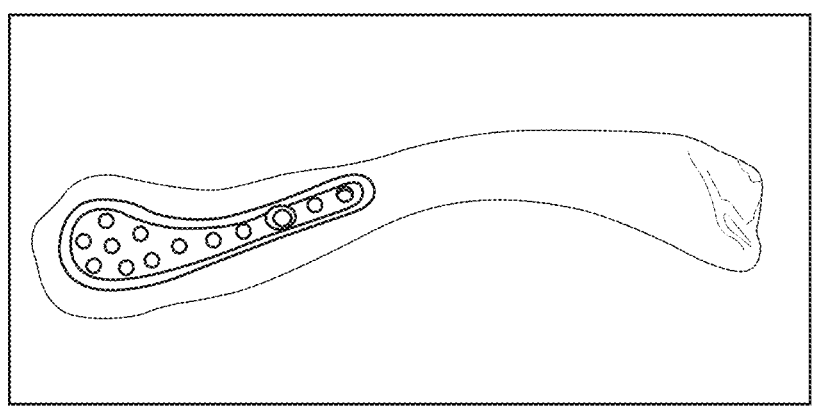
FIG. 110

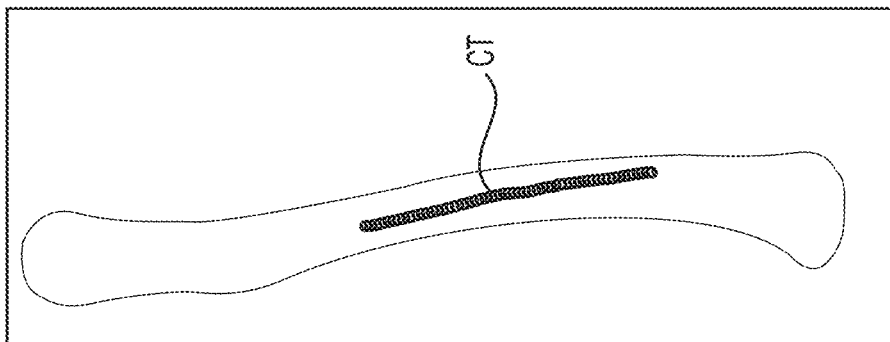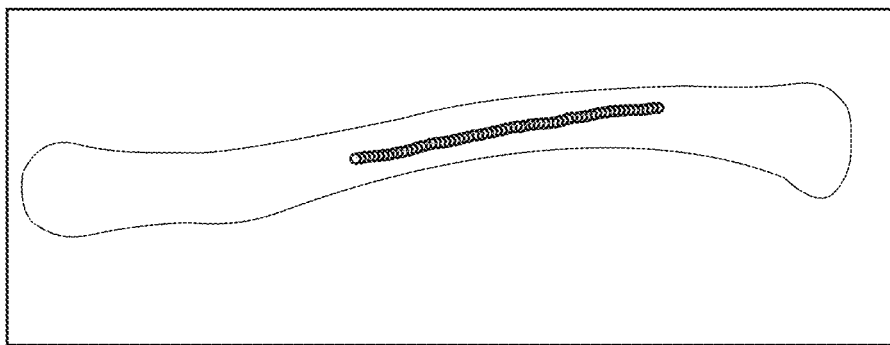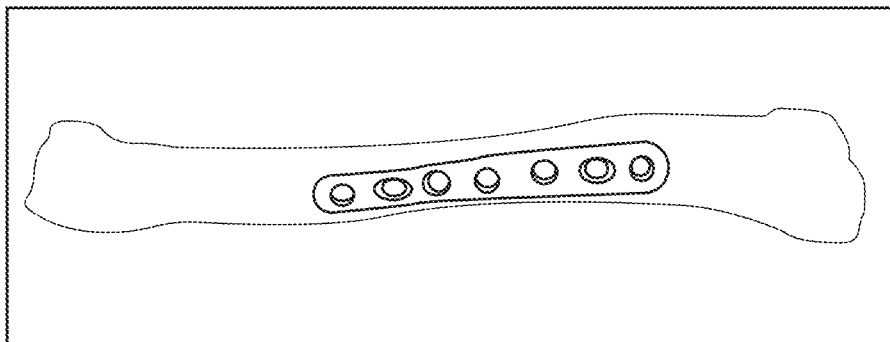
FIG. 111

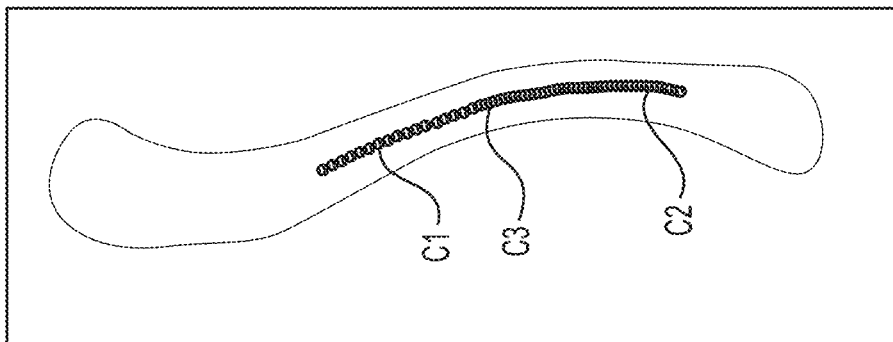
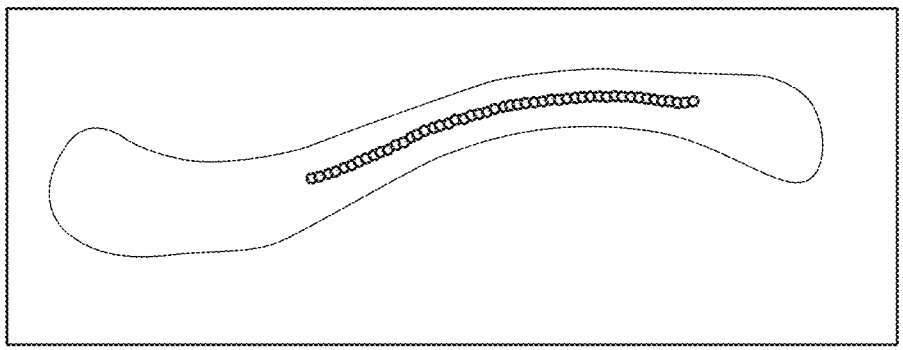
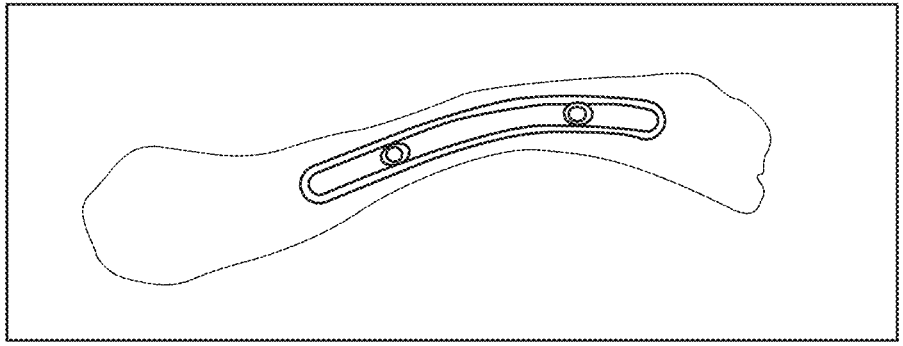
FIG. 112

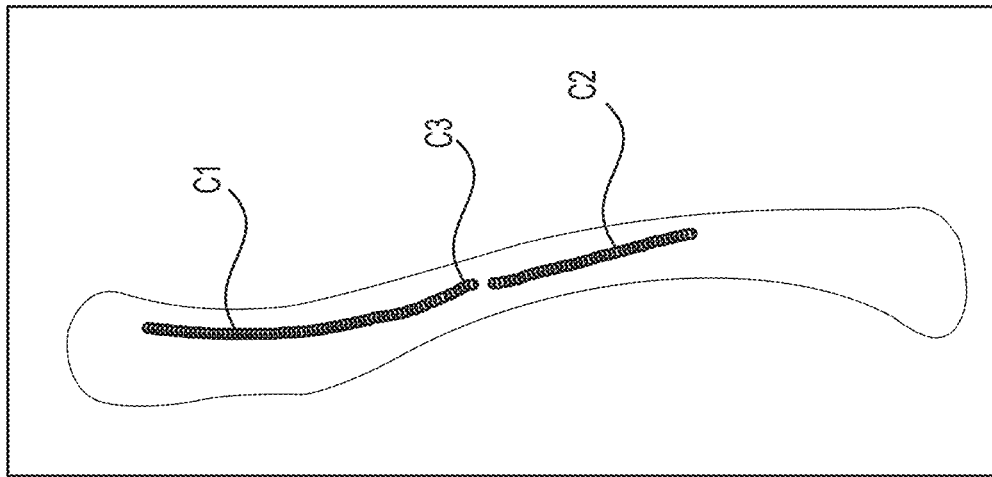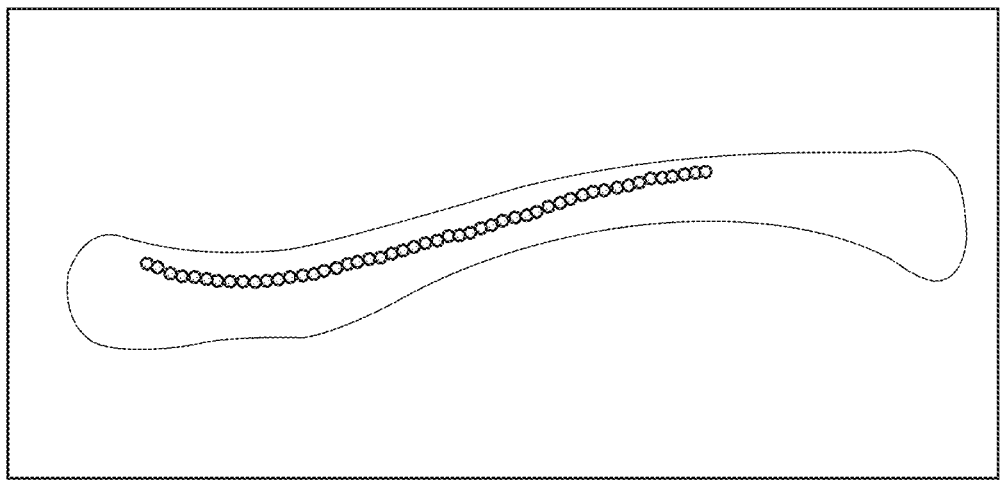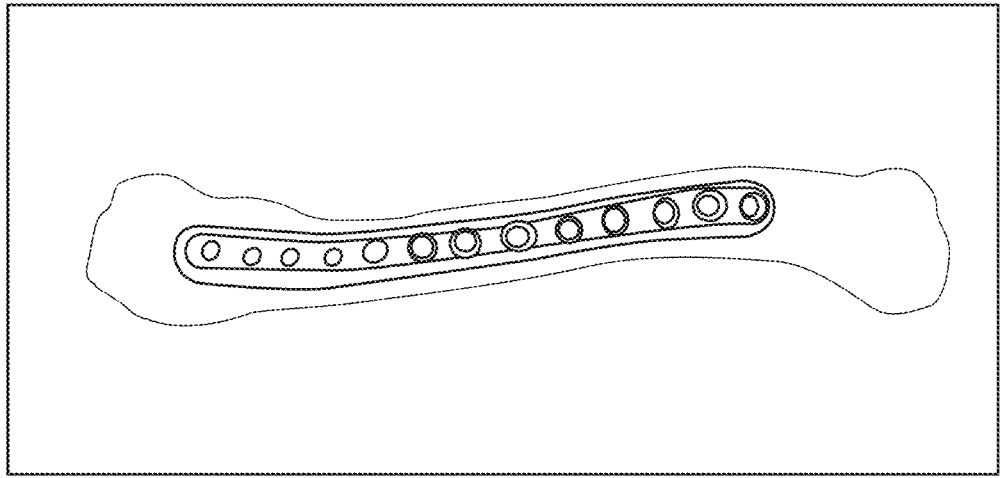
FIG. 113

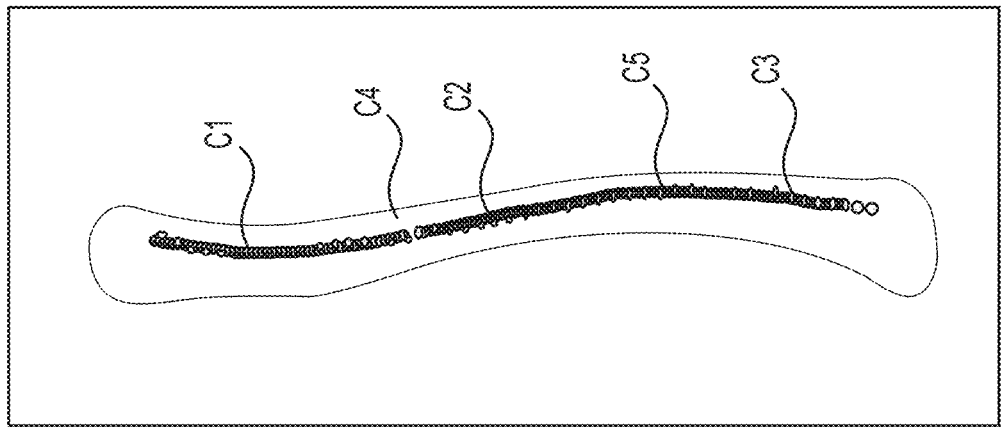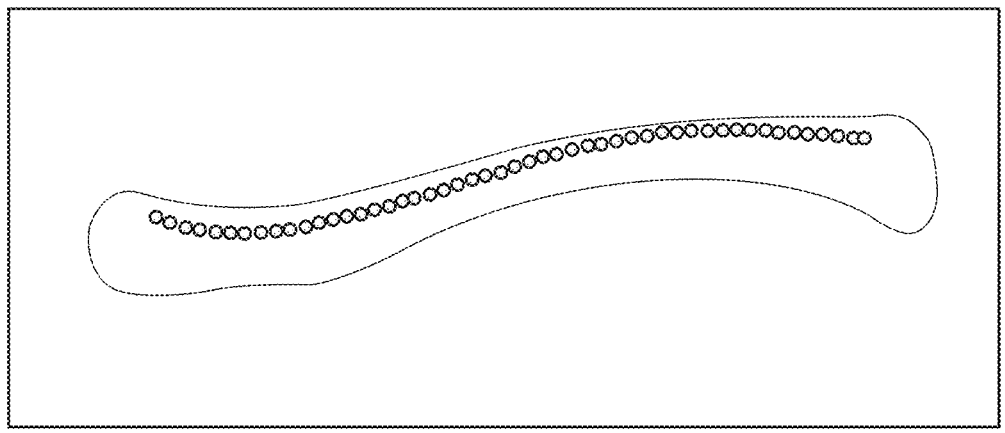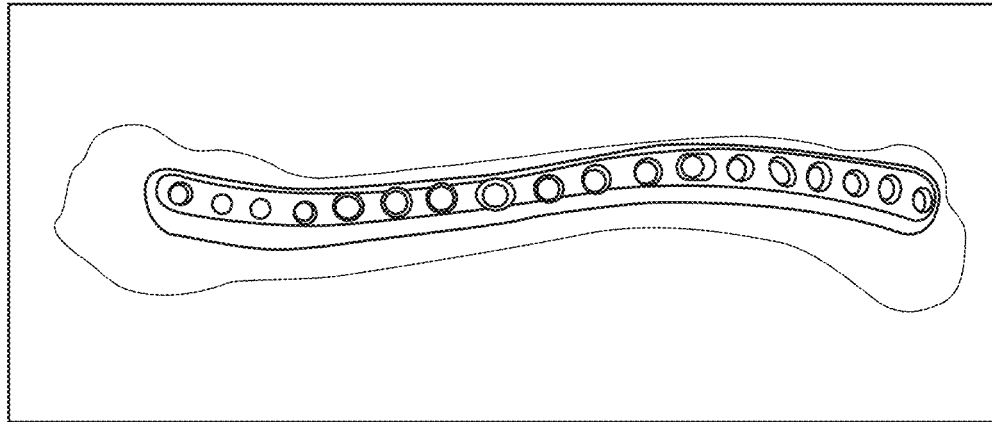
FIG. 114

METHODS AND DEVICES FOR BONE SURGERIES

CROSS REFERENCE TO RELATED APPLICATIONS

The present application is a continuation of continuation of U.S. patent application Ser. No. 17/130,015, entitled, "BONE RECONSTRUCTION AND ORTHOPEDIC IMPLANTS," filed Dec. 22, 2020, which is a continuation of, U.S. patent application Ser. No. 14/515,483, entitled, "BONE RECONSTRUCTION AND ORTHOPEDIC IMPLANTS," filed Oct. 15, 2014, now U.S. Pat. No. 11,426, 281, which claims the benefit of U.S. Provisional Patent Application Ser. No. 61/891,047, entitled "CRANIUM AND POSTCRANIAL BONE AND SOFT TISSUE RECONSTRUCTION," filed Oct. 15, 2013, the disclosures of which are incorporated herein by reference.

RELATED ART

Field of the Invention

The present disclosure is directed to various aspects of orthopedics including bone and tissue reconstruction, patient-specific and mass customized orthopedic implants, gender and ethnic specific orthopedic implants, cutting guides, trauma plates, bone graft cutting and placement guides, patient-specific instruments, utilization of inertial measurement units for anatomical tracking for kinematics and pathology, and utilization of inertial measurement units for navigation during orthopedic surgical procedures.

INTRODUCTION TO THE INVENTION

It is a first aspect of the present invention to provide a method of constructing a patient-specific orthopedic implant comprising: (a) comparing a patient-specific abnormal bone model, derived from an actual anatomy of a patient's abnormal bone, with a reconstructed patient-specific bone model, also derived from the anatomy of the patient's bone, where the reconstructed patient-specific bone model reflects a normalized anatomy of the patient's bone, and where the patient-specific abnormal bone model reflects an actual anatomy of the patient's bone including at least one of a partial bone, a deformed bone, and a shattered bone, wherein the patient-specific abnormal bone model comprises at least one of a patient-specific abnormal point cloud and a patient-specific abnormal bone surface model, and wherein the reconstructed patient-specific bone model comprises at least one of a reconstructed patient-specific point cloud and a reconstructed patient-specific bone surface model; (b) optimizing one or more parameters for a patient-specific orthopedic implant to be mounted to the patient's abnormal bone using data output from comparing the patient-specific abnormal bone model to the reconstructed patient-specific bone model; and, (c) generating an electronic design file for the patient-specific orthopedic implant taking into account the one or more parameters In a more detailed embodiment of the first aspect, the method further includes fabricating the patient-specific implant using the electronic design file. In yet another more detailed embodiment, the method further includes comparing the patient-specific abnormal bone model to the reconstructed patient-specific bone model to identify missing bone or deformed bone from the patient-specific abnormal bone model, and localizing the missing bone or deformed bone onto the reconstructed patient-specific bone model. In a further detailed embodiment, the method further includes generating the patient-specific abnormal bone model from data representative of the patient's abnormal bone, and generating the reconstructed patient-specific bone model from data representative of the patient's abnormal bone and from data from a statistical atlas, where the statistical atlas data comprises at least one of a point cloud and a surface model of a normal bone analogous to the patient's abnormal bone. In still a further detailed embodiment, the data representative of the patient's abnormal bone comprises at least one of magnetic resonance images, computerized tomography images, X-ray images, and ultrasound images. In a more detailed embodiment, the statistical atlas data is derived from at least one of magnetic resonance images, computerized tomography images, X-ray images, and ultrasound images of the normal bone. In a more detailed embodiment, the identified missing bone or the deformed bone comprises a set of bounding points, and localizing the missing bone or the deformed bone onto the reconstructed patient-specific bone model includes associating the set of bounding points with the reconstructed patient-specific bone model. In another more detailed embodiment, comparing the patient-specific abnormal bone model to the reconstructed patient-specific bone model to identify missing bone or deformed bone from the patient-specific abnormal bone model includes outputting at least two lists of data, where the at least two lists of data include a first list identifying the missing bone or the deformed bone, and a second list identifying bone in common between the patient-specific abnormal bone model and the reconstructed patient-specific bone model. In yet another more detailed embodiment, the first list comprises vertices belonging to the missing bone or the deformed bone from the patient-specific abnormal bone model, and the second list comprises vertices belong to bone in common between the patient-specific abnormal bone model and the reconstructed patient-specific bone model. In still another more detailed embodiment, the method further includes determining one or more patient-specific orthopedic implant fixation locations using data from the patient-specific abnormal bone model and data from the reconstructed patient-specific bone model.

In yet another more detailed embodiment of the first aspect, determining one or more patient-specific orthopedic implant fixation locations includes excluding any location where the missing bone or the deformed bone has been identified. In yet another more detailed embodiment, optimizing one or more parameters for a patient-specific orthopedic implant includes using an implant parameterizing template to establishing general parameters that are thereafter optimized using the reconstructed patient-specific bone model. In a further detailed embodiment, the parameters include at least one of angle parameters, depth parameters, curvature parameters, and fixation device location parameters. In still a further detailed embodiment, the method further comprises constructing an initial iteration of a surface model of the patient-specific orthopedic implant. In a more detailed embodiment, constructing the initial iteration of the surface model includes combining contours from the patient-specific abnormal bone model and contours from the reconstructed patient-specific bone model. In a more detailed embodiment, constructing the initial iteration of the surface model includes accounting for an intended implantation location for the patient-specific orthopedic implant. In another more detailed embodiment, the method further includes constructing a subsequent iteration of the surface model of the patient-specific orthopedic implant. In yet another more detailed embodiment, constructing the subsequent iteration of the surface model of the patient-specific orthopedic implant includes a manual review of the subsequent iteration of the surface model and the reconstructed patient-specific bone model to discern if a further iteration of the surface model is required. In still another more detailed embodiment, the electronic design file includes at least one of a computer aided design file, a computer numerical control file, and a rapid manufacturing instruction file.

In a more detailed embodiment of the first aspect, the method further comprises generating an electronic design file for a patient-specific implant placement guide using the one or more parameters optimized for the patient-specific orthopedic implant. In yet another more detailed embodiment, the method further includes fabricating the patient-specific implant placement guide using the electronic design file for the patient-specific implant placement guide. In a further detailed embodiment, the one or more parameters optimized for the patient-specific orthopedic implant includes at least one of a size parameter, a shape parameter, and a contour parameter. In still a further detailed embodiment, at least one contour parameter is in common among the patient-specific orthopedic implant and the patient-specific implant placement guide. In a more detailed embodiment, the method further comprises designing a patient-specific implant placement guide to include a surface shape that is a negative of a surface shape of the patient's bone where the patient-specific implant placement guide is intended to reside. In a more detailed embodiment, the patient-specific abnormal bone model comprises at least one of a patient-specific abnormal femur bone model and a patient-specific abnormal pelvis bone model derived from an actual anatomy of a patient's abnormal hip joint, the reconstructed patient-specific bone model comprises at least one of a reconstructed patient-specific femur bone model and a reconstructed patient-specific pelvis bone model derived from the anatomy of the patient's hip joint, the reconstructed patient-specific model reflects a normalized anatomy from the patient's hip joint, and the patient-specific abnormal bone model reflects an actual anatomy from the patient's hip joint. In another more detailed embodiment, the patient-specific abnormal bone model comprises the patient-specific abnormal femur bone model, the reconstructed patient-specific bone model comprises the reconstructed patient-specific femur bone model, the reconstructed patient-specific model reflects the normalized anatomy from a proximal femur of the patient, the patient-specific abnormal bone model reflects the actual anatomy from the proximal femur of the patient, and the patient-specific orthopedic implant comprises a femoral stem implant.

In a more detailed embodiment of the first aspect, the patient-specific abnormal bone model comprises the patient-specific abnormal pelvis bone model, the reconstructed patient-specific bone model comprises the reconstructed patient-specific pelvis bone model, the reconstructed patient-specific model reflects the normalized anatomy from the patient's pelvis, the patient-specific abnormal bone model reflects the actual anatomy from the patient's pelvis, and the patient-specific orthopedic implant comprises an acetabular cup implant. In yet another more detailed embodiment, the electronic design file for the patient-specific orthopedic implant includes at least one of a computer aided design file, a computer numerical control file, and a rapid manufacturing instruction file.

It is a second aspect of the present invention to provide a method of generating an electronic a reconstructed bone model of an abnormal bone comprising: (a) utilizing at least one of a point cloud and a surface model of an abnormal bone, where the abnormal bone includes at least one of a partial bone, a deformed bone, and a shattered bone, for at least one of identifying a bone from a statistical atlas that is similar to the abnormal bone, registering a bone from a statistical atlas to the abnormal bone, and morphing surface points on a reconstructed model of the abnormal bone onto at least one of the point cloud and the surface model of the abnormal bone; and, (b) generating the reconstructed model of the abnormal bone.

In a more detailed embodiment of the second aspect, the step of utilizing at least one of the point cloud and the surface model of an abnormal bone includes identifying the statistical atlas bone that is most similar to the abnormal bone. In yet another more detailed embodiment, the step of utilizing at least one of the point cloud and the surface model of an abnormal bone includes registering the statistical atlas bone to the abnormal bone. In a further detailed embodiment, the step of utilizing at least one of the point cloud and the surface model of an abnormal bone includes morphing surface points on the reconstructed model of the abnormal bone onto at least one of the point cloud and the surface model of the abnormal bone. In still a further detailed embodiment, identifying the statistical atlas bone that is most similar to the abnormal bone includes using one or more similarity metrics to identify the statistical atlas bone. In a more detailed embodiment, the statistical atlas includes a plurality of mathematical representations, where each of the plurality of mathematical representations is representative of a bone. In a more detailed embodiment, the statistical atlas includes a plurality of virtual models, where each of the plurality of virtual models is representative of a bone. In another more detailed embodiment, the method further comprises registering at least one of the point cloud and the surface model of the abnormal bone to an identified bone from the statistical atlas that is similar to the abnormal bone. In yet another more detailed embodiment, the method further comprises enhancement of shape parameters between (a) at least one of a point cloud and a surface model of an abnormal bone, and (b) an identified bone from the statistical atlas that is similar to the abnormal bone. In still another more detailed embodiment, enhancement of shape parameters includes interpolating between (a) at least one of a point cloud and a surface model of an abnormal bone, and (b) an identified bone from the statistical atlas that is similar to the abnormal bone, in order to identify missing bone or deformed bone in at least one of the point cloud and the surface model of the abnormal bone.

In yet another more detailed embodiment of the second aspect, enhancement of the shape parameters results in generating surface points corresponding to the missing bone or deformed bone. In yet another more detailed embodiment, the method further comprises morphing surface points, having been interpolated from the bone from the statistical atlas that is similar to the abnormal bone, with at least one of the point cloud and the surface model of the abnormal bone to generate the reconstructed model of the abnormal bone. In a further detailed embodiment, the abnormal bone comprises at least one of a deformed pelvis section, a shattered pelvis section, and a partial pelvis section missing bone, and the reconstructed model of the abnormal bone comprises at least a complete pelvis model section having remedied at least one of a bone deformity in the deformed pelvis section, a shattered bone comprising part of the shattered pelvis section, and a bone absence from the partial pelvis section. In still a further detailed embodiment, the complete pelvis model section includes an acetabular cup anatomy. In a more detailed embodiment, the abnormal bone comprises at least one of a deformed femur section, a shattered femur section, and a partial femur section missing bone, and the reconstructed model of the abnormal bone comprises at least a complete femur model section having remedied at least one of a bone deformity in the deformed femur section, a shattered bone comprising part of the shattered femur section, and a bone absence from the partial femur section. In a more detailed embodiment, the complete femur model section comprises a proximal femur having neck and ball anatomy. In yet another more detailed embodiment, the abnormal bone comprises at least one of a deformed humerus section, a shattered humerus section, and a partial humerus section missing bone, a deformed ulna section, a shattered ulna section, a partial ulna section missing bone, a deformed radius section, a shattered radius section, a partial radius section missing bone, a deformed cranium section, a shattered cranium section, a partial cranium section missing bone, a deformed vertebra section, a shattered vertebra section, and a partial vertebra section missing bone, and the reconstructed model of the abnormal bone comprises at least one of a complete humerus model section, a complete ulna model section, a complete radius model section a complete cranium model section, and a complete vertebra model section having remedied at least one of a bone deformity in the deformed ulna section, a shattered bone comprising part of the shattered ulna section, a bone absence from the partial ulna section, a bone deformity in the deformed radius section, a shattered bone comprising part of the shattered radius section, a bone absence from the partial radius section, a bone deformity in the deformed cranium section, a shattered bone comprising part of the shattered cranium section, a bone absence from the partial cranium section, a bone deformity in the deformed vertebra section, a shattered bone comprising part of the shattered vertebra section, and a bone absence from the partial vertebra section.

It is a third aspect of the present invention to provide a method of constructing a mass-customized orthopedic implant comprising: (a) identifying features, where the features comprise at least one of landmarks and shape features, across a statistical atlas population of bones; (b) generating descriptors relevant to implant design using the identified features across the statistical atlas population of bones; (c) grouping at least some of the descriptors into a group having similar descriptors; (d) parameterizing the group to extract parameters from the group; and, (e) generating an electronic design file for a mass-customized orthopedic implant.

In a more detailed embodiment of the third aspect, the method further includes fabricating the mass-customized orthopedic implant using the electronic design file. In yet another more detailed embodiment, the identification of features step is automatically carried out by a software program configured to calculate landmarks across a statistical atlas population of bones using location parameters embedded in a calculation logic. In a further detailed embodiment, the identification of features step is automatically carried out by a software program configured to calculate shape features across a statistical atlas population of bones using location parameters embedded in a calculation logic. In still a further detailed embodiment, the descriptors comprise mathematical descriptors that are calculated across the statistical atlas population of bones. In a more detailed embodiment, grouping at least some of the descriptors into a group having similar descriptors includes using a statistical analysis to establish the group. In a more detailed embodiment, the extracted descriptors from the group comprise design parameters for a shape of the mass-customized orthopedic implant. In another more detailed embodiment, the descriptors comprise mathematical descriptors, and parameterizing the group to extract descriptors from the group includes converting the mathematical descriptors into surface descriptors. In yet another more detailed embodiment, the electronic design file for a mass-customized orthopedic implant includes a virtual, three-dimensional model of the mass-customized orthopedic implant. In still another more detailed embodiment, parameterizing the group to extract descriptors from the group includes generating a virtual, three-dimensional model of the mass-customized orthopedic implant.

In yet another more detailed embodiment of the third aspect, the method further includes extracting three-dimensional cancellous bone features across the statistical atlas population of bones and generating a three dimensional bone model for each bone within the statistical atlas population of bones that incorporates the extracted cancellous bone features unique to that bone. In yet another more detailed embodiment, the method further includes conducting a porosity evaluation on each bone within the statistical atlas population of bones to determine cancellous bone size and pore size. In a further detailed embodiment, the method further includes conducting stress testing process that combines cancellous bone size data, pore size data, and surface descriptor parameters to generate the electronic design file for the mass-customized orthopedic implant. In still a further detailed embodiment, the electronic design file includes at least one of a computer aided design file, a computer numerical control file, and a rapid manufacturing instruction file. In a more detailed embodiment, the method further includes generating an electronic design file for a mass customized implant placement guide using at least one of the extracted parameters. In a more detailed embodiment, the method further includes fabricating the mass customized implant placement guide using the electronic design file for the mass customized implant placement guide. In another more detailed embodiment, the statistical atlas population of bones is ethnic specific. In yet another more detailed embodiment, the statistical atlas population of bones is gender specific. In still another more detailed embodiment, the statistical atlas population of bones comprises at least segments of femur bones. In yet another more detailed embodiment, the statistical atlas population of bones comprises at least segments of pelvis bones.

It is a fourth aspect of the present invention to provide a method of constructing a mass-customized trauma plate comprising: (a) establish a virtual boundary for a mass-customized trauma plate with respect to a virtual three dimensional bone model template; (b) select a plurality of surface points inside the virtual boundary corresponding to a surface location on the virtual three dimensional bone model template; (c) propagating the plurality of surface points across a statistical atlas containing a plurality of virtual three dimensional bone models; (d) using the plurality of surface points propagated onto each of the plurality of virtual three dimensional bone models to construct a virtual three dimensional bone plate fitted to that particular bone model; (e) extracting a plurality of curvatures representative of each virtual three dimensional bone plate created; (f) statistically analyze the plurality of curvatures extracted to deduce shape parameters for the mass-customized trauma plate; and, (g) generate an electronic design file for the mass-customized trauma plate using the shape parameters.

It is a fifth aspect of the present invention to provide a method of constructing a patient-specific cutting guide for preparing a bone for an orthopedic implant comprising: (a) processing patient-specific bone contours to determine a size of an orthopedic implant to be mounted to the patient's bone and the location of the implant when mounted relative to the patient's bone; (b) designing a patient-specific cutting guide using the size of the orthopedic implant and the location the implant when mounted to the patient's bone; and, (c) fabricating a cutting guide that is patient-specific that includes a shape that is a negative of the shape of the patient's bone to which the cutting guide is configured to be mounted.

BRIEF DESCRIPTION OF THE DRAWINGS

FIG. 70. Isolation of acetabular cup geometry.

FIG. 71. Acetabular cup anatomical templates.

FIG. 81. Multiple x-ray views used for reconstruction of pelvis and proximal femur.

FIG. 107. 3D surface distance map between plate surface and bone for evaluating plate fit.

FIG. 108. Validation of designed plate on cadaver to avoid muscle and ligament impingement.

FIG. 110. Superior lateral plate (left), plate midline curve (center) and midline plate curvature showing radius of curvature (right).

FIG. 111. Anterior mid-shaft 7h plate (left), plate midline curve (center) and midline plate curvature showing single radius of curvature (right).

FIG. 112. Superior mid-shaft plate (left), plate midline curve (center) and midline plate curvature showing differing radii of curvature (right).

FIG. 113. Anterior lateral plate (left), plate midline curve (center) and midline plate curvature showing differing radii of curvature (right).

FIG. 114. Anterior mid-shaft long plate (left), plate midline curve (center) and midline plate curvature showing differing radii of curvature (right).

DETAILED DESCRIPTION

The exemplary embodiments of the present disclosure are described and illustrated below to encompass various aspects of orthopedics including bone and tissue reconstruction, patient-specific and mass customized orthopedic implants, gender and ethnic specific orthopedic implants, cutting guides, trauma plates, bone graft cutting and placement guides, and patient-specific instruments. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Full Anatomy Reconstruction

Referring to FIGS. 1-8, reconstruction of a deformed anatomy or a partial anatomy is one of the complex problems facing healthcare providers. Loss of anatomy may be the result of birth conditions, tumors, diseases, personal injuries, or failure of previous surgeries. As part of providing treatment for various ailments, healthcare providers may find it advantageous to reconstruct an anatomy or construct an anatomy to facilitate treatment for various conditions that may include, without limitation, broken/shattered bones, bone degeneration, orthopedic implant revision, joint degeneration, and custom instrumentation design. For example, prior art hip reconstruction solution requires mirroring of the healthy patient anatomy which may not be an accurate reflection of the healthy anatomy due to naturally occurring asymmetry, as shown in FIG. 12-16.

The present disclosure provides a system and methods for bone and tissue reconstruction. In order to carry out this reconstruction, the system and associated methods utilizes anatomical images representative of one or more persons. These images are processed to create a virtual three dimensional (3D) tissue model or a series of virtual 3D tissue models mimicking the proper anatomy in question. Thereafter, the system and associated methods are utilized to create a mold and/or other devices (e.g., fixation devices, grafting devices, patient-specific implants, patient-specific surgical guides) for use with reconstructive surgery.

Figure 1:
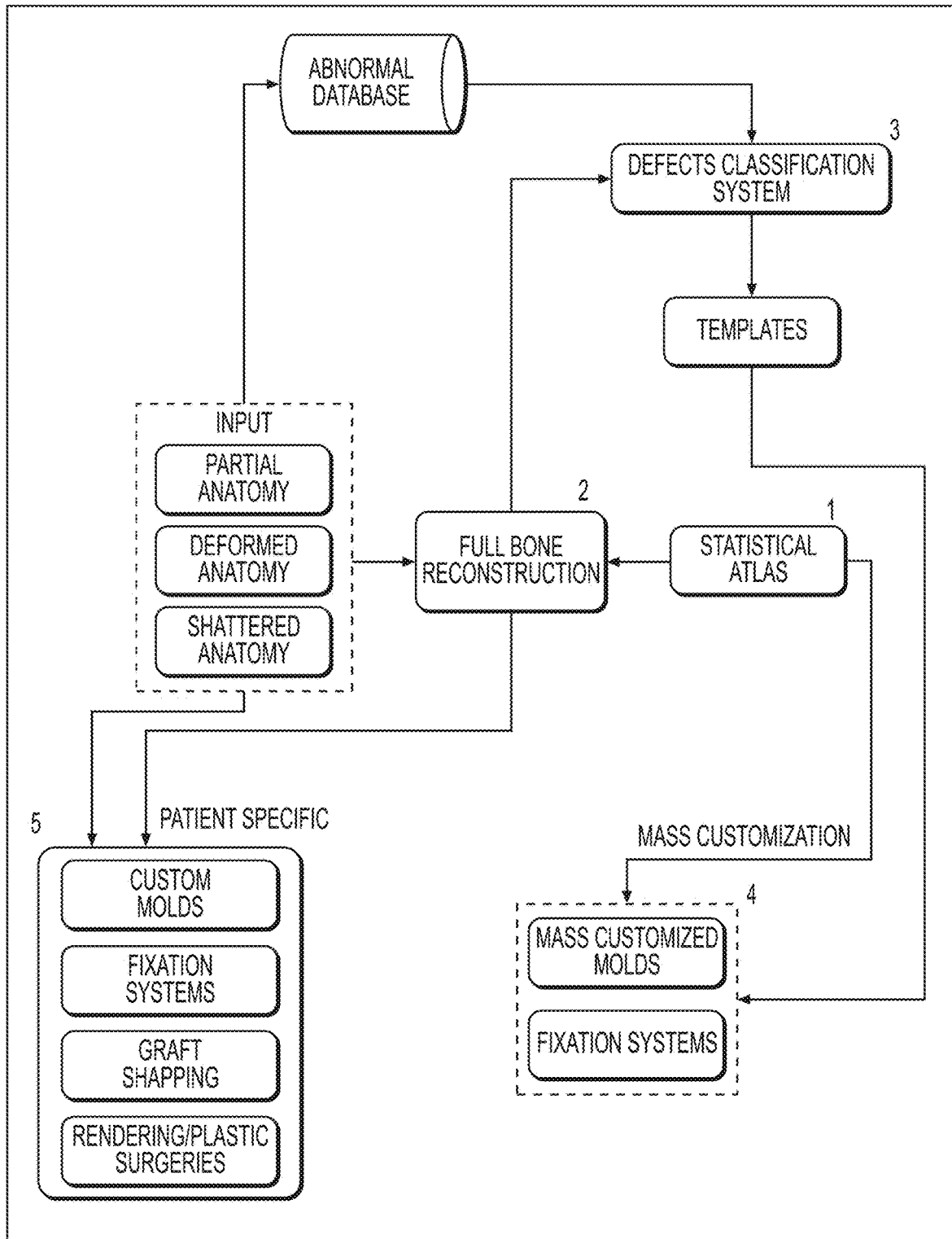
FIG. 1 is a schematic diagram of an overall process of generating mass customized and patient-specific molds from a partial anatomy.

As represented in FIG. 1, an overview of the exemplary system flow begins with receiving input data representative of an anatomy. This anatomy may comprise a partial anatomy in the case of tissue degeneration or tissue absence resulting from genetics, or this anatomy may comprise a deformed anatomy resulting from genetics or environmental conditions, or this anatomy may comprise a shattered tissue resulting from one or more anatomy breaks. Input anatomical data comprises two dimensional (2D) images or three dimensional (3D) surface representations of the anatomy in question that may, for example, be in the form of a surface model or point cloud. In circumstances where 2D images are utilized, these 2D images are utilized to construct a 3D virtual surface representation of the anatomy in question. Those skilled in the art are familiar with utilizing 2D images of anatomy to construct a 3D surface representation. Accordingly, a detailed explanation of this process has been omitted in furtherance of brevity. By way of example, input anatomical data may comprise one or more of X-rays, computed tomography (CT) scans, magnetic resonance images (MRIs), or any other imaging data from which a 3D surface representation of the tissue in question may be generated.

Figure 45:
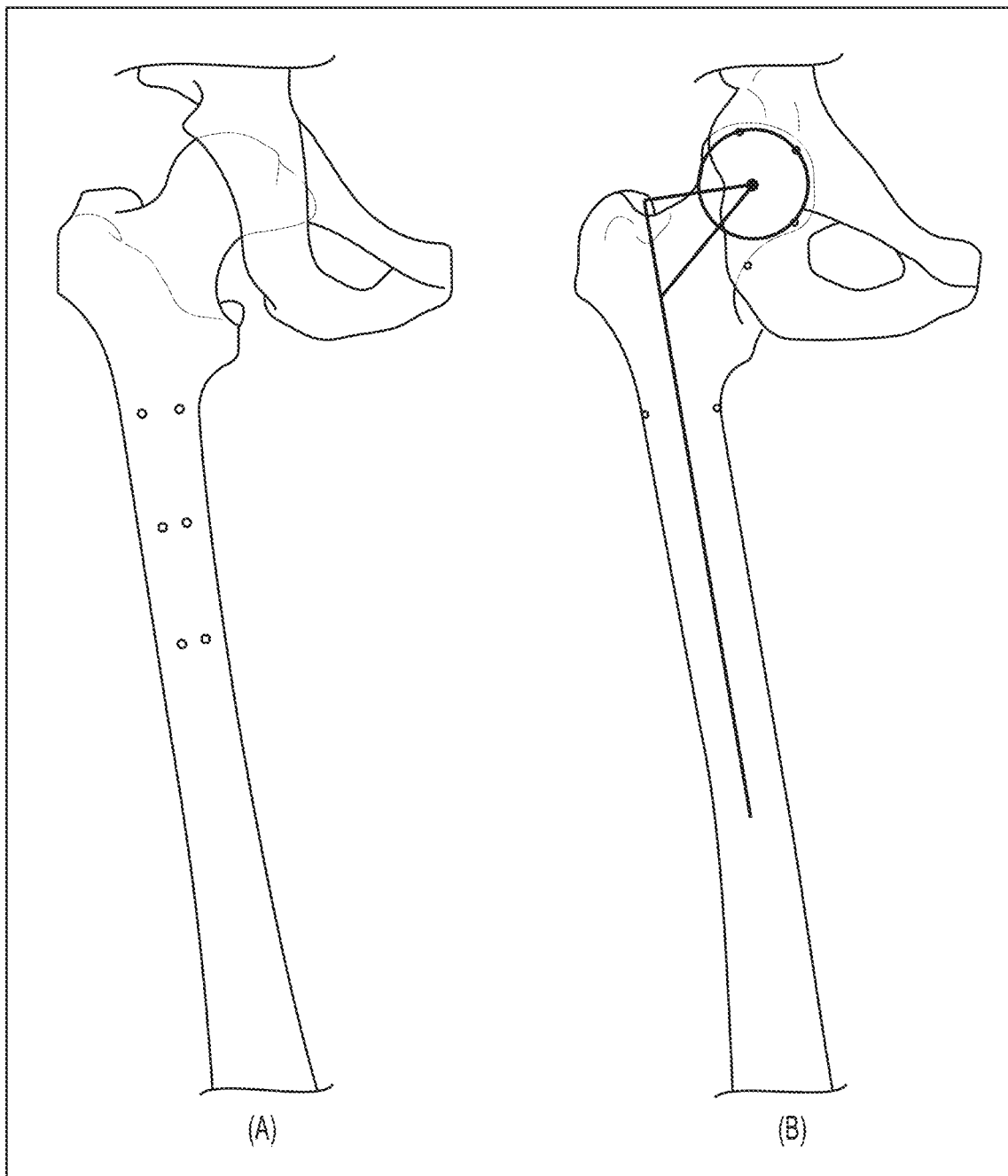
FIG. 45 is an X-ray depiction shown the IM width at 3 levels, and the proximal axis, head offset and femur head.
Figure 46:
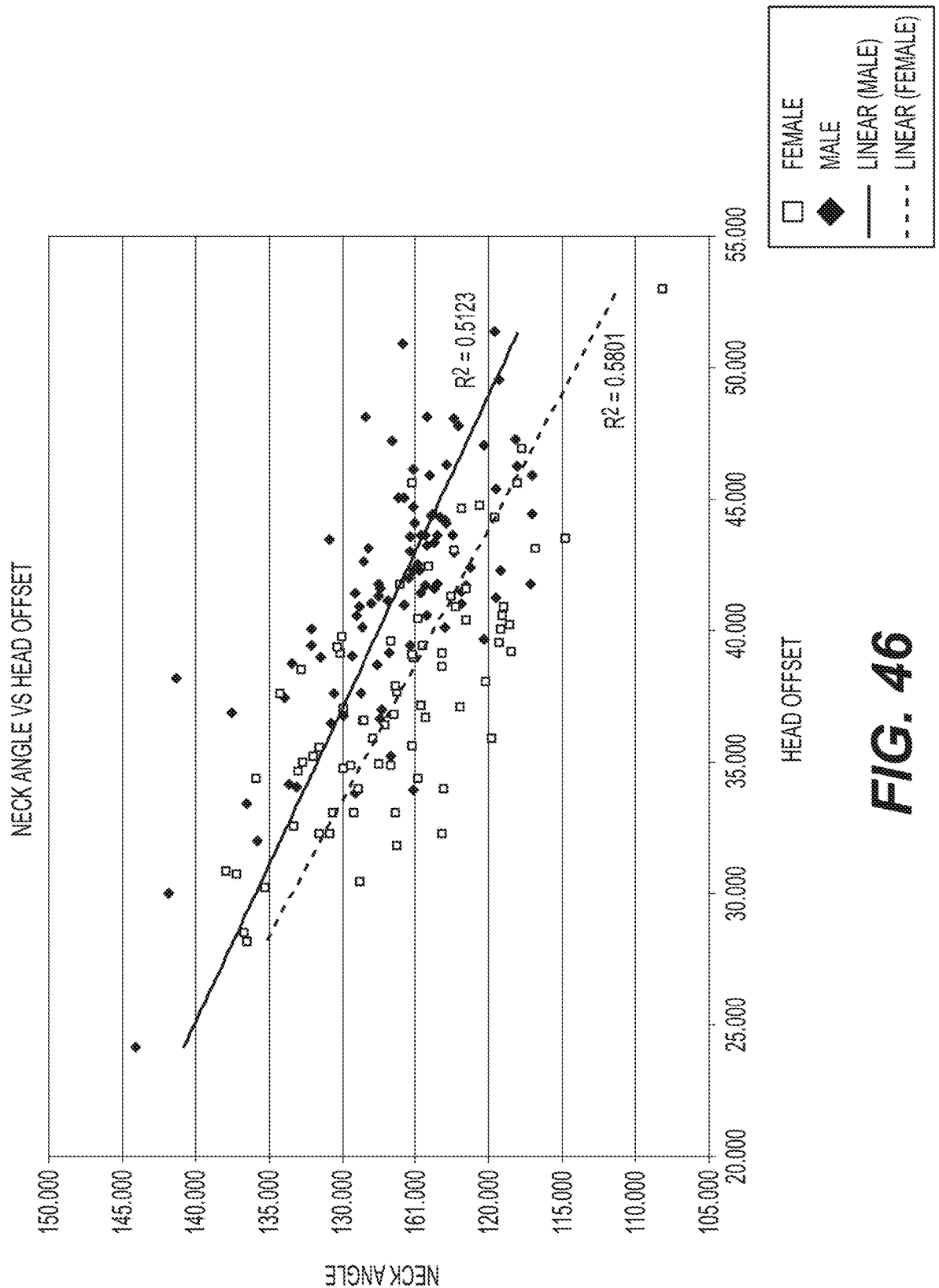
FIG. 46 is a plot of proximal angle versus head offset.
Figure 47:
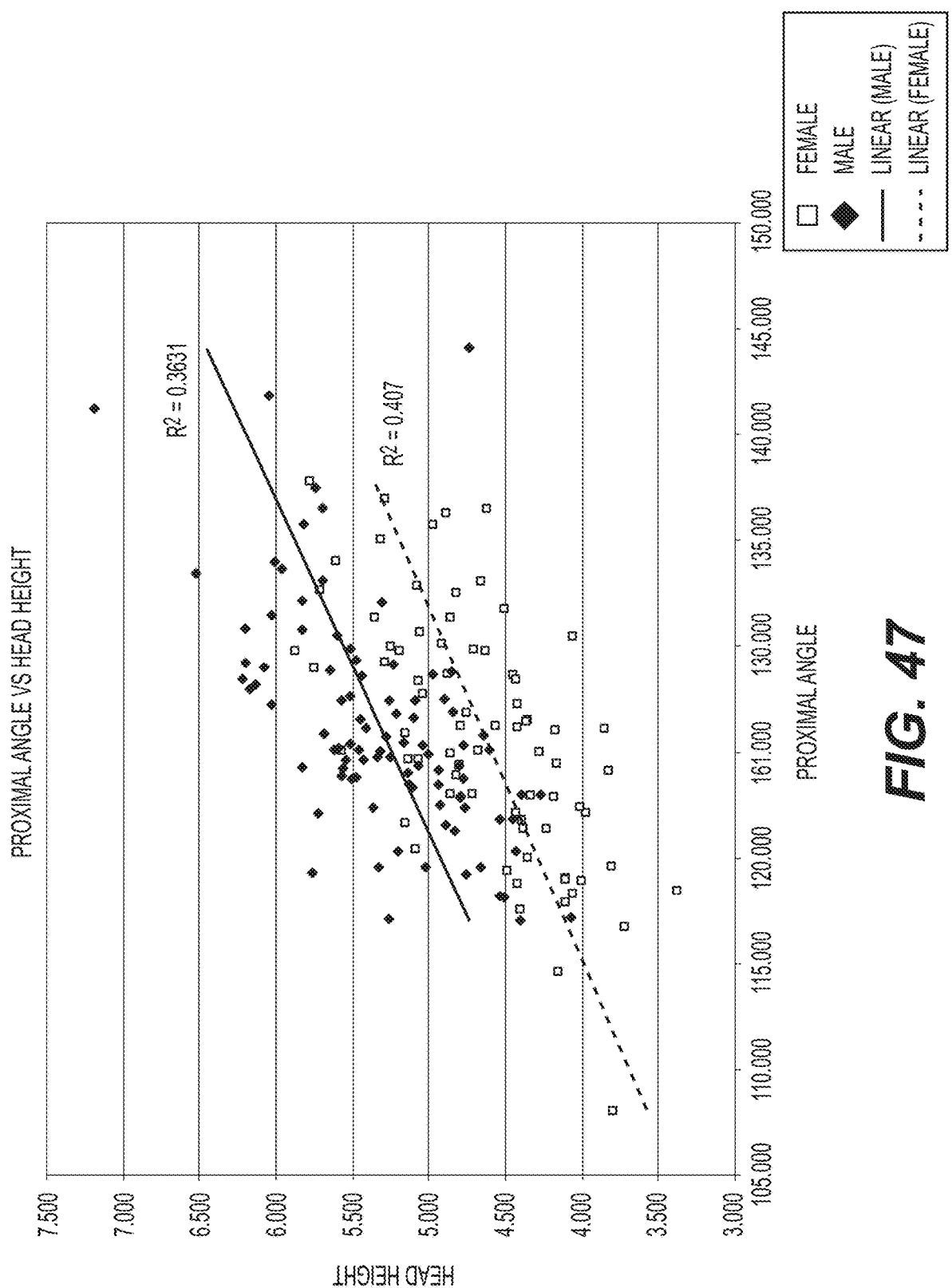
FIG. 47 is a plot of proximal angle versus head height.
Figure 48:
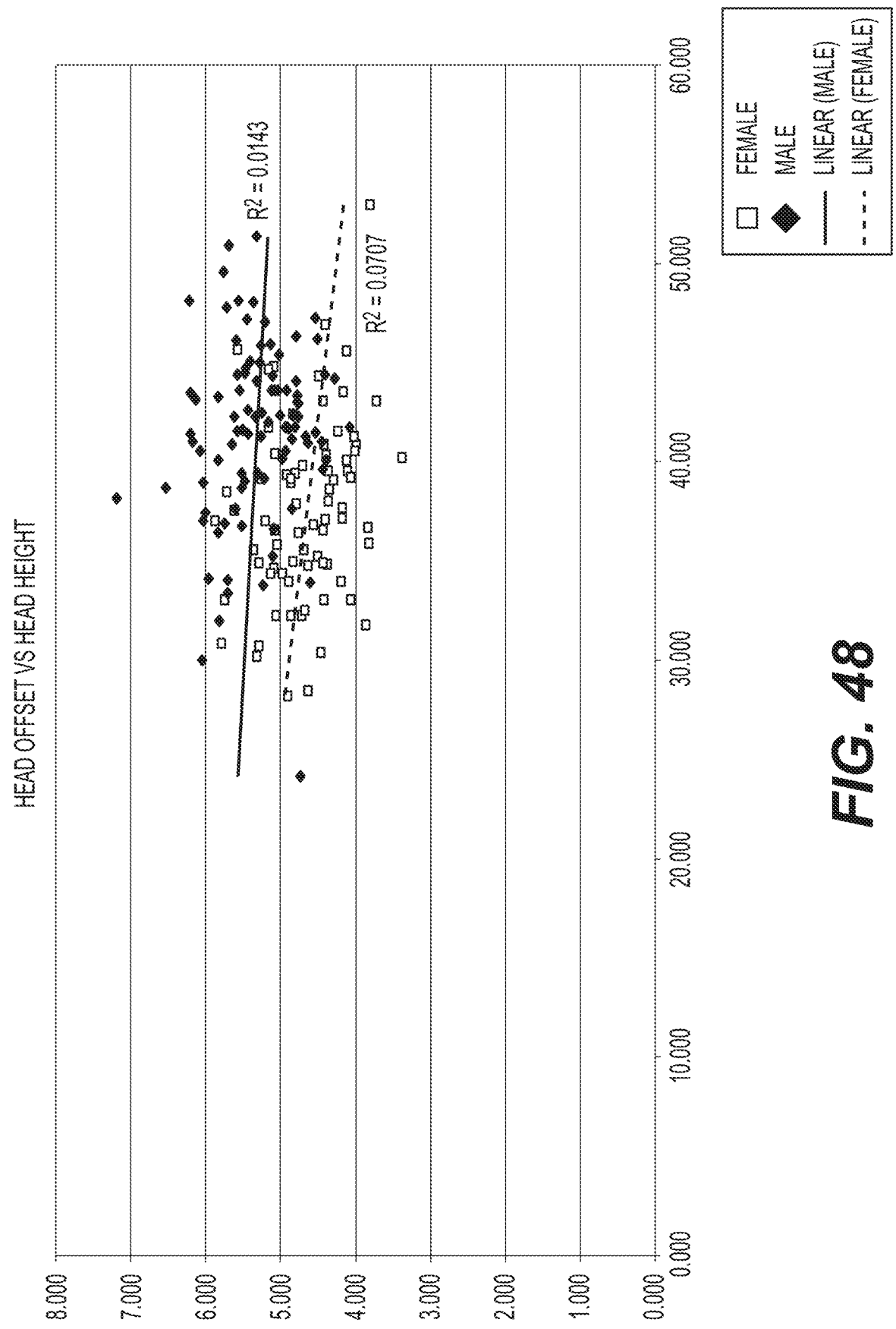
FIG. 48 is a plot of head offset versus head height.
Figure 49:
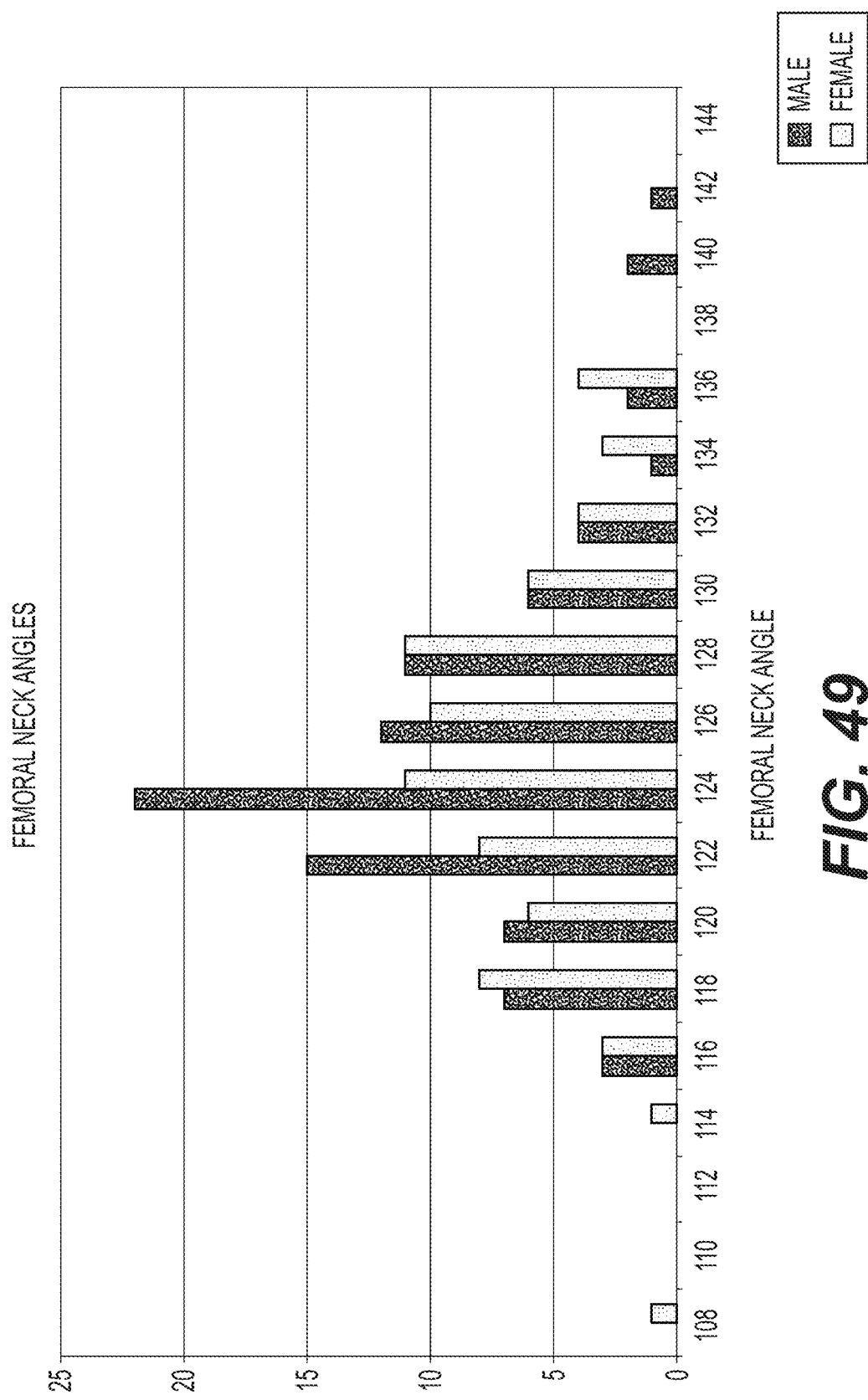
FIG. 49 is a proximal angle histogram.
Figure 50:
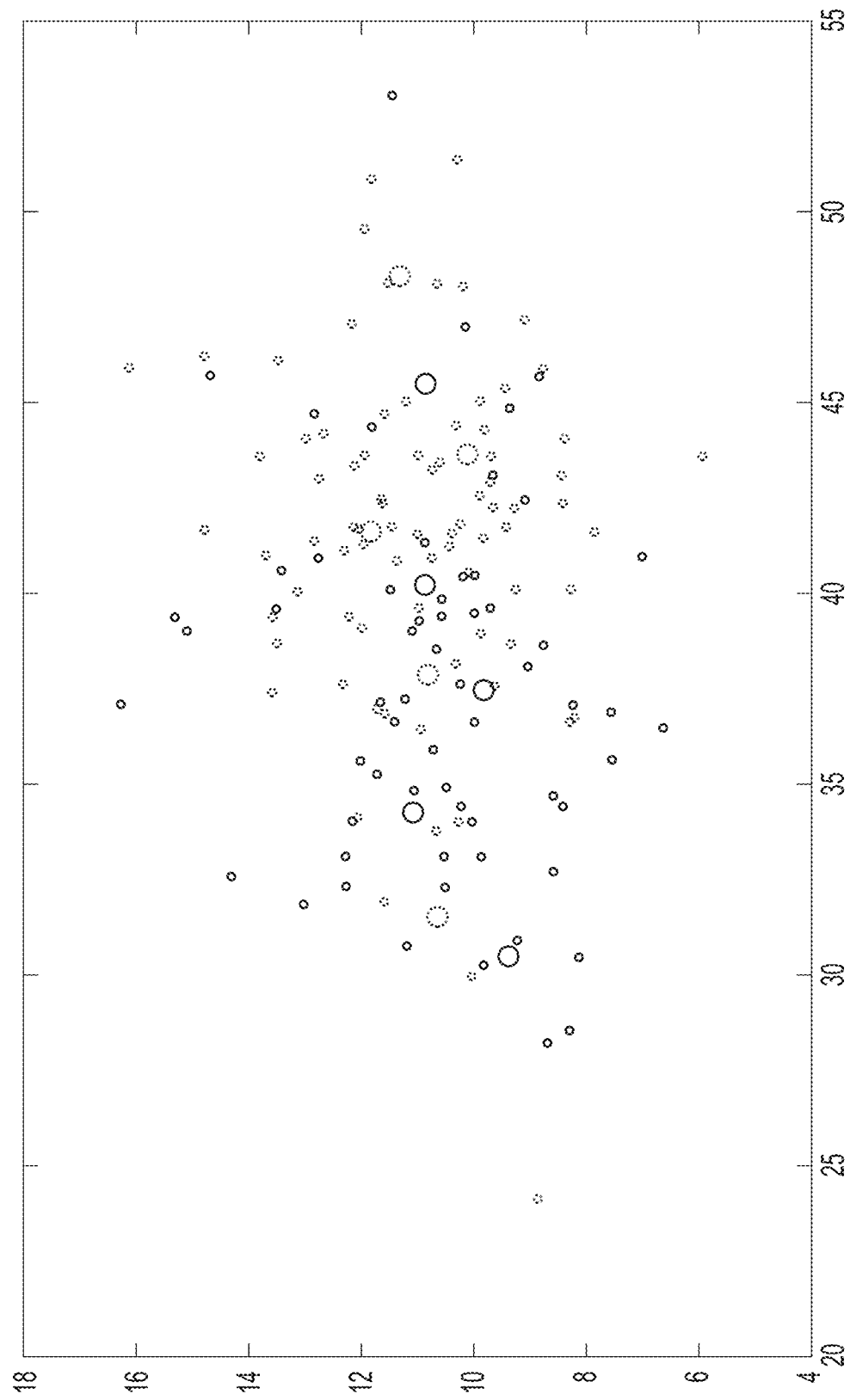
FIG. 50 is a plot depicting clusters of females and males for head offset and calcar diameter.
Figure 51:
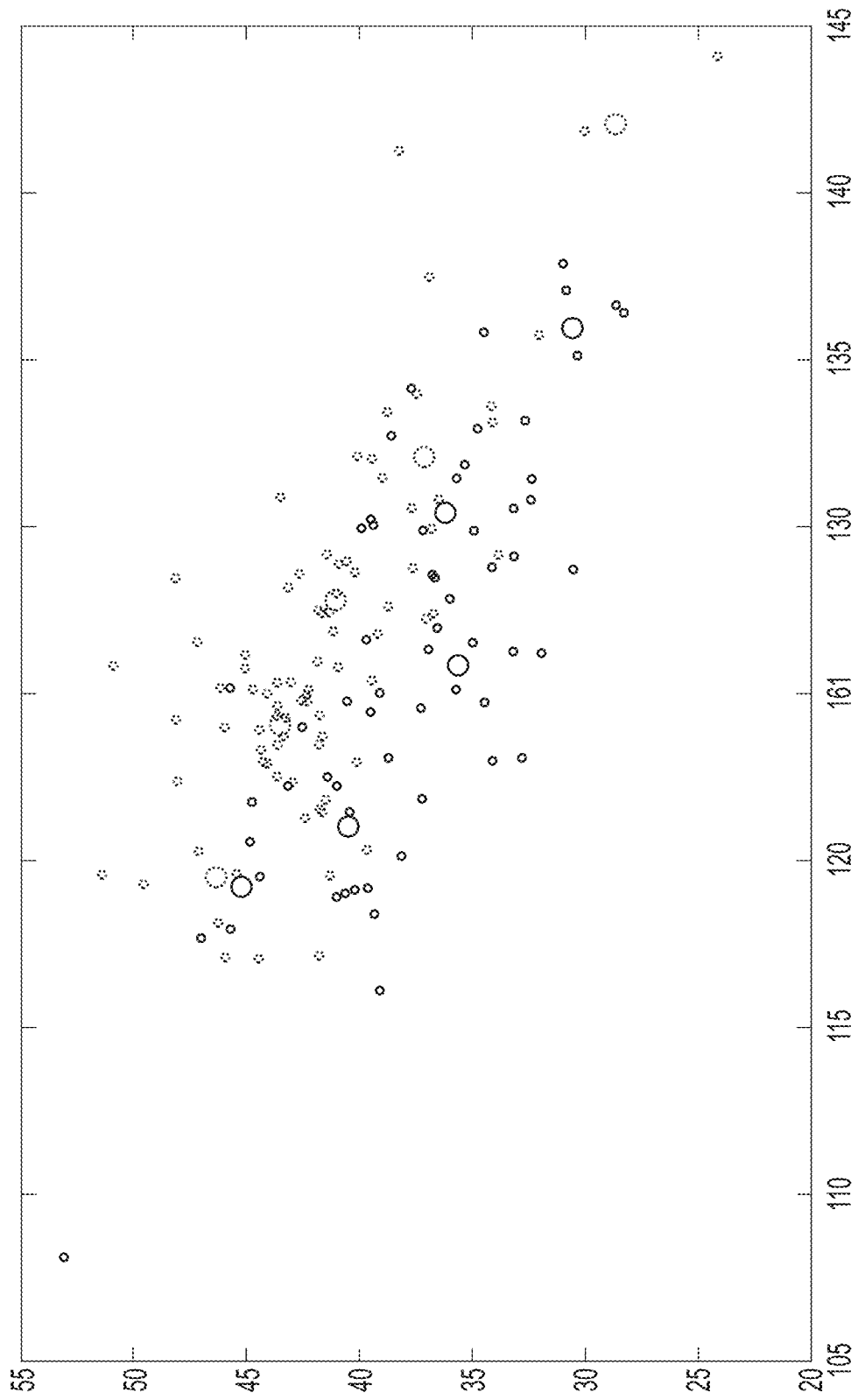
FIG. 51 is a plot depicting clusters of females and males for head offset and proximal angle.
Figure 52:
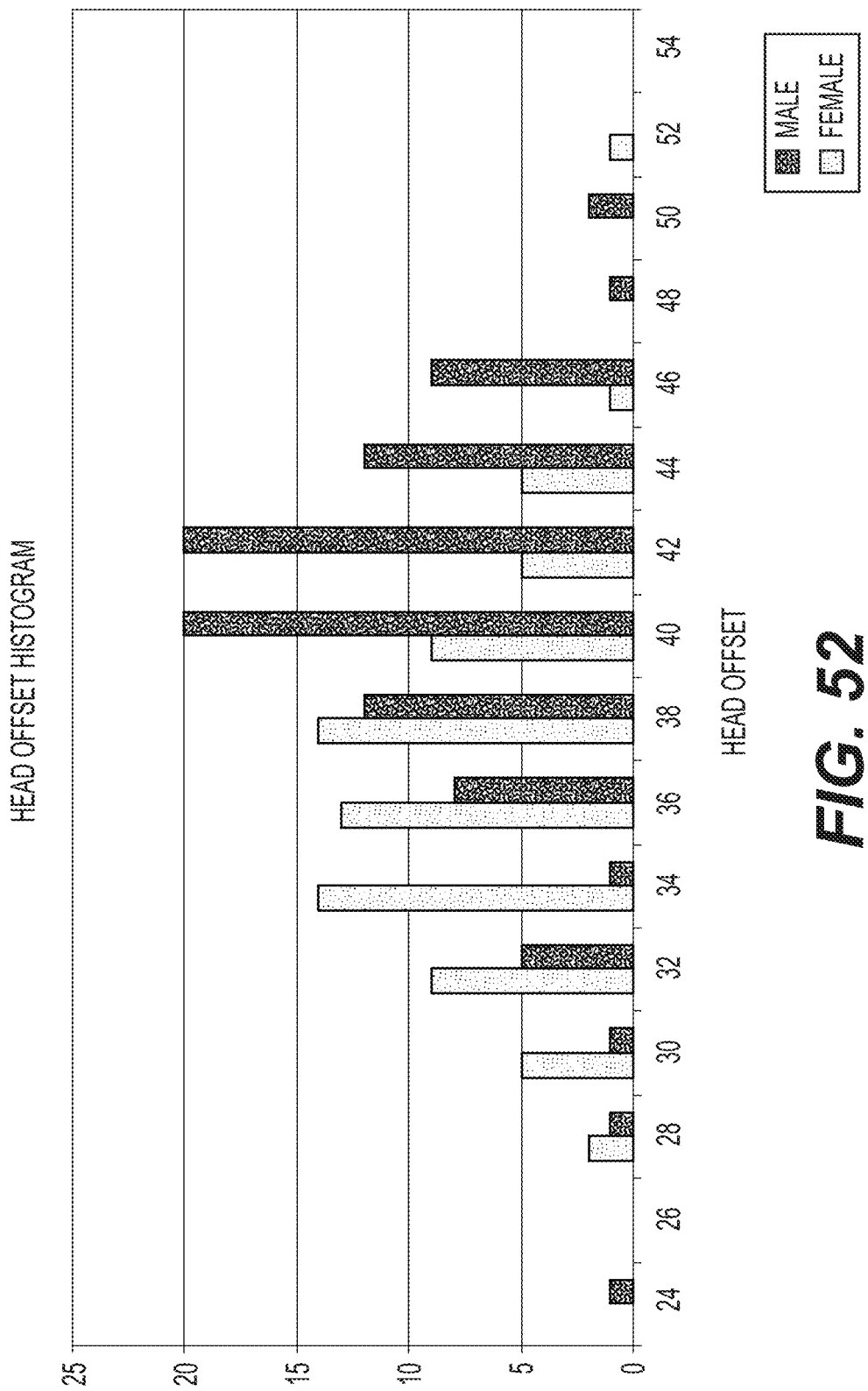
FIG. 52 is a head offset histogram.
Figure 53:
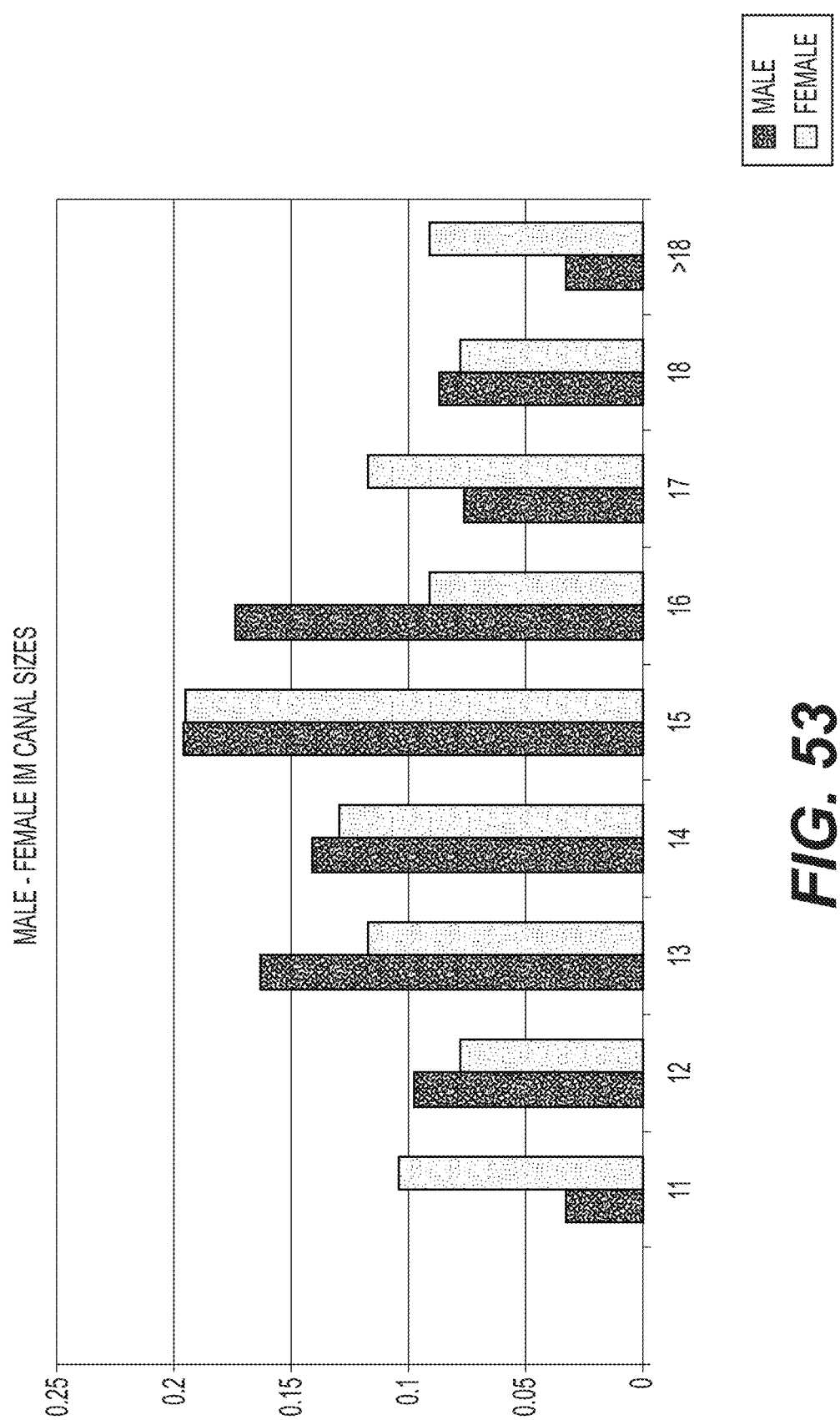
FIG. 53 is an IM sizes histogram.

Referring to FIG. 45 and Table I, in the context of X-ray images used to construct a virtual 3D bone model, it has been discovered that bone rotation during imaging plays an important role in correctly constructing the model. In other words, if one attempts to compile X-ray images in circumstances where bone rotation has occurred between images, the X-ray images need to be normalized to account for this bone rotation.

By way of example, in the context of a proximal femur, it has been discovered that bone rotation of six and fifteen degrees results in significant changes to the measurements extracted from X-ray images. By way of example, these measurements include, without limitation, proximal angle, head offset, and intramedullary canal width. As reflected in Table I, for the same femur, that was X-ray imaged at zero degrees (i.e., a starting point established by the initial X-ray), six degrees of rotation, and fifteen degrees of rotation exhibited differences proximal angle, head offset, and intramedullary canal width as measured using pixels, where each pixel size was approximately 0.29 millimeters. In particular, proximal angle increased with increasing rotation, as did head offset, but the same was not true for intramedullary width. In this exemplary table, three transverse planes were spaced apart along the longitudinal axis, where each plane corresponded to a location where the width of the intramedullary canal was measured. As reflected in Table I, the widths of the intramedullary canal for the same location change depending upon the angle of rotation. Consequently, as will be discussed in more detail hereafter, when constructing a 3D virtual model of a bone using X-rays, one must account for rotational deviation to the extent bone rotation occurs during imaging.

It should be understood, however, that the foregoing is an exemplary description of anatomies that may be used with the exemplary system and methods and, therefore, is in no way intended to limit other anatomies from being used with the present system pursuant to the disclosed methods. As used herein, tissue includes bone, muscle, ligaments, tendons, and any other definite kind of structural material with a specific function in a multicellular organism. Consequently, when the exemplary system and methods are discussed in the context of bone, those skilled in the art should realize the applicability of the system and methods to other tissue.

Referring back to FIG. 1, the anatomy data input to the system is directed to three modules, two of which involve processing of the anatomy data (full bone reconstruction module, patient-specific module), while a third (abnormal database module) catalogues the anatomy data as part of a database. A first of the processing modules, the full bone reconstruction module, processes the input anatomy data with data received from the statistical atlas module to generate a virtual, 3D model of the bone(s) in question. This 3D model is a full, normal reconstruction of the bone(s) in question. A second of the processing modules, the patient-specific module, processes the input anatomy data with data received from the full bone reconstruction module to generate one or more molds, fixation systems, graft shaping tools, and renderings, in addition to one or more final orthopedic implants. A rendering refers to visualization of reconstructed anatomy for feedback regarding expected surgical outcome. More specifically, the patient-specific module is adapted to generate fully customized devices, designed to precisely fit patient-specific anatomy, despite severe deviation of the patient's anatomy from normal. Moreover, the patient-specific module utilizes the virtual 3D reconstructed bone model from the full bone reconstruction module to automatically identify anatomical regions and features for device design parameters (e.g., fitting region and/or shape). In this fashion, patient-specific data is used to define design parameters so that the output instrument and any implant precisely fits the specific anatomy of the patient. Exemplary utilizations of the patient-specific module will be discussed in greater detail hereafter. In order to understand the functions and processes of the system in further detail, the following is an explanation of the modules of the system starting with the statistical atlas module.

Figure 2:
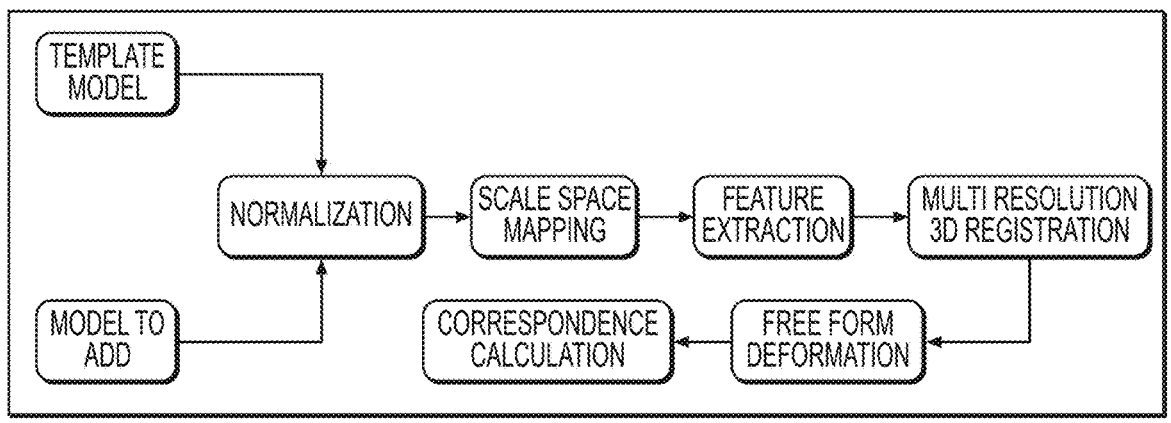
FIG. 2 is a schematic diagram detailing how to add a new anatomical structure to a statistical atlas in order to generate correspondence.

As shown in FIGS. 1 and 2, the statistical atlas module logs virtual, 3D models of one or more anatomies (e.g., bones) to capture the inherent anatomical variability in a given population. In exemplary form, the atlas logs mathematical representations of anatomical features of the one or more anatomies represented as a mean representation and variations about the mean representation. By representing the anatomical features as mathematical representations, the statistical atlas allows automated measurements of anatomies and, as will be discussed in more detail hereafter, reconstruction of missing anatomies.

In order to extract anatomical variations across a common anatomy, input anatomy data is compared to a common frame of reference across a population, commonly referred to as a template 3D model or anatomical 3D template model. This template 3D model is visually represented on a graphic display as a 3D model that can be rotated and otherwise visually manipulated, but comprises a mathematical representation of anatomical surface features/representations for all anatomies across the statistical atlas for the tissue in question (i.e., for a given bone all properties of the bone are shared across the population of the statistical atlas, which is generated from the template 3D model). The template 3D model can be a combination of multiple anatomical representations or a single representative instance and may represent the lowest entropy state of the statistical atlas. For each anatomy to be added to the statistical atlas (i.e., input anatomy data), an anatomical 3D model is created and both the anatomical 3D model and the template 3D model are subjected to a normalization process.

During the normalization process, the anatomical 3D model is normalized relative to the scale of the template 3D model. The normalization process may involve scaling one or both of the anatomical 3D model and the template 3D model to have a common unit scale. After normalization of the anatomical 3D model and the template 3D model, the normalized anatomical 3D model and template 3D model are rendered scale invariant, so that shape features can be utilized independent of scale (meaning size in this case). After normalization is complete, both 3D models are processed via a scale space mapping and feature extraction sequence.

Scale space mapping and feature extraction is essentially a multi-resolution feature extraction process. In particular, this process extracts shape-specific features at multiple feature scales. Initially, a plurality of anatomical features is selected, each representing features present at a different scale space. Thereafter, for each scale space representation of the selected anatomical feature, model specific features are extracted. These extracted features are used to draw out robust (as to noise) registration parameters between the template 3D model and the anatomical 3D model. Subsequent to this multi-resolution feature extraction process, the extracted data is processed via a multi-resolution 3D registration process.

Figure 5:
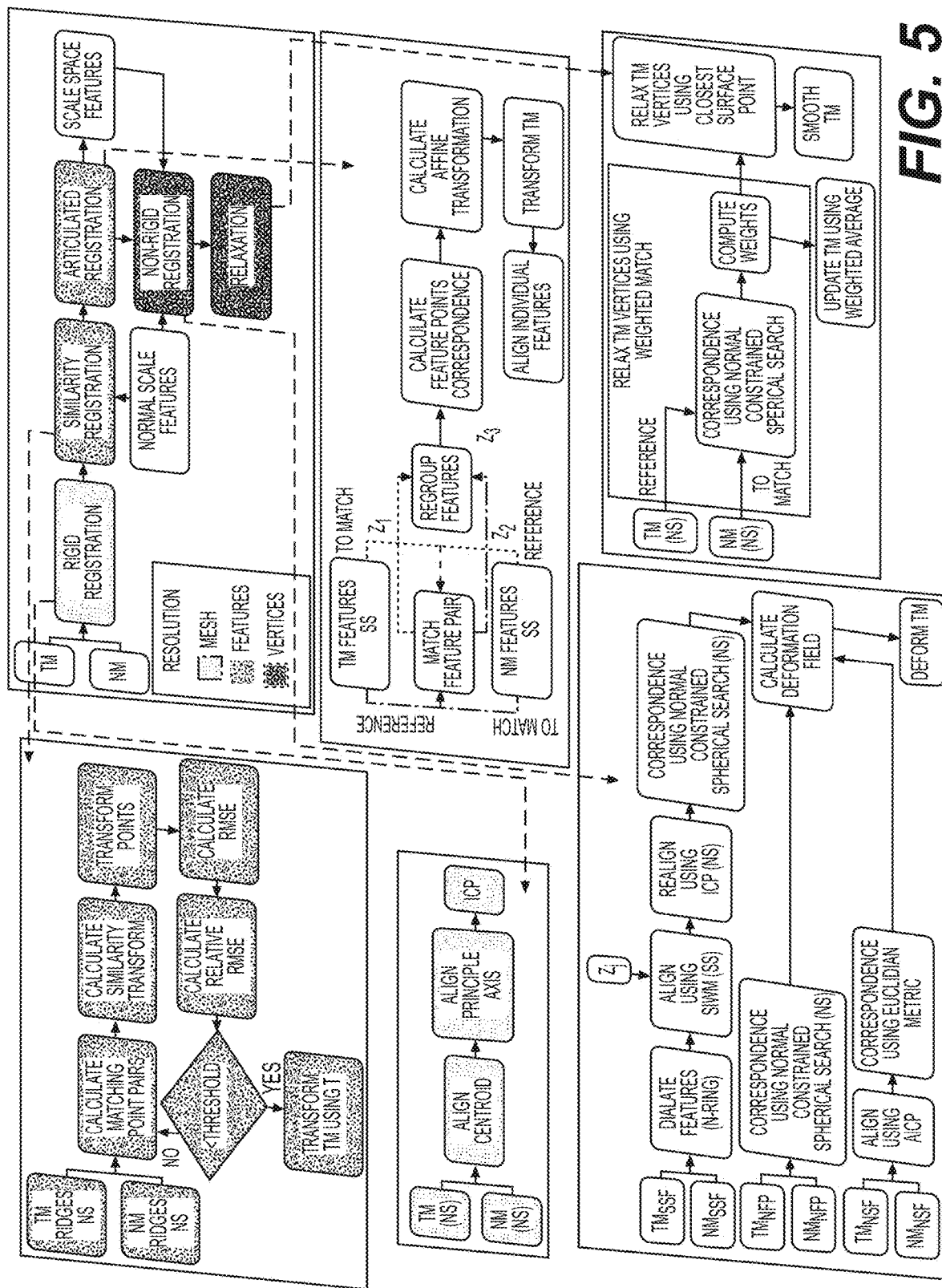
FIG. 5 is a low level break down of multi-resolution registration as outlined in FIG. 3.

Referring to FIGS. 2-5, the multi-resolution 3D registration process uses the scale space extracted features to carry out an affine registration calculation between the anatomical 3D model and template 3D model in order to register the two models. In particular, the anatomical 3D model and template 3D model are processed via a rigid registration process. As represented in FIG. 5, this rigid registration process is operative to align the anatomical 3D model and template 3D model to ensure both models are in the same space and with no pose singularity. In order to align the 3D models, the centroids associated with each model are aligned. In addition, the principle axes for each 3D model are aligned so that the major direction of both 3D models is the same. Finally, the pose difference between the 3D models is minimized by carrying out an iterative closest point calculation.

Post rigid registration, the 3D models are registered using a similarity registration process. This process involves aligning the template 3D model and the anatomical 3D model in normal scale iteratively by calculating a similarity transform that best aligns the normal scale features (i.e., ridges) for both the template 3D model and the anatomical 3D model. The iterative similarity alignment algorithm is a variant of iterative closest point. Within each iteration rotation, translation and scale are calculated between point pairs until convergence. Pair matching or correspondence between the two set of points is evaluated using distance query calculated using Kd-tree, or some other space partitioning data structure. In particular, the ridges for both models are utilized to carry out a calculate matching point pairs process. In this exemplary description, ridges refers to points on a 3D model where a single principle curvature has extrema along its curvature lines. As part of the calculate matching point pairs process, points are identified on ridges of the 3D models that match one another. Next, the ridges of both 3D models are subjected to a similarity transformation calculation process where rotation, translation, and scale are calculated that best align the ridges of both models. A transform points process follows, which is operative to apply the calculated rotation, translation, and scale to the template 3D model ridges. Thereafter, the root mean square error or distance error between each matched point set is calculated, followed by calculation of the change in relative root mean square error or distance error from the previous process. If the change in relative root mean square error or distance error is within a predetermined threshold, then a transformation process occurs to apply the final rotation, translation, and scale to the template 3D model.

An articulated registration process follows the similarity registration process and receives input data from a scale space features process. In the scale space feature process, feature are extracted from the template 3D model and the anatomical 3D model in different scale spaces. Each scale space is defined by convolving the original anatomical 3D model with Gaussian smoothing function.

The purpose of the articulated registration process is to match "n" scale space features of the template 3D model with "m" scale space features calculated on the anatomical 3D model. The difference between the number of detected features on the template 3D model and the anatomical 3D model is due to anatomical variation. This difference in a number of detected features may result in many relationships between the template 3D model and the anatomical 3D model. Therefore, a two-way, mutual feature matching is performed to accommodate such variation and achieve accurate matching between all mutual features. Specifically, feature sets are computed on the template 3D model in scale space. In this exemplary process, feature sets are connected sets of points that represent a prominent anatomical structure (e.g., acetabular cup in the pelvis, spine process in the lumbar). Likewise, feature sets are computed on the anatomical 3D model in scale space. A matching feature pair process matches the feature sets computed on the template 3D model to the feature sets on the anatomical 3D model using shape descriptors (e.g., curvature, shape index, etc.). The result of this process is an "n-m" mapping of feature sets between the template 3D model and the anatomical 3D model. If necessary, a regrouping process is carried out to regroup the matched feature sets into a single feature set (e.g., if acetabular cup was detected as two pieces, this process would regroup the two pieces into one single feature set). Thereafter, a calculation process is carried out to calculate the correspondence between each point in matched feature sets on the template 3D model and the anatomical 3D model. An affine calculation transformation process follows in order to calculate the rotation, translation, and shear that transform each matched feature set on the template 3D model to its corresponding feature set on the anatomical 3D model. Thereafter, the template 3D model is transformed using the calculated affine transformation parameters (i.e., rotation, translation, and shear). Finally, a rigid alignment process is carried out to align each matched feature set on the template 3D model and the anatomical 3D model.

A non-rigid registration process, occurring after the articulated registration process and the normal scale features process, involves matching all surface vertices on the template 3D model to vertices on the anatomical 3D model and calculating initial correspondence. This correspondence is then used to calculate deformation fields that move each vertex on the template 3D model to the matched point on the anatomical 3D model. Matching is done between vertices within the same class (i.e., scale space feature vertex; normal scale feature vertex, or non-feature vertex). In the context of the normal scale features process, shape features are calculated on the template 3D model and the anatomical 3D model in the original scale space (ridges), meaning the original input model.

Specifically, as part of the non-rigid registration process, the scale space features are calculated on the template 3D model (TMssf) and on the anatomical 3D model (NMssf). Each set of features on the template 3D model and on the anatomical 3D model are grown using "k" neighbor points. An alignment process is applied to the template 3D model scale space features to match its corresponding feature on the anatomical 3D model. Given two point clouds, reference (X) and moving (Y), the goal is to iteratively align the two point clouds to minimize overall error metric, under constraint of a minimum relative root mean squared error and maximum angle threshold. A realignment process is carried out to align feature sets on the template 3D model with the matching sets on the anatomical 3D model using iterative closest point in normal scale. Post realignment, the point correspondence between points in each feature set on the template 3D model with the matched feature set on the anatomical 3D model is calculated. The matched point on the anatomical 3D model should have a surface normal direction close to the template 3D model point. The output is forwarded to the calculate deformation fields step.

Parallel to the scale space features calculation course, template 3D model (TMnfp) and anatomical 3D model (NMnfp) non-feature points or the remaining set of points on the template 3D model surface that does not belong to either scale space features or normal scale features are processed pursuant to a correspondence calculation to calculate the point correspondence between non-feature points on the template 3D model and non-feature points on the anatomical 3D model. The matched point(s) on the new model should have a surface normal direction close to the template model point. The output is forwarded to the calculate deformation fields step.

Also parallel to the scale space features calculation course, normal scale features (i.e., ridges) on the template 3D model (TM nsf) are aligned with the normal scale features (i.e., ridges) on the anatomical 3D model (NM nsf) using AICP. AICP is a variant of the iterative closest point calculation where in each iteration translation, rotation, and scale are calculated between matched point sets. After the alignment process, a correspondence process is carried out.

The outputs from scale space features calculation course, the correspondence course, and the alignment course are subjected to a deformation process where the deformation field is calculated to move each point on the template 3D model to its matched point on the anatomical 3D model.

The output of the non-rigid registration process is a subjected to a relaxation process in order to move the vertices of the template 3D model mesh closer to surface of the anatomical 3D model after the multi-resolution registration step and smooth the output model. In particular, the template 3D model in normal space (TM ns) and the anatomical 3D model in normal space (NM ns) are processed via a correspondence calculation to compute the closest vertices on template 3D model to the anatomical 3D model using a normal constrained spherical search algorithm. This calculation, using the closest vertices for both models, generates a correspondence vector from each vertex in the template 3D model and its matched vertices in anatomical 3D model, which may result in more than one match point from the anatomical 3D model. Using the matched points for each vertex on the template 3D model, the weighted mean of the matched points on the anatomical 3D model is calculated based on the Euclidian distance from the point and matched points. At this point, the template 3D model is updated using the weighted average so as to move each point on template 3D model using the calculated weighted average distance. After the computed weights process, a relaxation process is carried out for every point on template model in order to find the closest point on the anatomical 3D model surface and move it to that point. Finally, a smoothing operation is performed on the deformed template 3D model to remove noise. The resultant registered 3D models (i.e., template and anatomical 3D models) are then subjected to a free form deformation process.

The free form deformation process morphs the surface of the template 3D model with the surface of the anatomical 3D model. More specifically, the surface of the template 3D model is iteratively moved on a weighted point-to-point basis using mutually matched points on both the template 3D model surface and the anatomical 3D model surface.

Figure 6:
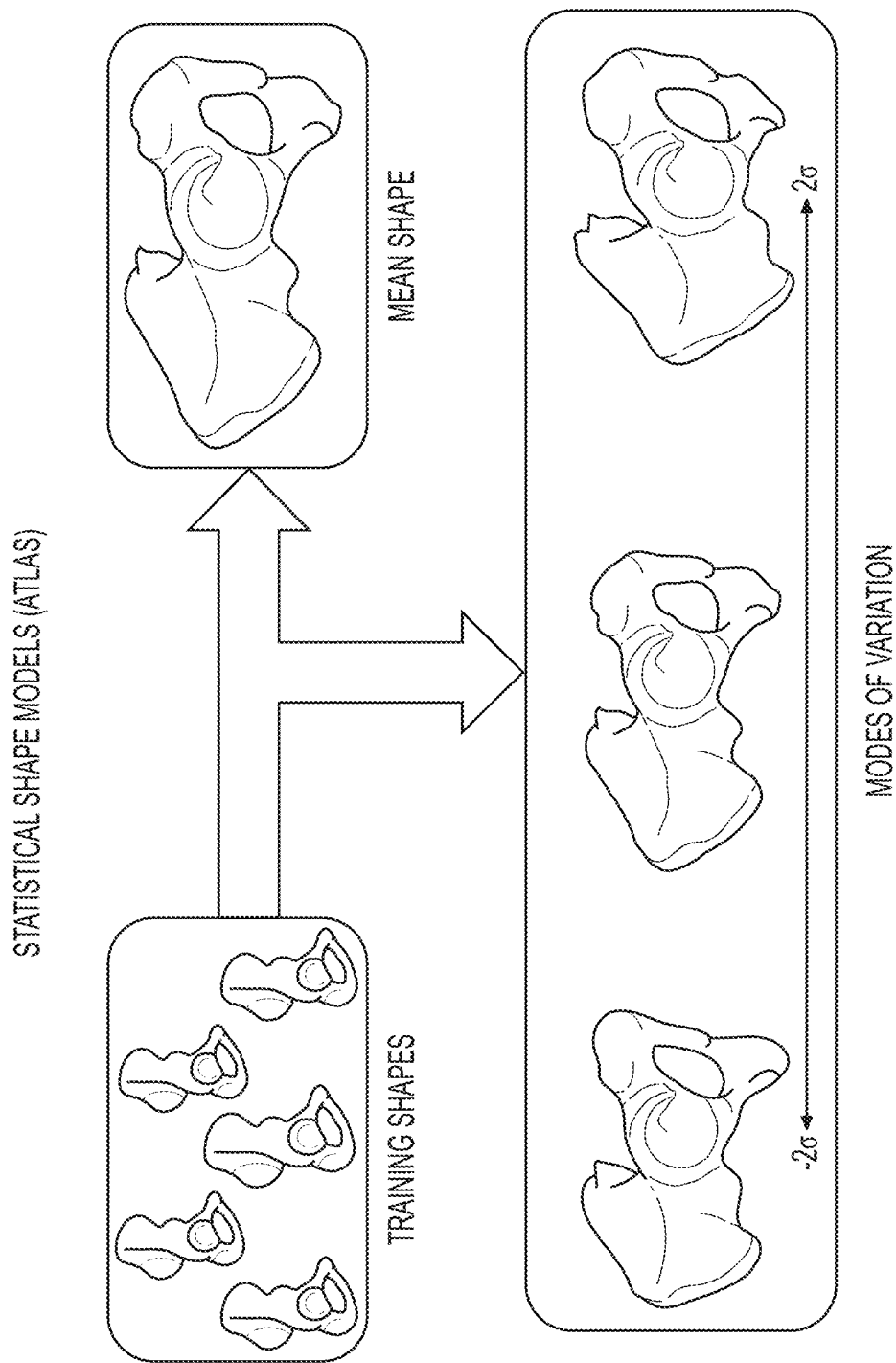
FIG. 6 is a graphical representation of capturing variation in population upon generation of correspondence

Referencing FIGS. 2 and 6, after the free form deformation process, the anatomical 3D model is subjected to a correspondence calculation process to determine the deviation between the anatomical 3D model and the morphed template 3D model. This correspondence calculation process refines the template 3D model from the free form deformation step to perform a final match of the selected landmark locations on the template deformed 3D model and the deformed anatomical 3D model. In this fashion, the correspondence calculation process calculates and records the variation in size and shape between the 3D models, which is recorded as deviation about the mean model. The output of this correspondence calculation process is the addition of a normalized anatomical 3D model and a revised template 3D model having been updated to account for the variations in the anatomical 3D model. In other words, the output of the process outlined in FIG. 2 is the normalized anatomical 3D model having been modified to have properties (e.g., point correspondence) consistent with the revised template 3D model to facilitate full anatomical reconstruction (e.g., full bone reconstruction).

Figure 7:
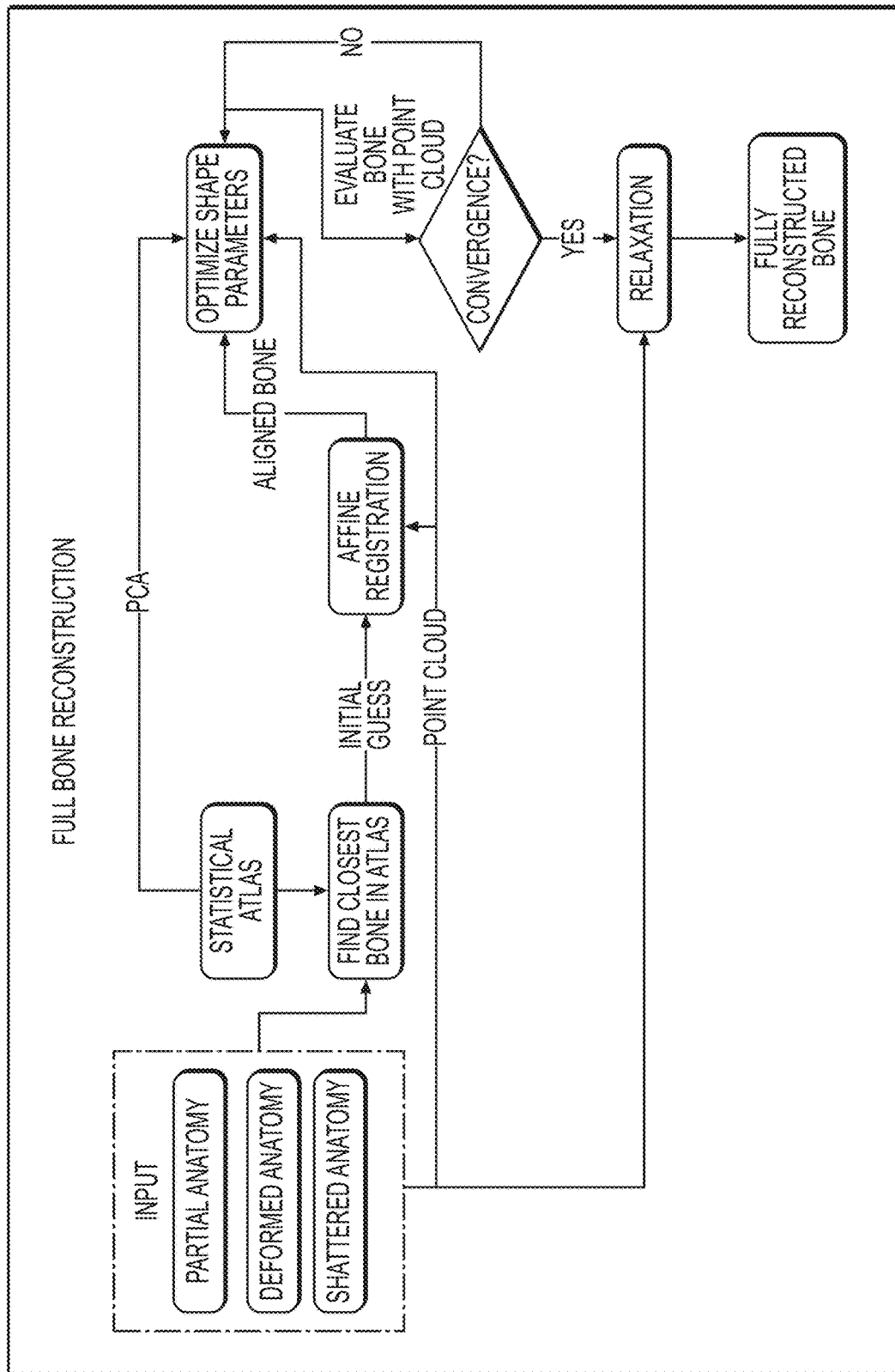
FIG. 7 is a schematic diagram of a full bone reconstruction process using partial, deformed or shattered anatomy.

Referring to FIGS. 1 and 7, inputs from the statistical atlas module and anatomy data are directed to a full anatomy reconstruction module. By way of example, the anatomy in question may be a bone or multiple bones. It should be noted, however, that anatomies other than bone may be reconstructed using the exemplary hardware, processes, and techniques described herein. In exemplary form, the full anatomy reconstruction module may receive input data as to a partial, deformed, or shattered pelvis. Input anatomical data comprises two dimensional (2D) images or three dimensional (3D) surface representations of the anatomy in question that may, for example, be in the form of a surface model or point cloud. In circumstances where 2D images are utilized, these 2D images are utilized to construct a 3D surface representation of the anatomy in question. Those skilled in the art are familiar with utilizing 2D images of anatomy to construct a 3D surface representation. Accordingly, a detailed explanation of this process has been omitted in furtherance of brevity. By way of example, input anatomical data may comprise one or more of X-rays, computed tomography (CT) scans, magnetic resonance images (MRIs), or any other imaging data from which a 3D surface representation may be generated. As will be discussed in more detail hereafter, this input anatomical data may be used, without limitation, for: (1) a starting point for identifying the closest statistical atlas 3D bone model; (2) registration using a set of 3D surface vertices; and, (3) a final relaxation step of reconstruction output.

Figure 3:
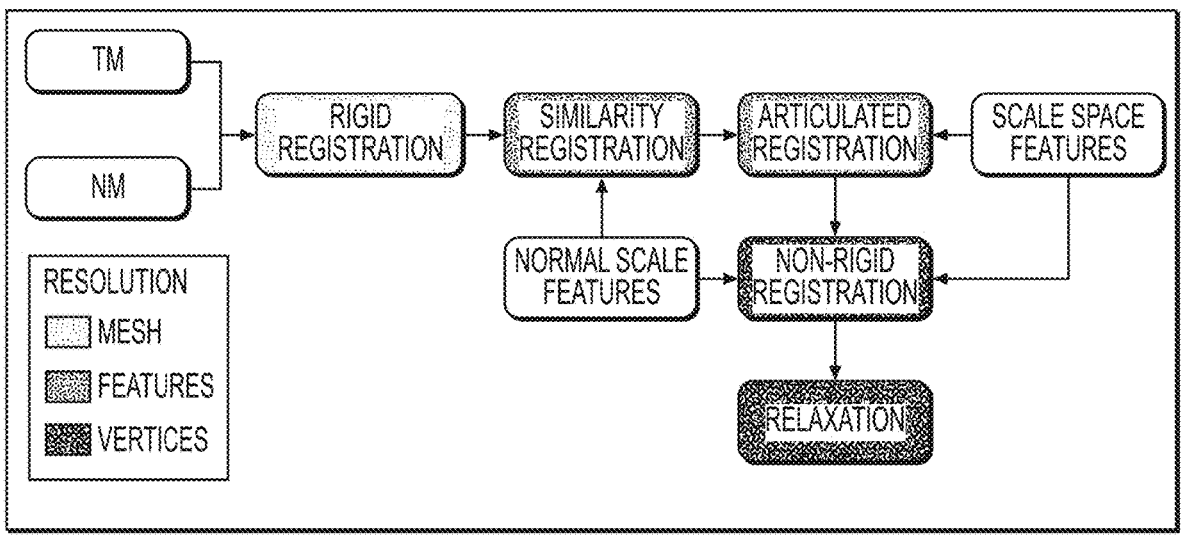
FIG. 3 is a multi-resolution 3D registration algorithm overview corresponding to the multi-resolution 3D registration in FIG. 2.
Figure 4:
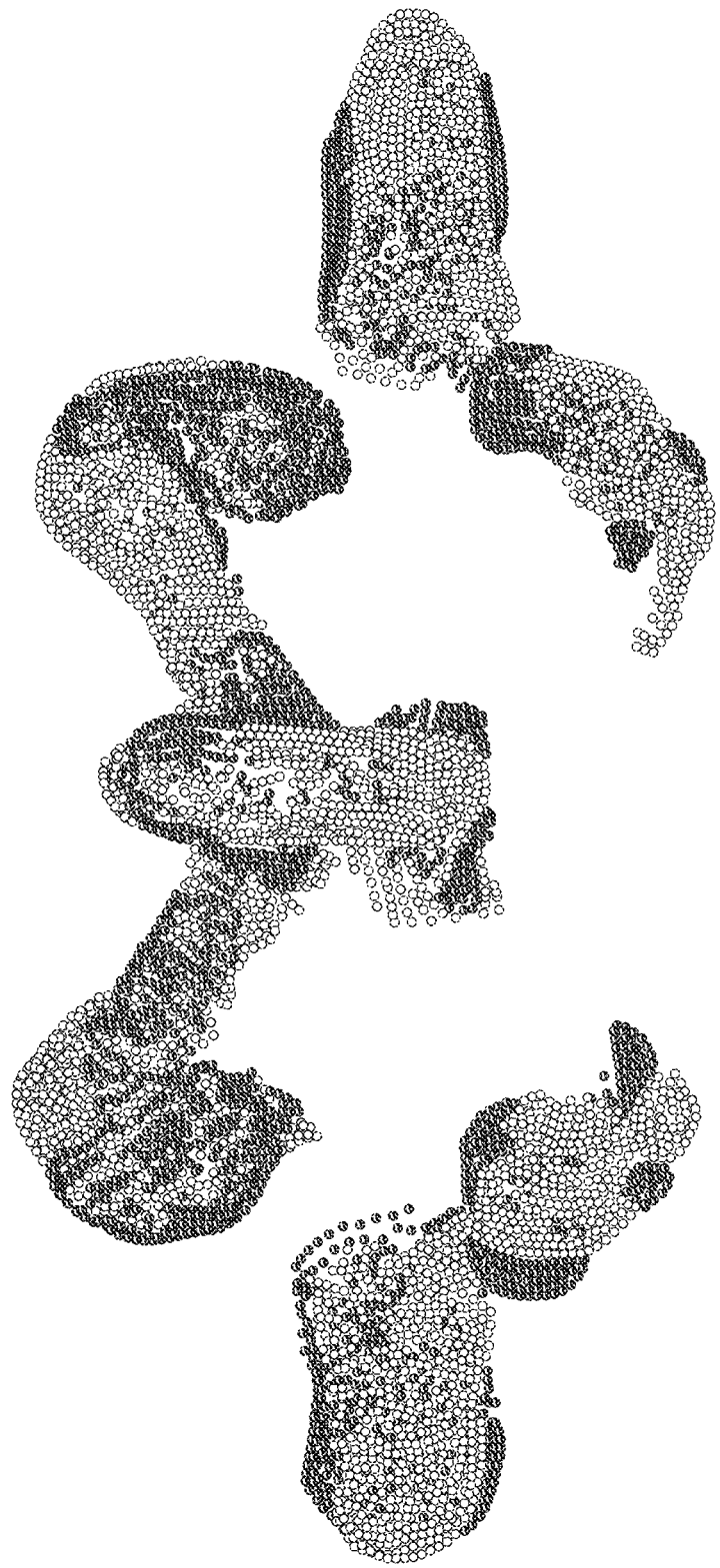
FIG. 4 is a multi-scale registration of feature points using multi-scale features.

As depicted in FIG. 7, the input anatomical data (e.g., bone model of the patient) is utilized to identify the anatomical model (e.g., bone model) in the statistical atlas that most closely resembles the anatomy of the patient in question. This step is depicted in FIG. 3 as finding the closest bone in the atlas. In order to initially identify a bone model in the statistical atlas that most closely resembles the patient's bone model, the patient's bone model is compared to the bone models in the statistical atlas using one or more similarity metrics. The result of the initial similarity metric(s) is the selection of a bone model from the statistical atlas that is used as an "initial guess" for a subsequent registration step. The registration step registers the patient bone model with the selected atlas bone model (i.e., the initial guess bone model) so that the output is a patient bone model that is aligned with the atlas bone model. Subsequent to the registration step, the shape parameters for aligned "initial guess" are optimized so that the shape matches the patient bone shape.

Shape parameters, in this case from the statistical atlas, are optimized so that the region of non-deformed or existing bone is used to minimize the error between the reconstruction and patient bone model. Changing shape parameter values allows for representation of different anatomical shapes. This process is repeated, at different scale spaces, until convergence of the reconstructed shape is achieved (possibly measured as relative surface change between iterations or as a maximum number of allowed iterations).

A relaxation step is performed to morph the optimized tissue to best match the original patient 3D tissue model. Consistent with the exemplary case, the missing anatomy from the reconstructed pelvis model that is output from the convergence step is applied to the patient-specific 3D pelvis model, thereby creating a patient-specific 3D model of the patient's reconstructed pelvis. More specifically, surface points on the reconstructed pelvis model are relaxed (i.e., morphed) directly onto the patient-specific 3D pelvis model to best match the reconstructed shape to the patient-specific shape. The output of this step is a fully reconstructed, patient-specific 3D tissue model representing what should be the normal/complete anatomy of the patient.

Referencing FIG. 1, the abnormal database is utilized as a data input and training for the defect classification module. In particular, the abnormal database contains data specific to an abnormal anatomical feature that includes an anatomical surface representation and related clinical and demographic data.

Figure 8:
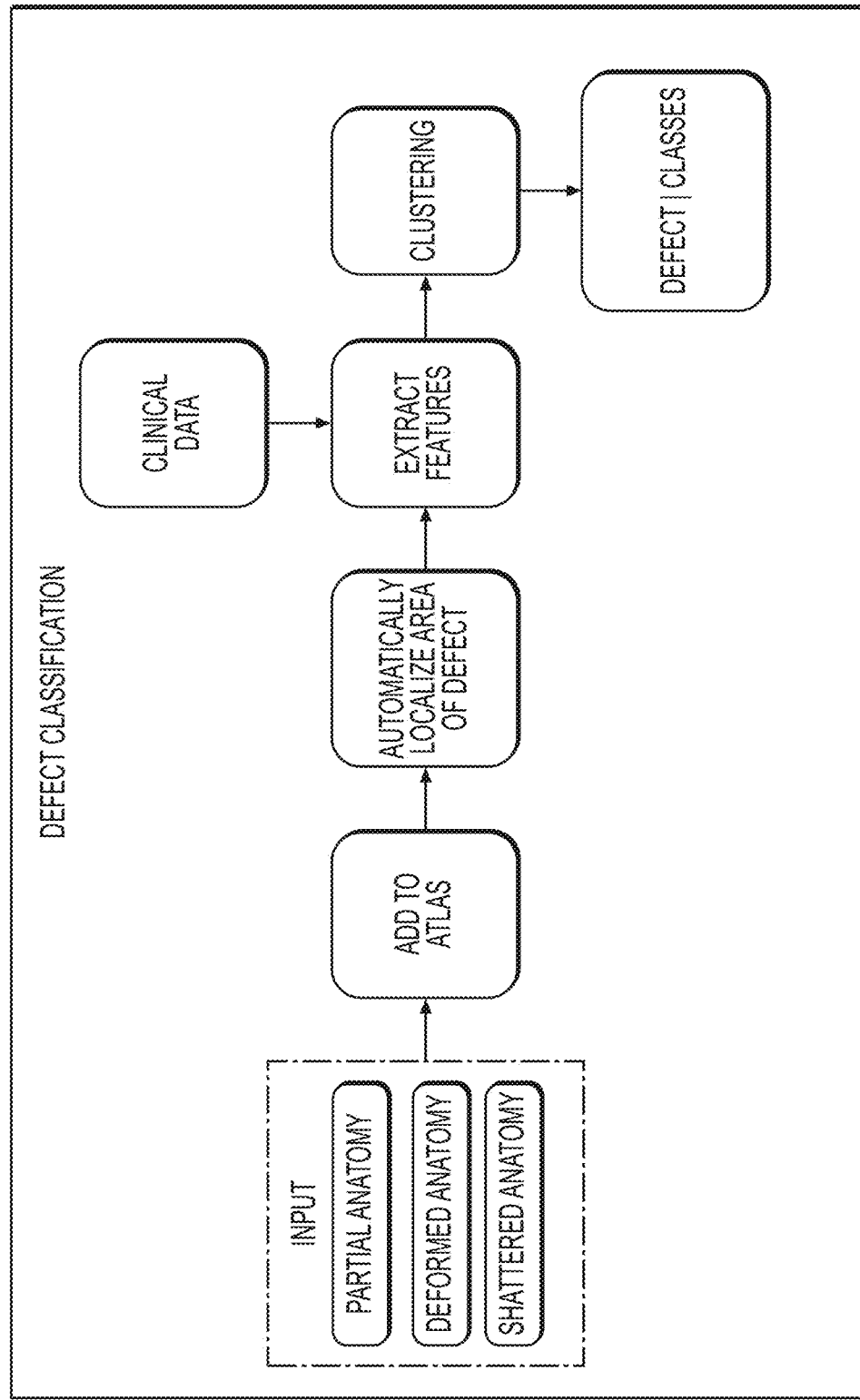
FIG. 8 is a schematic diagram of a defect classification process for generation of defect templates.
Figure 9:
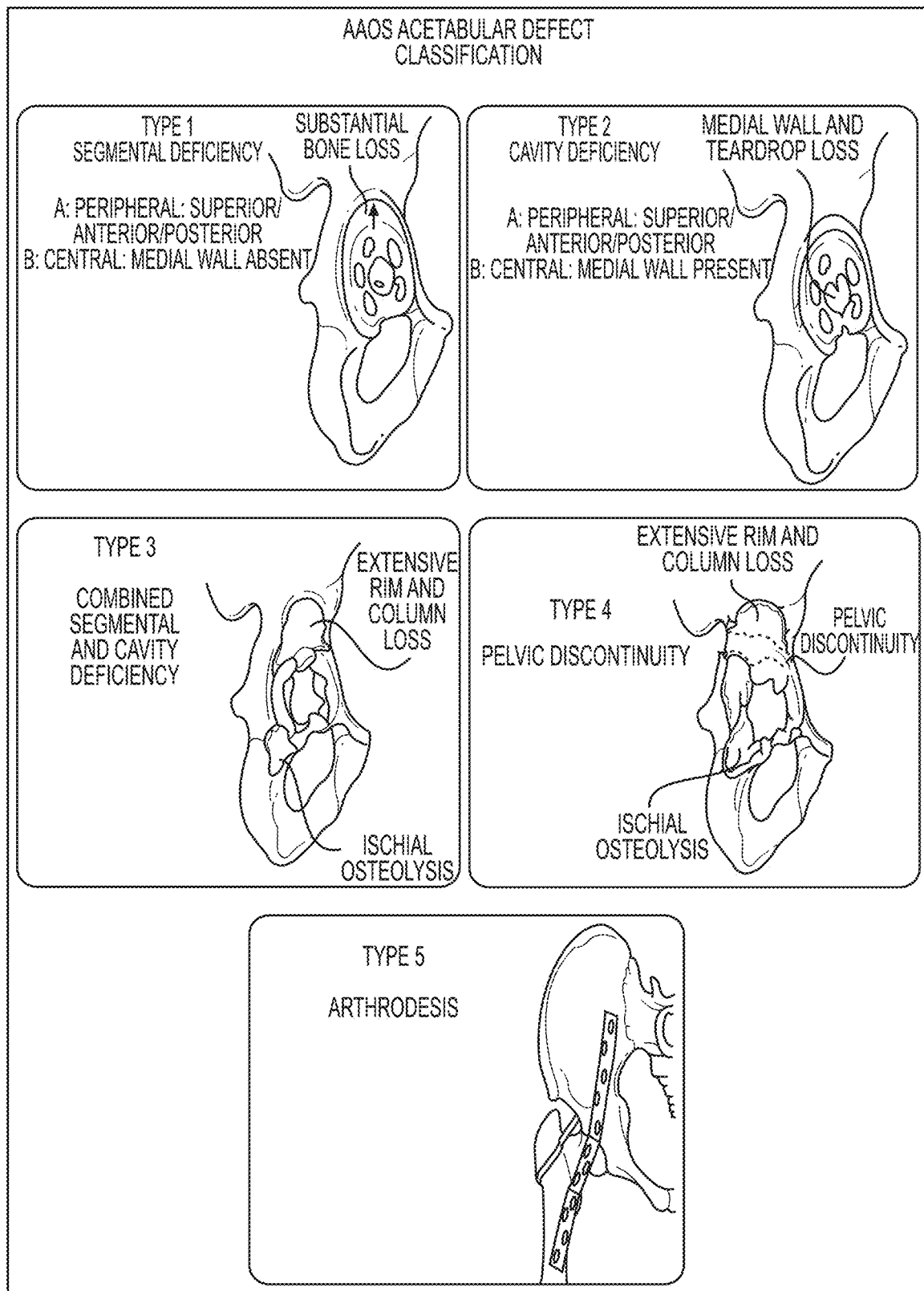
FIG. 9 is a graphical example of existing AAOS classifications for acetabular defects.
Figure 10:
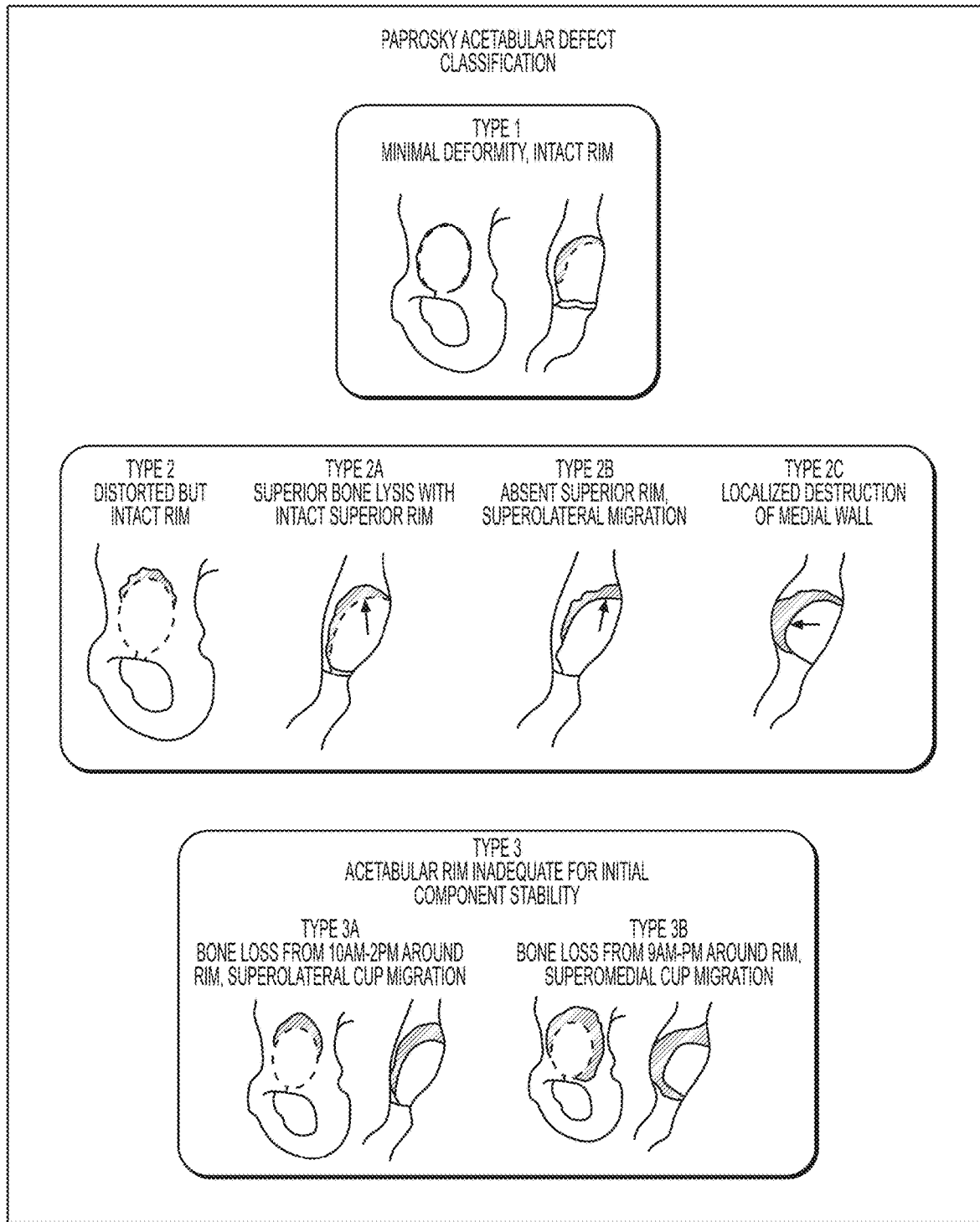
FIG. 10 is a graphical example of existing Paprosky acetabular defect classification.
Figure 11:
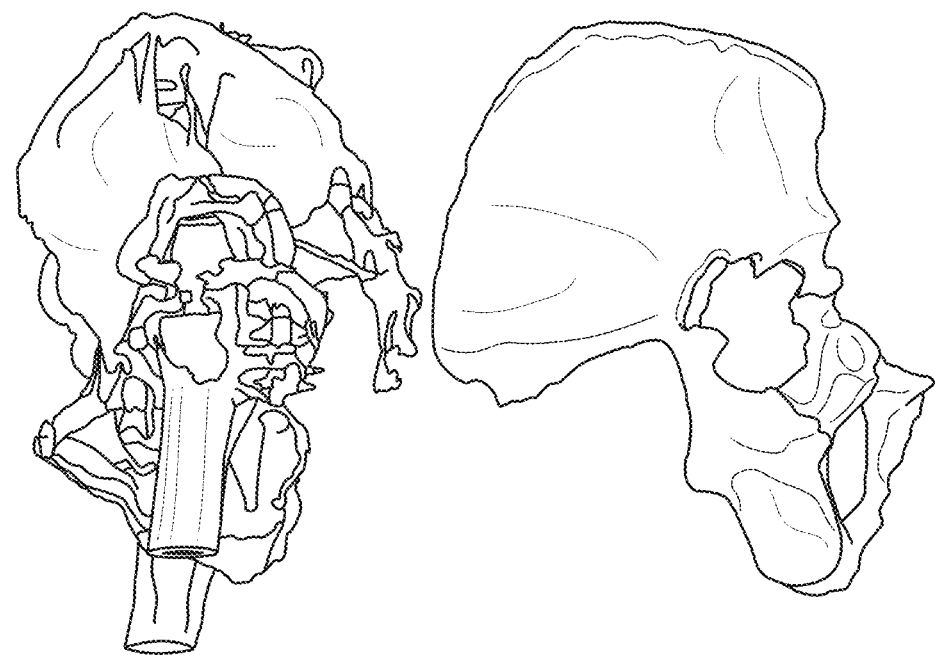
FIG. 11 is a three dimensional model representation of a patient with severe pelvis discontinuity on the left. On the right is an example of the three dimensional model of the patient's pelvis shown on the left.
Figure 12:
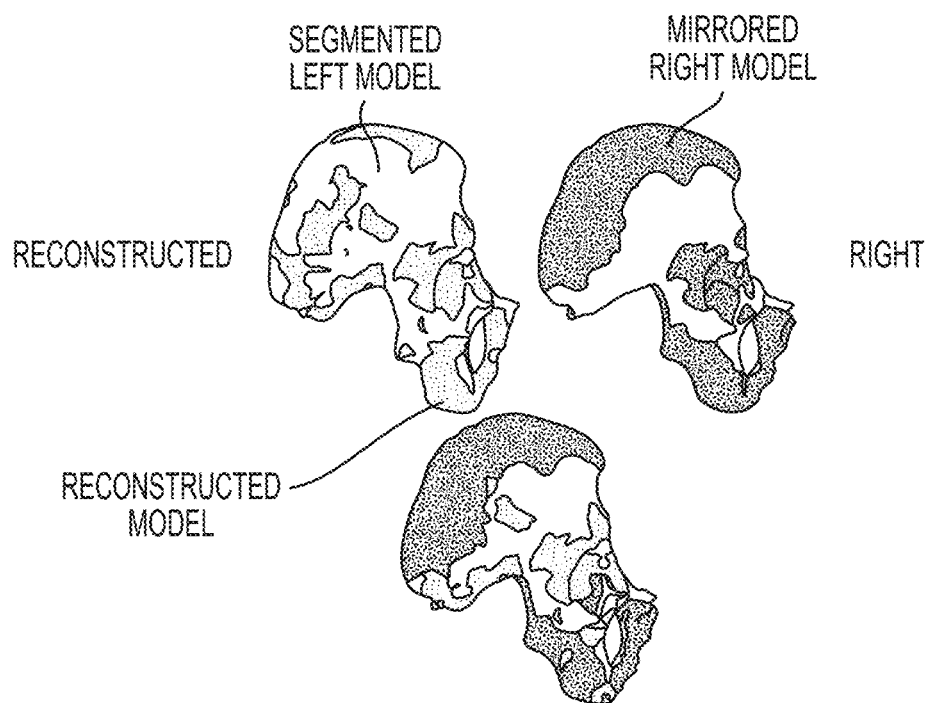
FIG. 12 is a comparison of the reconstructed left model and the original patient model, as well as right and left anatomy.
Figure 13:
FIG. 13 is a distance map between a reconstructed model and a mirror image of the pelvis model reconstructed.
Figure 14:
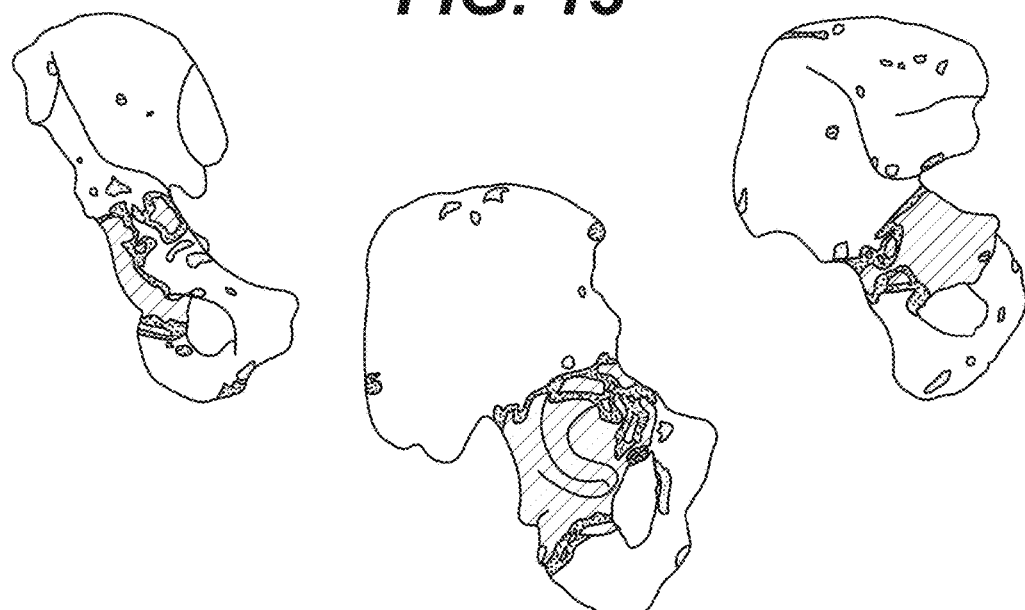
FIG. 14 is a patient with complete pelvis discontinuity and results of reconstruction with rms error of 1.8 mm.
Figure 15:
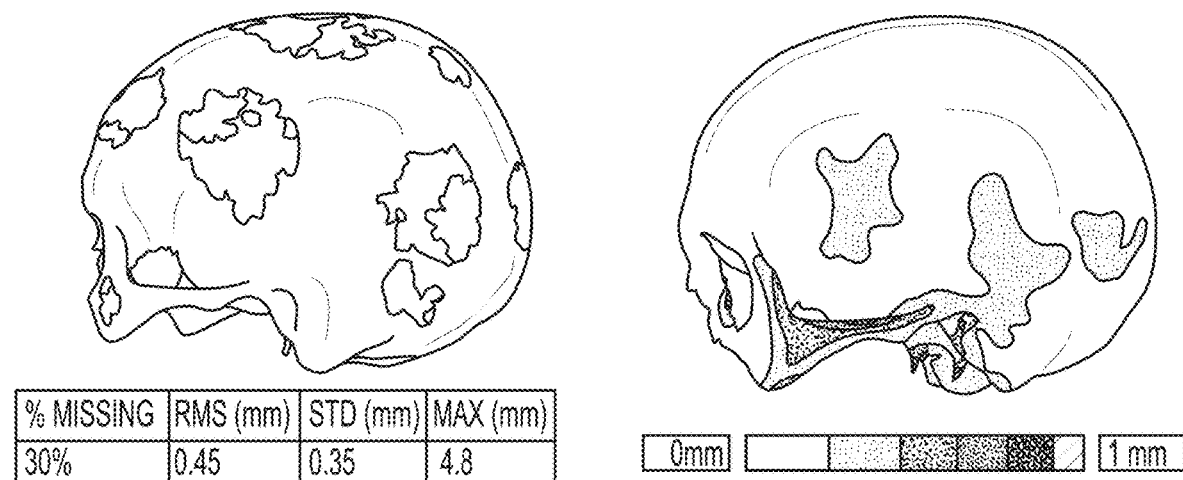
FIG. 15 are the results of reconstruction on partial skulls and mean distance map for reconstruction error.
Figure 16:
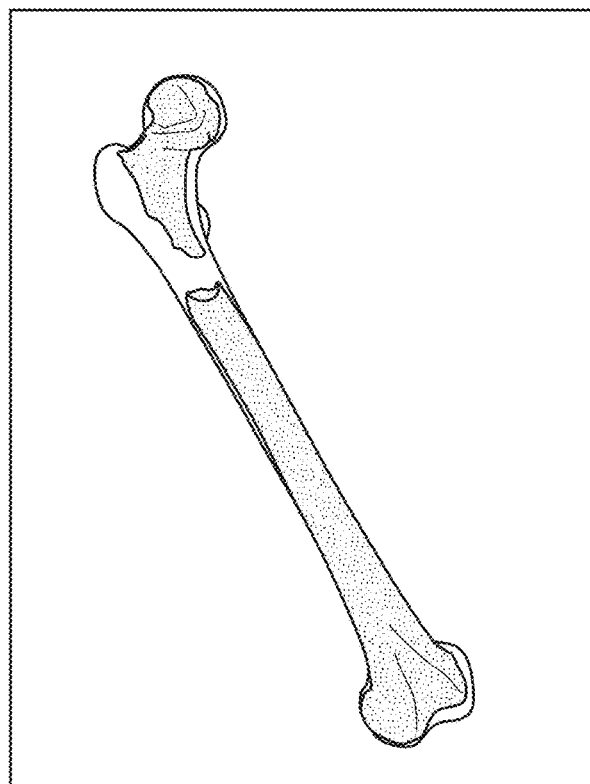
FIG. 16 are the results of reconstruction of shattered femur.

Referencing FIGS. 1 and 8, the fully reconstructed, patient-specific 3D tissue model representing the normal/complete tissue and input anatomical data (i.e., 3D surface representation or data from which a 3D surface representation may be generated) representing abnormal/incomplete tissue from the abnormal database are input to the defect classification module. This anatomical data from the abnormal database may be a partial anatomy in the case of tissue degeneration or tissue absence resulting from genetics, or this anatomy may be a deformed anatomy resulting from genetics or environmental conditions (e.g., surgical revisions, diseases, etc.), or this anatomy may be a shattered tissue resulting from one or more anatomy breaks. By way of example, input anatomical data may comprise one or more of X-rays, computed tomography (CT) scans, magnetic resonance images (Mills), or any other imaging data from which a 3D surface representation may be generated.

The defect classification module pulls a plurality of abnormal 3D surface representations from abnormal database coupled with the normal 3D representation of the anatomy in question to create a quantitative defect classification system. This defect classification system is used to create "templates" of each defect class or cluster. More generally, the defect classification module classifies the anatomical deficiency into classes which consist of closely related deficiencies (referring to those with similar shape, clinical, appearance, or other characteristics) to facilitate the generation of healthcare solutions which address these deficiencies. The instant defect classification module uses software and hardware to classify the defects automatically as a means to eliminate or reduce discrepancies between pre-operative data and intra-operative observer visualization. Traditionally, pre-operative radiographs have been taken as a means to qualitatively analyze the extent of anatomical reconstruction necessary, but this resulted in pre-operative planning that was hit-or-miss at best. Currently, intra-operative observers make the final determination of the extent of anatomy deficiency and many times conclude that the pre-operative planning relying on radiographs was defective or incomplete. As a result, the instant defect classification module improves upon current classification systems by reducing interobserver and intraobserver variation related to defect classification and providing quantitative metrics for classifying new defect instances.

As part of the defect classification module t, the module is may take as input one or more classification types to be used as an initial state. For example, in the context of a pelvis, the defect classification module may use as input defect features corresponding to the American Academy of Orthopaedic Surgeons (AAOS) D'Antonio et al. bone defect classification structure. This structure includes four different classes as follows: (1) Type I, corresponding to segmental bone loss; (2) Type II, corresponding to cavitary bone loss; (3) Type III, corresponding to combined segmental and cavitary bone loss; and, (4) Type IV, corresponding to pelvis discontinuity. Alternatively, the defect classification module may be programmed with the Paprosky bone defect classification structure. This structure includes three different classes as follows: (1) Type I, corresponding to supportive rim with no bone lysis; (2) Type II, corresponding to distorted hemispheres with intact supportive columns and less than two centimeters of superomedial or lateral migration; and, (3) Type III, corresponding to superior migration greater than two centimeters and sever ischial lysis with Kohler's line broken or intact. Moreover, the defect classification module may be programmed with the Modified Paprosky bone defect classification structure. This structure includes six different classes as follows: (1) Type 1, corresponding to supportive rim with no component migration; (2) Type 2A, corresponding to distorted hemisphere but superior migration less than three centimeters; (3) Type 2B, corresponding to greater hemisphere distortion having less than ⅓ rim circumference and the dome remaining supportive; (4) Type 2C, corresponding to an intact rim, migration medial to Kohler's line, and the dome remains supportive; (5) Type 3A, corresponding to superior migration, greater than three centimeters and severe ischial lysis with intact Kohler's line; and, (6) Type 3B, corresponding to superior migration, greater than three centimeters and severe ischial lysis with broken Kohler's line and rim defect greater than half the circumference. Using the output classification types and parameters, the defect classification module compares the anatomical data to that of the reconstructed data to discern which of the classification types the anatomical data most closely resembles, thereby corresponding to the resulting assigned classification.

As an initial step, the add to statistical atlas step involves generating correspondence between normal atlas 3D bone model and the abnormal 3D bone model. More specifically, the 3D bone models are compared to discern what bone in the normal 3D model is not present in the abnormal 3D model. In exemplary form, the missing/abnormal bone is identified by comparing points on the surface of each 3D bone model and generating a list of the discrete points on the surface of the normal 3D bone model that are not present on the abnormal 3D bone model. The system may also record and list (i.e., identify) those surface points in common between the two models or summarily note that unless recorded as points being absent on the abnormal 3D bone model, all other points are present in common in both bone models (i.e., on both the normal and abnormal bone models). Accordingly, the output of this step is the abnormal 3D bone model with statistical atlas correspondence and a list of features (points) from the normal atlas 3D bone model indicating if that feature (point) is present or missing in the abnormal 3D bone model.

After generating correspondence between the normal atlas 3D bone model (generated from the full bone reconstruction module) and the abnormal 3D bone model (generated from the input anatomical data), the missing/abnormal regions from the abnormal 3D bone model are localized on the normal atlas 3D bone model. In other words, the normal atlas 3D bone model is compared to the abnormal 3D bone model to identify and record bone missing from the abnormal 3D bone model that is present in the normal atlas 3D bone model. Localization may be carried out in a multitude of fashions including, without limitation, curvature comparison, surface area comparisons, and point cloud area comparisons. Ultimately, in exemplary form, the missing/abnormal bone is localized as a set of bounding points identifying the geometrical bounds of the missing/abnormal region(s).

Using the bounding points, the defect classification module extracts features from the missing/abnormal region(s) using input clinical data. In exemplary form, the extracted features may include shape information, volumetric information, or any other information used to describe the overall characteristics of the defective (i.e., missing or abnormal) area. These features may be refined based on existing clinical data, such as on-going defect classification data or patient clinical information not necessarily related to the anatomical feature (demographics, disease history, etc.). The output of this step is a mathematical descriptor representative of the defective area(s) that are used in a subsequent step to group similar tissue (e.g., bone) deformities.

The mathematical descriptor is clustered or grouped based upon a statistical analysis. In particular, the descriptor is statistically analyzed and compared to other descriptors from other patients/cadavers to identify unique defect classes within a given population. Obviously, this classification is premised upon multiple descriptors from multiple patients/cadavers that refine the classifications and identifications of discrete groups as the number of patients/cadavers grows. The output from this statistical analysis is a set of defect classes that are used to classify new input anatomical data and determines the number of templates.

The output of the defect classification module is directed to a template module. In exemplary form, the template module includes data that is specific as to each of the defect classifications identified by the defect classification module. By way of example, each template for a given defect classification includes surface representations of the defective bone, location(s) of the defect(s), and measurements relating to the defective bone. This template data may be in the form of surface shape data, point cloud representations, one or more curvature profiles, dimensional data, and physical quantity data. Outputs from the template module and the statistical atlas are utilized by a mass customization module to design, test, and allow fabrication of mass customized implants, fixation devices, instruments or molds. Exemplary utilizations of the mass customization module will be discussed in greater detail hereafter.

Patient-Specific Reconstruction Implants

Figure 17:
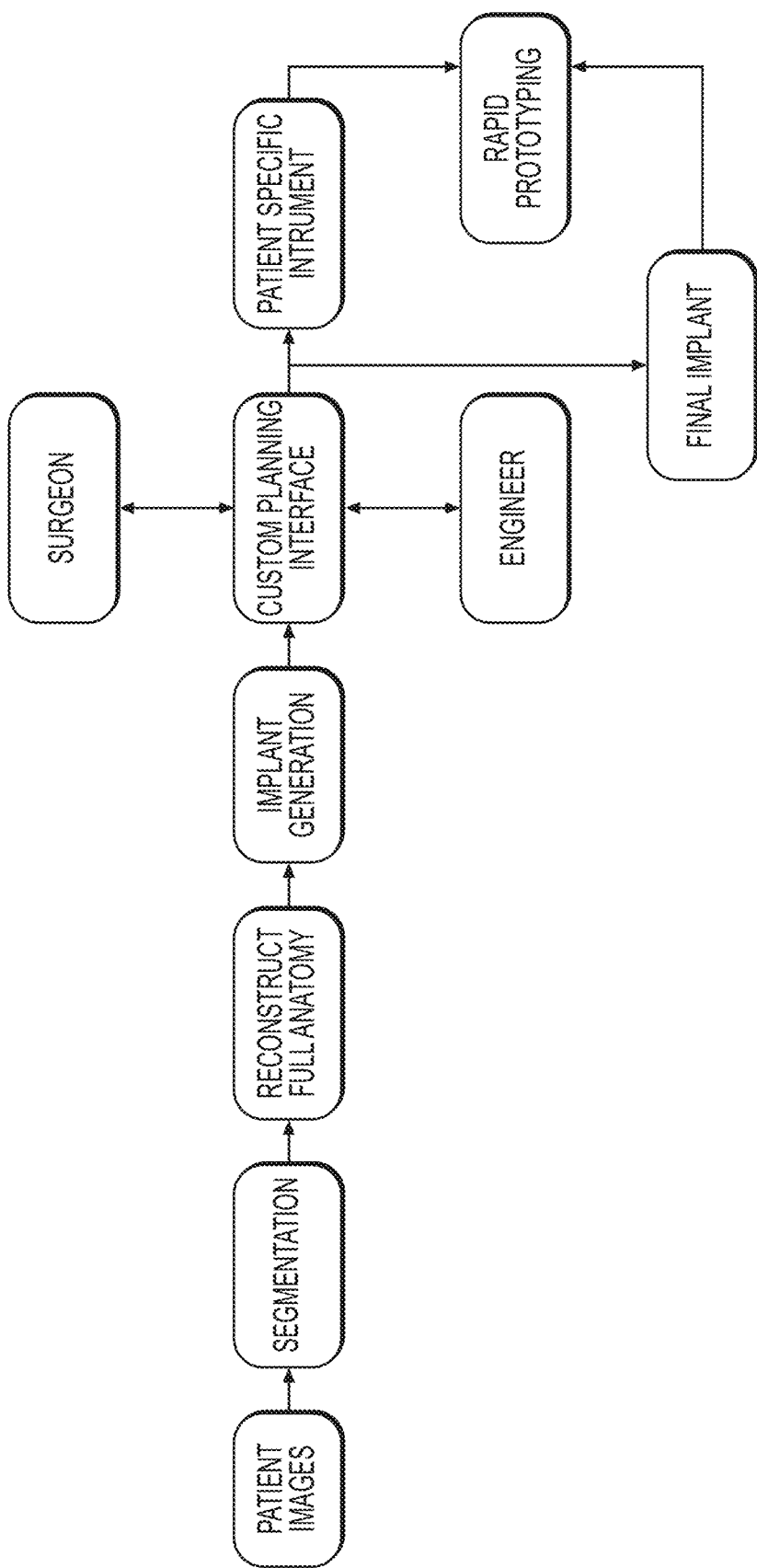
FIG. 17 is a schematic diagram of the process of creating a patient-specific reconstructive implant.

Referring to FIGS. 1 and 17, an exemplary process and system are described for generating patient-specific orthopedic implant guides and associated patient-specific orthopedic implants for patients afflicted with partial, deformed, and/or shattered anatomies. For purposes of the exemplary discussion, a total hip arthroplasty procedure will be described for a patient with a partial anatomy. It should be understood, however, that the exemplary process and system are applicable to any orthopedic implant amenable to patient-specific customization in instances where incomplete or deformed anatomy is present. For example, the exemplary process and system are applicable to shoulder replacements and knee replacements where bone degeneration (partial anatomy), bone deformation, or shattered bones are present. Consequently, though a hip implant is discussed hereafter, those skilled in the art will understand the applicability of the system and process to other orthopedic implants, guides, tools, etc. for use with original orthopedic or orthopedic revision surgeries.

Pelvis discontinuity is a distinct form of bone loss most often associated with total hip arthroplasty (THA), in which osteolysis or acetabular fractures can cause the superior aspect of the pelvis to become separated from the inferior portion. The amount and severity of bone loss and the potential for biological in-growth of the implant are some of the factors that can affect the choice of treatment for a particular patient. In the case of severe bone loss and loss of pelvic integrity, a custom tri-flange cup may be used. First introduced in 1992, this implant has several advantages over existing cages. It can provide stability to pelvic discontinuity, eliminate the need for structural grafting and intraoperative contouring of cages, and promote osseointegration of the construct to the surrounding bone.

Regardless of the context, whether partial, deformed, and/or shattered anatomies of the patient are at issue, the exemplary system and process for generating patient-specific implants and/or guides utilizes the foregoing exemplary process and system of 3D bone model reconstruction (see FIGS. 1-7 and the foregoing exemplary discussion of the same) to generate a three dimensional model of the patient's reconstructed anatomy. More specifically, in the context of total hip arthroplasty where pelvis discontinuity is involved, the exemplary patient-specific system utilizes the patient pelvis data to generate a 3D model of the patient's complete pelvis, which is side specific (right or left). Consequently, a discussion of the system and process for utilizing patient anatomy data for a partial anatomy and generating a 3D reconstructed model of the patient's anatomy is omitted in furtherance of brevity. Accordingly, a description of the process and system for generating patient-specific orthopedic implant guides and associated patient-specific orthopedic implants for patients afflicted with partial, deformed, and/or shattered anatomies will be described post formation of the three dimensional reconstructed model.

Referring specifically to FIGS. 17-19 and 23, after the patient-specific reconstructed 3D bone model of the pelvis and femur are generated, both the incomplete patient-specific 3D bone model (for pelvis and femur) and the reconstructed 3D bone model (for pelvis and femur) are utilized to create the patient-specific orthopedic implant and a patient-specific placement guide for the implant and/or its fasteners. In particular, the extract defect shape step includes generating correspondence between the patient-specific 3D model and the reconstructed 3D model (correspondence between pelvis models, and correspondence between femur models, but not between one femur model and a pelvis model). More specifically, the 3D models are compared to discern what bone in the reconstructed 3D model is not present in the patient-specific 3D model. In exemplary form, the missing/abnormal bone is identified by comparing points on the surface of each 3D model and generating a list of the discrete points on the surface of the reconstructed 3D model that are not present on the patient-specific 3D model. The system may also record and list (i.e., identify) those surface points in common between the two models or summarily note that unless recorded as points being absent on the patient-specific 3D model, all other points are present in common in both models (i.e., on both the reconstructed and patient-specific 3D models).

Figure 18:
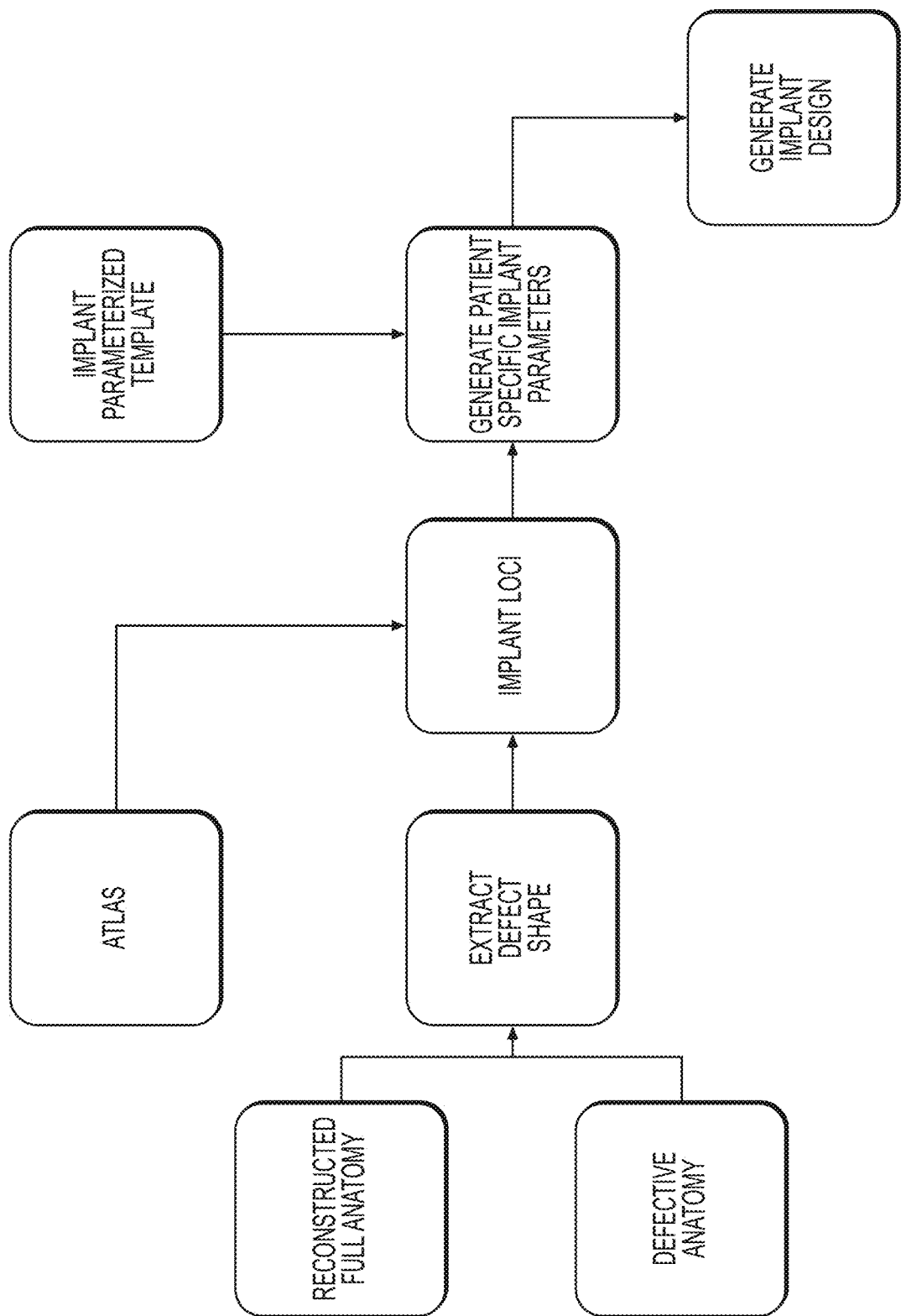
FIG. 18 is a schematic diagram of the process for implant generation depicted in FIG. 17.

Referring to FIG. 18, after generating correspondence between the reconstructed 3D model (generated from the full bone reconstruction module) and the patient-specific 3D model (generated from the input anatomical data), the missing/abnormal regions from the patient-specific 3D model are localized on the reconstructed 3D model. In other words, the reconstructed 3D model is compared to the patient-specific 3D model to identify and record bone missing from the patient-specific 3D model that is present in the reconstructed 3D model. Localization may be carried out in a multitude of fashions including, without limitation, curvature comparison, surface area comparisons, and point cloud area comparisons. Ultimately, in exemplary form, the missing/abnormal bone is localized and the output comprises two lists: (a) a first list identifying vertices corresponding to bone of the reconstructed 3D model that is absent or deformed in the patient-specific 3D model; and, (b) a second list identifying vertices corresponding to bone of the reconstructed 3D model that is also present and normal in the patient-specific 3D model.

Figure 19:
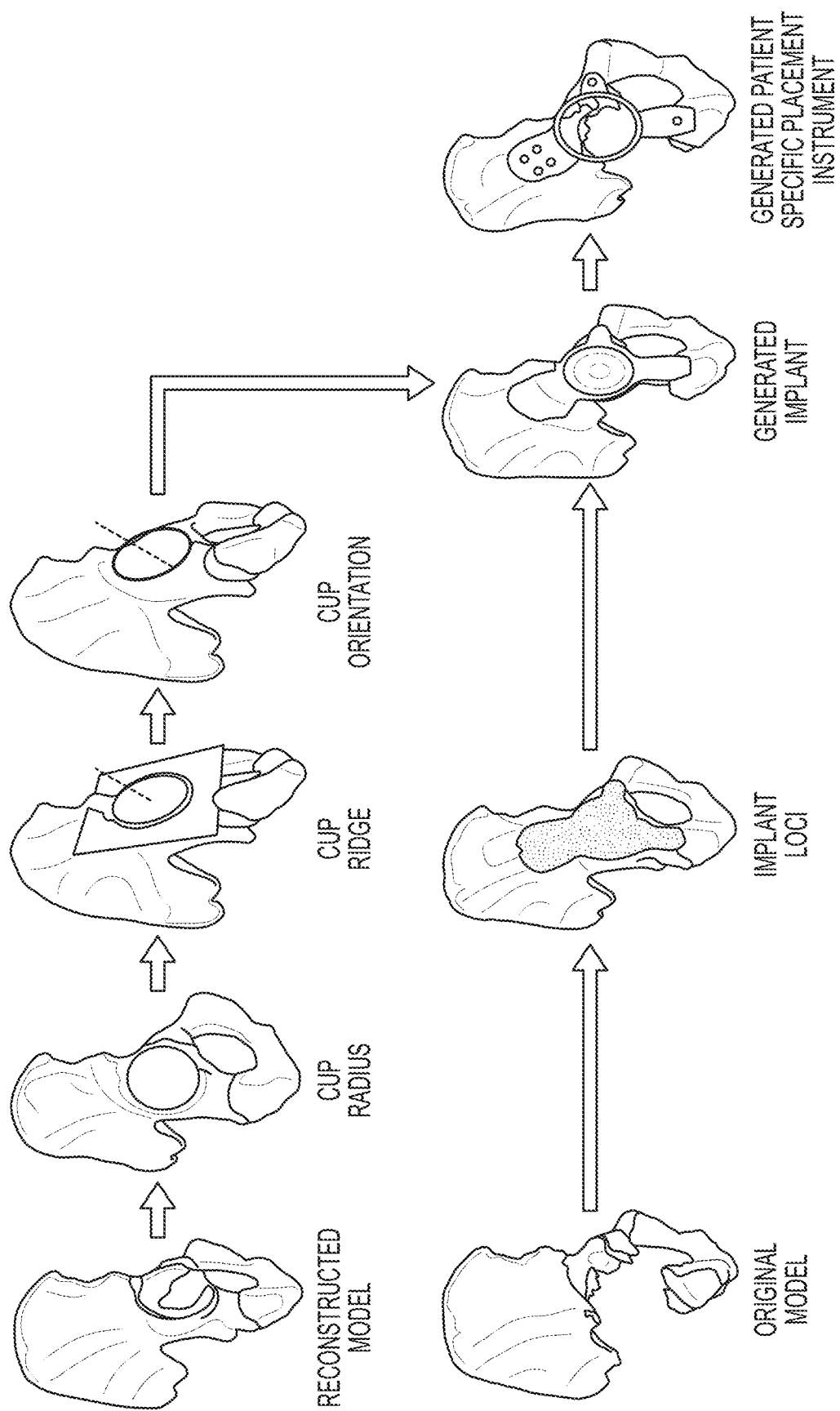
FIG. 19 is a process flow diagram showing various steps for reconstruction of patient full anatomy from partial anatomy and generation of patient specific cup implant for pelvis discontinuity.
Figure 23:
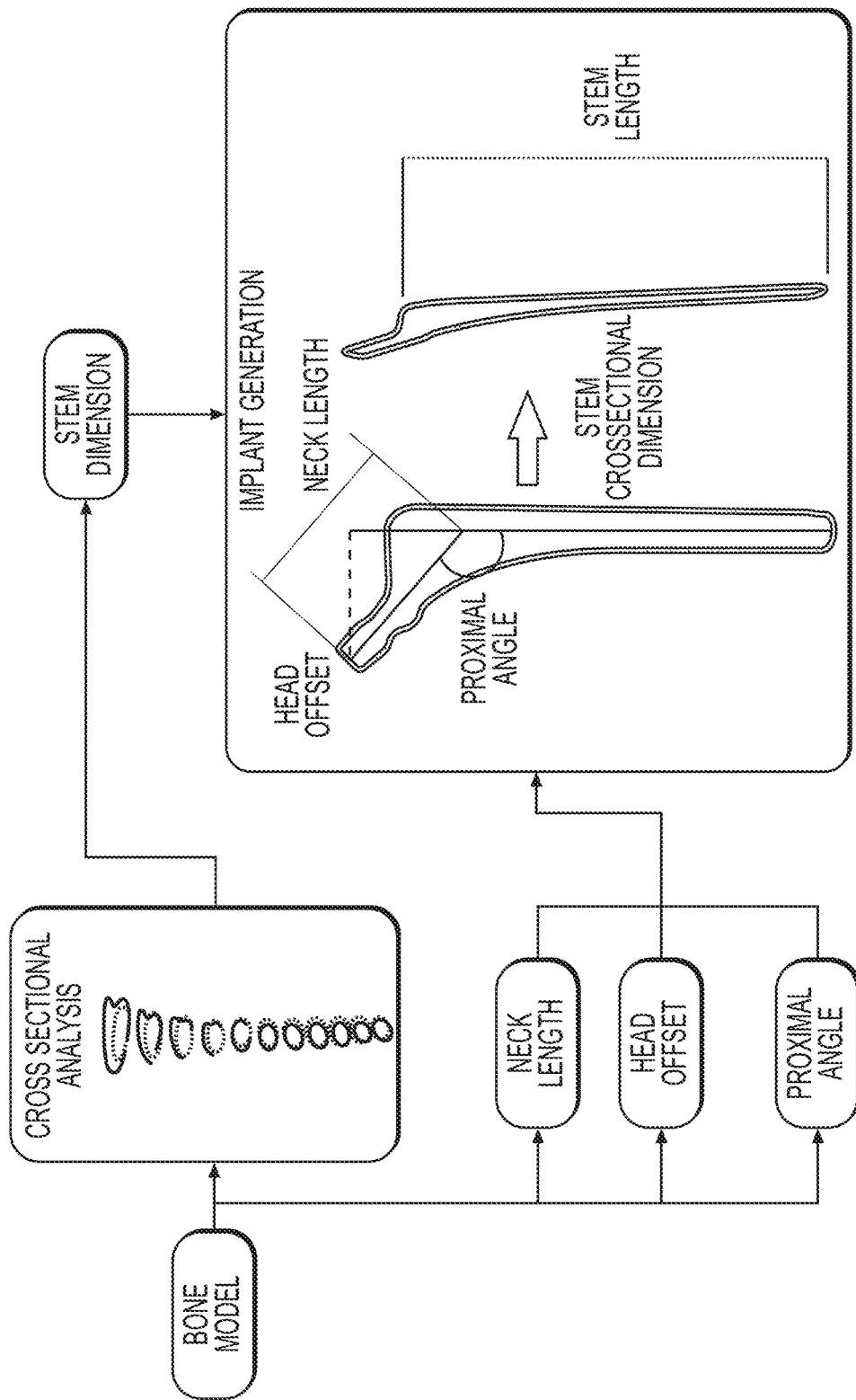
FIG. 23 is a schematic diagram of a process for generating a patient-specific hip stem for reconstructive surgeries.

Referencing FIGS. 18, 19, and 23, following the extract defect shape step, an implant loci step is performed. The two vertices lists from the extract defect shape step and a 3D model of a normal bone (e.g., pelvis, femur, etc.) from the statistical atlas (see FIGS. 1 and 2, as well as the foregoing exemplary discussion of the same) are input to discern the fixation locations for a femoral or pelvic implant. More specifically, the fixation locations (i.e., implant loci) are automatically selected so that each is positioned where a patient has residual bone. Conversely, the fixation locations are not selected in defect areas of the patient's residual bone. In this manner, the fixation locations are chosen independent of the ultimate implant design/shape. The selection of fixation locations may be automated using shape information and statistical atlas locations.

As show in FIG. 18, after the implant loci step, the next step is to generate patient-specific implant parameters. In order to complete this step, an implant parameterized template is input that defines the implant by a set number of parameters that are sufficient to define the underlying shape of the implant. By way of example, in the case of a pelvis reconstruction to replace/augment an absent or degenerative acetabulum, the implant parameterized template includes angle parameters for the orientation of the replacement acetabular cup and depth parameters to accommodate for dimensions of the femoral head. Other parameters for an acetabular implant may include, without limitation, the acetabular cup diameter, face orientation, flange locations and shapes, location and orientation of fixation screws. In the case of porous implants, the location and structural characteristics of the porosity should be included. By way of example, in the case of a femoral reconstruction to replace/augment an absent or degenerative femur, the implant parameterized template includes angle parameters for the orientation of the replacement femoral head, neck length, head offset, proximal angle, and cross-sectional analysis of the exterior femur and intercondylar channel. Those skilled in the art will understand that the parameters chosen to define the underlying shape of the implant will vary depending upon the anatomy being replaced or supplemented. Consequently, an exhaustive listing of parameters that are sufficient to define the underlying shape of an implant is impractical. Nevertheless, as depicted in FIG. 19 for example, the reconstructed 3D pelvis model may be utilized to obtain the radius of the acetabular cup, identification of pelvic bone comprising the acetabular cup circumferential upper ridge, and identification of the orientation of the acetabular cup with respect to the residual pelvis. Moreover, the parameters may be refined taking into account the implant loci so that the implant best/better fits the patient-specific anatomy.

Subsequent to finalizing the set number of parameters that are sufficient to define the underlying shape of the implant, the design of the implant is undertaken. More specifically, an initial iteration of the overall implant surface model is constructed. This initial iteration of the overall implant surface model is defined by a combination of patient-specific contours and estimated contours for the implanted region. The estimated contours are determined from the reconstructed 3D bone model, missing anatomical bone, and features extracted from the reconstructed 3D bone model. These features and the location of the implant site, which can be automatically determined, are used to determine the overall implant shape, as depicted for example in FIG. 19 for an acetabular cup implant.

Referring back to FIG. 17, the initial iteration of the overall implant surface model is processed pursuant to a custom (i.e., patient-specific) planning sequence. This custom planning sequence may involve inputs from a surgeon and an engineer as part of an iterative review and design process. In particular, the surgeon and/or engineer may view the overall implant surface model and the reconstructed 3D bone model to determine if changes are needed to the overall implant surface model. This review may result in iterations of the overall implant surface model until agreement is reached between the engineer and surgeon. The output from this step is the surface model for the final implant, which may be in the form of CAD files, CNC machine encoding, or rapid manufacturing instructions to create the final implant or a tangible model.

Figure 20:
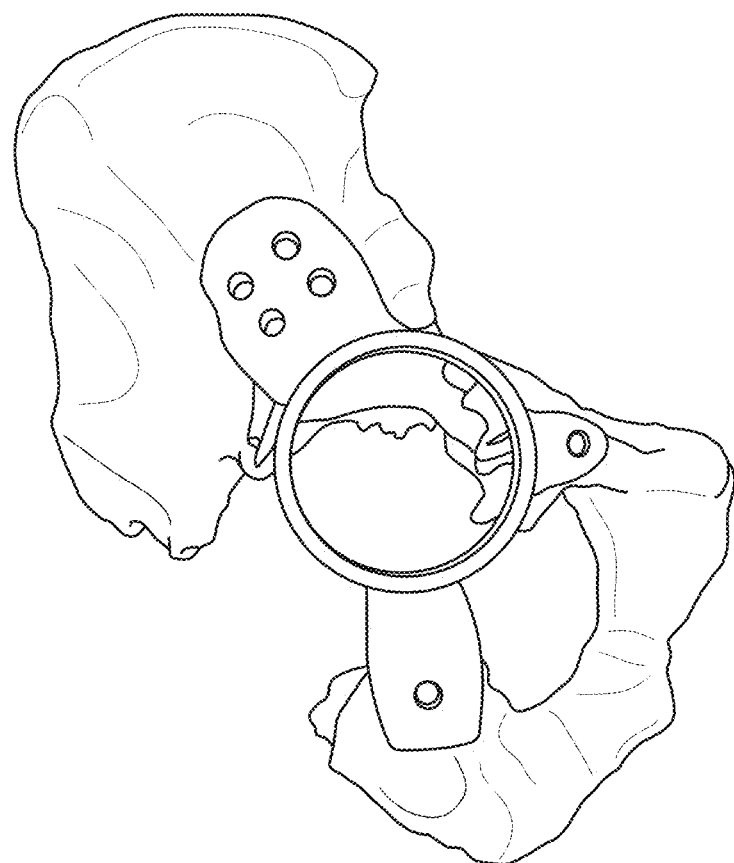
FIG. 20 is a graphical representation of a patient-specific placement guide for a patient-specific acetabular implant.
Figure 21:
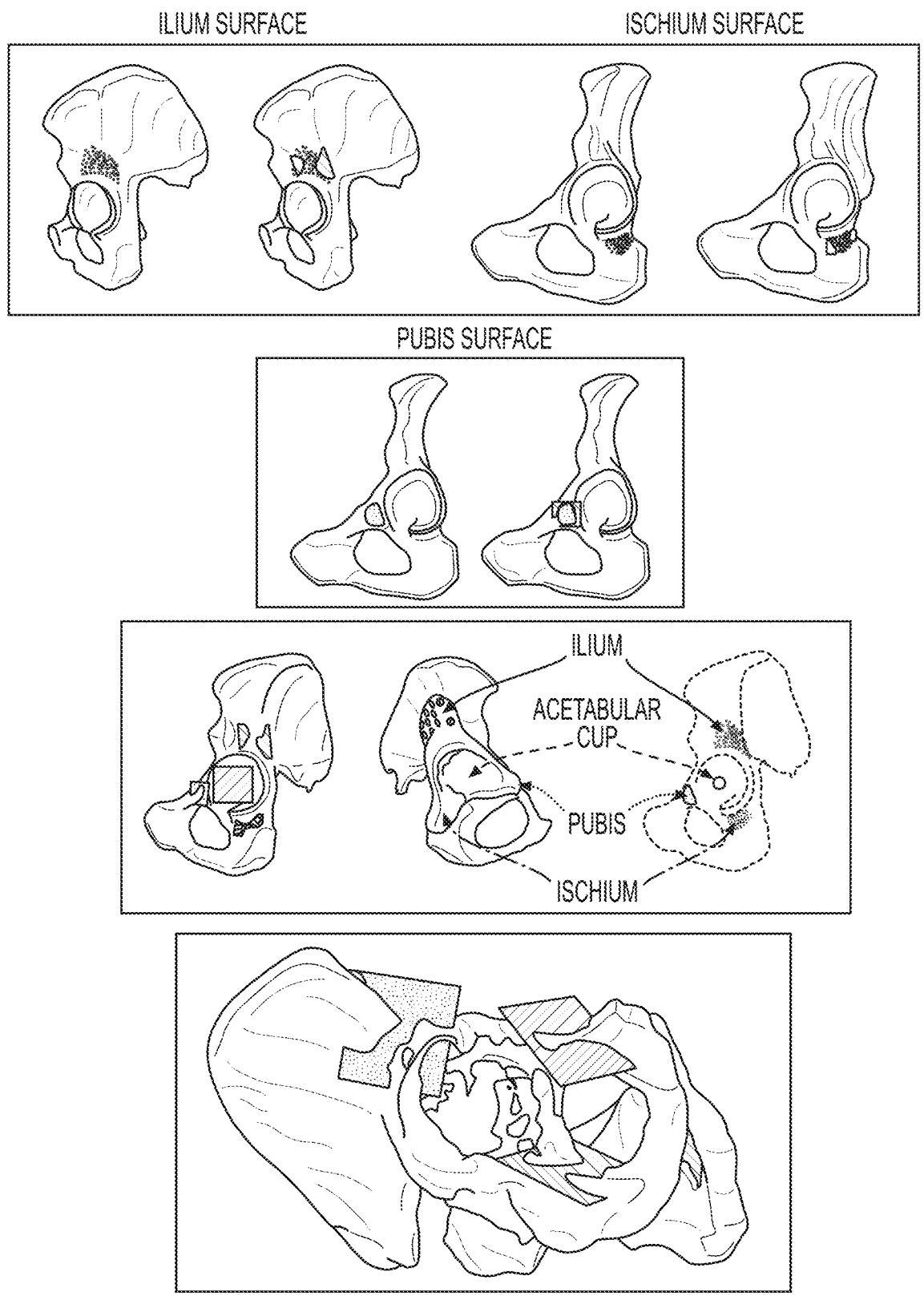
FIG. 21 comprises images studying the relationship between the three attachment sites of an implant and the cup orientation for mass customization.

Referring to FIGS. 17, 19, and 20, contemporaneous with or after the design of the patient-specific orthopedic implant is the design of a patient specific placement guide. In the context of an acetabular cup implant, as discussed in exemplary form above, one or more surgical instruments can be designed and fabricated to assist in placing the patient-specific acetabular cup. Having designed the patient-specific implant to have a size and shape to match that of the residual bone, the contours and shape of the patient-specific implant may be utilized and incorporated as part of the placement guide.

In exemplary form, the acetabular placement guide comprises three flanges that are configured to contact the ilium, ischium, and pubis surfaces, where the three flanges are interconnected via a ring. Moreover, the flanges of the placement guide may take on the identical shape, size, and contour of the acetabular cup implant so that the placement guide will take on the identical position as planned for the acetabular cup implant. In other words, the acetabular placement guide is shaped as the negative imprint of the patient anatomy (ilium, ischium, and pubis partial surfaces), just as the acetabular cup implant is, so that the placement guide fits on the patient anatomy exactly. But the implant guide differs from the implant significantly in that it includes one or more fixation holes configured to guide drilling for holes and/or placement of fasteners. In exemplary form, the placement guide includes holes sized and oriented, based on image analysis (e.g., microCT), to ensure proper orientation of any drill bit or other guide (e.g., a dowel) that will be utilized when securing the acetabular cup implant to the residual pelvis. The number of holes and orientation varies depending upon the residual bone, which impacts the shaped of the acetabular cup implant too. FIG. 20 depicts an example of a patient-specific placement guide for use in a total hip arthroplasty procedure. In another instance, the guide can be made so that it fits into the implant and guides only the direction of the fixation screws. In this form, the guide is shaped as the negative of the implant, so that it can be placed directly over the implant. Nevertheless, the incorporation of at least part of the patient-specific reconstructed implant size, shape, and contour is a theme that carries over regardless of the intended bone to which the patient-specific implant will be coupled.

Utilizing the exemplary system and method described herein can provide a wealth of information that can result in higher orthopedic placement accuracy, better anatomical integration, and the ability to pre-operatively measure true angles and plane orientation via the reconstructed three dimensional model.

Creation of Customized Implants Using Massively Customizable Components

Figure 22:
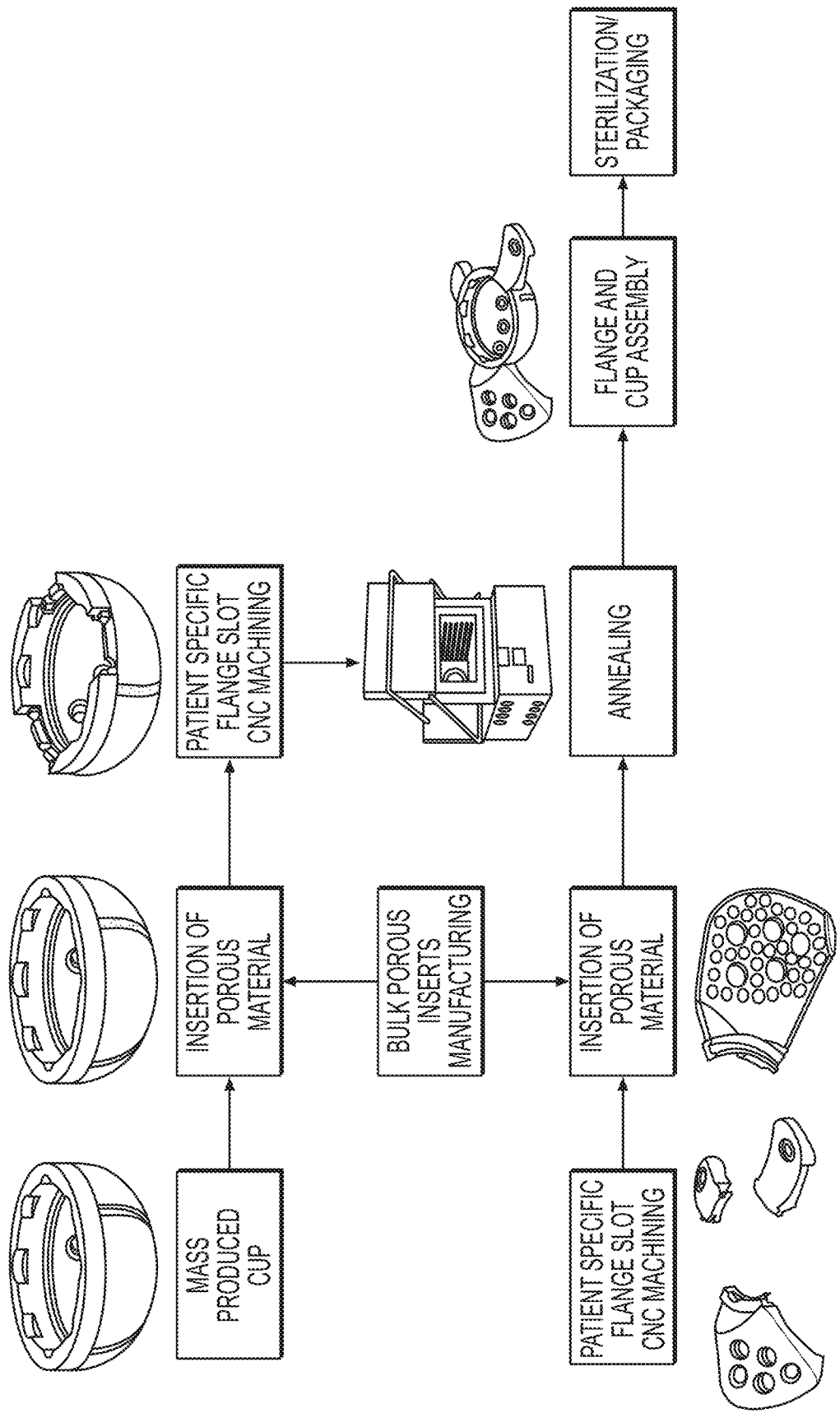
FIG. 22 is a schematic diagram for a method for manufacturing a mass produced custom acetabular component using a modular design.

Referring to FIG. 22, an exemplary process and system are described for generating customized orthopedic implants using massively customizable components. For purposes of the exemplary discussion, a total hip arthroplasty procedure will be described for a patient with severe acetabular defects. It should be understood, however, that the exemplary process and system are applicable to any orthopedic implant amenable to mass customization in instances where incomplete anatomy is present.

Severe acetabular defects require specialized procedures and implant components to repair. One approach is the custom triflange, which a fully custom implant consisting of an acetabular cup and three flanges that are attached to the ilium, ischium, and pubis. In contrast to the exemplary process and system, prior art triflange implants comprise a single complex component, which is cumbersome to manufacture and requires that the entire implant be redesigned for every case (i.e., completely patient-specific). The exemplary process and system generates a custom triflange implant that makes use of massively customizable components in addition to fully custom components in a modular way to allow custom fitting and porosity.

A preplanning step in accordance with the exemplary process is performed to determine the orientation of the three flanges relative to the cup, the flange contact locations, and the acetabular cup orientation and size. This preplanning step is conducted in accordance with the "Patient-specific Implants" discussion immediately preceding this section. By way of example, specific locations of implant fixation are determined pursuant to an implant loci step and using its prefatory data inputs as discussed in the immediately preceding section. By way of recall, as part of this implant loci step, the two vertices lists from the extract defect shape step and a 3D model of a normal pelvis from the statistical atlas (see FIGS. 1 and 2, as well as the foregoing exemplary discussion of the same) are input to discern the fixation locations for the custom triflange. More specifically, the fixation locations (i.e., implant loci) are selected so that each is positioned where a patient has residual bone. In other words, the fixation locations are not selected in defect areas of the patient's residual pelvis. In this manner, the fixation locations are chosen independent of the ultimate implant design/shape.

After determining the fixation locations, the triflange components (i.e., flanges) are designed using the "Patient-specific Implants" discussion immediately preceding this section. The flanges are designed to be oriented relative to the replacement acetabular cup so that the cup orientation provides acceptable joint functionality. Additionally, the contact surfaces of the flanges are contoured to match the patient's pelvis anatomy in that the contact surfaces of the triflanges are shaped as a "negative" of the pelvis's bony surface. The exemplary process of FIG. 20 utilizes the final step of the process depicted in FIG. 17 to rapid prototype the flanges (or use conventional computer numerical control (CNC) equipment). After the flanges are fabricated, further machining or steps may be performed to provide cavities within which porous material may be added to the triflanges.

One portion of the triflange system that does not need to be a custom component is the acetabular cup component. In this exemplary process, a family of acetabular cups is initially manufactured and provides the foundation on which to build the triflange system. These "blank" cups are retained in inventory for use as needed. If a particular porosity for the cup is desired, mechanical features are added to the cup that allows press fitting of porous material into the cup. Alternatively, if a particular porosity for the cup is desired, the cup may be coated using one or more porous coatings.

After the blank cup is formed and any porosity issues are addressed as discussed above, the cup is rendered patient-specific by machining the cup to accept the flanges. In particular, using the virtual model of the flanges, the system software constructs virtual locking mechanisms for the flanges, which are transformed into machine coding so that the locking mechanisms are machined into the cup. These locking mechanisms allow the cup to be fastened to the flanges so that when the flanges are mounted to the patient's residual bone, the cup is properly oriented with respect to the residual pelvis. This machining may use conventional CNC) equipment to form the locking mechanisms into the blank cups.

Subsequent to fabrication of the locking mechanisms as part of the blank cup, the flanges are mounted to the cup using the interface between the locking mechanisms. The triflange assembly (i.e., final implant) is subjected to an annealing process to promote strong bonding between the components. Post annealing of the triflange implant, a sterilization process occurs followed by appropriate packaging to ensure a sterile environment for the triflange implant.

Creation of Mass Customized Implants

Figure 24:
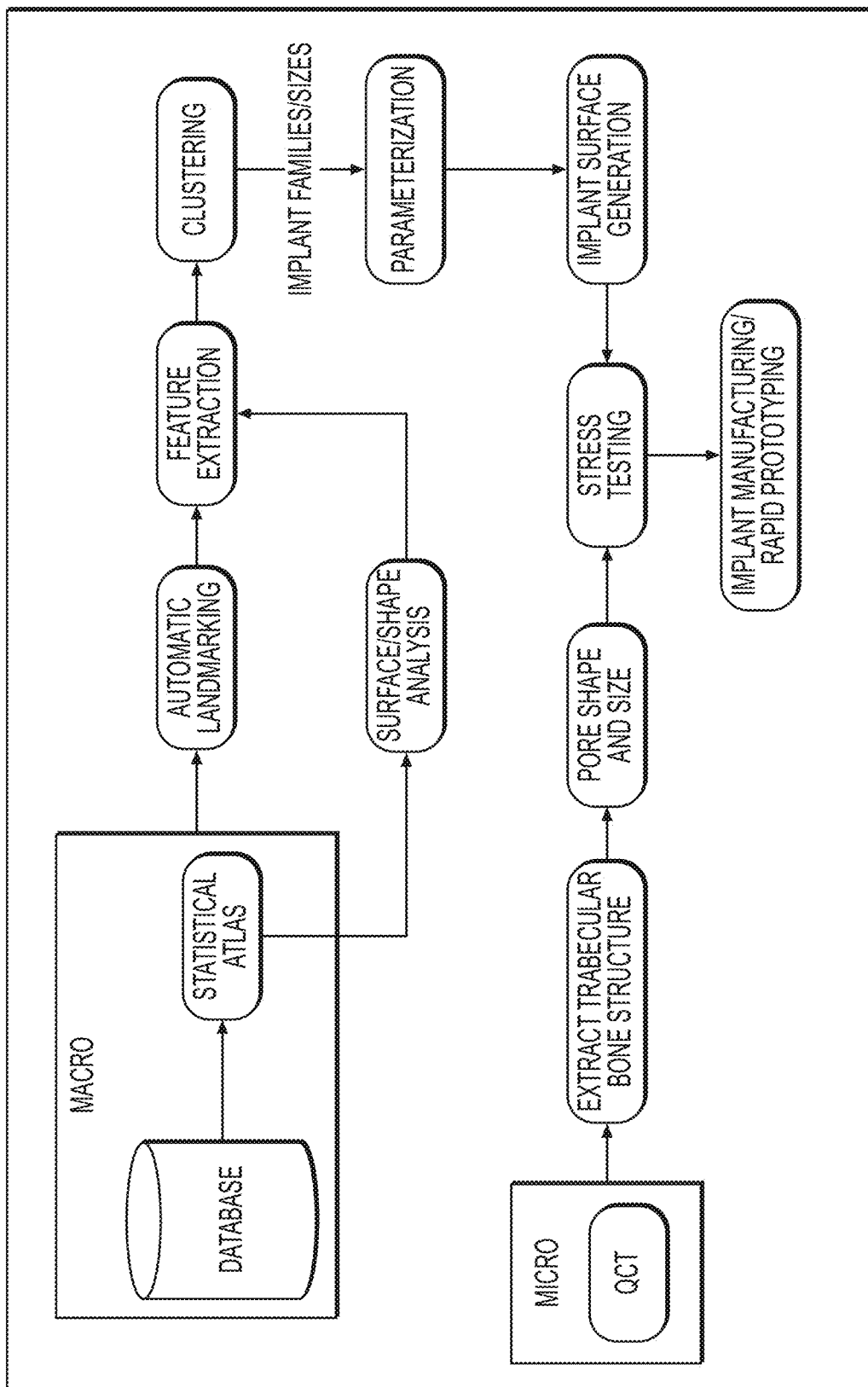
FIG. 24 is a schematic diagram of a process for mass customized implant generation.

Referring to FIG. 24, an exemplary process and system are described for generating mass customized orthopedic implant guides and associated mass customized orthopedic implants for patients afflicted with partial, deformed, and/or shattered anatomies. For purposes of the exemplary discussion, a total hip arthroplasty procedure will be described for a patient needing primary joint replacement. It should be understood, however, that the exemplary process and system are applicable to any orthopedic implant and guides amenable to mass customization in instances where incomplete anatomy is present. For example, the exemplary process and system are applicable to shoulder replacements and knee replacements where bone degeneration (partial anatomy), bone deformation, or shattered bones are present. Consequently, though a hip implant is discussed hereafter, those skilled in the art will understand the applicability of the system and process to other orthopedic implants, guides, tools, etc. for use with primary orthopedic or orthopedic revision surgeries.

The exemplary process utilizes input data from a macro perspective and a micro perspective. In particular, the macro perspective involves determination of the overall geometric shape of the orthopedic implant and corresponding anatomy. Conversely, the micro perspective involves accounting for the shape and structure of cancellous bone and its porosity.

The macro perspective includes a database communicating with a statistical atlas module that logs virtual, 3D models of one or more anatomies (e.g., bones) to capture the inherent anatomical variability in a given population. In exemplary form, the atlas logs mathematical representations of anatomical features of the one or more anatomies represented as a mean representation and variations about the mean representation for a given anatomical population. Reference is had to FIG. 2 and the foregoing discussion of the statistical atlas and how one adds anatomy to the statistical atlas of a given population. Outputs from the statistical atlas are directed to an automatic landmarking module and to a surface/shape analysis module.

The automatic landmarking module utilizes inputs from the statistical atlas (e.g., regions likely to contain a specific landmark) and local geometrical analyses to calculate anatomical landmarks for each instance of anatomy within the statistical atlas. This calculation is specific to each landmark. The approximate shape of the region is known, for example, and the location of the landmark being searched for is known relative to the local shape characteristics. For example, locating the medial epicondylar point of the distal femur is accomplished by refining the search based on the approximate location of medial epicondylar points within the statistical atlas. Accordingly, it is known that the medial epicondylar point is the most medial point within this search window, so a search for the most medial point is performed as to each bone model within the medial epicondylar region defined in the statistical atlas, with the output of the search being identified as the medial epicondylar point landmark. After the anatomical landmarks are automatically calculated for each virtual, 3D model within the statistical atlas population, the virtual, 3D models of the statistical atlas are directed to a feature extraction module, along with shape/surface analysis outputs.

The shape/surface outputs come from a shape/surface module also receiving inputs from the statistical atlas. In the context of the shape/surface module, the virtual, 3D models within the statistical atlas population are analyzed for shape/surface features that are not encompassed by the automatic landmarking. In other words, features corresponding to the overall 3D shape of the anatomy, but not belonging to features defined in the previous automatic landmarking step are calculated as well. For example, curvature data is calculated for the virtual 3D models.

Outputs from the surface/shape analysis module and the automatic landmarking module are directed to a feature extraction module. Using a combination of landmarks and shape features, mathematical descriptors (i.e., curvature, dimensions) relevant to implant design are calculated for each instance in the atlas. These descriptors are used as input to a clustering process.

The mathematical descriptor is clustered or grouped based upon a statistical analysis. In particular, the descriptor is statistically analyzed and compared to other descriptors from the remaining anatomy population to identify groups (of anatomies) having similar features within the population. Obviously, this clustering is premised upon multiple descriptors from multiple anatomies across the population. As new instances are presented to the clustering, which were not present in the initial clustering, the output clusters are refined to better represent the new population. The output from this statistical analysis is a finite number of implants (including implant families and sizes) covering all or the vast majority of the anatomical population.

For each cluster, a parameterization module extracts the mathematical descriptors within the cluster. The mathematical descriptors form the parameters (e.g., CAD design parameters) for the eventual implant model. The extracted mathematical descriptors are fed into an implant surface generation module. This module is responsible for converting the mathematical descriptors into surface descriptors to generate a 3D, virtual model of the anatomy for each cluster. The 3D, virtual model complements the micro perspective prior to stress testing and implant manufacturing.

On the micro perspective, for each anatomy of a given population, data is obtained indicative of structural integrity. In exemplary form, this data for a bone may comprise microCT data providing structural information as to the cancellous bone. More specifically, the microCT data may comprise images of the bone in question (multiple microCT images for multiple bones across a population). These images are thereafter segmented via the extract trabecular bone structure module in order to extract the three dimensional geometry of the cancellous bones and create virtual, 3D models for each bone within the population. The resulting 3D virtual models are input to a pore size and shape module. As depicted graphically in FIG. 76, the 3D virtual models include porous size and shape information, which is evaluated by the pore size and shape module to determine pore size and size for the cancellous bone. This evaluation is useful to analyze the porous size and shape of the bone within the intramedullary canal so that the stem of the femoral implant can be treated with a coating or otherwise processed to exhibit a porous exterior to promote integration between the residual bone of the femur and the femoral implant. The output from this module, in combination with the 3D virtual model output from the implant surface generation module, is directed to a virtual stress testing module.

The stress testing module combines implant porosity data from the pore size and shape module and implant shape data from the implant surface generation module to define the final implant shape model and properties. For example, the shape and properties include providing a porous coating for the final implant model that roughly matches the cancellous bone porosity for the bone in question. Once the shape and properties are incorporated, the final implant model undergoes virtual stress testing (finite-element and mechanical analysis) to verify the functional quality of the model. To the extent the functional quality is unacceptable, the parameters defining the implant shape and porosity are modified until acceptable performance is achieved. Presuming the final implant model satisfies the stress testing criteria, the final implant model is utilized to generate machine instructions necessary to convert the virtual model into a tangible implant (that may be further refined by manufacturing processes known to those skilled in the art). In exemplary form, the machine instructions may include rapid manufacturing machine instructions to fabricate the final implant through a rapid prototyping process (to properly capture porous structure) or a combination of traditional manufacturing and rapid prototyping.

Creation of Gender/Ethnic Specific Hip Implants

Figure 25:
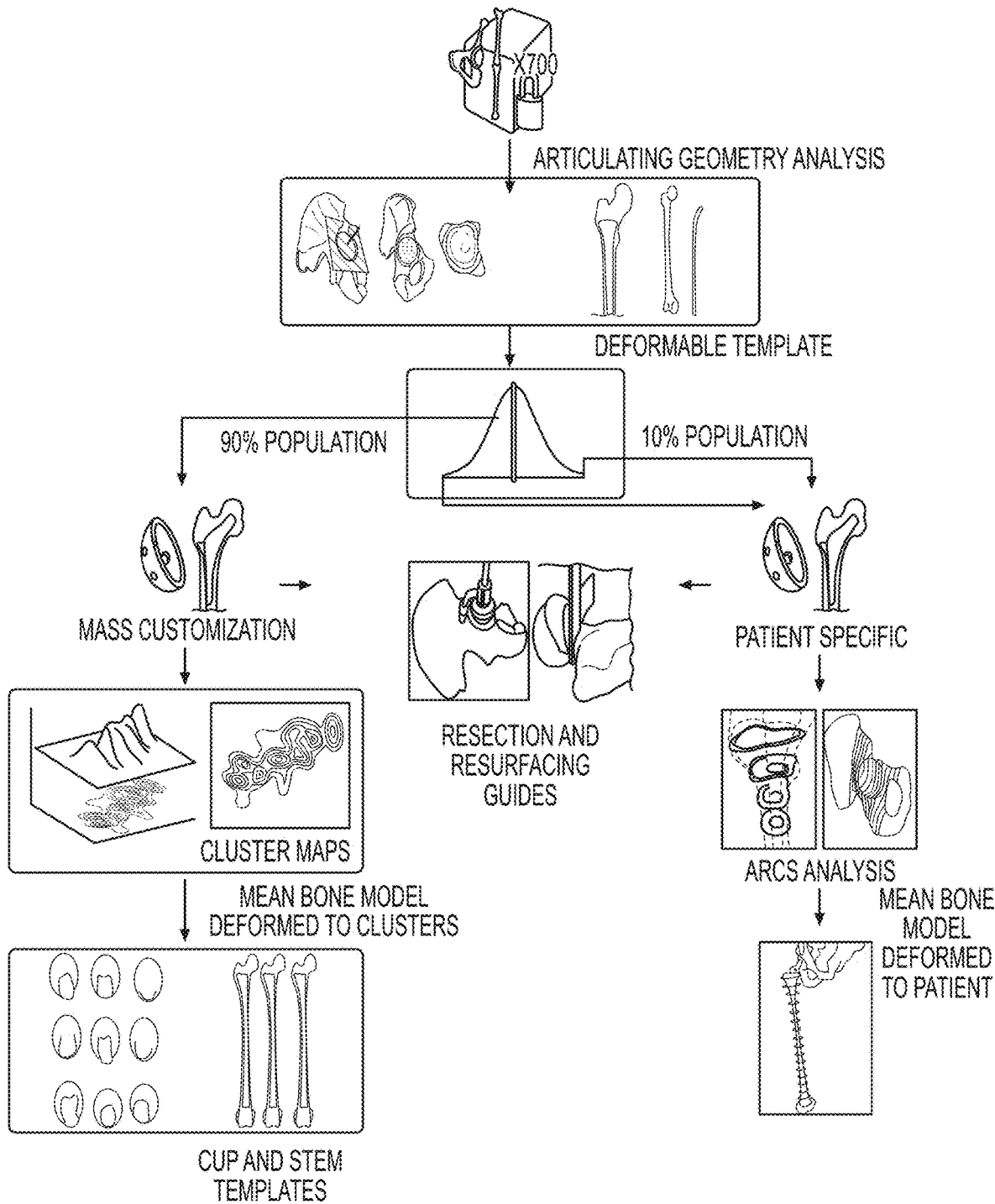
FIG. 25 is a schematic diagram depicting a process for using a statistical atlas for generation of both mass customized and patient-specific hip implants.
Figure 76:
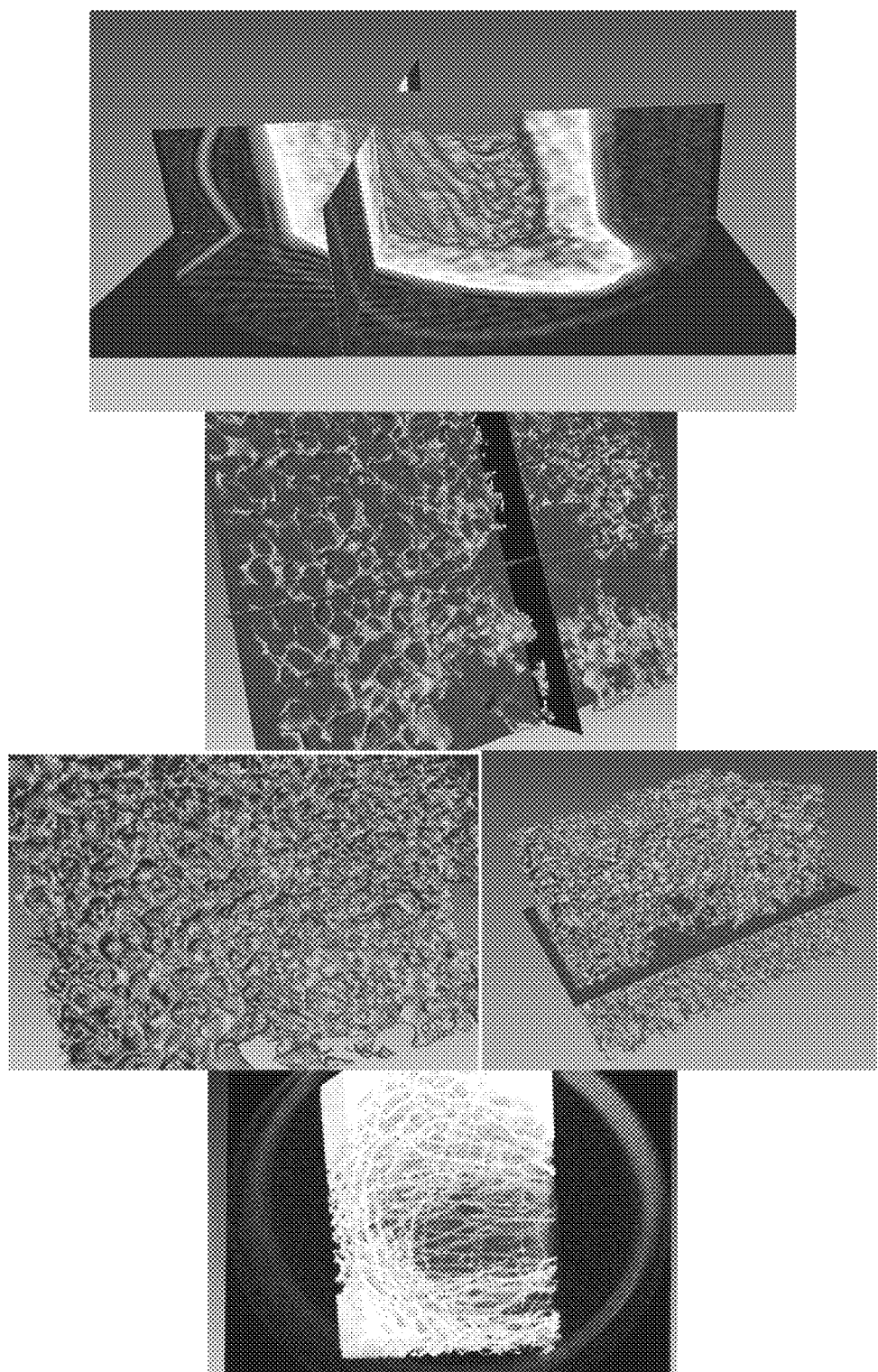
FIG. 76. Extracting porous shape and sizes to match bone anatomy from Micro-CT.

Referring to FIGS. 25-76, an exemplary process and system are described for generating gender and/or ethnic specific implants. For purposes of the exemplary discussion, a total hip arthroplasty procedure will be described for a patient with requiring primary joint replacement. It should be understood, however, that the exemplary process and system are applicable to any orthopedic implant amenable to customization. For example, the exemplary process and system are applicable to shoulder replacements and knee replacements and other primary joint replacement procedures. Consequently, though a hip implant is discussed hereafter, those skilled in the art will understand the applicability of the system and process to other orthopedic implants, guides, tools, etc. for use with original orthopedic or orthopedic revision surgeries.

The hip joint is composed of the head of the femur and the acetabulum of the pelvis. The hip joint anatomy makes it one of the most stable joints in the body. The stability is provided by a rigid ball and socket configuration. The femoral head is almost spherical in its articular portion that forms two-thirds of a sphere. Data has shown that the diameter of the femoral head is smaller for females than males. In the normal hip, the center of the femoral head is assumed to coincide exactly with the center of the acetabulum and this assumption is used as the basis for the design of most hip systems. However, the native acetabulum is not deep enough to cover all of the native femoral head. The almost rounded part of the femoral head is spheroidal rather than spherical because the uppermost part is flattened slightly. This spheroidal shape causes the load to be distributed in a ring-like pattern around the superior pole.

The geometrical center of the femoral head is traversed by three axes of the joint: the horizontal axis; the vertical axis; and, the anterior/posterior axis. The femoral head is supported by the neck of the femur, which joints the shaft. The axis of the femoral neck is obliquely set and runs superiorly medially and anteriorly. The angle of the inclination of the femoral neck to the shaft in the frontal plane is the neck shaft angle. In most adults, this angle varies between 90 to 135 degrees and is important because it determines the effectiveness of the hip abductors, the length of the limb, and the forces imposed on the hip joint.

An angle of inclination greater than 125 degrees is called coxa valga, whereas an angle of inclination less than 125 degrees is called coxa vara. Angles of inclination greater than 125 degrees coincide with lengthened limbs, reduced effectiveness of the hip abductors, increased load on the femoral head, and increased stress on the femoral neck. In a case of coxa vara, angles of inclination less than 125 degrees coincide with shortened the limbs, increased effectiveness of the hip abductors, decreased load on the femoral head, and decreased stress on the femoral neck. The femoral neck forms an acute angle with the transverse axis of the femoral condyles. This angle faces medially and anteriorly and is called angle of anteversion. In adult humans, this angle averages approximately 7.5 degrees.

The acetabulum lies on the lateral aspect of the hip where the ilium, ischium, and pubis meet. These three separate bones join into the formation of the acetabulum, with the ilium and ischium contributing approximately two-fifths each and the pubis one-fifth of the acetabulum. The acetabulum is not a deep enough socket to cover all of the femoral head and has both articulating and non-articulating portions. However, the acetabular labrum deepens the socket to increase stability. Together with labrum, the acetabulum covers slightly more than 50% of the femoral head. Only the sides of the acetabulum are lined with articular cartilage, which is interrupted inferiorly by the deep acetabular notch. The center part of the acetabular cavity is deeper than the articular cartilage and is nonarticular. This center part is called the acetabular fossae and is separated from the interface of the pelvic bone by a thin plate. The acetabular fossae is a region unique for every patient and is used in creating patient-specific guide for reaming and placement of the acetabular cup component. Additionally, variation of anatomical features further warrant the need for population specific implant designs.

Some of the problems associated with prior art use of cementless components can be attributed to the wide variation in size, shape, and orientation of the femoral canal. One of the challenges to orthopedic implant design of the femoral stem is large variation in the mediolateral and anteroposterior dimensions. There is also significant variation in the ratio of the proximal to distal canal size. The different combination of various arcs, taper angles, curves, and offsets in the normal population is staggering. However, that is not the only problem.

Ancestral differences in femora morphology and a lack of definite standards for modern populations makes designing the proper hip implant system problematic. For example, significant differences in anterior curvature, torsion, and cross-sectional shape exist between American Indians, American blacks, and American whites. Differences between Asian and Western populations in the femora are found in the anterior bow of the femora, where Chinese are more anteriorly bowed and externally rotated with smaller intramedullary canals and smaller distal condyles than Caucasian femora. Likewise, Caucasian femora are larger than Japanese femora in terms of length distal condyle dimensions. Ethnic differences also exist in the proximal femur mineral bone density (BMD) and hip axis length between American blacks and whites. The combined effects of higher BMD, shorter hip axis length, and shorter intertrochanteric width may explain the lower prevalence of osteoporotic fractures in American black women compared to their white counterparts. Similarly, elderly Asian and American black men were found to have thicker cortices and higher BMD than white and Hispanic men, which may contribute to greater bone strength in these ethnic groups. In general, American blacks have thicker bone cortices, narrower endosteal diameters, and greater BMD than American whites.

Combining the femur and the pelvic ancestral (and ethnic) differences becomes even more challenging to primary hip systems. Revision surgery creates more complexity. Added to these normal anatomic and ethnic variations, the difficulties faced by the surgeon who performs revision operation are compounded by: (a) distortion of the femoral canal caused by bone loss around the originally placed prostheses; and, (b) iatrogenic defects produced by the removal of the components and cement.

All of the foregoing factors have led a number of hip surgeons to look for ways to improve design of uncemented femoral prostheses. In total hip replacement (primary or revision), the ideal is to establish an optimal fit between the femoral ball and acetabular cup. The femoral stem neck should have a cruciform cross section to reduce stiffness. The stem length should be such that the stem has parallel contact with the walls of the femur over two to three internal canal diameters. The proximal one third of the stem is porous coated or hydroxylapatite (HA) coated. The stem is cylindrical (i.e. not tapered) to control bending loads and to allow transmission of all rotational and axial loads proximally. The femoral head position should reproduce the patient's own head center, unless it is abnormal.

One way to attempt to satisfy these goals is to manufacture femoral prostheses individually for each patient. In other words, make a prosthesis that is specific to a particular patient rather than trying to reshape the patient's bone to fit a readymade prosthesis.

There are some common design rules for patient-specific (or mass customization) primary and revision hip replacements. Among these design rules are: (1) the hip stem should be collarless (except in revision) to allow uniform distribution of load to the femur; (2) the hip stem should have a modified rhomboidal cross section to maximize fit/fill, but should maintain rotational stability; (3) the hip stem should be bowed when necessary to conform to patient's bone; (4) the hip stem should be inserted along a curved path, with no gaps between the prosthesis and the bone; (5) the hip stem neck should have cruciform cross section to reduce stiffness; (6) the hip stem length should be such that the stem has parallel contact with the walls of the femur over two to three internal canal diameters; (7) the proximal one third of the hip stem is porous coated or hydroxylapatite (HA) coated; (8) the hip stem is cylindrical (i.e. not tapered) to control bending loads and to allow transmission of all rotational and axial loads proximally; (9) the femoral head position of the hip stem should reproduce the patient's own head center, unless it is abnormal.

The following is an exemplary process and system for generating mass customized orthopedic implant for patients needing primary joint replacement taking into account the gender and/or ethnicity of the patient population. For purposes of the exemplary discussion, a total hip arthroplasty procedure will be described for a patient with a partial anatomy. It should be understood, however, that the exemplary process and system are applicable to any orthopedic implant amenable to mass customization in instances where incomplete anatomy is present. For example, the exemplary process and system are applicable to shoulder replacements and knee replacements where bone degeneration (partial anatomy), bone deformation, or shattered bones are present. Consequently, though a femoral component of a hip implant is discussed hereafter, those skilled in the art will understand the applicability of the system and process to other orthopedic implants, guides, tools, etc. for use with original orthopedic or orthopedic revision surgeries.

Referring to FIG. 25, an overall process flow is depicted for using a statistical atlas for generation of both mass customized and patient-specific hip implants. Initially, the process includes the statistical atlas including several instances of one or more bones being analyzed. In the exemplary context of a hip implant, the statistical atlas includes several instances of bone models for the pelvis bone and the femur bone. An articulating surface geometry analysis is conducted at least for the acetabular component (i.e., acetabulum) and the proximal femoral component (i.e., femoral head). In particular, the articulating surface geometry analysis involves calculation of landmarks, measurements, and shape features on each bone from a given population of the statistical atlas. In addition, the articulating surface geometry analysis includes generating quantitative values, such as statistics, representative of the calculations. From these calculations, a distribution of the calculations is plotted and parsed based the distribution. For a bell-shaped distribution, for example, it may be observed that approximately ninety percent (90%) of the population is grouped so that a non-patient-specific implant (e.g., a mass customized implant) may be designed and adequately fit this grouping, thereby reducing the costs for patients compared with patient-specific implants. For the remaining ten percent (10%) of the population, a patient-specific implant may be a better approach.

In the context of a mass customized implant, the statistical atlas may be utilized to quantitatively assess how many different groups (i.e., different implants) are able to encompass the overwhelming majority of a given population. These quantitative assessments may result in clusters of data indicating the general parameters for a basic implant design that, while not patient-specific, would be more specific than an off-the-shelf alternative.

In the context of a patient-specific implant, the statistical atlas may be utilized to quantitatively assess what a normal bone embodies and differences between the patient's bone and a normal bone. More specifically, the statistical atlas may include curvature data that is associated with a mean or template bone model. This template bone model can then be used to extrapolate what the form of the patient's correct bone would be and craft the implant and surgical instruments used to carry out the implant procedure.

Figure 26:
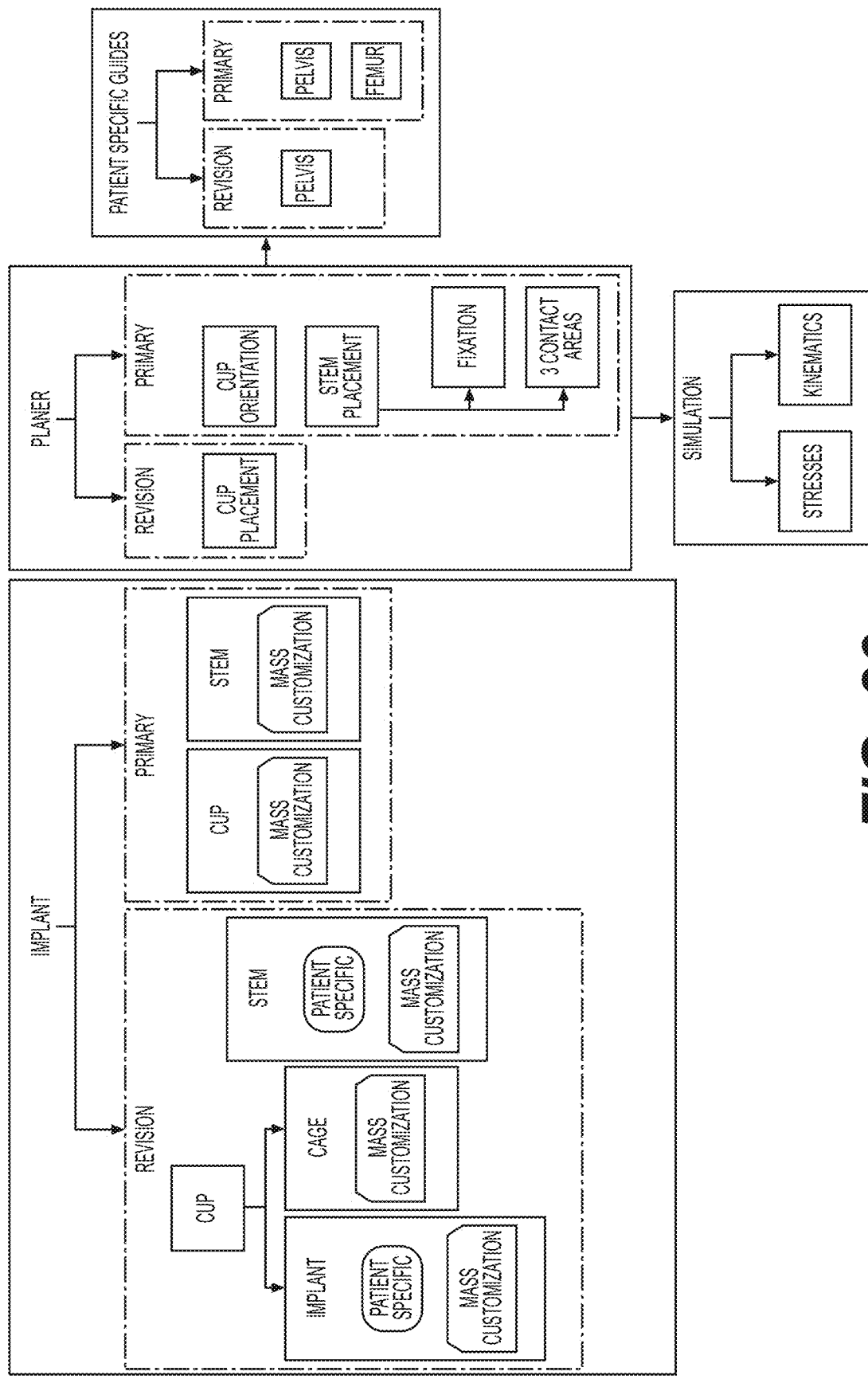
FIG. 26 is a schematic diagram depicting a process for using a statistical atlas for generation of both mass customized and patient-specific hip implant.

FIG. 26 graphically summarizes the utilization of a statistical atlas in designing mass customized and patient-specific hip implants. In the context of the implant box, reference is had back to FIGS. 17 and 18 and the associated discussion for these figures. Similarly, in the context of the planner box, reference is had back to FIG. 17 and the associated discussion of the custom planning interface. Finally, in the context of the patient-specific guides box, reference is had back to FIG. 19 and the associated discussion for this figure.

Figure 27:
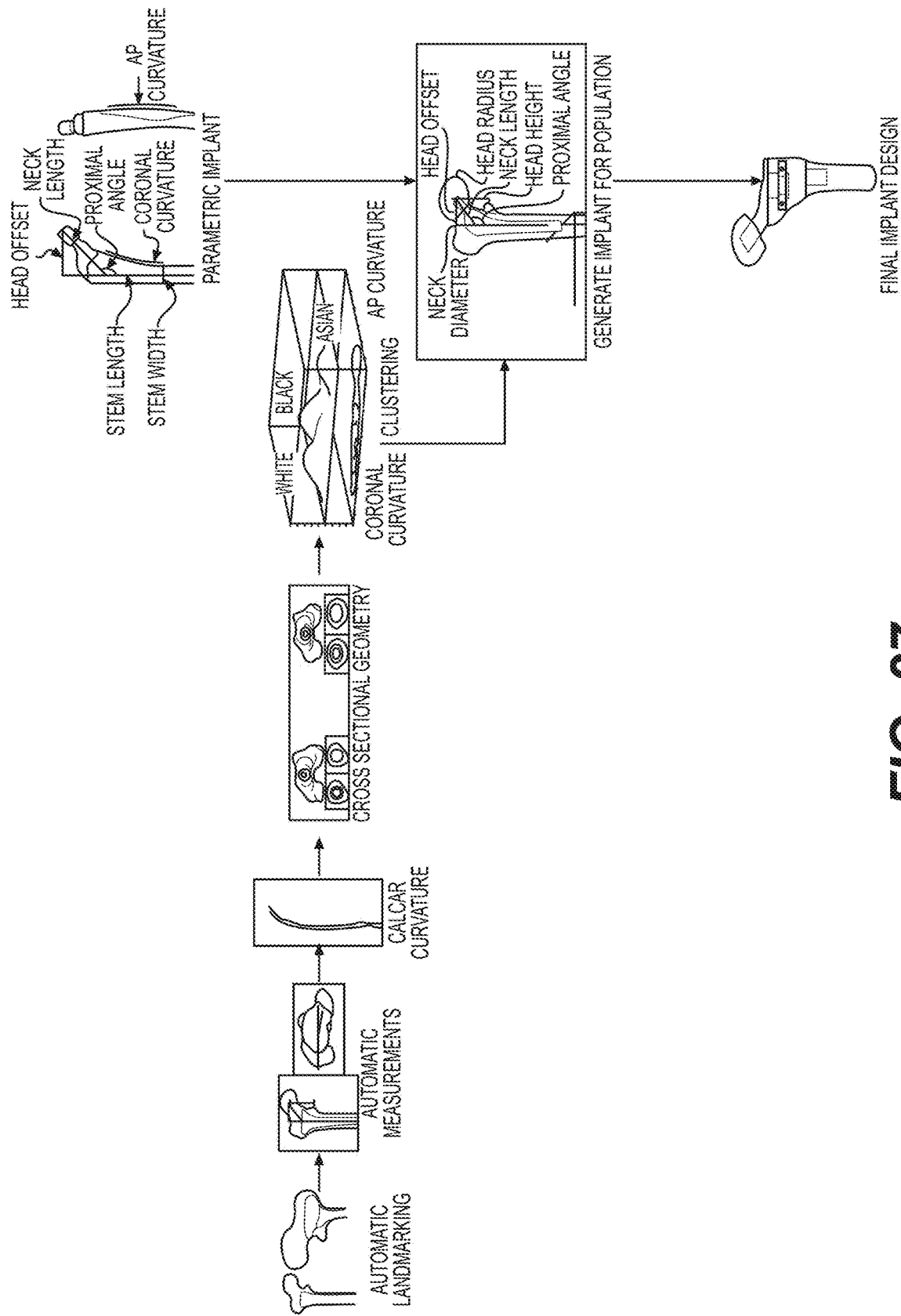
FIG. 27 is a schematic diagram depicting an outline of a process for designing population specific hip stem components.
Figure 28:
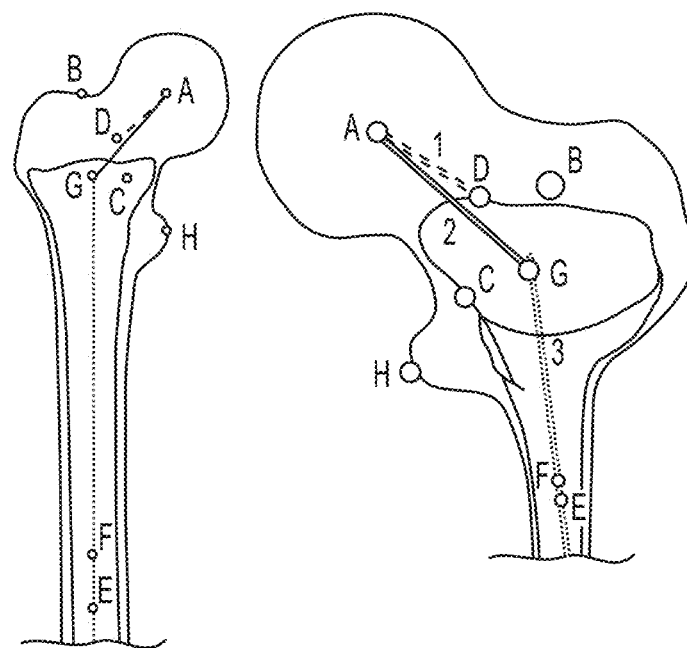
FIG. 28 is a graphical representation showing where the proximal femur landmarks are located.
Figure 29:
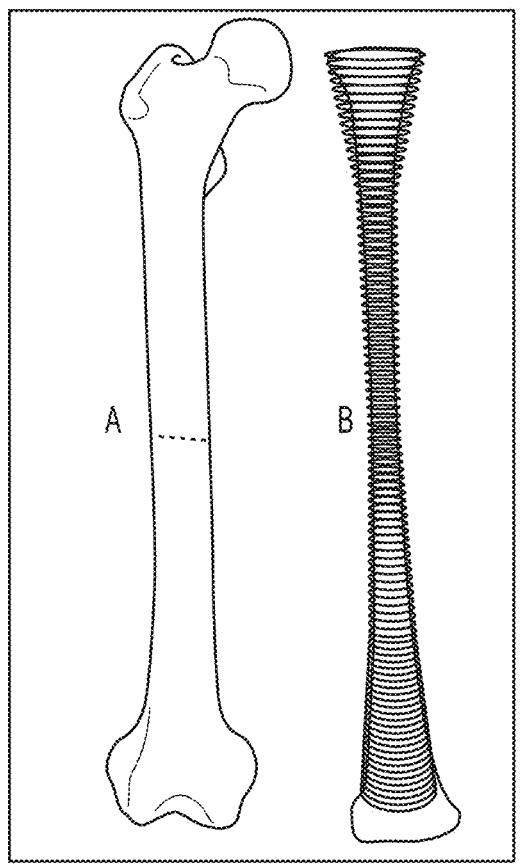
FIG. 29 is a 3D model of a femur showing canal waist in the middle of the femur and femur waist along the length of the femur.
Figure 30:
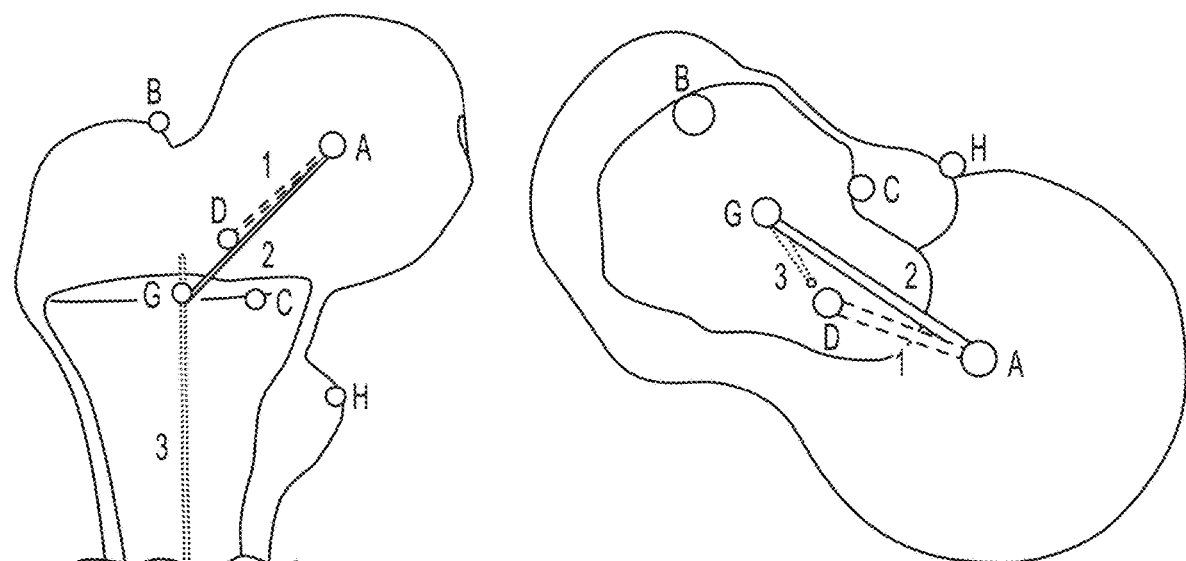
FIG. 30 is a graphical representation showing where the proximal femur axes are located.
Figure 31:
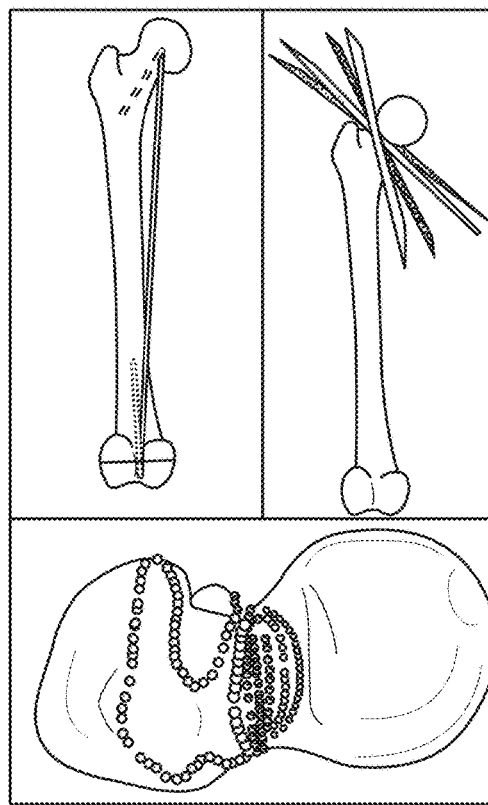
FIG. 31 is a graphical representation showing where the neck center calculation is located.
Figure 32:
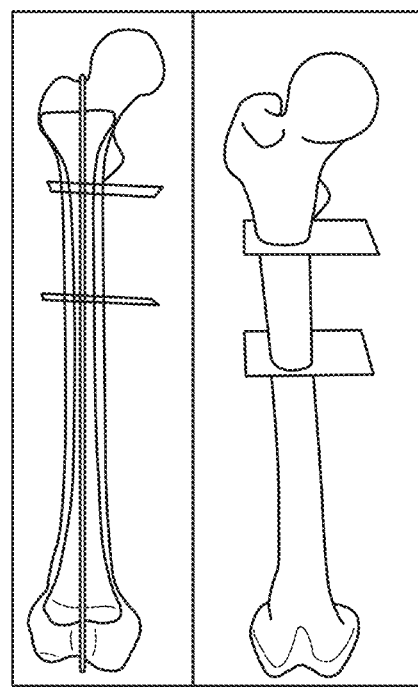
FIG. 32 is a graphical representation of two points used to define a femur proximal anatomical axis.
Figure 33:
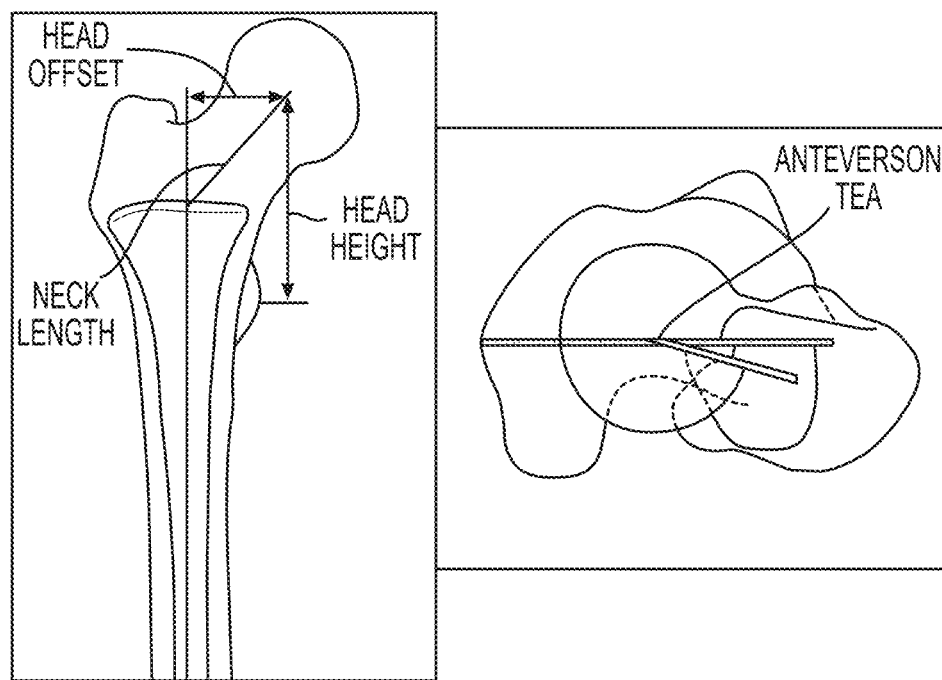
FIG. 33 is a graphical representation of 3D proximal femur measurements.
Figure 34:
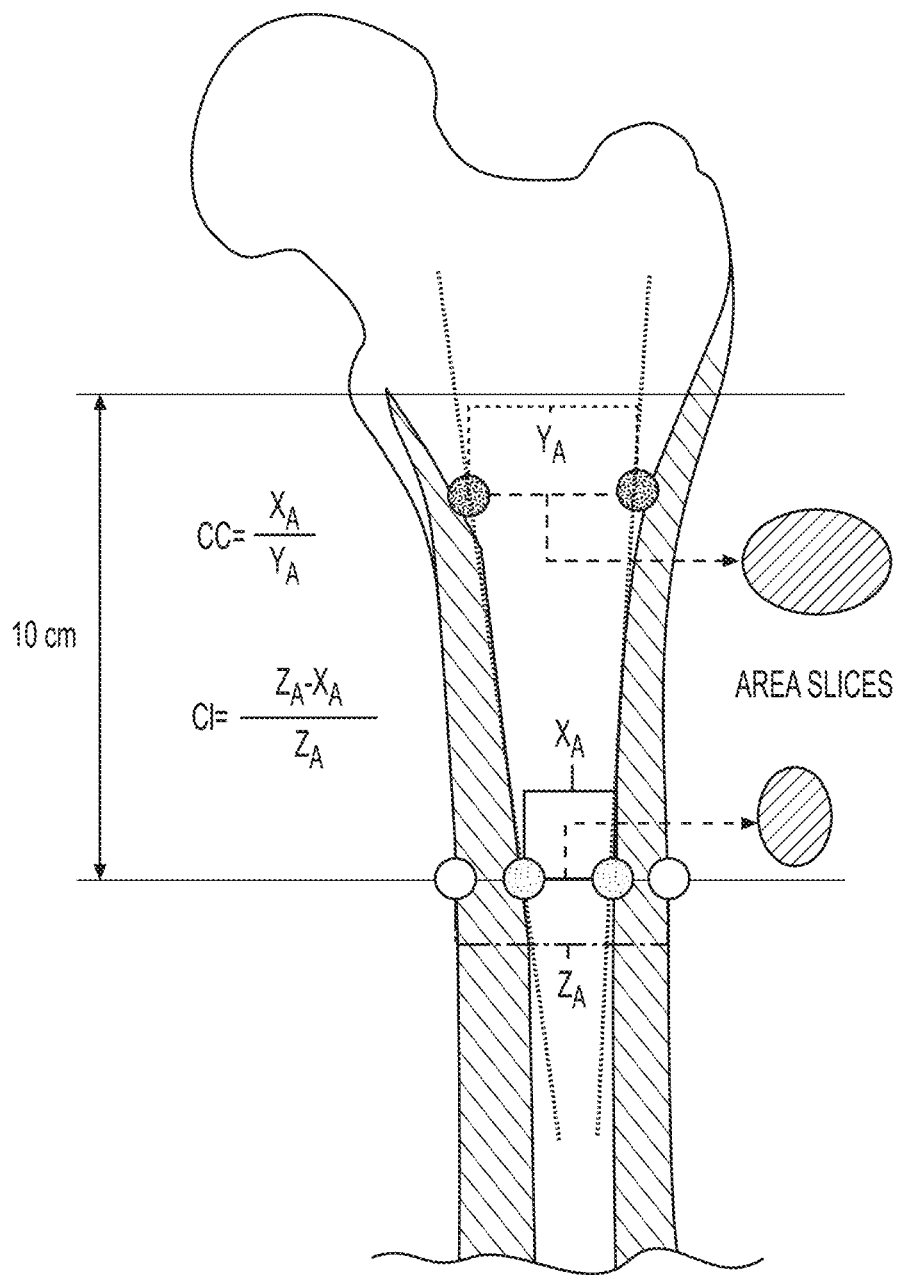
FIG. 34 shows an exemplary Don ratio, which is generally in 2D (from XR).
Figure 35:
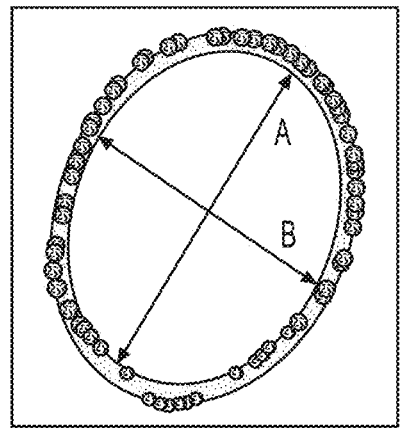
FIG. 35 is a graphical representation of the B/A ratio at the IM Isthmus.
Figure 36:
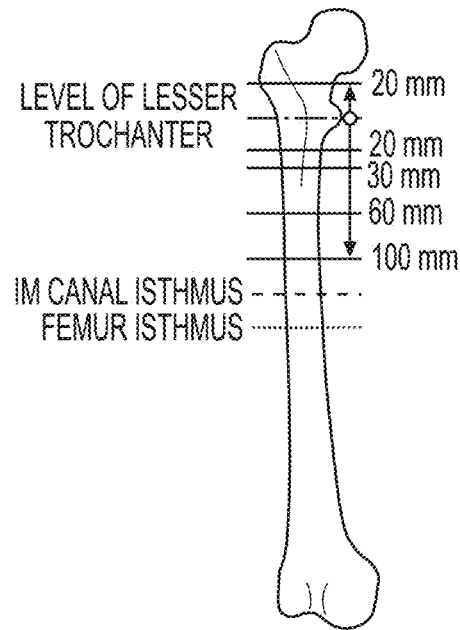
FIG. 36 is a graphical representation of IM canal measurements.
Figure 37:
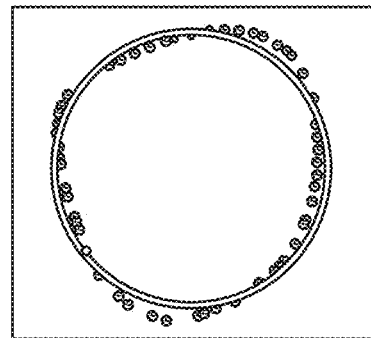
FIG. 37 is a contour and a fitted circle.
Figure 38:
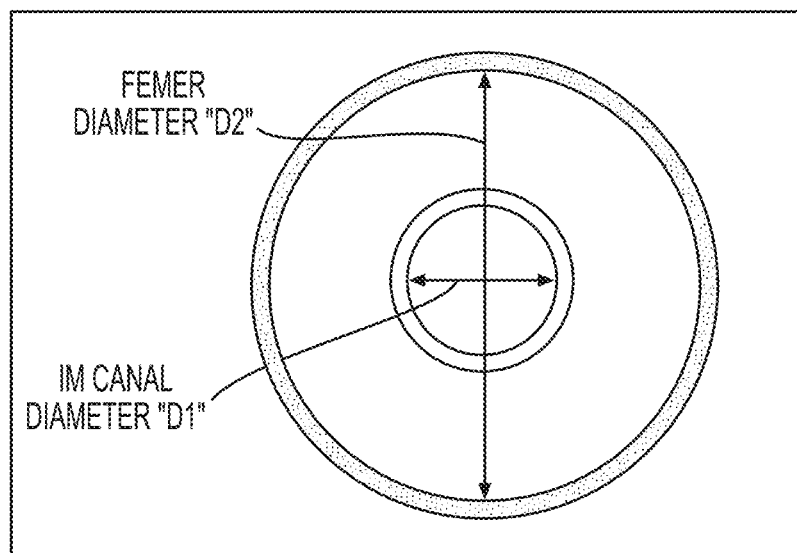
FIG. 38 is a graphical representation of the measurements taken to obtain the IM canal femur radii ratio.
Figure 39:
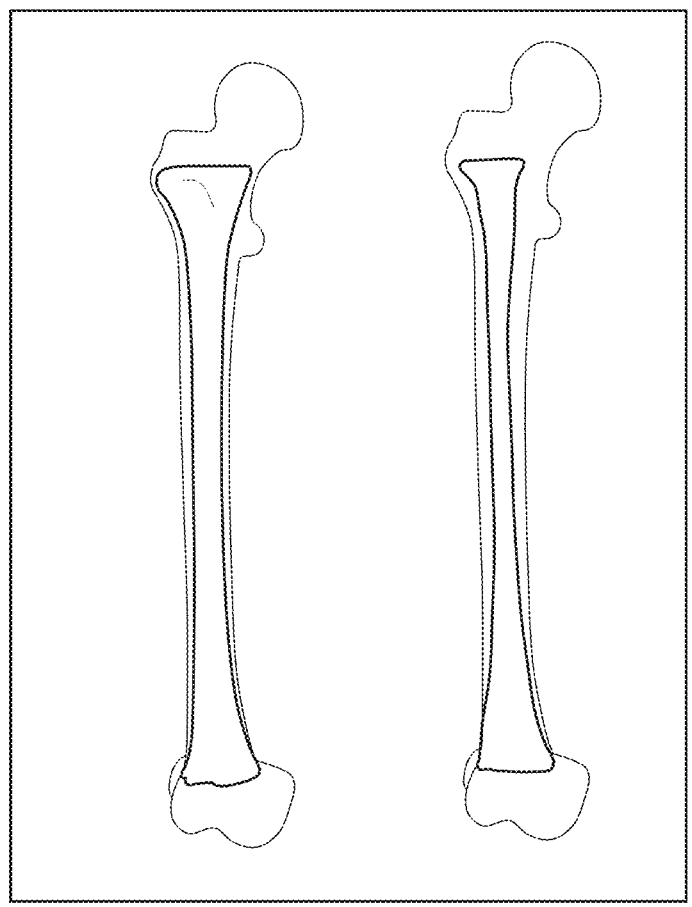
FIG. 39 depicts two femur models showing the effect of the change in the radii ratio, with the one on the left having a radii ratio of 0.69, and the one on the right having a radii ratio of 0.38.
Figure 40:
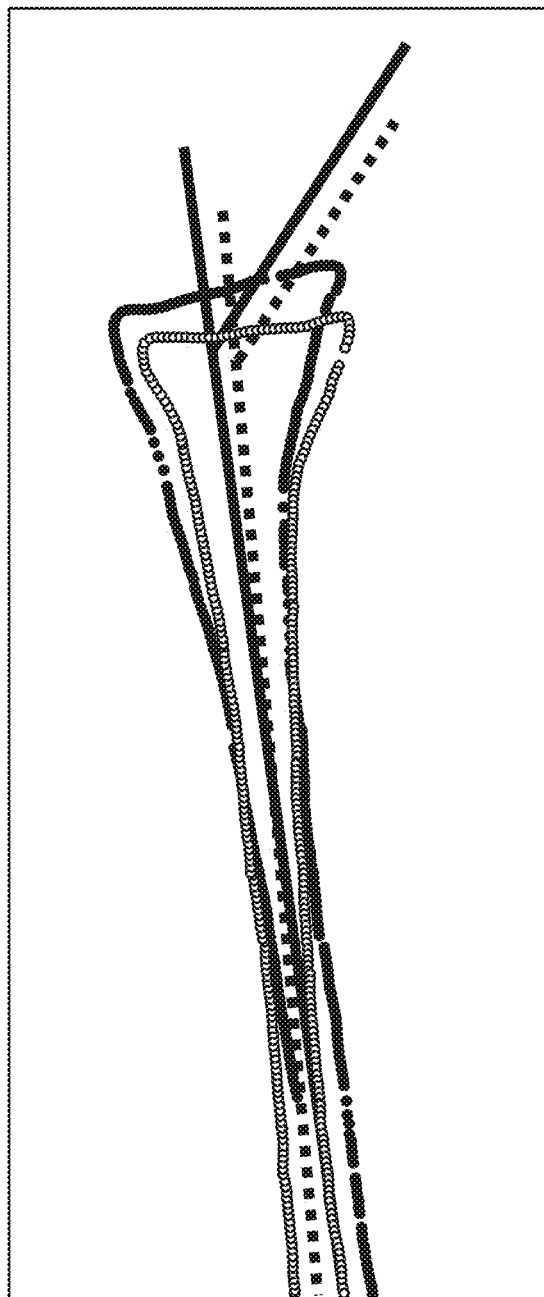
FIG. 40 is a graphical representation of medial contours, neck axis and head point of a proximal femur before alignment.
Figure 41:
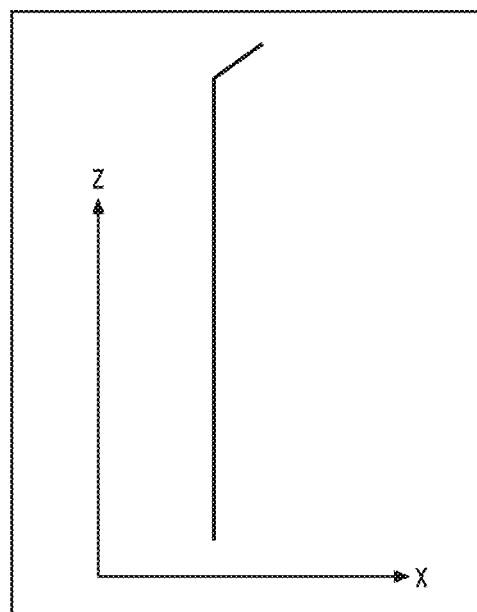
FIG. 41 is a graphical representation of an anatomical axis alignment with the Z-direction.
Figure 42:
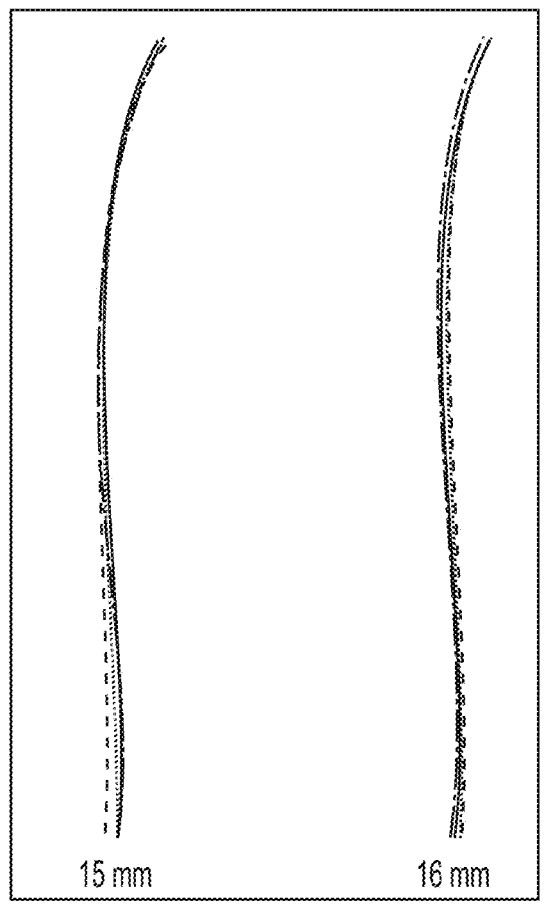
FIG. 42 is a graphical representation of medial contours aligned using the femoral neck pivot point.

As depicted in FIG. 27, a flow chart is depicted for an exemplary process that may be utilized to design and fabricate gender and/or ethnic specific hip implants. In particular, the process includes utilization of a statistical atlas containing various specimens of a proximal femur (i.e., femur including femoral head) that have been identified by associated data as being from either a male or a female and the ethnicity of the person from which the bone pertains. Moreover, the statistical atlas module logs virtual, 3D models of one or more anatomies (e.g., bones) to capture the inherent anatomical variability in a given gender and/or ethnic population. In exemplary form, the atlas logs mathematical representations of anatomical features of the one or more anatomies represented as a mean representation and variations about the mean representation for a given anatomical population that may have a common gender and/or ethnicity (or grouped to have one of a plurality of ethnicities for which anatomical commonalities exist). Reference is had to FIG. 2 and the foregoing discussion of the statistical atlas and how one adds anatomy to the statistical atlas for a given population. Outputs from the statistical atlas are directed to an automatic landmarking module and to a surface/shape analysis module.

Referring to FIGS. 27-39, the automatic landmarking module utilizes inputs from the statistical atlas (e.g., regions likely to contain a specific landmark) and local geometrical analyses to calculate anatomical landmarks for each instance of anatomy within the statistical atlas. By way of example, various proximal femur landmarks are calculated for each 3D virtual model of a femur that include, without limitation: (1) femoral head center, which is the center point of a femoral head approximated by a sphere; (2) greater trochanter point, which is the point on the greater trochanter having the minimum distance to the plane passing through the neck shaft point perpendicular to the anatomical neck center line; (3) osteotomy point, which is the point fifteen millimeters from the end of the lesser trochanter (approximately thirty millimeters from the lesser trochanter point); (4) neck shaft point, which is the point on the head sphere whose tangential plane encloses the minimum femoral neck cross-sectional area; (5) femur waist, which is the cross-section with the smallest diameter along the femur shaft; (6) intramedullary canal waist, which is the cross-section with the smallest diameter along the intramedullary canal; (7) femoral neck pivot point, which is the point on the femoral anatomical axis that forms with the femoral head center and the distal end of the femoral anatomical axis an angle equal to the femoral neck angle; and, (8) lesser trochanter point, which is the point on the lesser trochanter region that most protrudes outward. By way of further example, various proximal femur axes are calculated for each 3D virtual model of a femur using the identified anatomical landmarks that include, without limitation: (a) femoral neck anatomical axis, which is coaxial with a line connecting the femur head center with the femur neck center; (b) femoral neck axis, which is coaxial with a line joining the femur head center point and the femoral neck pivot point; and, (c) femoral anatomical axis, which is coaxial with a line connecting two points lying at a distance twenty-three percent and forty percent of the total femur length starting from the proximal end of the femur. By way of yet further example, various proximal femur measurements are calculated for each 3D virtual model of a femur using the identified anatomical landmarks and axes that include, without limitation: (i) proximal angle, which is the 3D angle between femoral anatomical axis and femoral neck anatomical axis; (ii) head offset, which is the horizontal distance between the femoral anatomical axis and the femoral head center; (iii) head height, which is the vertical distance between the lesser trochanter point (referenced previously) and femoral head center; (iv) greater trochantor to head center distance, which is the distance between the head center and the greater trochanter point (referenced previously); (v) neck length, which is the distance between the head center and the neck-pivot point (referenced previously); (vi) the head radius, which is the radius of the sphere fitted to femoral head; (vii) neck diameter, which is the diameter of the circle fitted to the neck cross section at plane normal to femoral neck anatomical axis and passing through neck center point (referenced previously); (viii) femoral neck anteversion transepicondylar angle, which is the angle between the transepicondylar axis and femoral neck axis; (ix) femoral neck anteversion posteriorcondylar angle, which is the angle between the posteriorcondylar axis and femoral neck axis; (x) LPFA, which is the angle between mechanical axis and vector pointing to the greater trochanter; (xi) calcar index area, which is defined by the equation: $(Z-X)/Z$, where Z is the femur area at 10 centimeters below the mid lesser trochanter point and X is the intramedullary canal area at 10 centimeters below the mid lesser trochanter point; (xii) canal calcar ratio area, which is the ratio between the intramedullary canal area at 3 centimeters below the mid-lesser trochanter level to the intramedullary canal area at 10 centimeters below the mid-lesser trochanter; (xiii) XYR area, which is the ratio between the intramedullary canal area at 3 centimeters below the mid-lesser trochanter to the intramedullary canal area at 10 centimeters below the mid-lesser trochanter; (xiv) minor/major axes ratio, which is the ratio between the minor axis and major axis of a fitted ellipse to the intramedullary canal cross-section at the narrowest point on intramedullary canal; and, (xv) femur radii to intramedullary canal radii ratio, which is the ratio of circle radii, using circles best fit to the circumference of the outer circumference of the femur and intramedullary canal within a plane normal to the femoral anatomical axis (this ratio reflects the thickness of the cortical bone and, accordingly, cortical bone loss in cases of osteoporosis).

Referencing FIGS. 27 and 40-42, using the output from the automatic landmarking module, parameters for the femoral stem are assessed for a given population. In particular, regardless of whether the population is grouped based upon ethnicity, gender, or a combination of the two, the medial contour, neck angle, and head offset are assessed.

In the case of the medial contour, this contour with respect to the intramedullary canal for each femur within the population is generated by intersecting the intramedullary canal with a plane extending through the femoral pivot point and having a normal axis perpendicular to both the femoral anatomical axis and the neck axis (vectors cross product). After the contours are generated for each femur within the population, the population is subdivided into groups using intramedullary canal size. When subdivided, the contours may be out of plane, so an alignment process is carried out to align all the contours with respect to a common plane (e.g., an X-Z plane). The alignment process includes aligning the axis which is normal to both the femoral neck axis and anatomical axis to the Y axis then aligning the anatomical axis to the Z axis. In this fashion, all contours are translated relative to a specific point in order for the contours to have a common coordinate frame.

After the contours have a common coordinate frame, the femoral neck point is utilized to verify that the points of the contours are in plane. In particular, the femoral neck point is a consistent point that reflects real anatomy and guarantees the points on the contours are in plane. By verifying the points of the contour are in plane, alignment variability between population femurs can be significantly reduced, which facilitates utilization of the contours for head offset and implant angle design.

Figure 43:
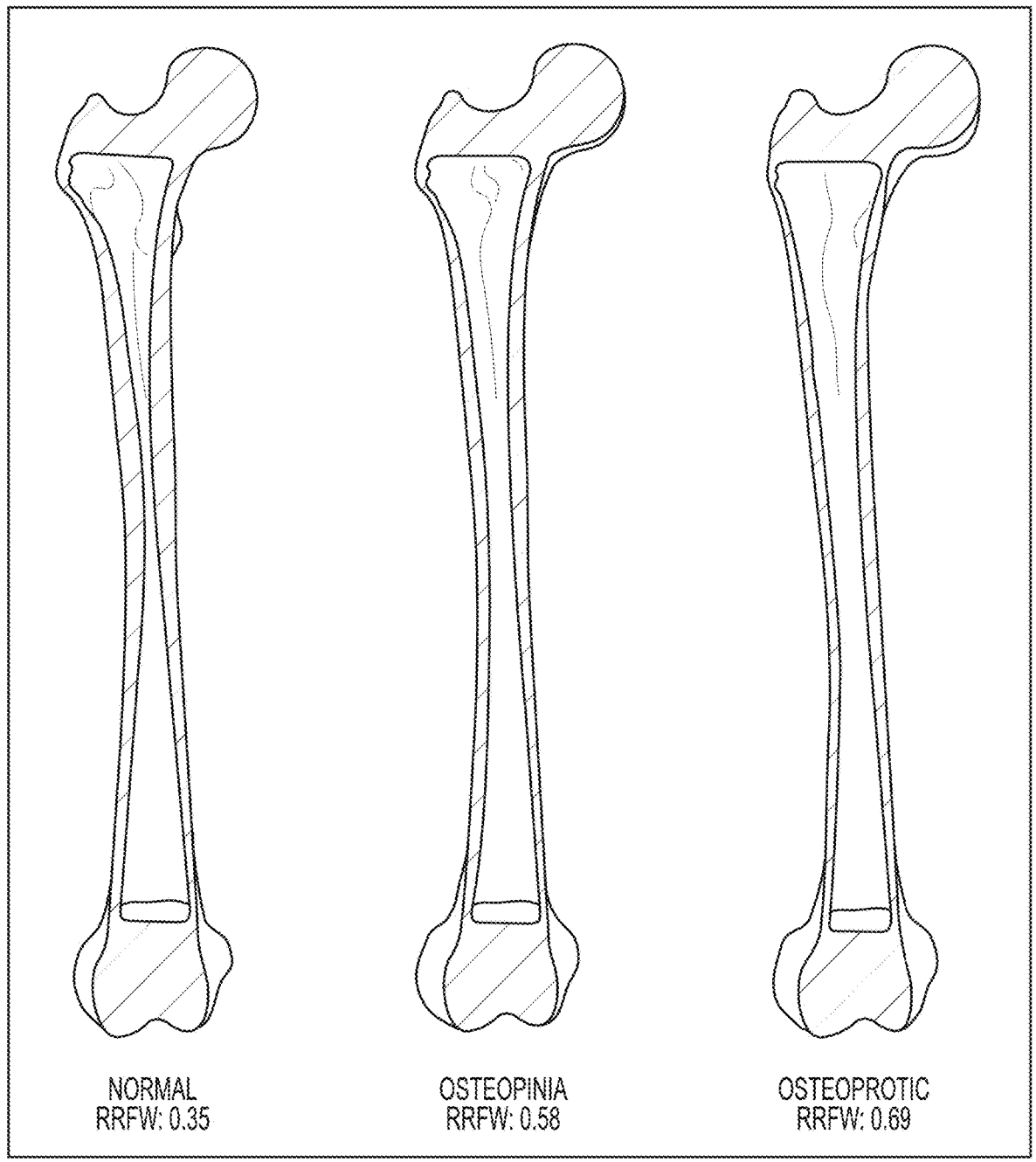
FIG. 43 is a graphical representation of different models generated using interpolation between models to show the smoothness of interpolation.
Figure 44:
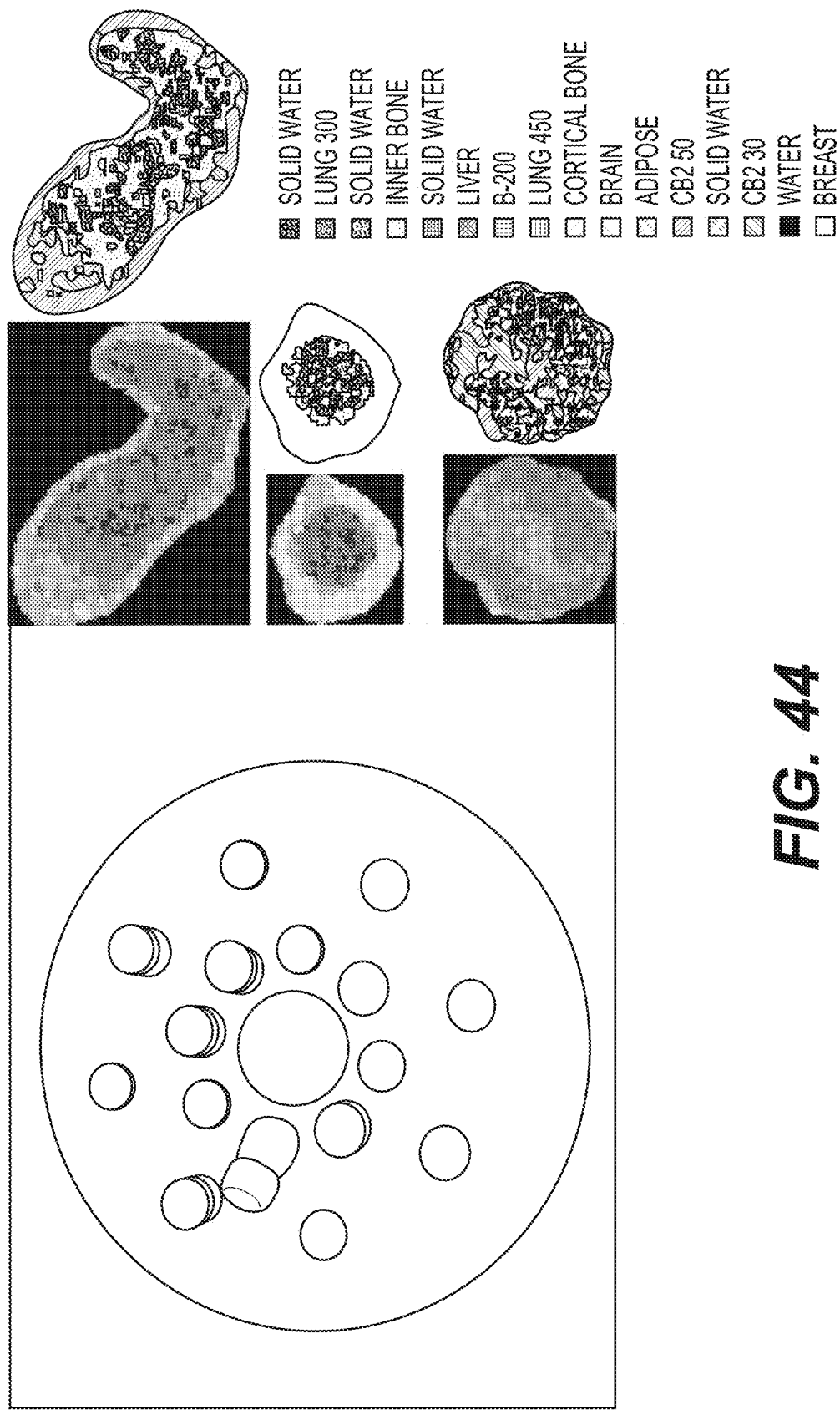
FIG. 44 is a graphical and pictorial representation of three dimensional mapping of bone density.

Referring to FIG. 43, the statistical atlas may also be useful to interpolate between normal and osteoporotic bones. When designing and sizing a femoral stem, one of the key considerations is intramedullary canal dimensions. In instances of normal bone, with respect to the femur, the intramedullary canal is significantly narrower than compared to a femur exhibiting osteoporosis. This narrower intramedullary canal dimension is the result, at least in part, of bone thicknesses (measured transverse to the dominant axis of the femur) decreasing, which correspondingly results in receding of the interior surface of the femur delineating the intramedullary channel. In this method, a synthetic population is created by interpolating between healthy and severely osteoporotic bone thicknesses and generating virtual 3D models having said thicknesses. This dataset thusly contains bones corresponding to different stages of osteoporosis. This dataset can now be used as an input to implant stem design.

In exemplary form, the statistical atlas includes a population of normal, non-osteoporotic bones and osteoporotic bones, in this case the bone is a femur. Each of these normal femurs of the atlas is quantified and represented as a 3D virtual model, in accordance with the process described herein for adding bones to a statistical atlas. Likewise, each of the osteoporotic bones of the atlas is quantified and represented as a 3D virtual model, in accordance with the process described herein for adding bones to a statistical atlas. As part of the 3D models for normal and osteoporotic bones, intramedullary canal dimensions are recorded along the longitudinal length of the femur. Using atlas point correspondence, the intramedullary canal is identified on the atlas bones as spanning a fixed percentage of the overall bone length (say 5%) proximal to the lesser trochanter and a second fixed percentage (say 2%) proximal to the distal cortex point. Additionally, points on the external bone surface falling within these proximal and distal bounds are used for determining bone thickness, defined as the distance from the external point to the nearest point on the IM canal.

Figure 54:
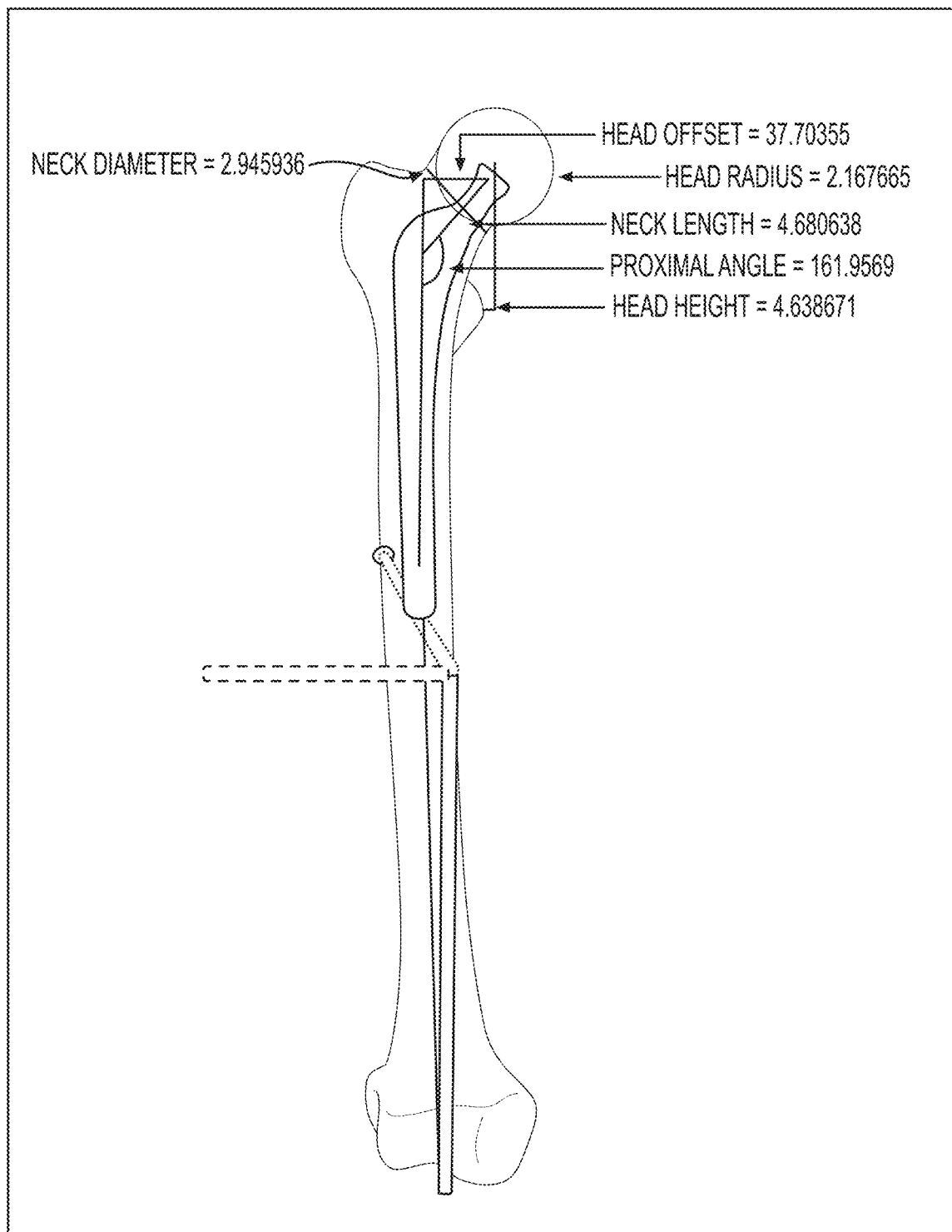
FIG. 54 is a graphical representation of female measurements with respect to a proximal femur.
Figure 55:
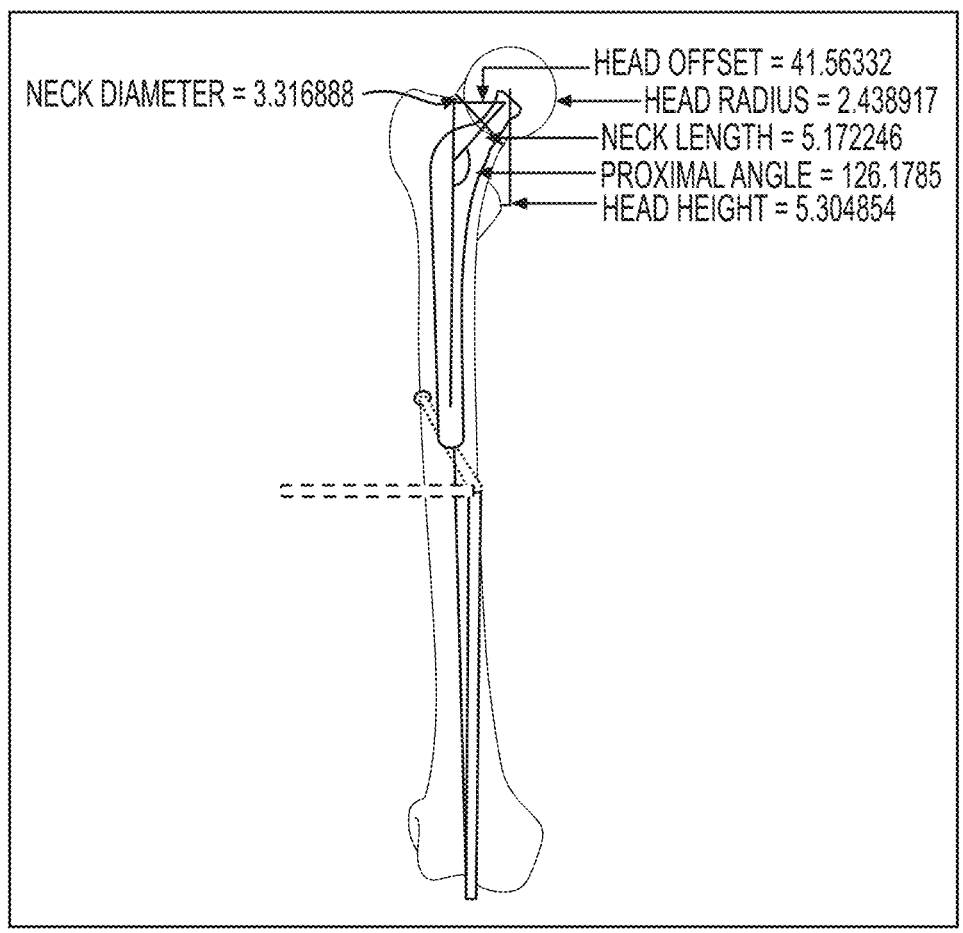
FIG. 55 is a graphical representation of male measurements with respect to a proximal femur.
Figure 56:
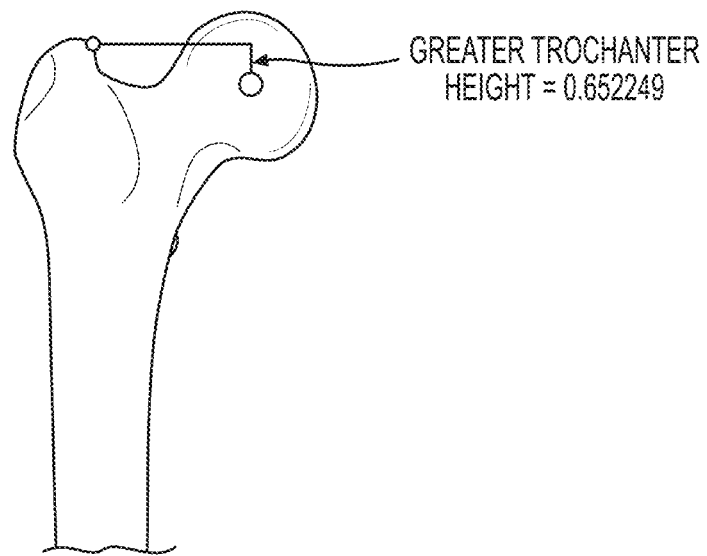
FIG. 56 is a graphical representation of female measurements with respect to the greater trochanter height.
Figure 57:
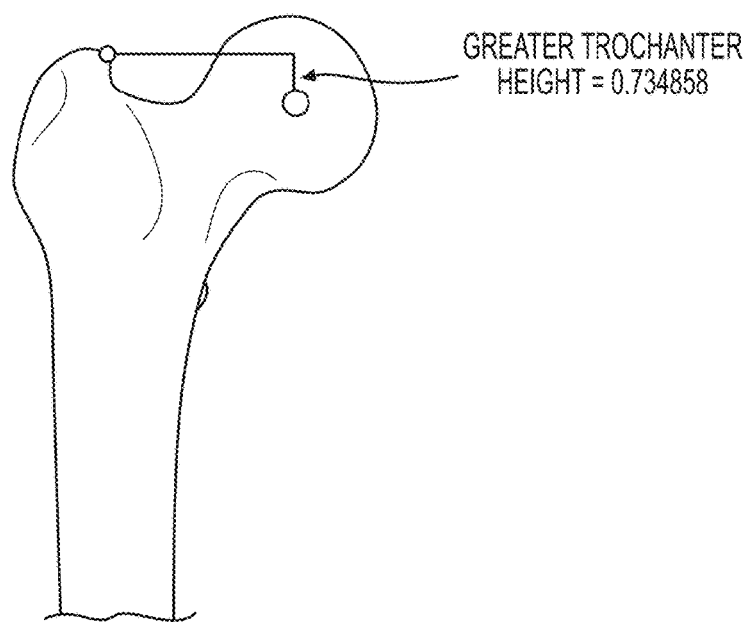
FIG. 57 is a graphical representation of male measurements with respect to the greater trochanter height.
Figure 58:
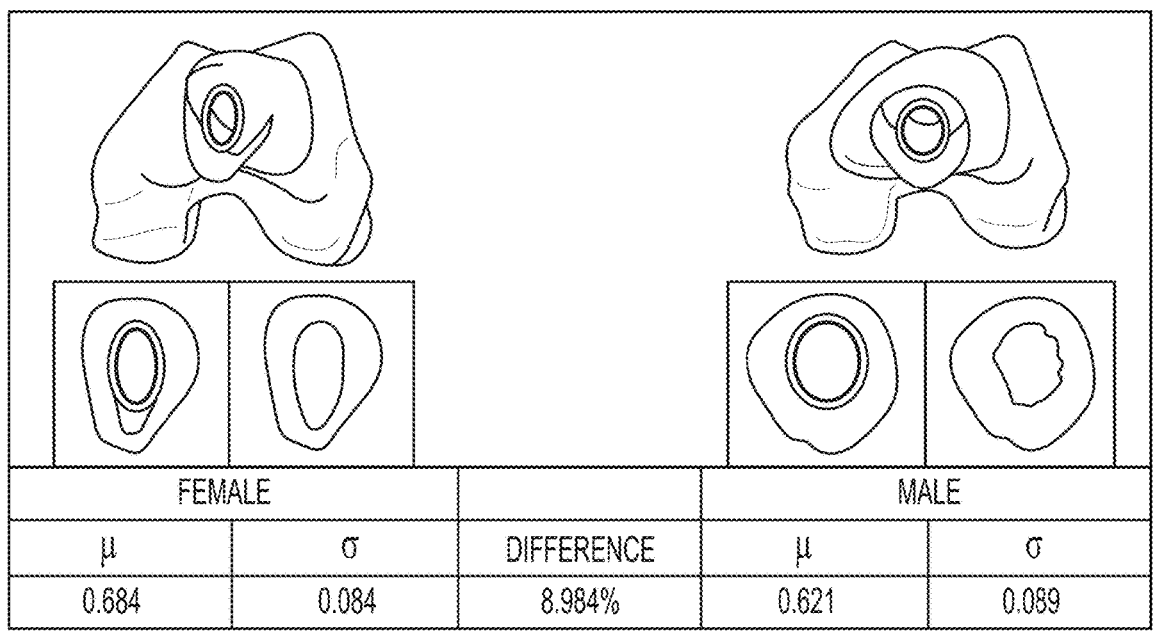
FIG. 58 IM canal shape difference between gender.
Figure 59:
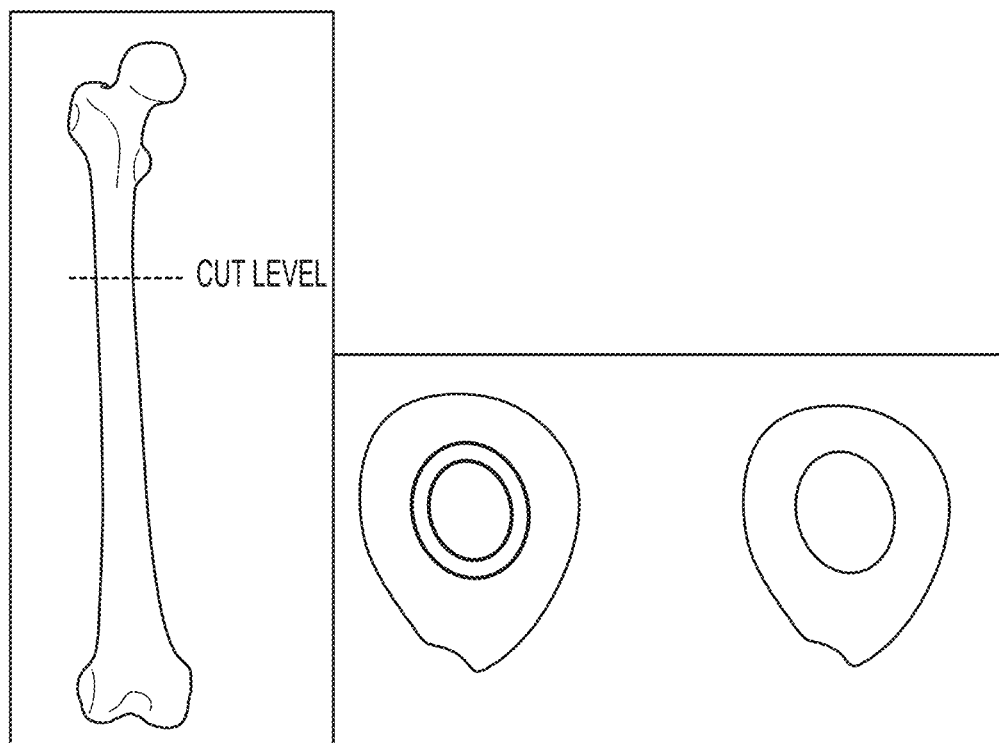
FIG. 59 Normal Female: T-score 1.1
Figure 60:
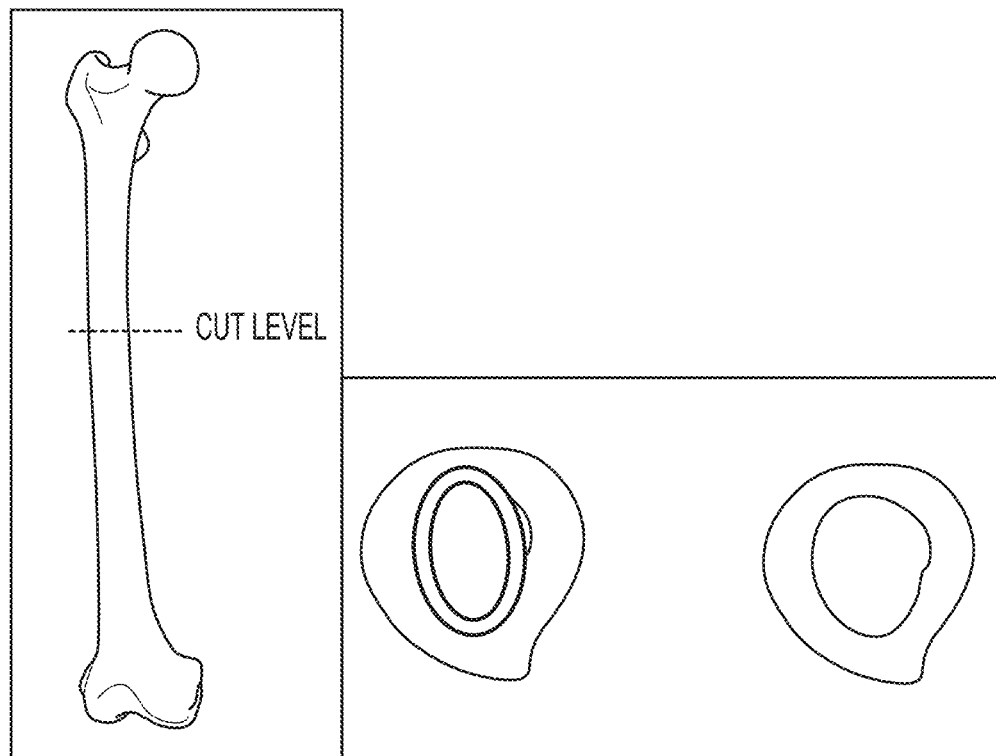
FIG. 60 Osteopinia Female: T-score −1.3
Figure 61:
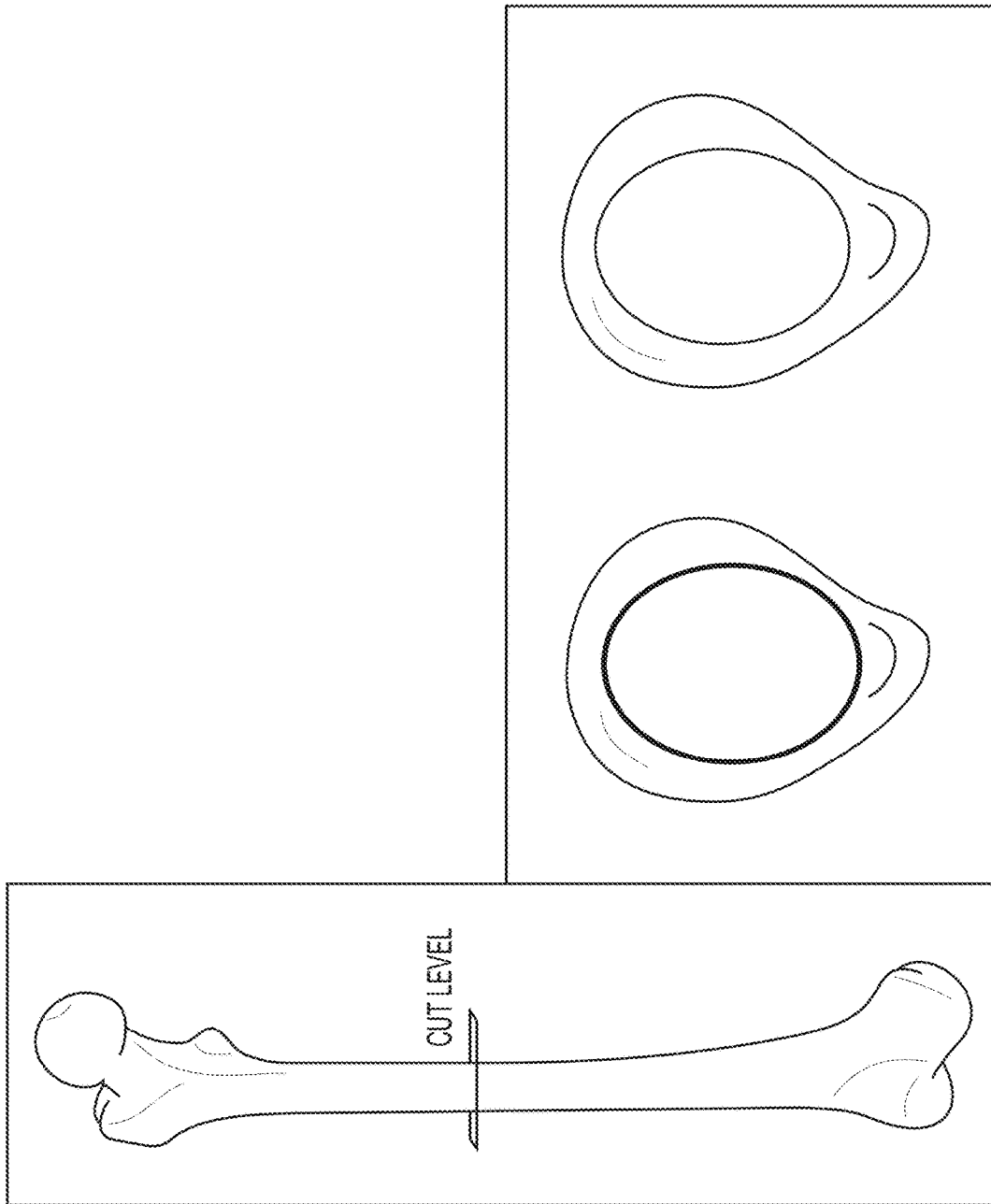
FIG. 61 Osteoporosis Female: T-score −3
Figure 62:
FIG. 62 Interpolated dataset headoffsets histogram.
Figure 63:
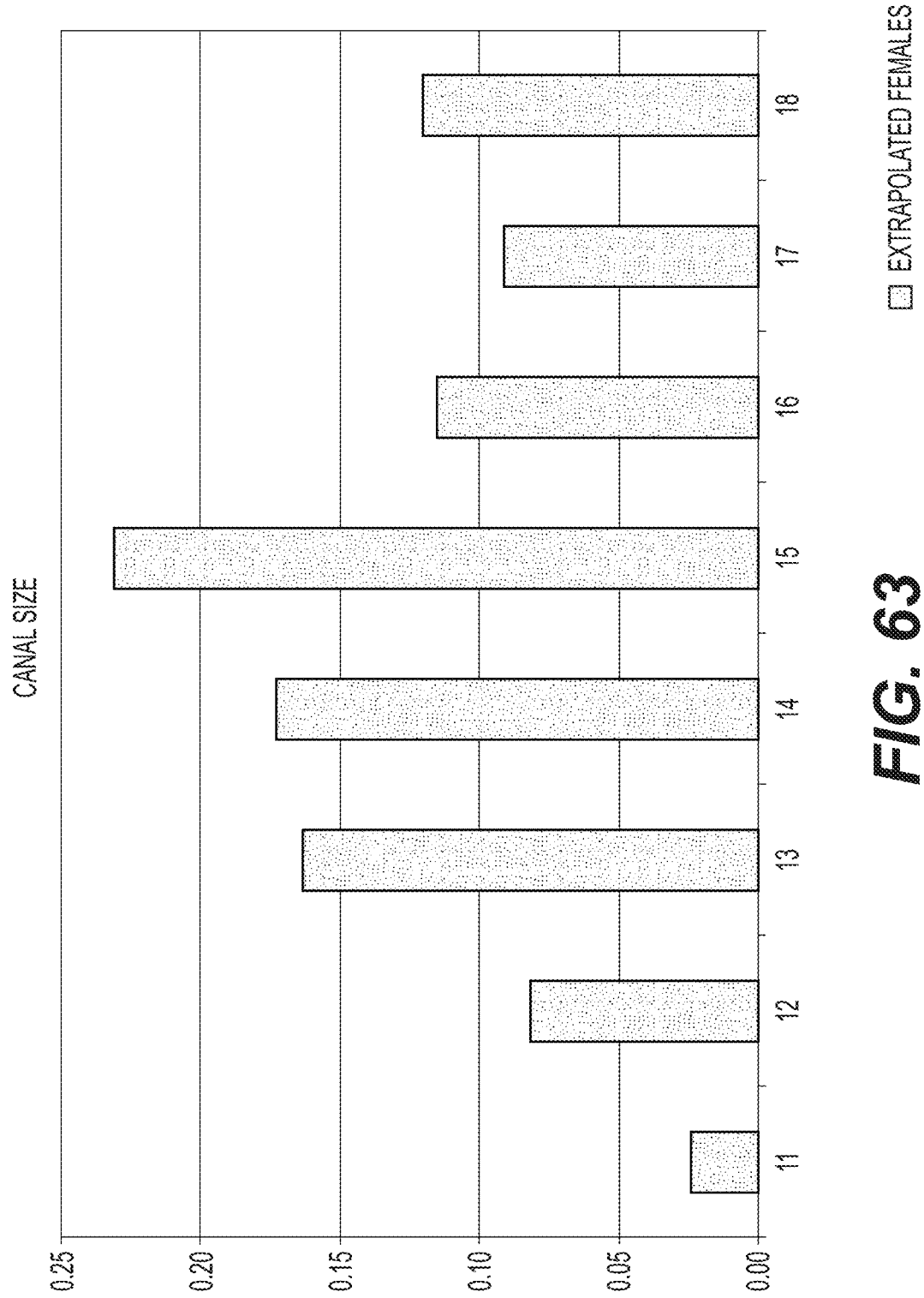
FIG. 63 dataset Canal Sizes histogram.

In the context of a proximal femur, FIGS. 46-57 confirm that gender differences exist across any ethnic population. As depicted in FIGS. 54 and 55, the template 3D model of the statistical atlas for a proximal femur of a woman exhibits statistical significant measurements when compared to the template 3D model of a proximal femur for a male. In particular, the head offset is approximately 9.3% less for females than for males. In current implants head offset increases with stem size, which is acceptable in normal female cases. But a problem arises when accounting for head offset in cases of osteoporosis and osteopinia where the bone loss leads to increase of intramedullary canal size, which means larger stem size and larger offset. Similarly, the neck diameter and head radius are approximately 11.2% less for females than for males. And the neck length is approximately 9.5% less for females than for males. In addition, the proximal angle is approximately 0.2% less for females than for males. Finally, the femoral head height is approximately 13.3% less for females than for males. Consequently, the gender bone data confirms that simply scaling a generic, femoral implant (i.e., gender neutral) will not account for differences in bone geometries and, hence, a gender based femoral implant is needed.

Referring to FIGS. 58-63, not only do the dimensions of the proximal femur widely vary across gender lines, but so too does the cross-sectional shape of the femur along the length of the intramedullary canal. In particular, across a given population within a statistical atlas of male and female femurs, males have intramedullary canal cross-sections that are closer to circular than females. More specifically, females have intramedullary canal cross-sections that are 8.98% more eccentric than for males. As will be discussed in more detail hereafter, this gender specific data comprises part of the feature extraction data that is plotted to arrive at clusters from which the number and general shape parameters are extracted to arrive at the gender specific femoral implants.

Figure 64:
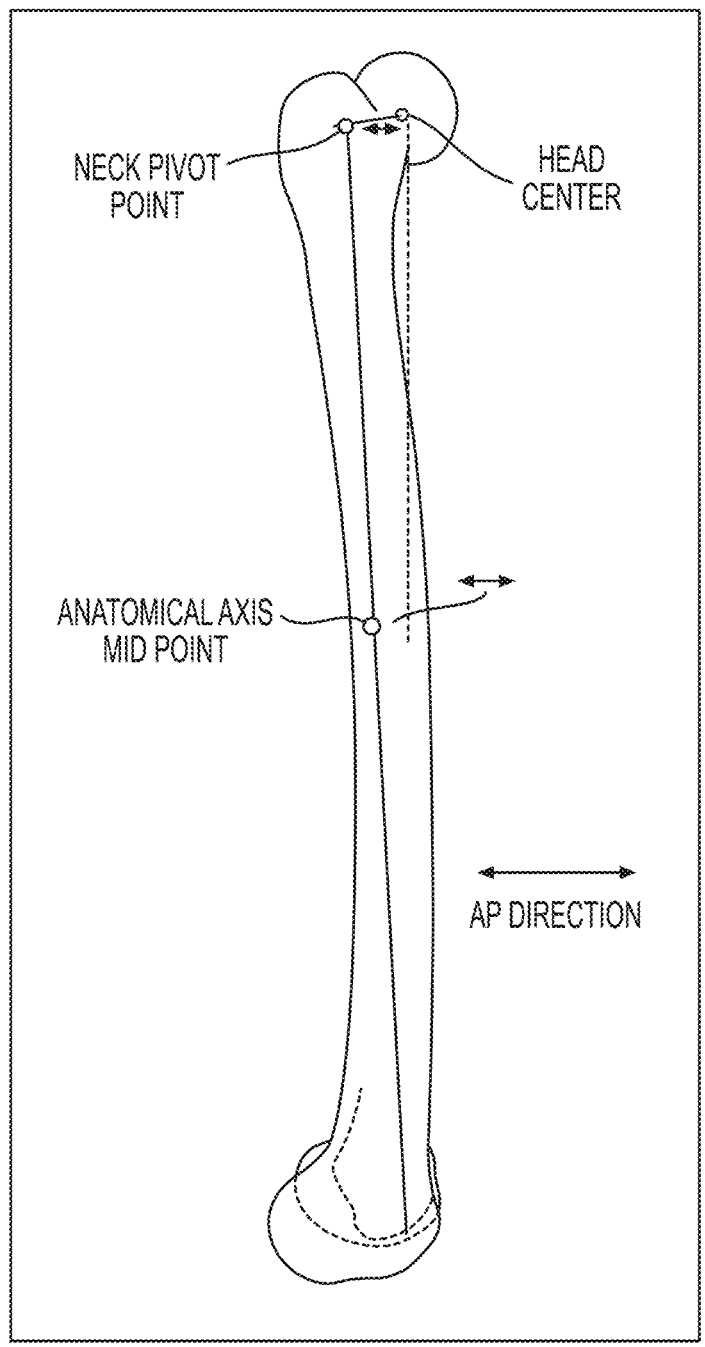
FIG. 64 AP Head height measurement.
Figure 65:
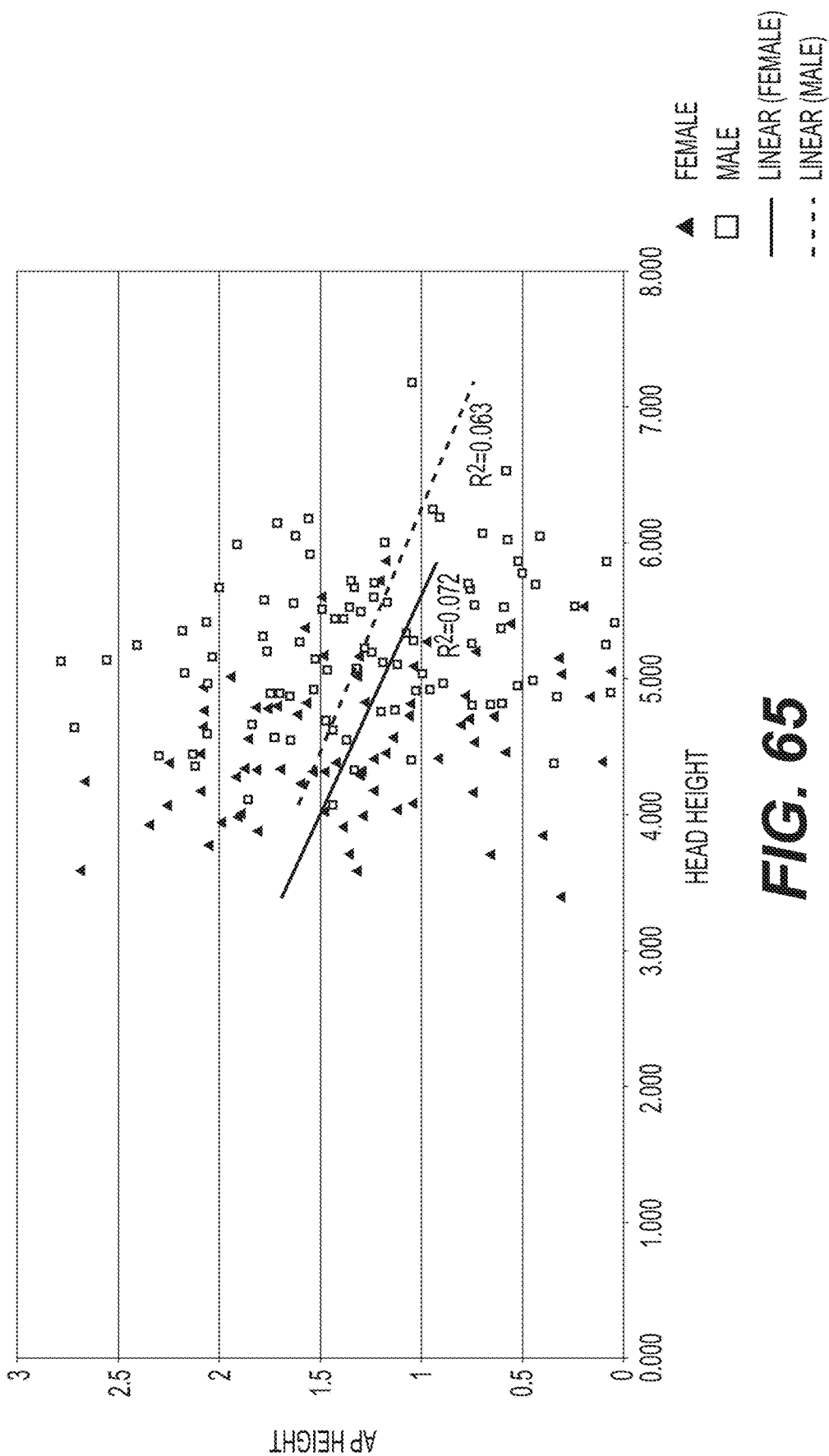
FIG. 65 Head Height Vs AP Head height relative to pivot point.
Figure 66:
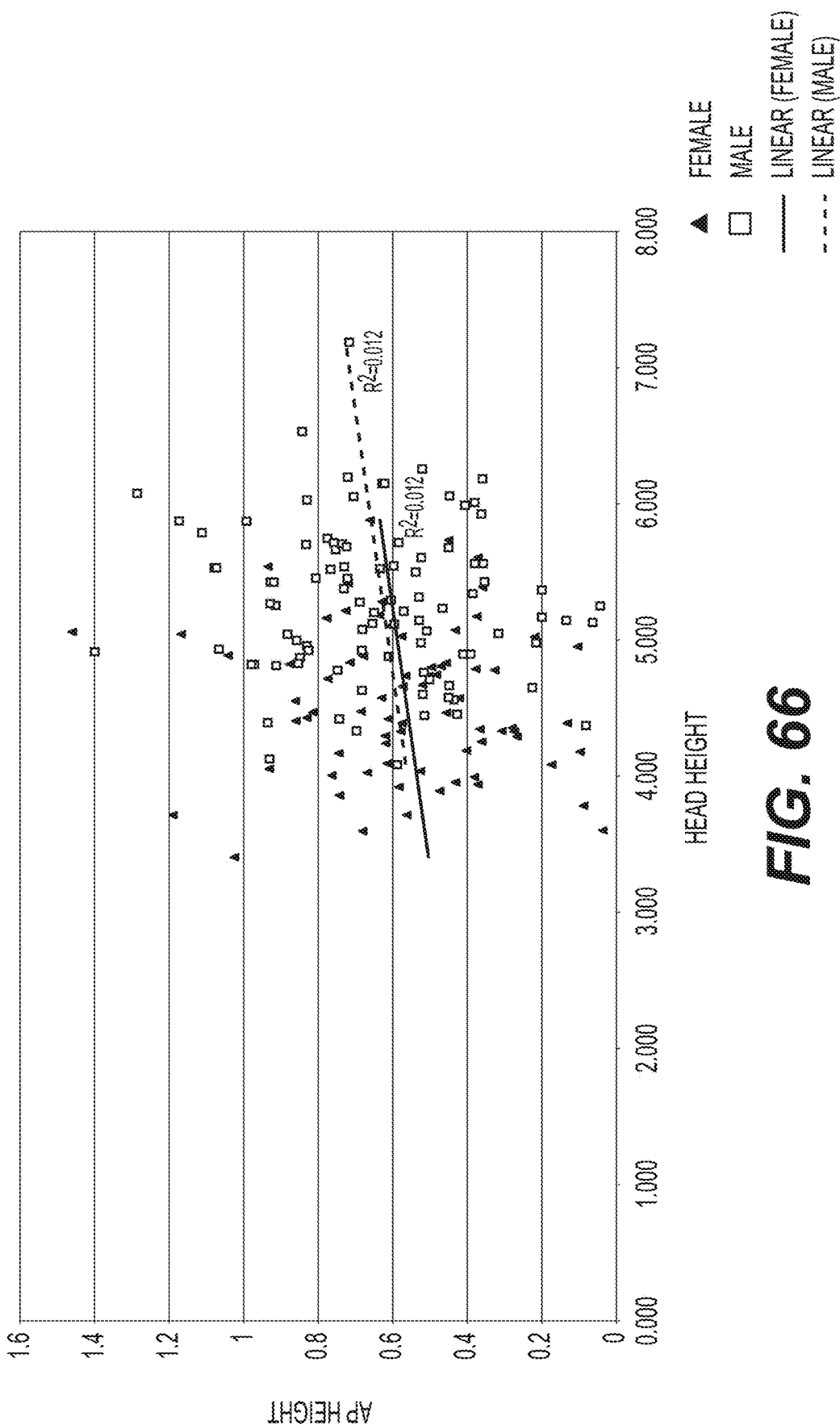
FIG. 66 Head Height Vs AP Head height relative to anatomical axis mid-point.
Figure 67:
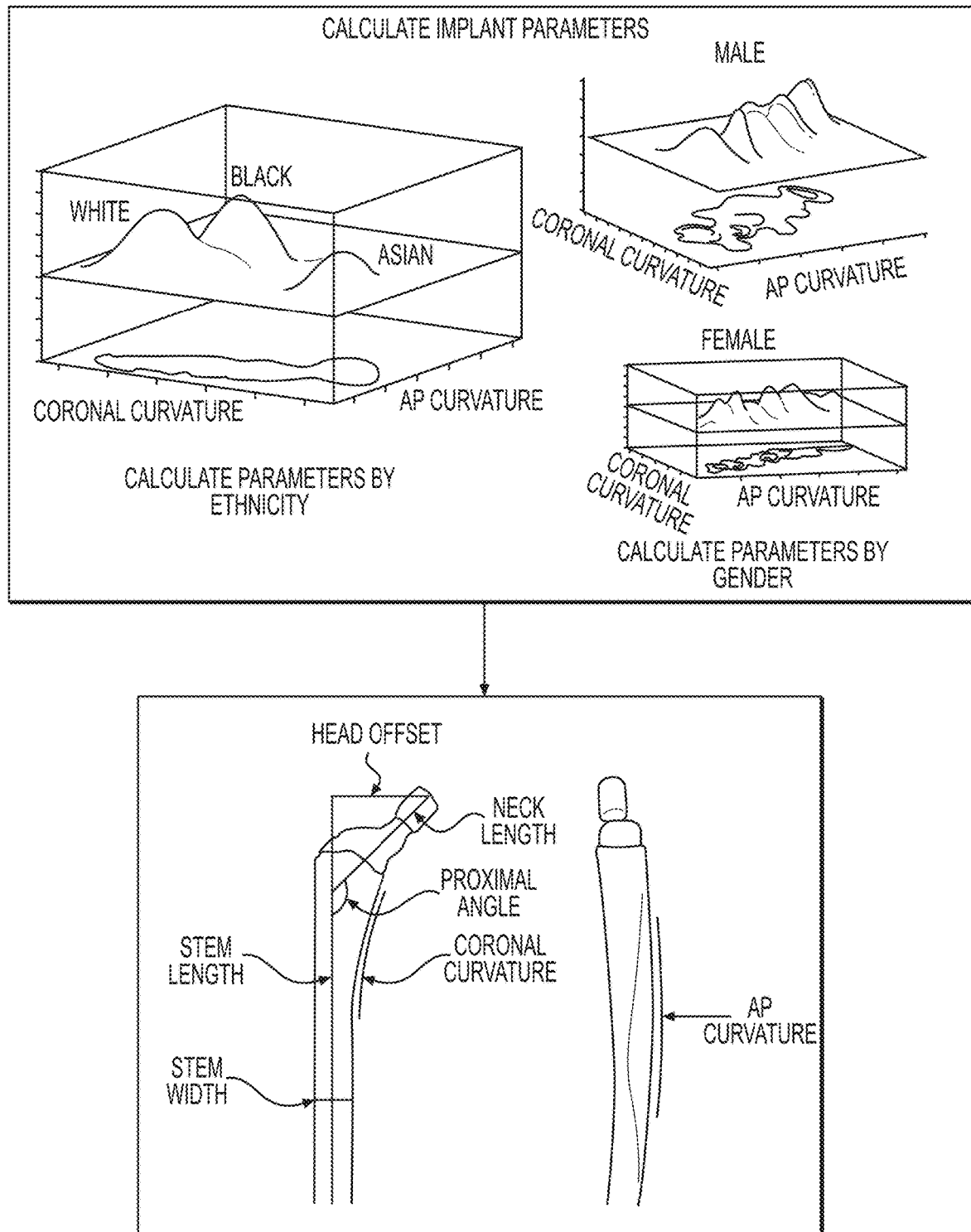
FIG. 67 Parameters used for creation of mass customized hip stem implant family that accommodates differences in both ethnicity and gender from clustering.

As depicted in FIGS. 64-66, the statistical atlas includes calculations that correspond to measurements across a given population of femurs (divided by gender) as to the head center offset in the anterior-posterior (AP) direction. In exemplary form, AP direction was determined by a vector that points anteriorly perpendicular to both the mechanical axis and the posterior condylar axis. Offset was measured between the femoral head center and two reference points, with the first reference point being the midpoint of the anatomical axis, and the second reference point being the femur neck pivot point. In summary, AP head height relative to the neck pivot point and anatomical axis midpoint did not exhibit significant differences between male and female femurs. Again, this gender specific data comprises part of the feature extraction data that is plotted to arrive at clusters from which the number and general shape parameters are extracted to arrive at the gender specific femoral implants.

Referring back to FIGS. 24 and 27, the head center offset, cross-sectional shape data of the intramedullary canal, and medial contour data for the femurs within the statistical atlas population comprise part of the extracted feature data that is plotted to discern the number of clusters present across a given population (one that is gender specific, a second that is ethnic specific presuming the statistical atlas includes data as to the ethnicity associated with each bone) in order to design a gender and/or ethnic specific, mass customized implant consistent with the flow chart and associated discussion for FIG. 24. The identified clusters that are gender and/or ethnic specific are utilized to extract the parameters necessary to design a mass customized femoral implant.

Figure 68:
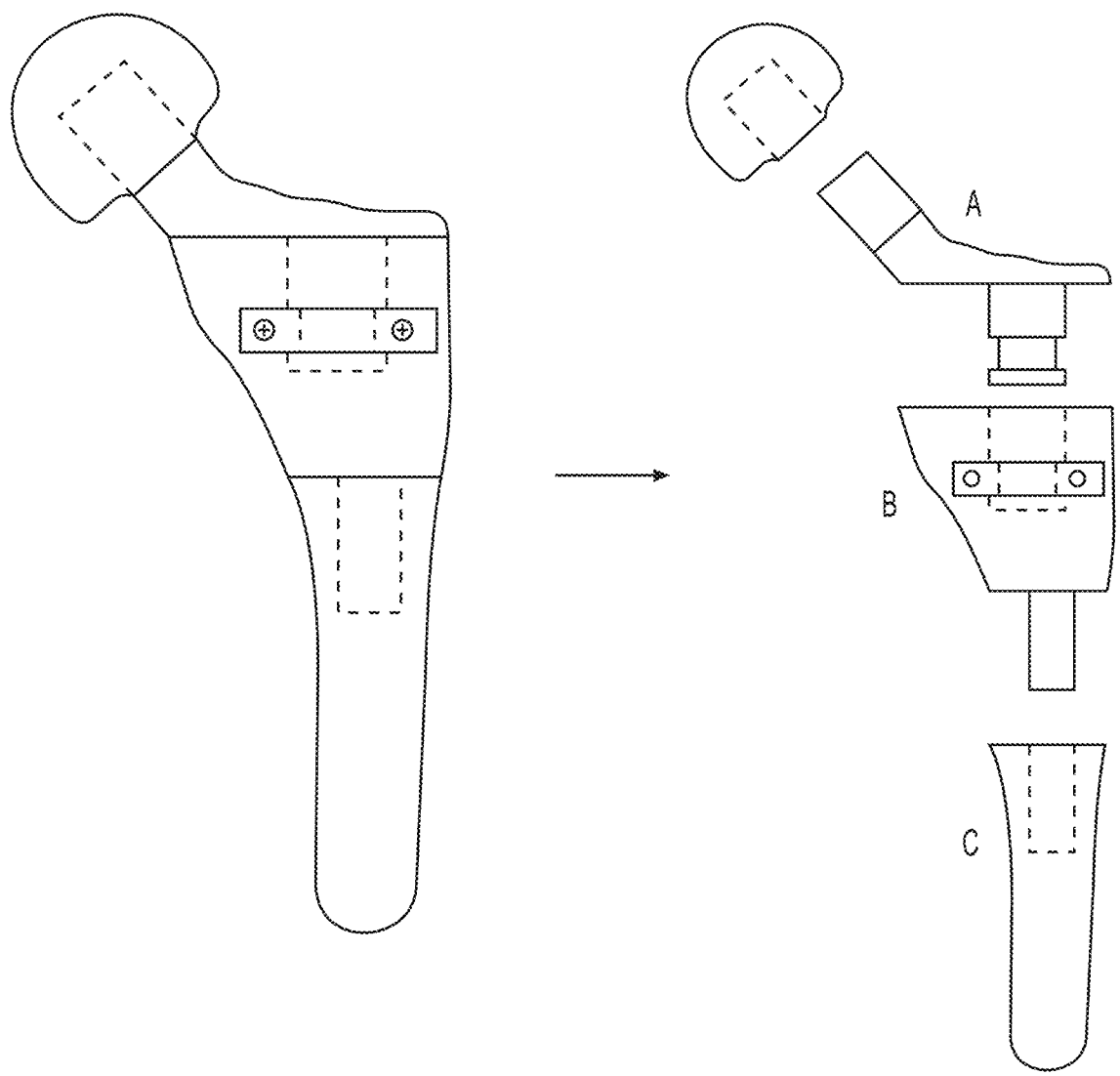
FIG. 68. Primary hip stem, assembled and exploded views.

Referring to FIG. 68, an exemplary mass-customized femoral component in accordance with the instant disclosure is depicted. In particular, the mass-customized femoral component comprises four primary elements that include a ball, neck, proximal stem, and distal stem. Each of the primary elements includes an interchangeable interface to allow interchangeable balls, necks, and stems with the other interchangeable elements. In this fashion, if a larger femoral ball is needed, only the femoral ball would be exchanged. Likewise, if a greater neck offset was desired, the neck element would be exchanged for a different neck element providing the requisite offset, while retaining the other three elements if appropriate. In this manner, the femoral component can, within certain limits, be customized to fit the patient without necessarily sacrificing the fit or kinematics that would otherwise be surrendered by using a one-size-fits-all implant. Accordingly, all of the femoral elements can be exchanged for other mass customized elements to better suit the patient anatomy.

In this exemplary embodiment, the neck is configured to rotate about the axis of the proximal stem so that the rotational orientation of the neck with respect to the proximal stem may be adjusted intraoperativly. In particular, preoperative measurements may establish the planned rotational position of the neck with respect to the proximal stem. Nevertheless, intraoperative considerations such as in-vivo kinematic testing may result in the surgeon changing the pre-operative rotational orientation to provide improved kinematics or avoidance of a particular impingement. By way of example, the neck includes a cylindrical stud having an inset circumferential groove having a textured surface. This cylindrical stud is received within an axial cylindrical channel of the proximal stem. In addition to this cylindrical channel, a second channel intersects the cylindrical channel and is shaped to receive a plate having a semi-circular groove that is also textured and configured to engage the textured surface of the inset circumferential groove. A pair of screws fastened to the proximal stem pushes the plate into engagement with the cylindrical stud so that eventually, rotational motion of the cylindrical stud with respect to the proximal stem is no longer possible. Accordingly, when this fixed engagement is reached, the screws may be loosened to allow rotational motion between the cylindrical stud and the proximal stem, such as would be necessary to make rotational adjustments intraoperatively.

Engagement between the neck and ball may be conventional, whereas engagement between the proximal stem and the distal stem is unconventional. In particular, the proximal stem includes a distal shank that is threaded and engaged to be threadably received within a threaded opening extending into the distal stem. Accordingly, the proximal stem is mounted to the distal stem by rotation of the proximal stem with respect to the distal stem so that the threads of the shank engage the threads of the distal stem opening. Rotation of the proximal stem with respect to the distal stem is concluded when the proximal stem abuts the distal stem. However, if rotational adjustment is necessary between the proximal stem and the distal stem, washers may be utilized to provide a spacer corresponding to the correct rotational adjustment. By way of further example, if greater rotational adjustment is required, the washer will be greater in thickness, whereas a thinner washer will provide correspondingly less rotational adjustment.

Each of the primary elements may be fabricated in predetermined alternatives that account for size and contour variations within a given gender and/or ethnicity. In this fashion, the alternatives of the primary elements may be mixed and matched to approximate a patient-specific implant that more closely configures to the anatomy of the patient than conventional mass customized femoral components, but at a fraction of the cost and process utilized to generate a patient-specific femoral implant.

Figure 69:
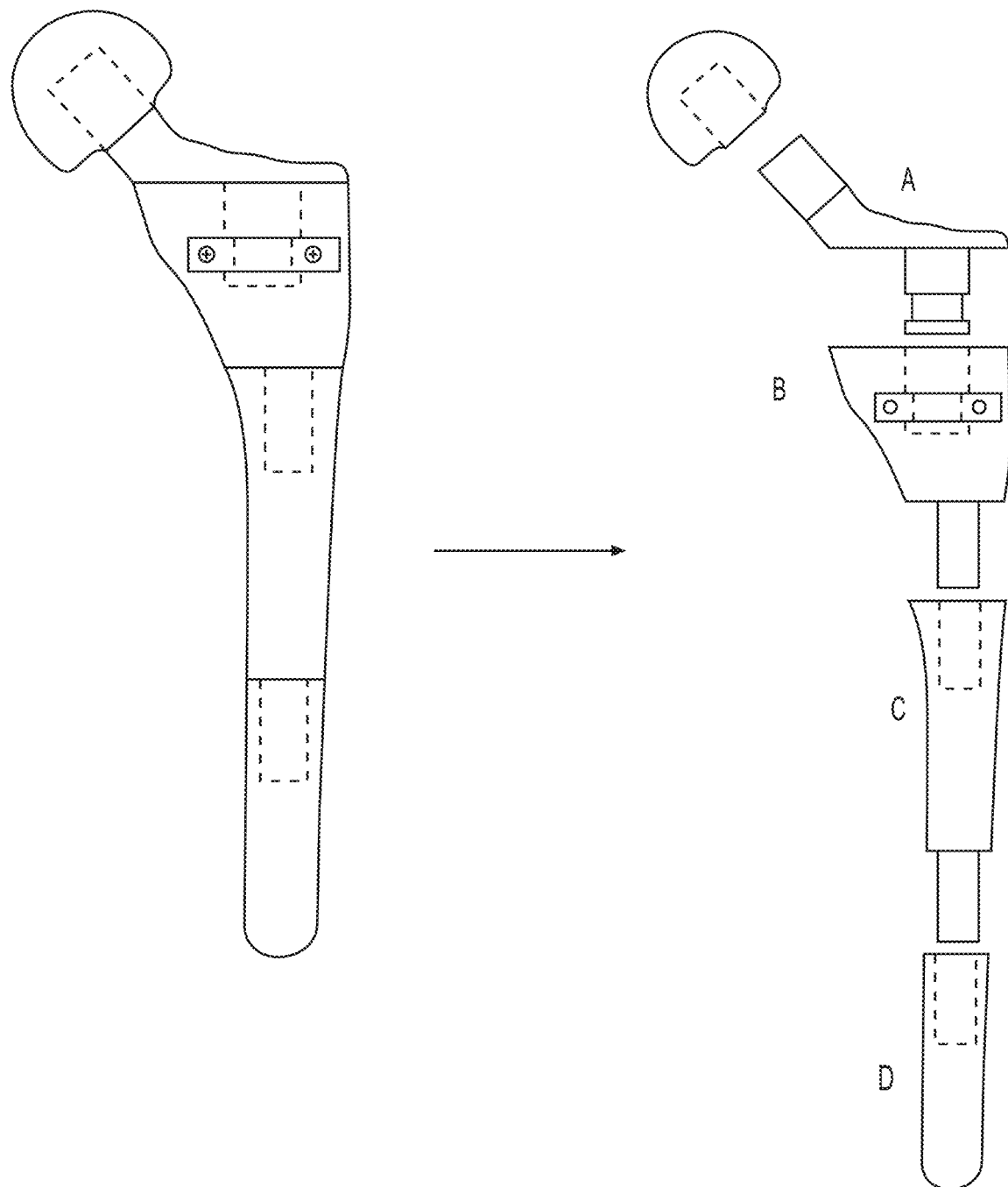
FIG. 69. Revision hip stem, assembled and exploded views.

FIG. 69 depicts a further alternate exemplary mass-customized femoral component in accordance with the instant disclosure is depicted. In particular, the mass-customized femoral component comprises five primary elements that include a ball, neck, proximal stem, intermediate stem, and distal stem. Each of the primary elements includes an interchangeable interface to allow interchangeable balls, necks, and stems with the other interchangeable elements. Those skilled in the art will understand that by increasing the number of elements of the mass-customized femoral component, akin to stacking slices of the patient's natural femur to reproduce this bone, one can increasingly approach the fit of a patient-specific implant by using mass-customized elements.

Figure 72:
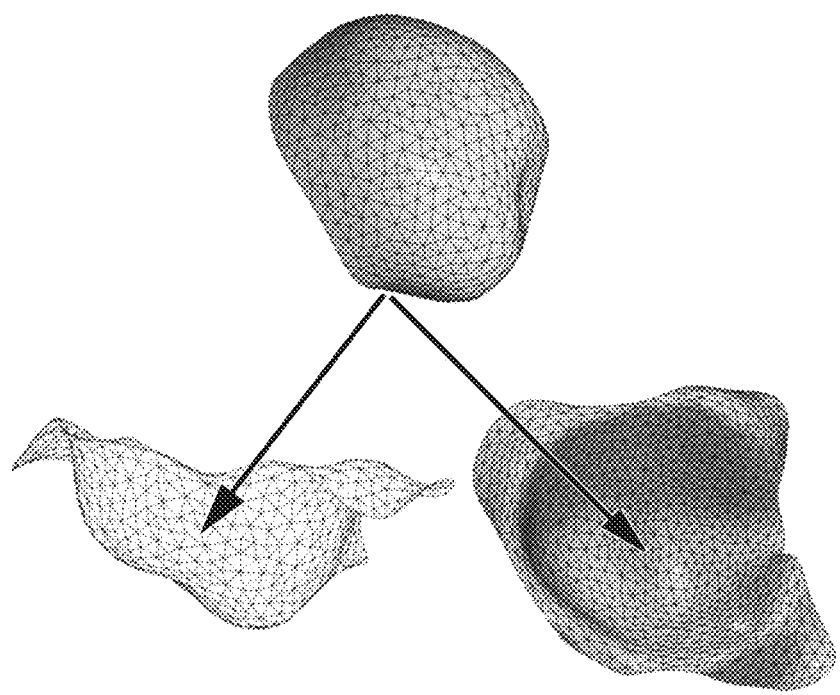
FIG. 72. Anatomical acetabular cup and femoral stem ball shape exhibiting multiple cup radii.
Figure 73:
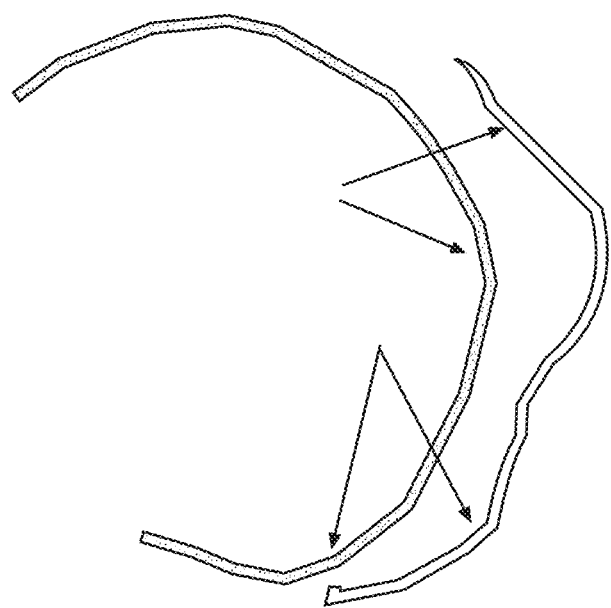
FIG. 73. Curvature matching between acetabular cup and femoral head curvature affects kinematics and constraints.
Figure 74:
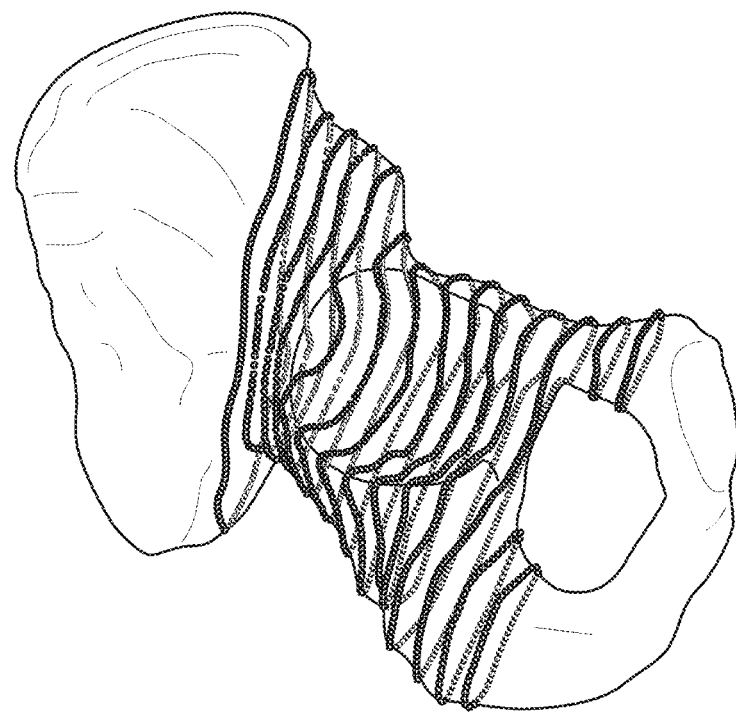
FIG. 74. Contours defining cross sectional analysis of acetabular cup
Figure 75:
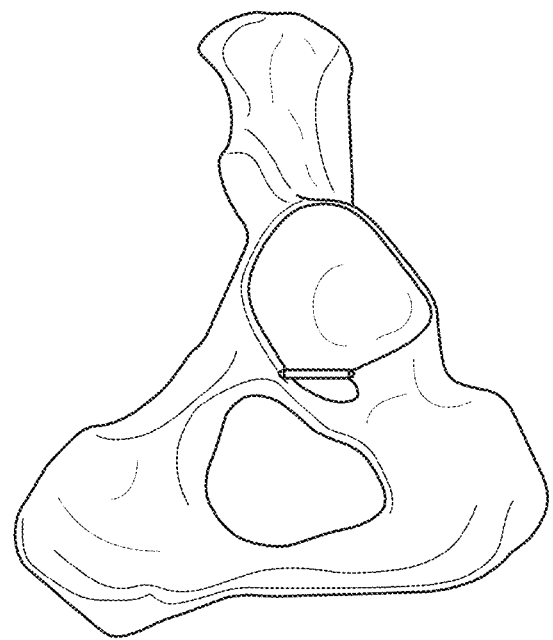
FIG. 75. Transverse acetabular ligament automatically detected as method for cup orientation.

Similar to the anatomical differences between genders and ethnicities for the proximal femur, FIGS. 70-75 confirm that gender and ethnic differences exist across a general pelvis population within a statistical atlas. Referring back to FIG. 24, a series of mass customized acetabular cup implants are designed and fabricated by using statistical atlas data (i.e., pelvis population) grouped based upon at least one of gender and ethnicity. The grouped atlas data is subjected to an automatic landmarking process and a surface/shape analysis process to isolate the geometry of the acetabular cup within the population, as depicted graphically in FIG. 70. In addition, as depicted graphically in FIGS. 74 and 75, the landmarking (for location of acetabular ligament) and contour analysis (for evaluating the contours of the acetabular cup) processes lead to feature extraction, from which the anatomical cup implant surfaces are ultimately generated, as shown in FIG. 71. This analysis shows that the acetabular cup and femoral head are not composed of a single radius of curvature, but several radii, as shown in FIGS. 72 and 73.

Creation of Animal-Specific Implants

Figure 77:
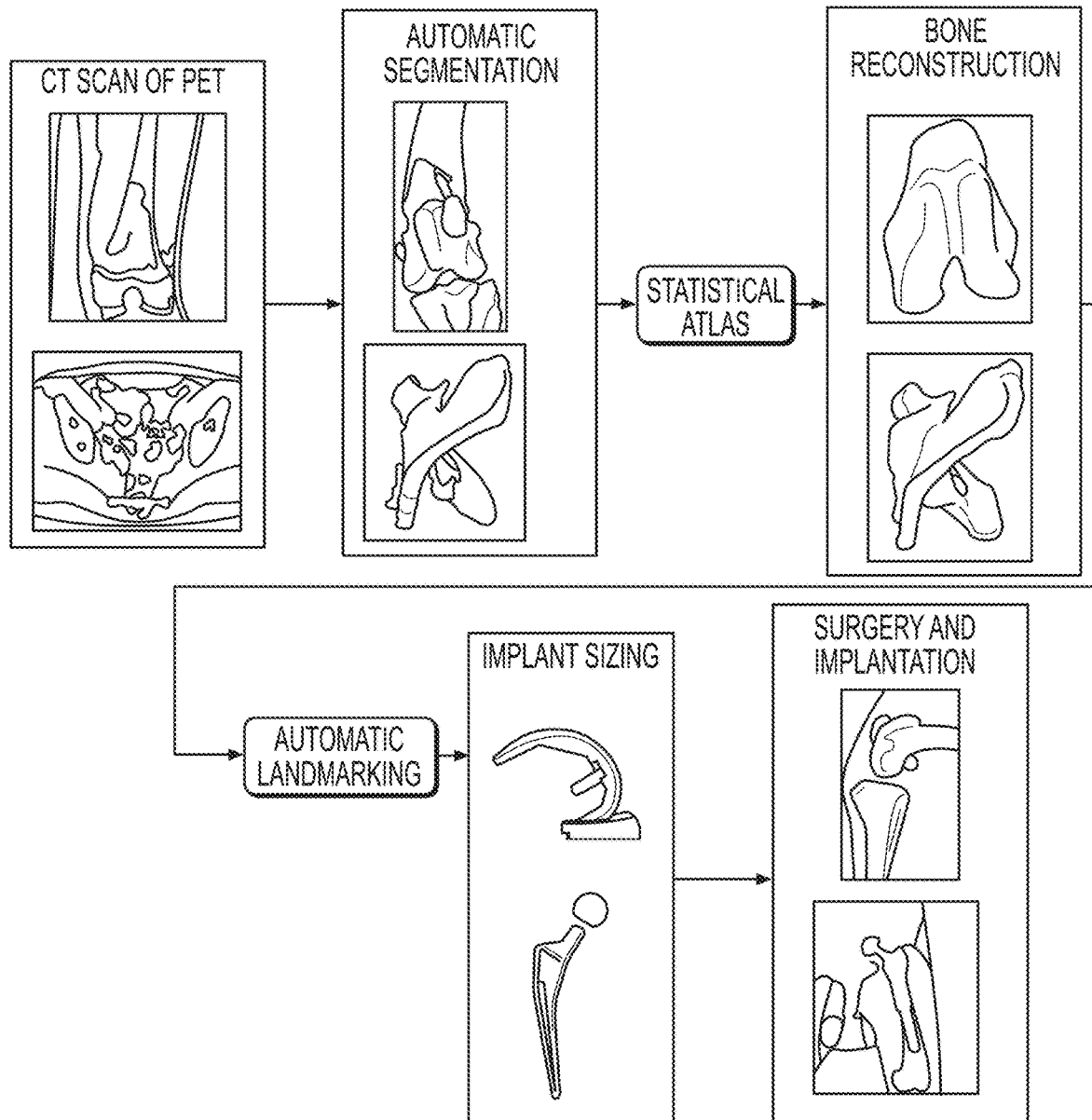
FIG. 77. Pet specific implants and cutting guides.

Referring to FIG. 77, an exemplary system and methods for designing and fabricating an animal-specific (i.e., patient-specific for an animal) implant and associated instrumentation is similar to the process depicted and explained previously with respect to FIG. 17, which is incorporated herein. As a prefatory matter, images of the animal anatomy are taken and automatically segmented to yield a virtual 3D bone model. Though graphically depicted as CT scan images, it should be understood that other imaging modalities besides CT may be utilized such as, without limitation, MM, ultrasound, and X-ray. The virtual 3D bone model of the affected anatomy is loaded into the statistical atlas, in accordance with the previous exemplary disclosure. Thereafter, inputs from the statistical atlas are utilized to reconstruct the bone(s) and create a reconstructed virtual 3D bone model. Bone landmarks are calculated on the surface of the reconstructed virtual 3D bone model to allow determination of the correct implant size. Geometry of affected bone is then mapped and converted to parametric form, which is then used to create an animal-specific implant that mimics the residual anatomical geometry. In addition to the animal-specific implant, animal-specific instrumentation is fabricated and utilized for preparation of the animal's residual bone and placement of the animal-specific implant.

Figure 78:
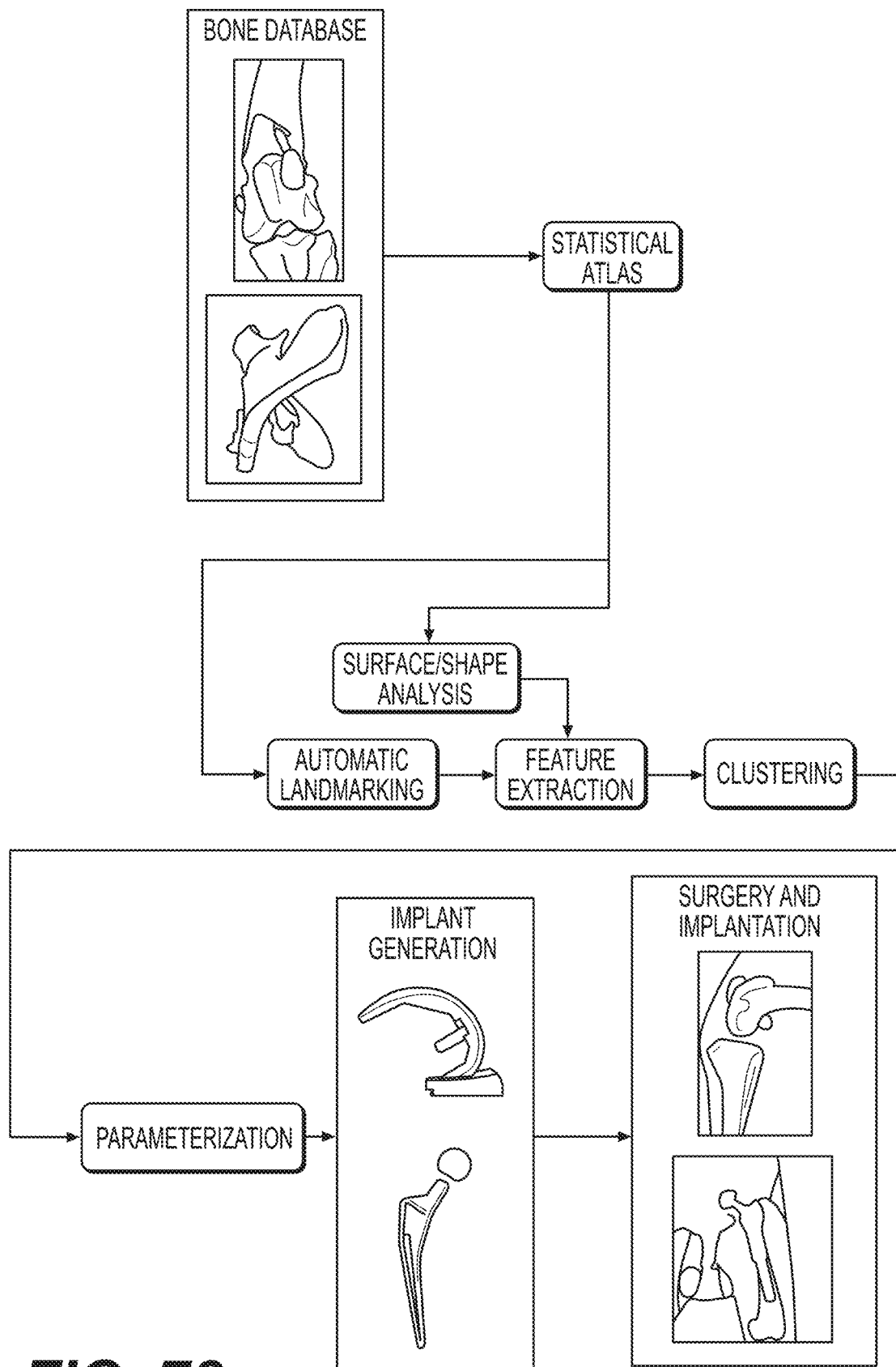
FIG. 78. Mass customized orthopedic implants for pets using statistical atlases.

Referring to FIG. 78, an exemplary system and methods for designing and fabricating a mass customized animal implant is similar to the process depicted and explained previously with respect to FIG. 24, which is incorporated herein. As a prefatory matter, 3D animal bone models from the statistical atlas pertinent to the bone(s) in question are subjected to an automatic landmarking and surface/shape analysis. The automatic landmarking process uses information stored in the atlas (e.g., regions likely to contain a specific landmark) and local geometrical analyses to automatically calculate anatomical landmarks for each 3D animal bone model. For each animal bone in question within the statistical atlas, the shape/surface analysis directly extracts features the surface geometry of the 3D virtual animal bone models. Thereafter, each of the 3D animal bone models have a feature extraction process carried out thereon that uses a combination of landmarks and shape features to calculate features relevant to implant design. These features are used as inputs to a clustering process, where the animal bone population is divided into groups having similar features using a predetermined clustering methodology. Each resulting cluster represents those instances used to define the shape and size of a single animal implant. A parameterization process follows for each cluster center (implant size) in order to extract the parameters for an overall implant model (e.g., computer aided design (CAD) parameters). Thereafter, using the extracted parameters, the overall implant surface and size are generated for each cluster. Depending upon the cluster the animal patient falls into, the mass-customized implant is selected from the requisite group and implanted.

Creation of Patient-Specific Cutting Guides

Referring to FIGS. 79-94, an exemplary process and system are described for integration of multidimensional medical imaging, computer aided design (CAD), and computer graphics features for designing patient-specific cutting guides. For purposes of exemplary explanation only, the patient-specific cutting guides are described in the context of a total hip arthroplasty procedure. Nevertheless, those skilled in the art will realize that the exemplary process and system are applicable to any surgical procedure for which cutting guides may be utilized.

Figure 79:
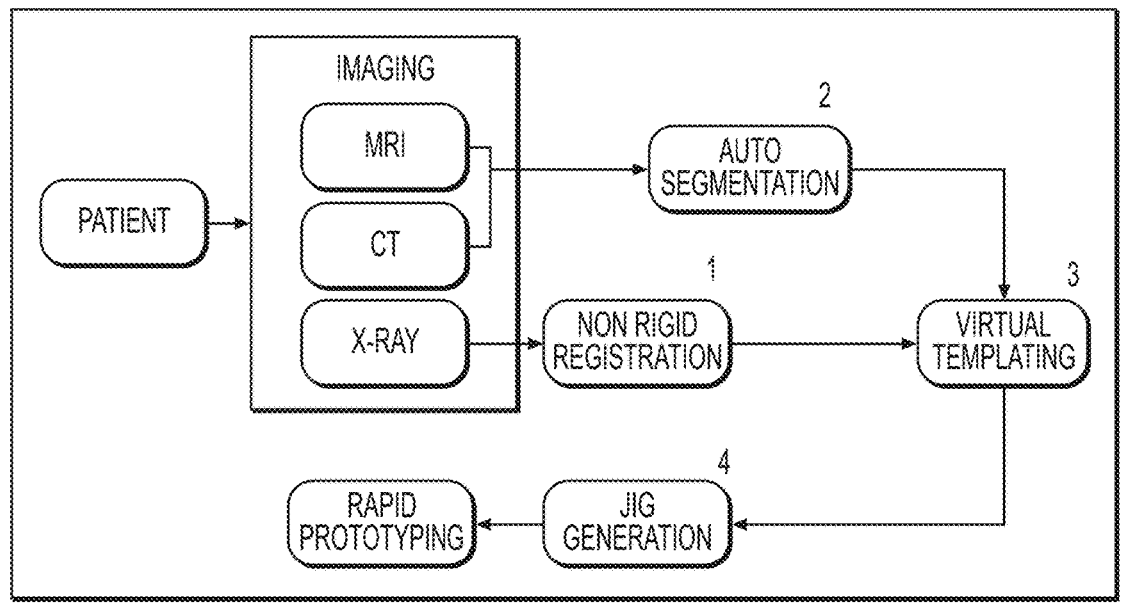
FIG. 79. Process of generation of patient specific cutting and placement guides for hip system.

As represented in FIG. 79, an overview of the exemplary system flow begins with receiving input data representative of an anatomy. Input anatomical data comprises two dimensional (2D) images or three dimensional (3D) surface representations of the anatomy in question that may, for example, be in the form of a surface model or point cloud. In circumstances where 2D images are utilized, these 2D images are utilized to construct a 3D surface representation of the anatomy in question. Those skilled in the art are familiar with utilizing 2D images of anatomy to construct a 3D surface representation. Accordingly, a detailed explanation of this process has been omitted in furtherance of brevity. By way of example, input anatomical data may comprise one or more of X-rays (taken from at least two views), computed tomography (CT) scans, magnetic resonance images (Mills), or any other imaging data from which a 3D surface representation may be generated. In exemplary form, the anatomy comprises a pelvis and a femur.

It should be understood, however, that the following is an exemplary description of anatomies that may be used with the exemplary system and in no way is intended to limit other anatomies from being used with the present system. As used herein, tissue includes bone, muscle, ligaments, tendons, and any other definite kind of structural material with a specific function in a multicellular organism. Consequently, when the exemplary system and methods are discussed in the context of bones involved with the hip joint, those skilled in the art will realize the applicability of the system and methods to other tissue.

The femur and pelvis input anatomy data of the system is directed to one of two modules depending upon the type of input data. In the case of X-ray data, the 2D X-ray images are input to a non-rigid module in order to extract 3d bone contours. If the input data is in the form of CT scans or MRI images, these scans/images are directed to an auto segmentation module where the scans/images are automatically segmented to extract the 3D bone contours (and 3D cartilage contours).

Figure 80:
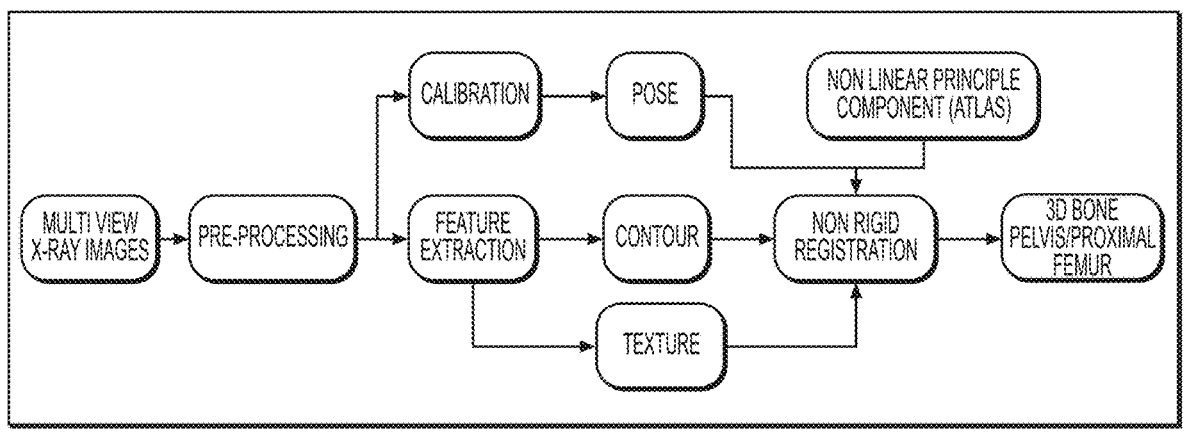
FIG. 80. Process of non-rigid registration for creation of patient specific three dimensional pelvis and proximal femur models from x-ray.
Figure 82:
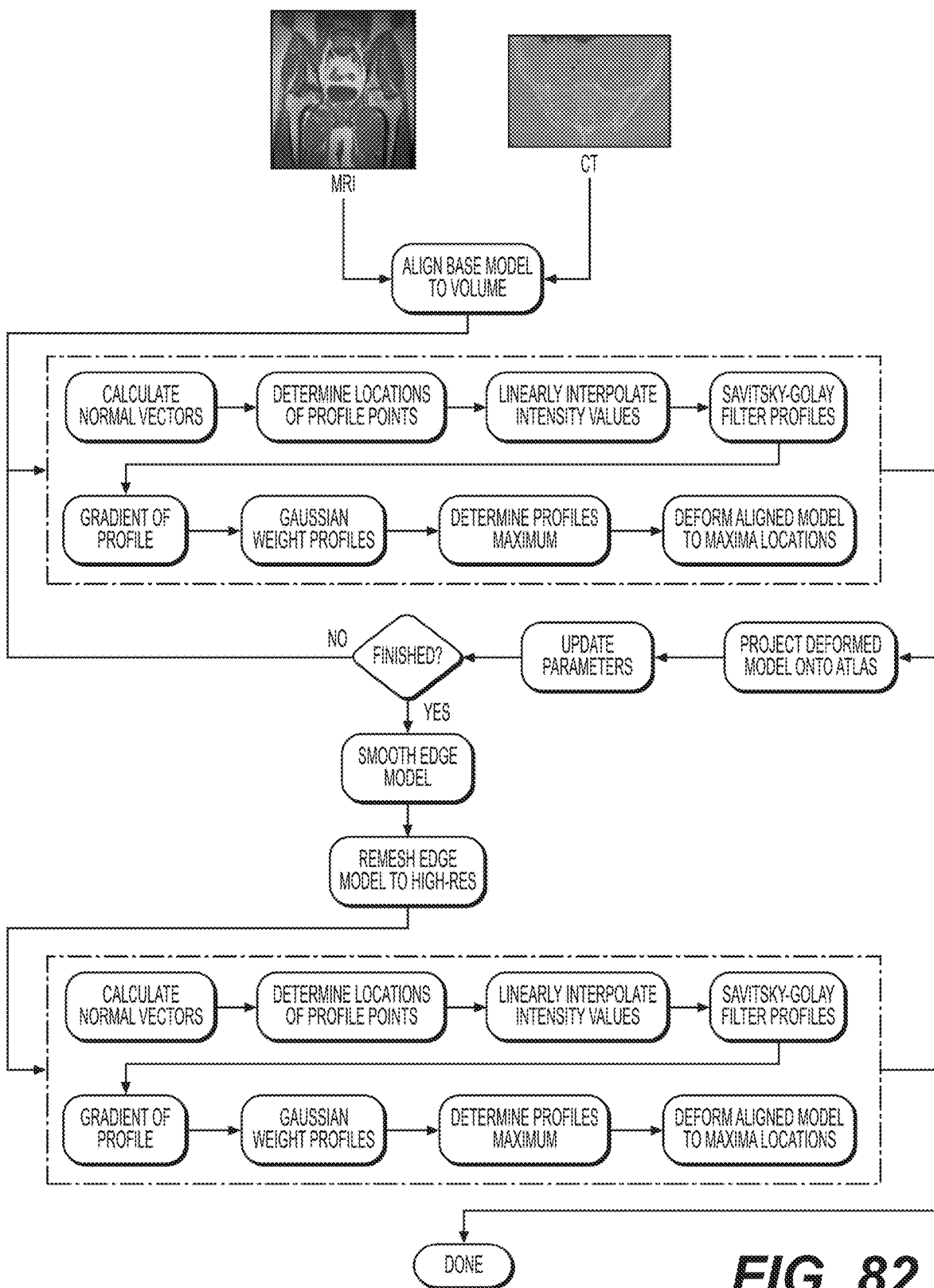
FIG. 82. Automatic segmentation of pelvis and proximal femur from MRI and CT scans, as described in FIG. 79.

Referring to FIG. 80, the non-rigid module uses the multiple X-ray images taken from at least two different views are subjected to one or more pre-processing steps. These steps may include one or more of the following: noise reduction and image enhancement. The resultant pre-processed X-ray images are subjected to a calibration step in order to register the X-ray images. Preferably, the X-ray images have been taken in the presence of a fixed position calibration device so that the X-ray images are registered with respect to this fixed position calibration device. But when no fixed position calibration device is present in the X-ray images, the images may nonetheless be calibrated using common detected features across multiple images. From this calibration process, the output is the position of the anatomy relative to the imager, which is identified by the "Pose" reference in FIG. 80.

The resultant pre-processed X-ray images are subjected to a feature extraction step. This feature extraction step comprises one or more computations of image features utilizing the pre-processed X-ray images. By way of example, these computations may include gradient features, contours, textural components, or any other image derived feature. In this exemplary process, the feature extraction step outputs the outline of the anatomy (e.g., bone shape) as represented by the "Contour" reference in FIG. 80, as well as image features as represented by the "Texture" reference, derived from the X-ray images. Both the outlined anatomy and image feature data is directed to a non-rigid registration step.

The non-rigid registration step registers the outputs from the feature extraction step and the calibration step to a 3D template model of the anatomy in question from a statistical atlas. By way of example, the 3D template model is generated responsive to non-linear principal components from an anatomical database comprising part of the statistical atlas. During the non-rigid registration step, the 3D template model has its shape parameters (non-linear principal components) optimized to match the shape parameters of the X-ray images resulting from the pose, contour, and texture data. The output from the non-rigid registration step is a 3D patient-specific bone model, which is directed to a virtual templating module, similar to the 3D patient-specific bone model output from the auto segmentation module for CT scans or MRI images.

Figure 83:
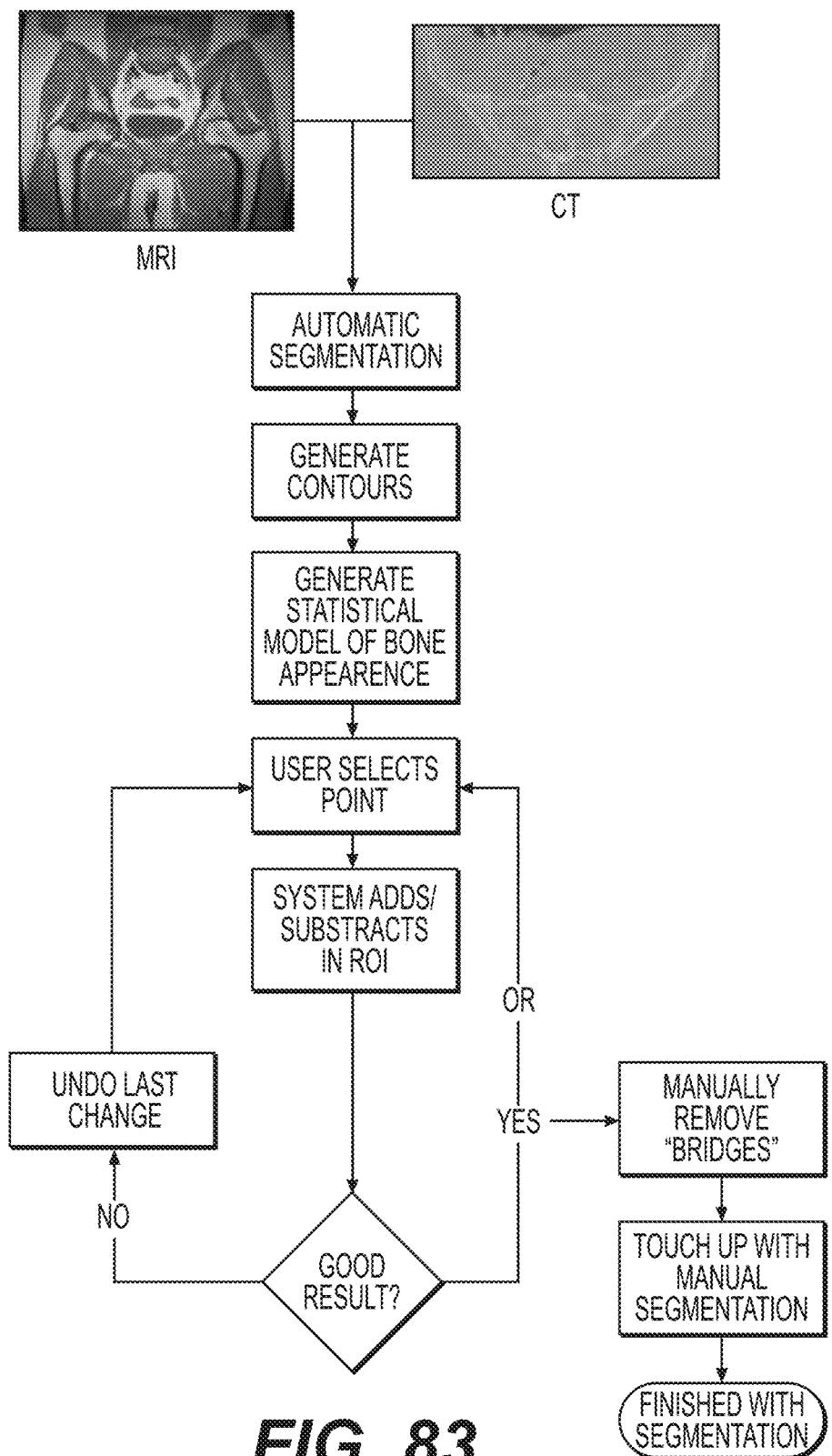
FIG. 83. Automatic segmentation of complex and shattered anatomy from MRI or CT, as outlined in FIG. 79.

Referencing FIG. 83, the auto segmentation process is initialized by taking the CT scans or MM images, for example, and carrying out an automatic segmentation sequence. With specific reference to FIG. 82, the automatic segmentation sequence includes aligning the scans/images with respect to a base or starting 3D model of the anatomy in question. After alignment of the scans/images to the base 3D model, the scans/images are processed via an initial deformation process to calculate the normal vectors, determine locations of the profile points, linearly interpolate the intensity values, filter the resulting profiles using a Savitsky-Golay filter, generate a gradient of the profiles, weigh the profiles using a Gaussian weight profile equation, determine the maximum profiles, and use these maximum profiles to deform the base 3D model. The resulting deformed 3D model is projected onto the template 3D model from a statistical atlas for the anatomy in question. Using the parameters of the template 3D model, the deformed 3D model is further deformed in a secondary deformation process to resemble features unique o the template 3D model. After this latter deformation process, the deformed 3D model is compared to the scans/images to discern whether significant differences exist.

In circumstances where significant differences exist between the deformed 3D model and the scans/images, the deformed 3D model and the scans/images are again subjected to the initial deformation process followed by the secondary deformation process. This looping process is continued until the deformed 3D model is within a predetermined tolerance(s) for differences between the deformed 3D model and the scans/images.

After the deformed 3D model has been determined to exhibit less than significant differences with respect to the previous iteration or a maximum number of iterations is achieved, the surface edges of the deformed 3D model as smoothed, followed by a higher resolution remeshing step to further smooth the surfaces to create a smoothed 3D model. This smoothed 3D model is subjected to an initial deformation sequence (identical to the foregoing initial deformation process prior to surface smoothing) to generate a 3D segmented bone model.

Referring back to FIG. 83, the 3D segmented bone model is processed to generate contours. In particular, the intersection of the 3D segmented bone model and the scans/images are calculated, which result in binary contours at each image/scan plane.

The 3D segmented bone model is also processed to generate a statistical 3D model of the bone appearance that is patient-specific. In particular, the appearance of the bone and any anatomical abnormality is modeled based on image information present in within the contours and external to the contours.

The bone contours are thereafter reviewed by a user of the segmentation system. This user may be a segmentation expert or infrequent user of the segmentation system that notices one or more areas of the 3D model that do not correlate with the segmented regions. This lack of correlation may exist in the context of a missing region or a region that is clearly inaccurate. Upon identification of one or more erroneous regions, the user may select a "seed point" on the model indicating the center of the area where the erroneous region exists, or manually outlines the missing regions. The software of the system uses the seed point to add or subtract from the contour local to the seed point using the initial scans/images of the anatomy from CT or Mill. For example, a user could select a region where an osteophyte should be present and the software will compare the scans/images to the region on the 3D model in order to add the osteophyte to the segmentation sequence. Any changes made to the 3D model are ultimately reviewed by the user and verified or undone. This review and revision sequence may be repeated as many times as necessary to account for anatomical differences between the scans/images and the 3D model. When the user is satisfied with the 3D model, the resulting model may be manually manipulated to remove bridges and touch up areas of the model as necessary prior to being output to the virtual templating module.

Figure 84:
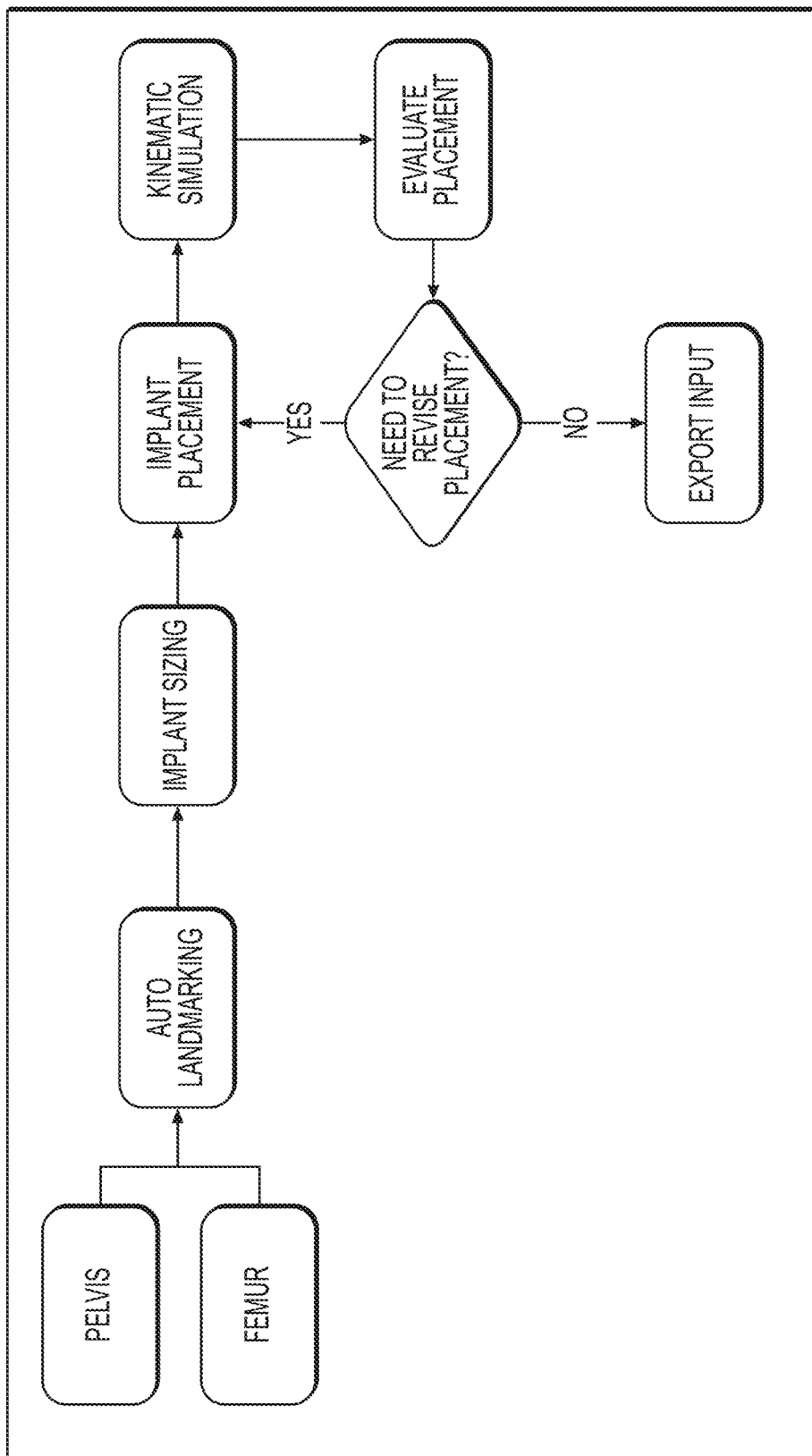
FIG. 84. Process of virtual templating for both acetabular cup and femoral stem components.

As shown in FIGS. 79 and 84, the virtual templating module receives 3D patient-specific models from either or both the auto segmentation module and the non-rigid registration module. In the context of a hip joint, the 3D patient-specific models include the pelvis and the femur, which are both input to an automatic landmarking process. This automatic landmarking step calculates anatomical landmarks relevant to implant placement on the femur and pelvis 3D models using regions from similar anatomy present in a statistical atlas and local geometrical searches.

Figure 85:
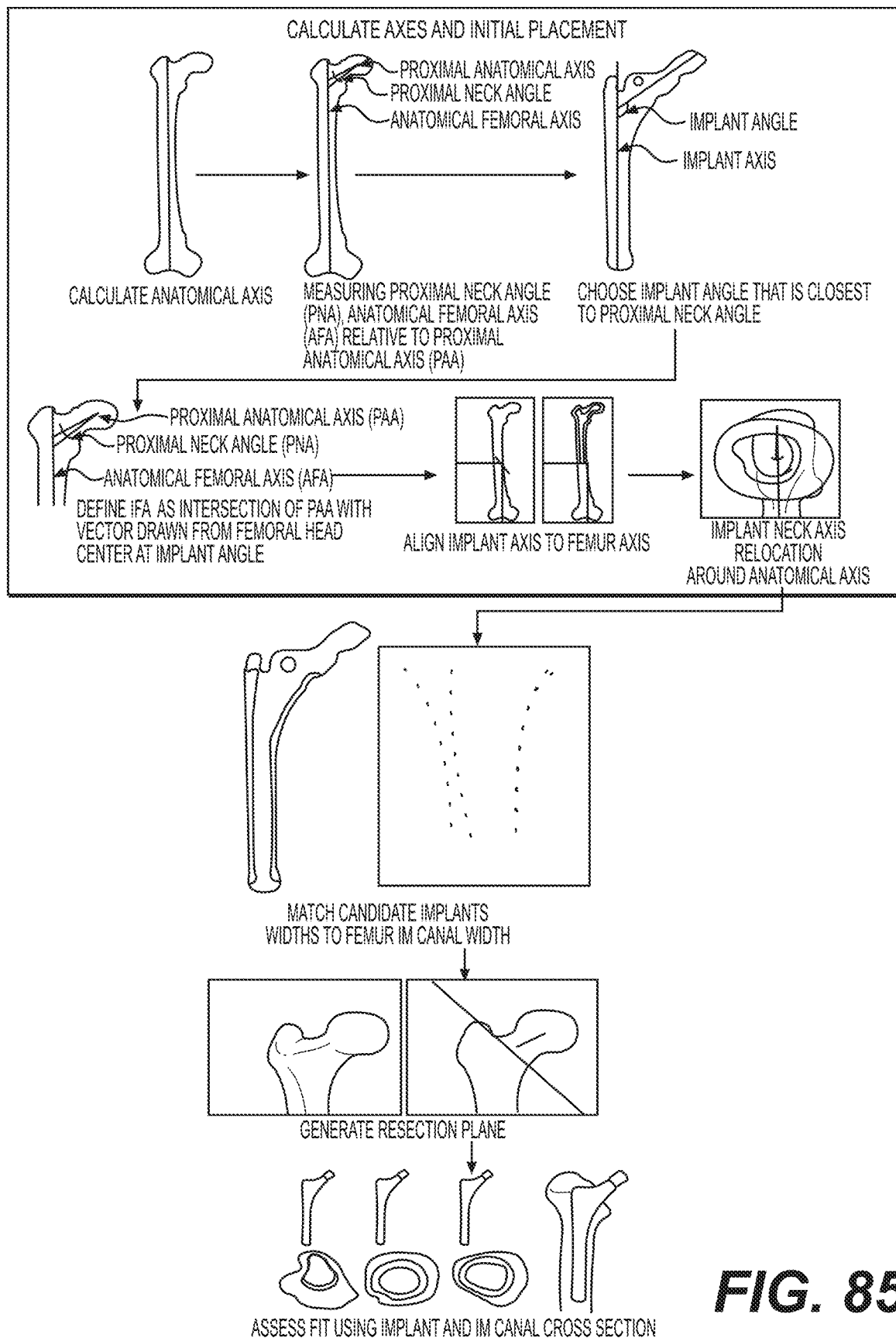
FIG. 85. Stem automatic placement using distal fixation.

In the context of automatic placement of the femoral stem using distal fixation, as shown in FIG. 85, the automatic landmarking includes definition of axes on the femur and the implant. With respect to the femur, the anatomical femoral axis (AFA) is calculated, followed by the proximal anatomical axis (PAA). The proximal neck angle (PNA) is then calculated, which is defined as the angle between the AFA and PNA. With respect to the femoral implant, the implant axis is along the length of the implant stem and the implant neck axis is along the length of the implant neck. Similar to the PNA of the femur, the implant angle is defined as the angle between the implant axis and the implant neck axis. The implant is then chosen which has an implant angle that is closest to the PNA. The implant fitting angle (IFA) is then defined as the intersection of the proximal anatomical axis with a vector drawn from the femoral head center at the chosen implant angle.

When using automatic placement of the femoral stem using distal fixation and the calculated anatomical landmarks, as shown in FIG. 85, an implant sizing step determines/estimates for the appropriate implant sizes for femoral components. The implant size is chosen by comparing the width of the implant to the width of the intramedullary canal and selecting the implant with the most similar width to the intramedullary canal. Thereafter, the system moves forward to an implant placement step.

In the implant placement step for a distal fixation femoral stem, based on surgeon preferred surgical technique and previously calculated anatomical landmarks, the initial implant position is determined/chosen for all relevant implanted components. A resection plane is created to simulate the proximal femur osteotomy and the implant fit is assessed. Fit assessment is conducted by analyzing the cross sections of the aligned implant and femur intramedullary canal at varying levels along the implant axis. The implant is aligned to the femur by aligning the implant axis to the anatomic femur axis then translating the implant so that the neck of the implant is in the general location of the proximal femur neck. The implant is then rotated about the anatomic femur axis to achieve desired anteversion.

As part of this implant placement step, an iterative scheme is utilized that includes using an initial "educated guess" as to implant placement as part of a kinematic simulation to evaluate the placement of the "educated guess." In exemplary form, the kinematic simulation takes the implant (based upon the placement of the implant chosen) through a range of motion using estimated or measured joint kinematics. Consequently, the kinematic simulation may be used to determine impingement locations and estimate the resulting range of motion of the implant post implantation. In cases where the kinematic simulation results in unsatisfactory data (e.g., unsatisfactory range of motion, unsatisfactory mimicking of natural kinematics, etc.), another location for implant placement may be utilized, followed by a kinematic analysis, to further refine the implant placement until reaching a satisfactory result. After the implant position is determined/chosen for all relevant implanted components, the template data is forwarded to a jig generation module.

Figure 86:
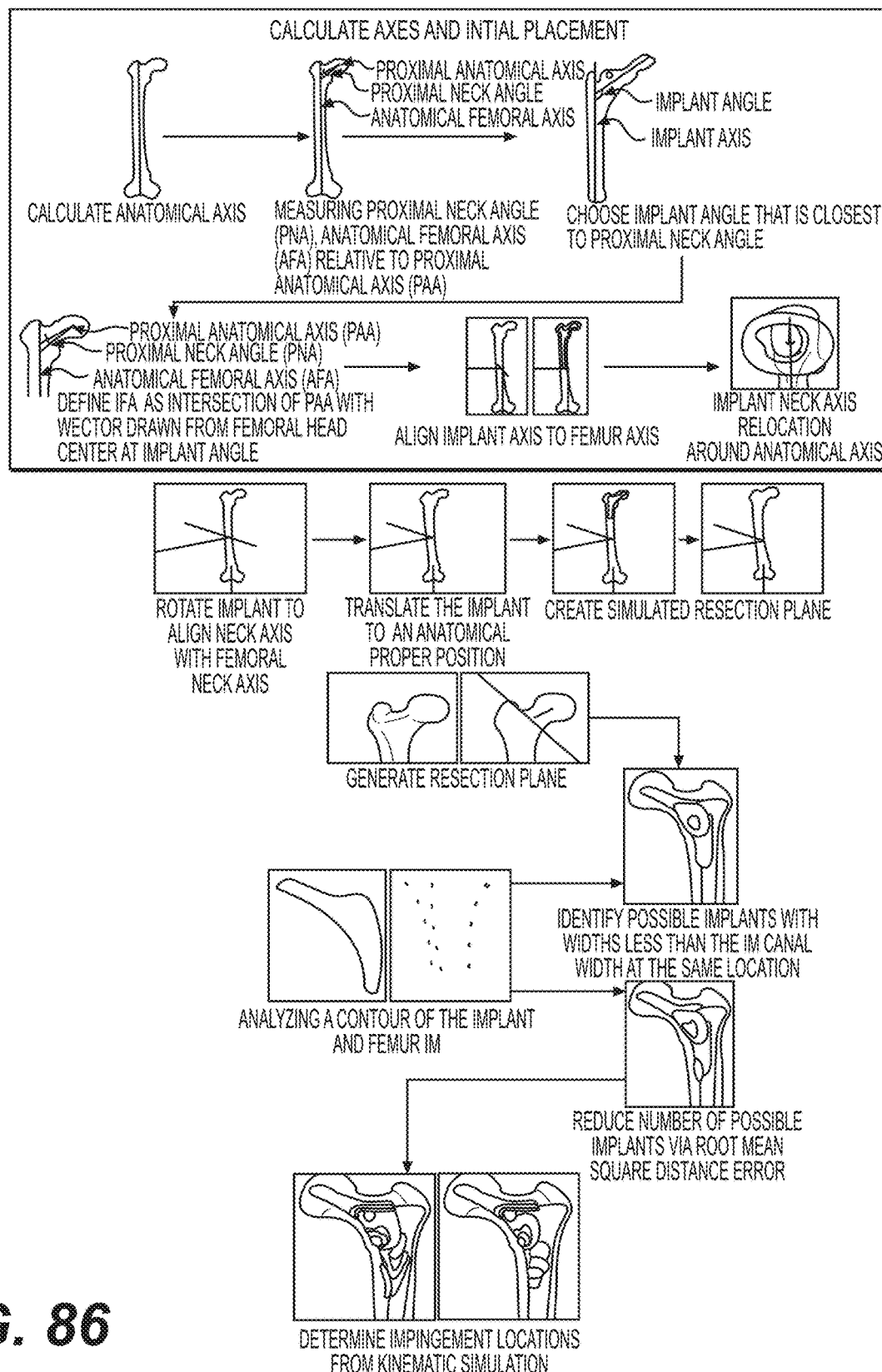
FIG. 86. Stem automatic placement using press fit and three contacts.
Figure 87:
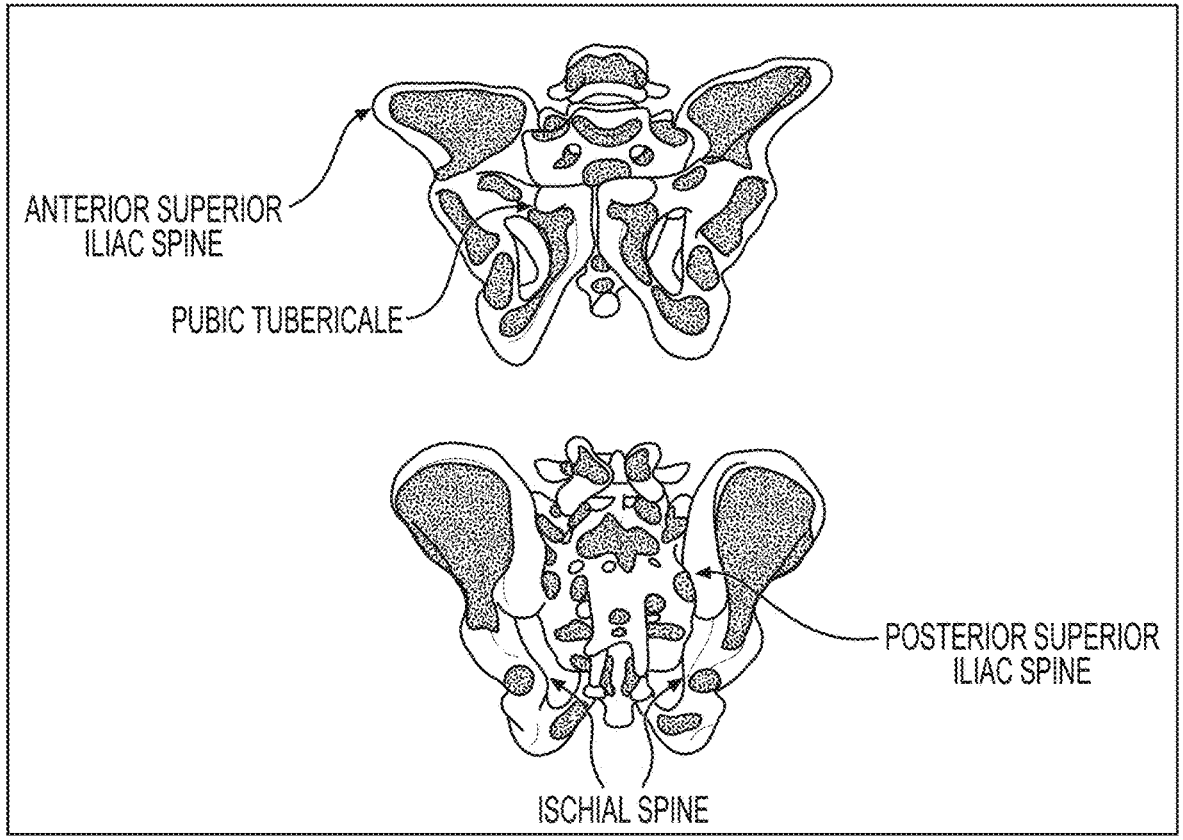
FIG. 87. Automatic pelvis landmarking.
Figure 88:
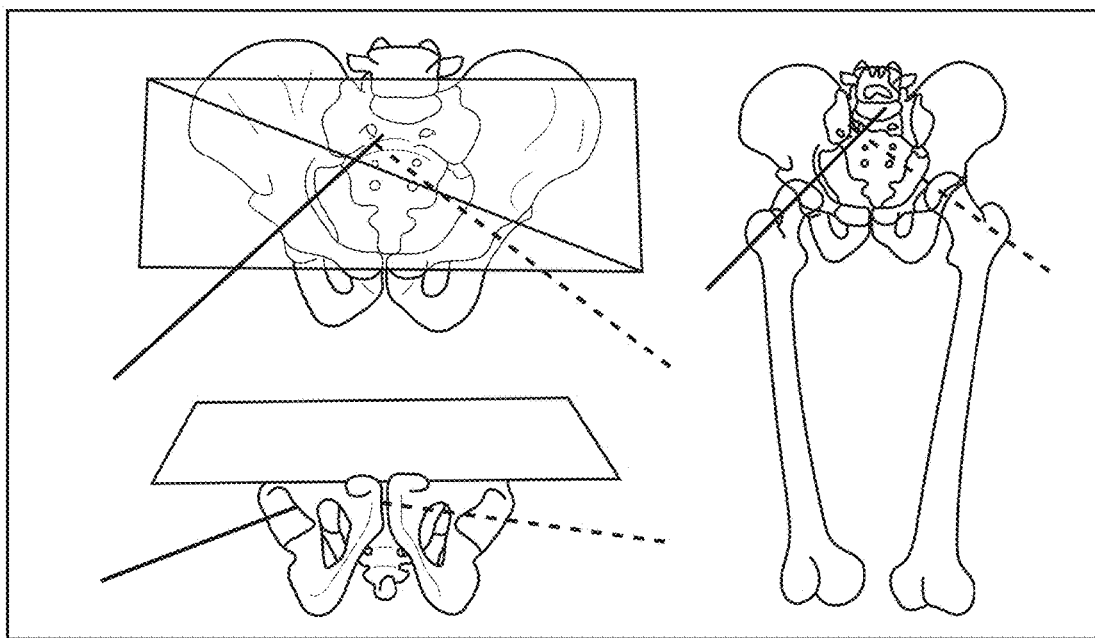
FIG. 88. Automatic calculation of cup orientation and placement.
Figure 89:
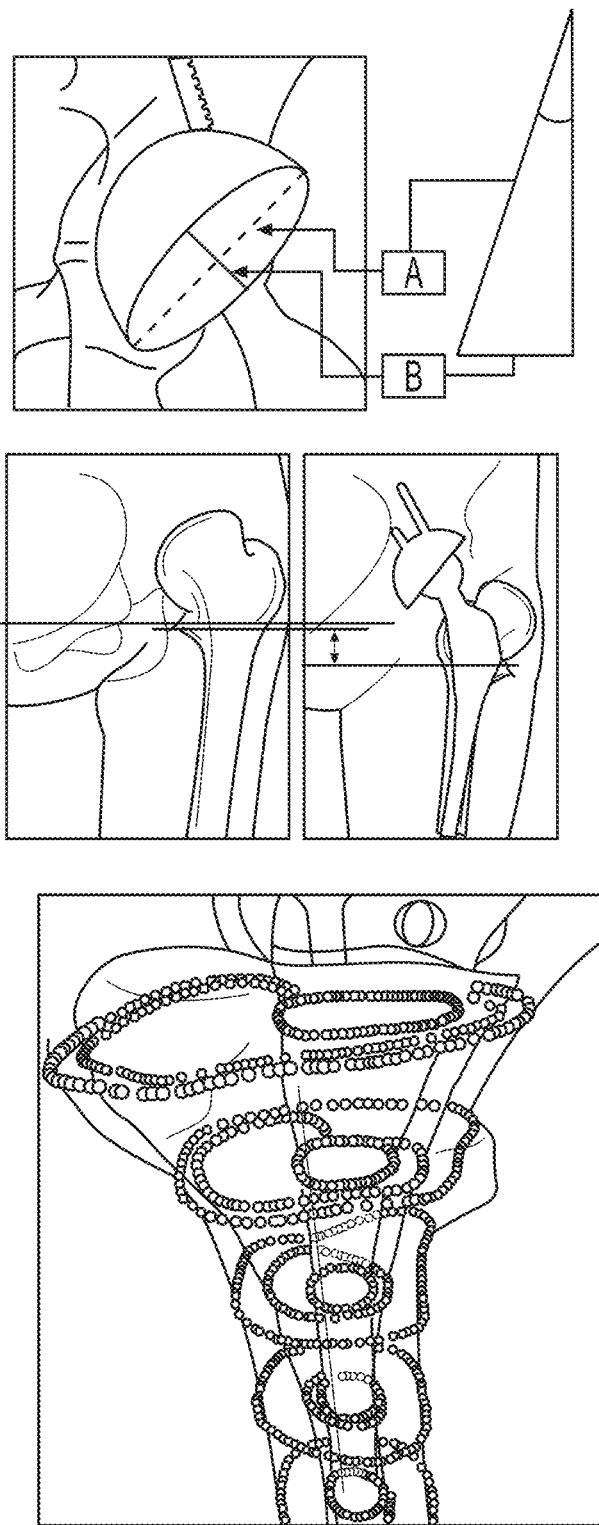
FIG. 89. Cup and stem placement evaluation.
Figure 90:
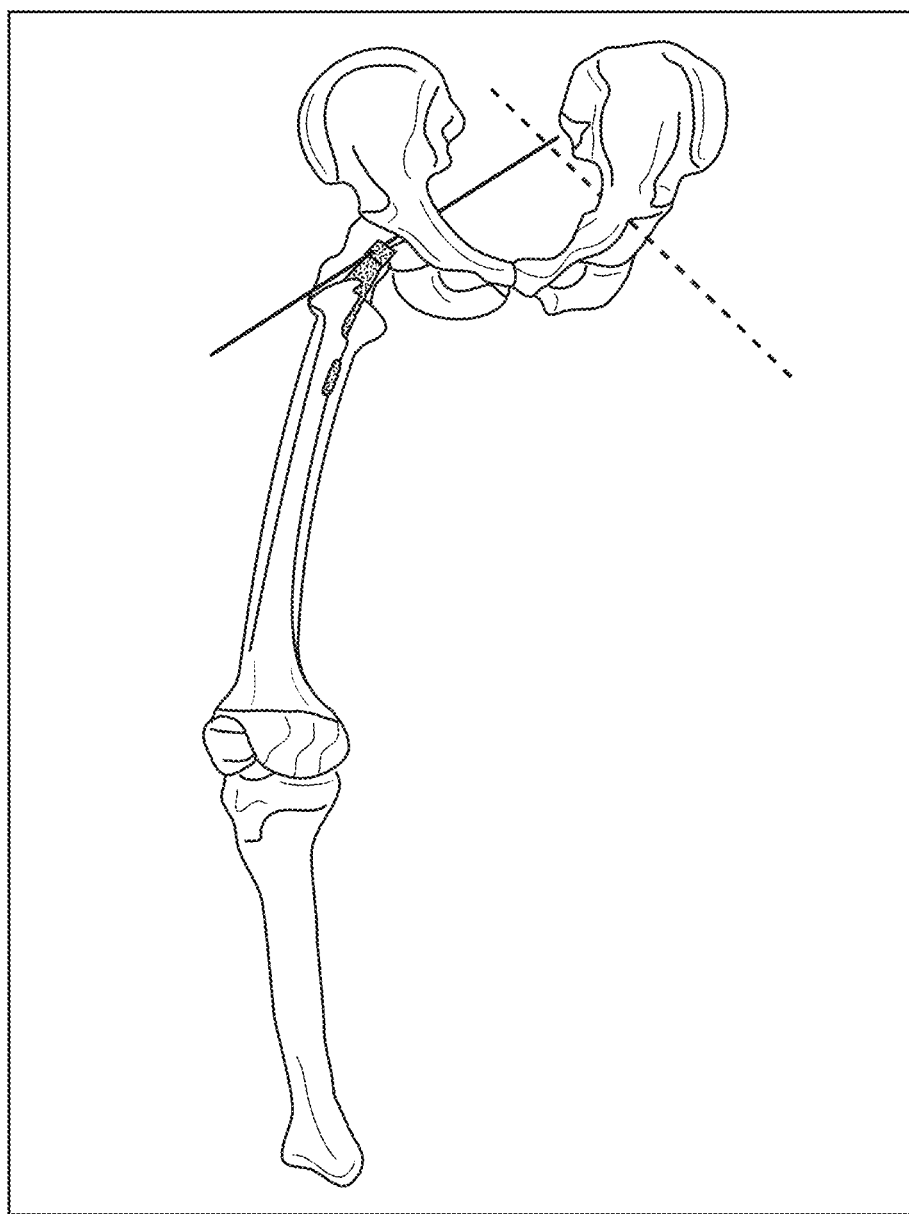
FIG. 90. Assessment of cup and stem placement to ensure overall limb length restoration and orientation.
Figure 91:
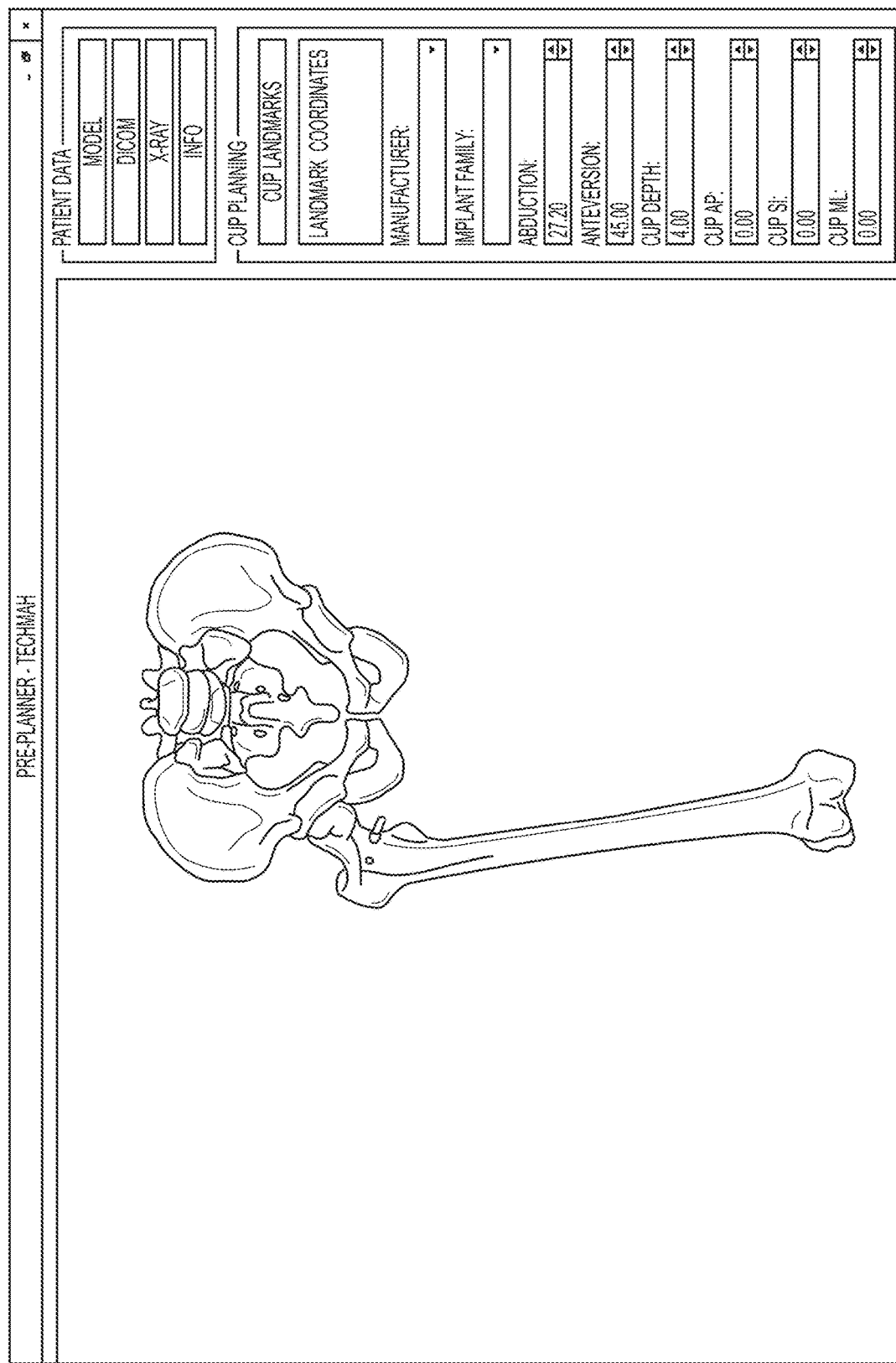
FIG. 91. Preplanning interface for evaluating and modifying implant placement and sizing.

In the context of automatic placement of the femoral stem using press fit and three contacts, as shown in FIG. 86, the automatic landmarking includes definition of axes on the femur and the implant. With respect to the femur, the anatomical femoral axis (AFA) is calculated, followed by the proximal anatomical axis (PAA). The proximal neck angle (PNA) is then calculated, which is defined as the angle between the AFA and PNA. With respect to the femoral implant, the implant axis is along the length of the implant stem and the implant neck axis is along the length of the implant neck. Similar to the PNA of the femur, the implant angle is defined as the angle between the implant axis and the implant neck axis. The implant is then chosen which has an implant angle that is closest to the PNA. The implant fitting angle (IFA) is then defined as the intersection of the proximal anatomical axis with a vector drawn from the femoral head center at the chosen implant angle.

When using automatic placement of the femoral stem using press fit, three contacts, and the calculated anatomical landmarks, as shown in FIG. 86, an implant sizing step determines/estimates for the appropriate implant sizes for pelvis and femoral components. The implant size is chosen by aligning the implant to the femur by aligning the implant axis to the anatomic femur axis. The implant is then rotated to align its neck axis with the femoral neck axis. The implant is then translated to be in an anatomically proper position within the proximal femur. Thereafter, the system moves forward to an implant placement step.

In the implant placement step for a press fit femoral stem, based on surgeon preferred surgical technique and previously calculated anatomical landmarks, the initial implant position is determined/chosen for all relevant implanted components. A resection plane is created to simulate the proximal femur osteotomy and the implant fit is assessed. Fit assessment is conducted by analyzing a contour of the implant and femur intramedullary canal. The contour is created by intersecting the intramedullary canal with a plane normal to both anatomical axis and femoral neck axis, passing through the point of intersection of the anatomical axis and femur neck axis, producing a contour. When the implant and intramedullary canal contours are generated, only the implants with widths less than the intramedullary canal width at the same location are kept, resulting in many possible correct implant sizes. The group of possible sizes is reduced through two strategies reducing mean square distance error between the implant and the intramedullary canal. The first strategy minimizes the mean square error (MSE) or other mathematical error metric of the distance between both medial and lateral sides of the implant and the intramedullary canal. The second strategy minimizes the MSE of the distance between the lateral side of the implant and the intramedullary canal.

As part of this implant placement step, an iterative scheme is utilized that includes using an initial "educated guess" as to implant placement as part of a kinematic simulation to evaluate the placement of the "educated guess." In exemplary form, the kinematic simulation takes the implant (based upon the placement of the implant chosen) through a range of motion using estimated or measured joint kinematics. Consequently, the kinematic simulation may be used to determine impingement locations and estimate the resulting range of motion of the implant post implantation. In cases where the kinematic simulation results in unsatisfactory data (e.g., unsatisfactory range of motion, unsatisfactory mimicking of natural kinematics, etc.), another location for implant placement may be utilized, followed by a kinematic analysis, to further refine the implant placement until reaching a satisfactory result. After the implant position is determined/chosen for all relevant implanted components, the template data is forwarded to a jig generation module.

Referring back to FIG. 79, the jig generation module generates a patient-specific guide model. More specifically, from the template data and associated planning parameters, the shape and placement of a patient-specific implant is known with respect to the patient's residual bone. Consequently, the virtual templating module, using the patient-specific 3D bone model, calculates the position of the implant with respect to the patient's residual bone and, thus, provides the jig generation module with information as to how much of the patient's residual bone is intended to be retained. Consistent with this bone retention data, the jig generation module utilizes the bone retention data to assign one or more bone cuts to reduce the patient's current bone to the residual bone necessary to accept the implant as planned. Using the intended bone cut(s), the jig generation module generates a virtual 3D model of a cutting guide/jig having a shape configured to mate with the patient's bone in a single location and orientation. In other words, the 3D model of the cutting jig is created as a "negative" of the anatomical surface of the patient's residual bone so that the tangible cutting guide precisely matches the patient anatomy. In this fashion, any guesswork associated with positioning of the cutting jig is eliminated. After the jig generation module generates the virtual 3D model of the cutting jig, the module outputs machine code necessary for a rapid prototyping machine, CNC machine, or similar device to fabricate a tangible cutting guide. By way of example, the exemplary cutting jig for resection of the femoral head and neck comprises a hollow slot that forms an associated guide to constrain a cutting blade within a certain range of motion and maintains the cutting blade at a predetermined orientation that replicates the virtual cuts from the surgical planning and templating modules. The jig generation module is also utilized to create a placement jig for the femoral stem.

Figure 92:
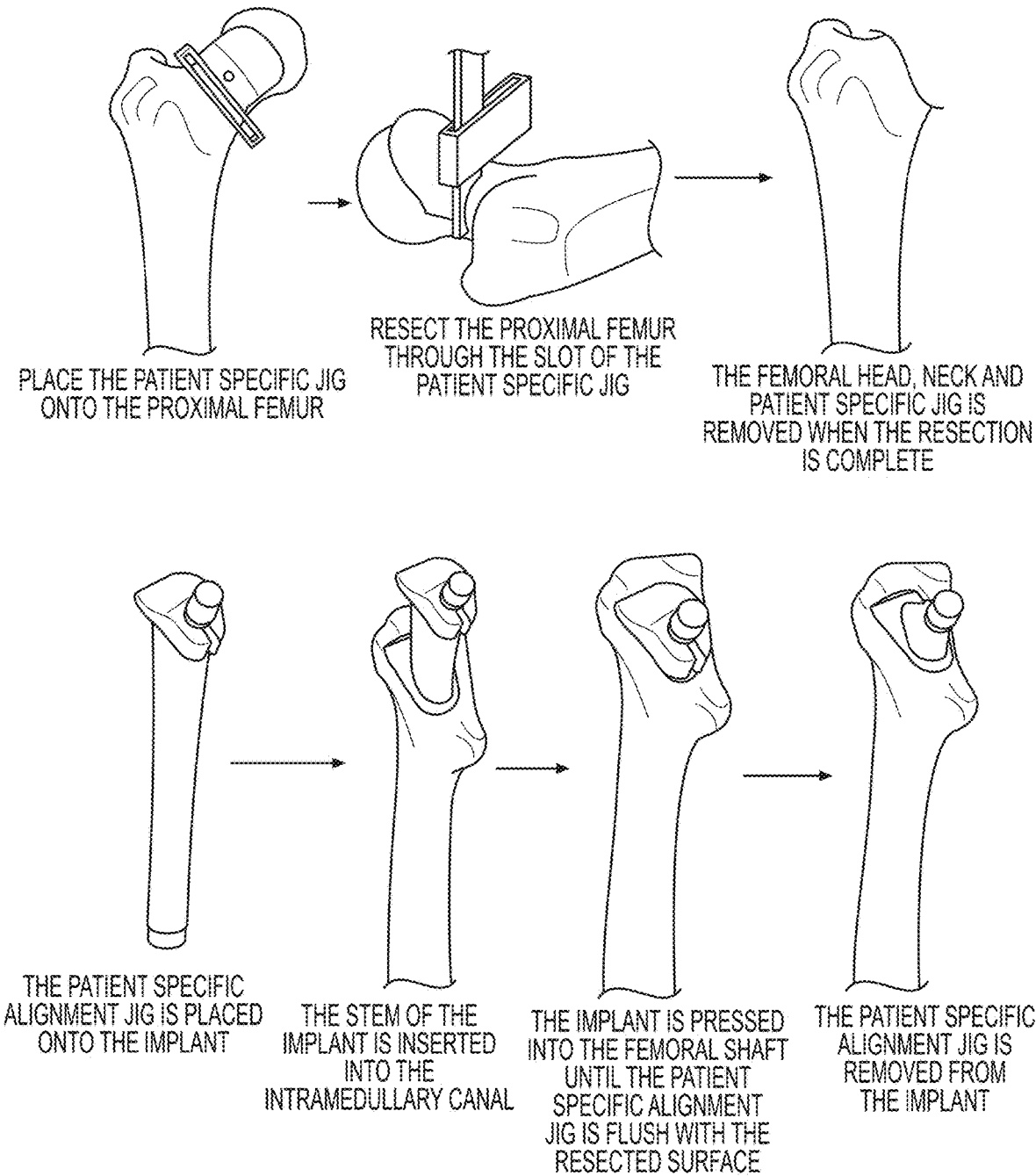
FIG. 92. Process of using patient specific guide for resection and placement of femoral stem.

Referring to FIG. 92, subsequent to resecting the femoral head and neck, intramedullary reaming followed by femoral stem insertion takes place. In order to prepare the femur for insertion of the femoral implant, reaming of the intramedullary canal needs to take place along an orientation consistent with the orientation of the femoral implant. If the reaming is offset, the orientation of the femoral implant may be compromised. To address this concern, the jig generation module generates a virtual guide that is a "negative" of the anatomical surface of the patient's residual or resected bone so that a rapid prototyping machine, CNC machine, or similar device can fabricate the cutting guide that precisely matches the patient anatomy. By way of example, the reaming jig may include an axial guide along which the reamer may longitudinally traverse. Using this reaming jig, the surgeon performing the reaming operation is ensured of reaming in the proper orientation.

The intramedullary canal may receive the femoral stem. Again, to ensure the femoral stem is properly positioned both from a rotational perspective and an angular perspective within the intramedullary canal, the jig generation module generates a femoral stem placement guide. By way of example, the femoral stem placement guide concurrently is a "negative" of the anatomical surface of the patient's residual or resected bone as well as the top of the femoral stem. In this manner, the placement guide slides over the femoral shaft (portion of femoral stem that the femoral ball is connected to) and concurrently includes a unique shape to interface with the patient's residual or resected bone so that only a single orientation of the femoral stem is possible with respect to the patient's femur, thereby ensuring proper implantation of the femoral stem consistent with pre-operative planning. It should be noted, however, that while the exemplary jigs have been described in the context of a primary hip implant, those skilled in the art should understand that the foregoing exemplary process and system are not limited to primary hip implants or limited to hip implant or revision surgical procedures. Instead, the process and system are applicable to any hip implants in addition to surgical procedures involving other areas of the body including, without limitation, knee, ankle, shoulder, spine, head, and elbow.

Figure 93:
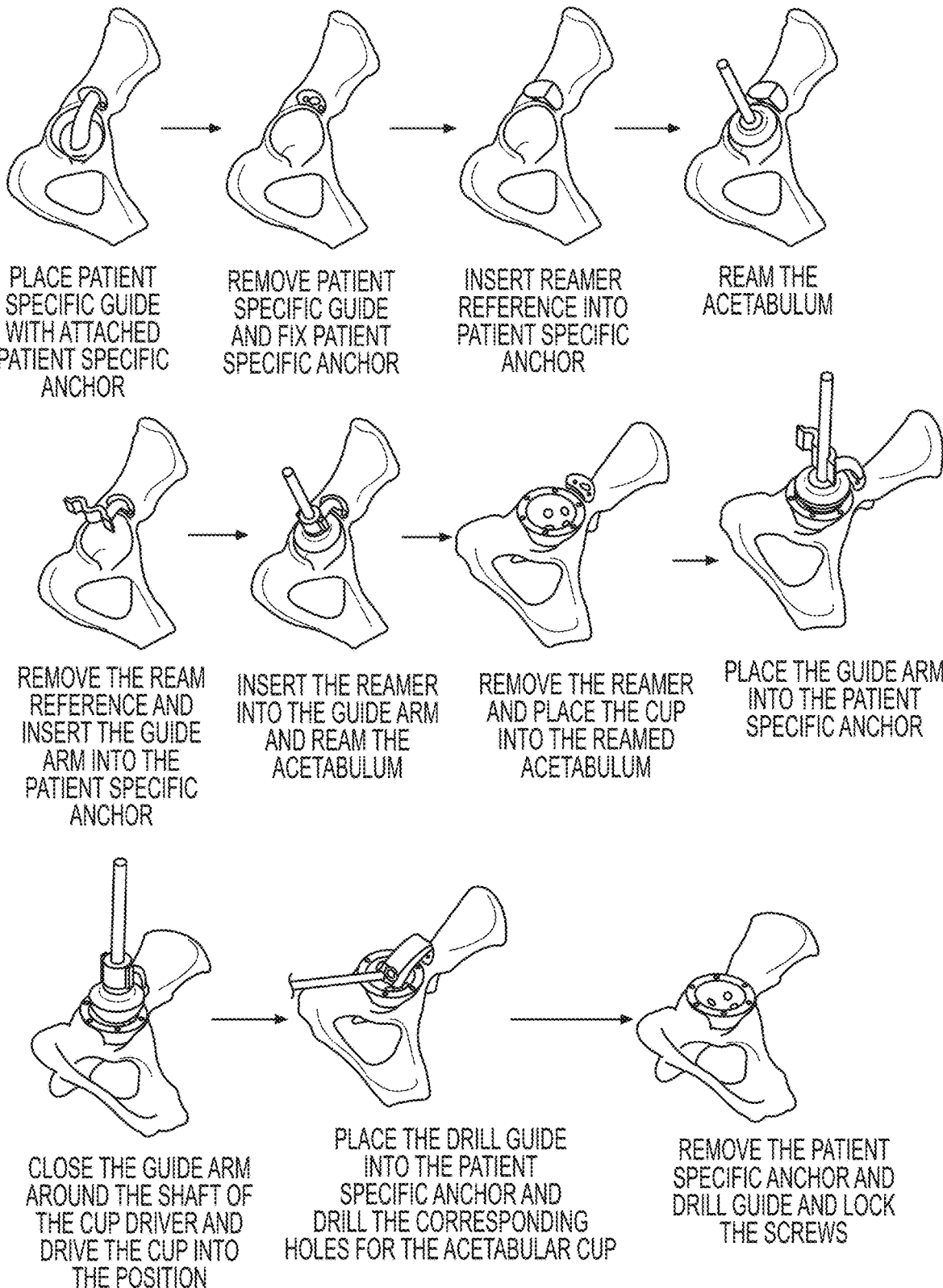
FIG. 93. Process of using patient specific guide for reaming and placement of acetabular cup.
Figure 94:
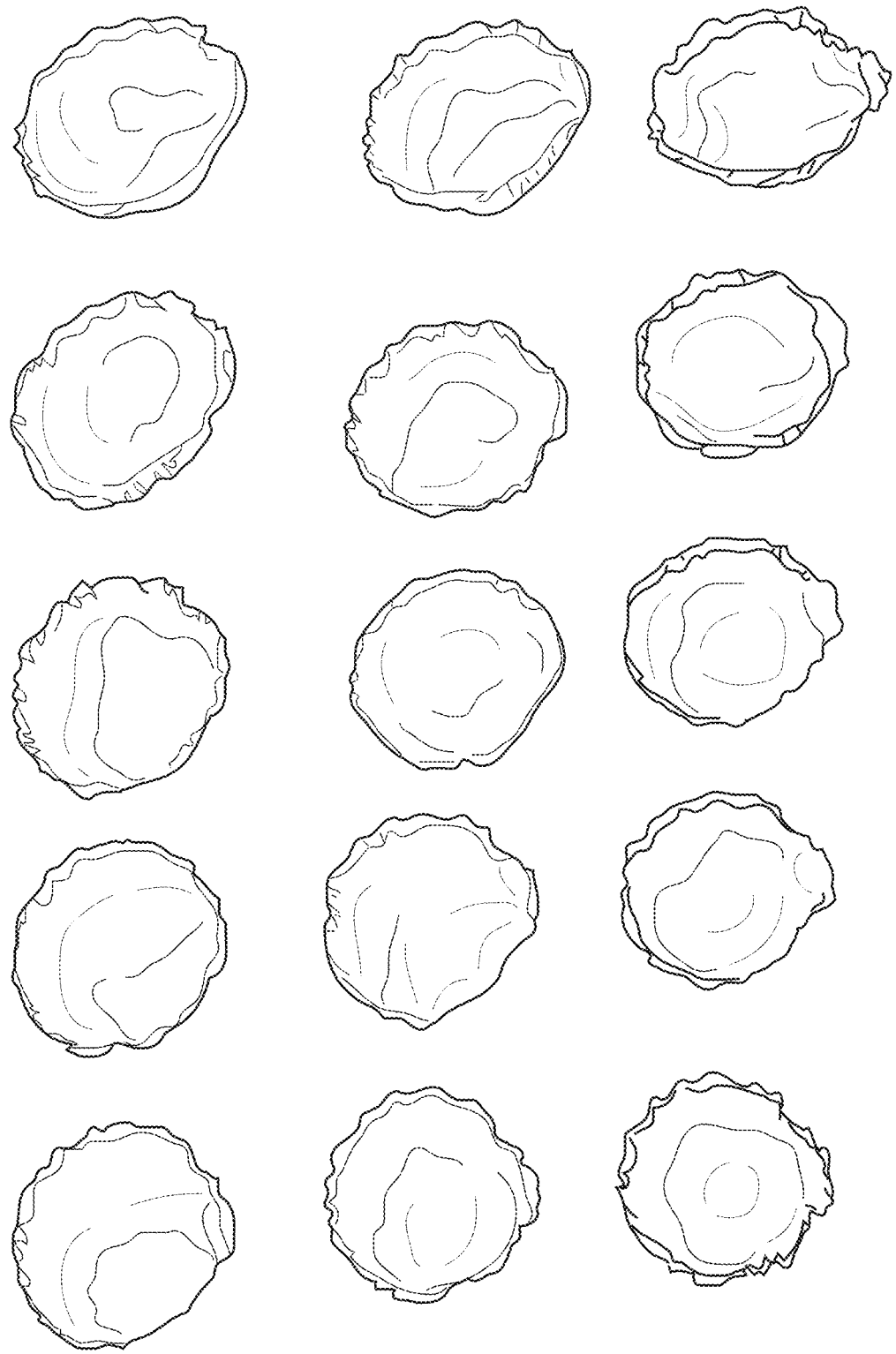
FIG. 94. Mapping of patient specific labrum attachment site, in this example the acetabulum, which is used for generation of patient specific guide and locking mechanism. A statistical atlas, or templates, can be used to determine patient specific guide mating sites.
Figure 95:
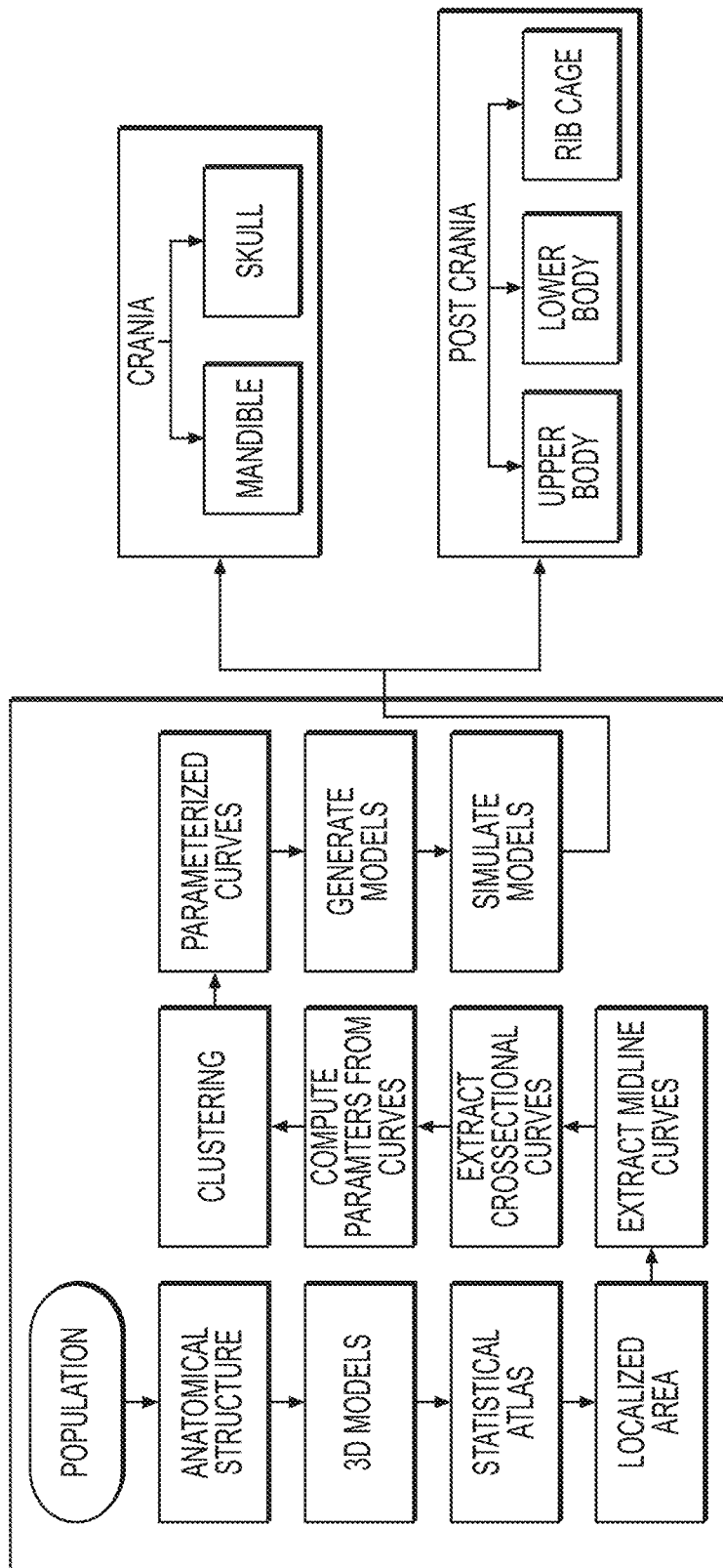
FIG. 95. Process of creating trauma plates and fixation devices for a population.
Figure 96:
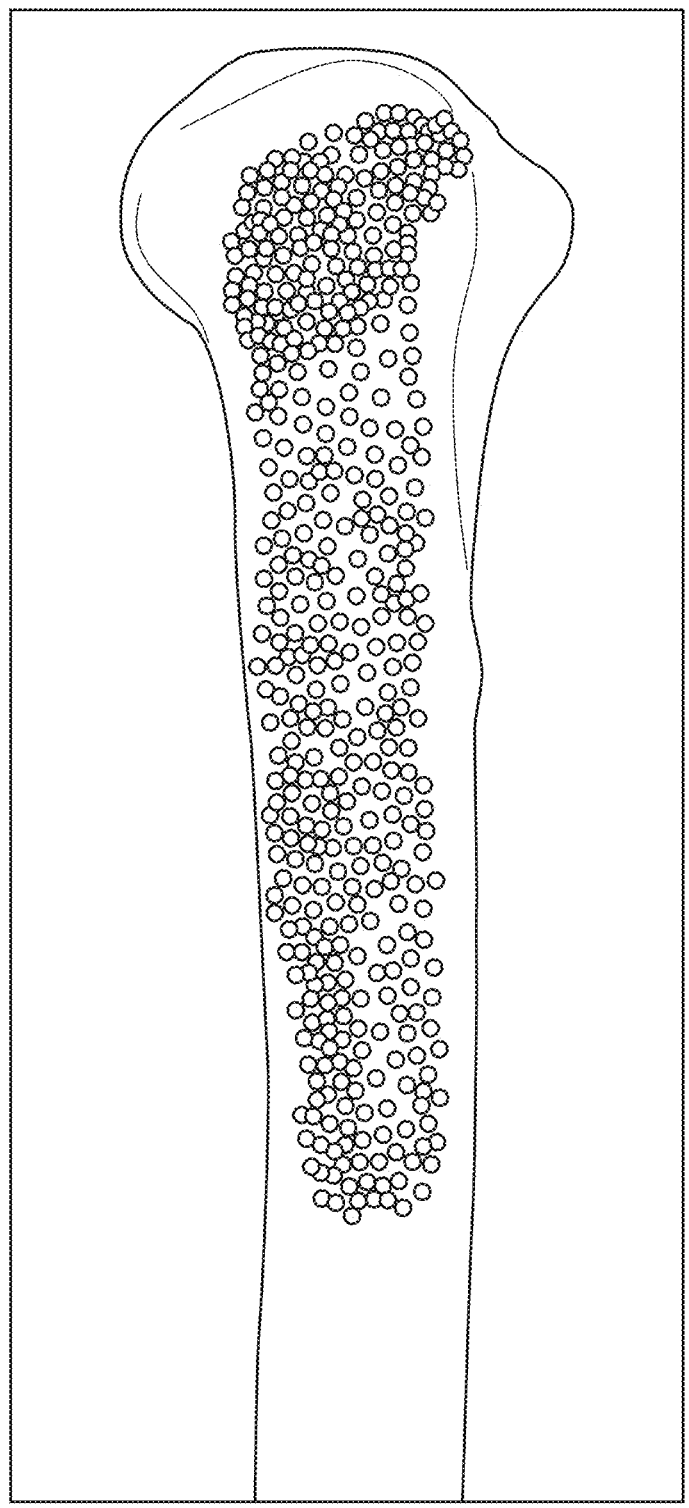
FIG. 96. Localization of plate shape on atlas mean bone.
Figure 97:
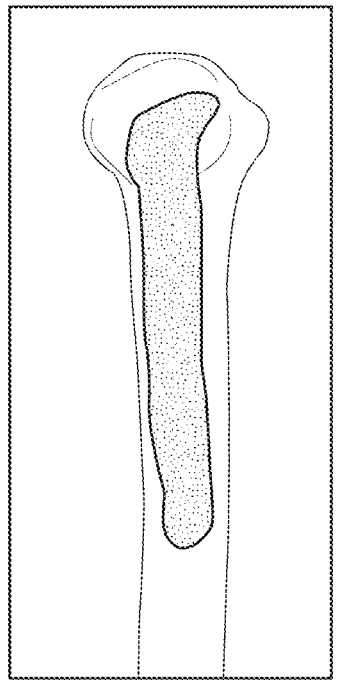
FIG. 97. Propagation of plate loci on entire population, here shown on a single instance.
Figure 98:
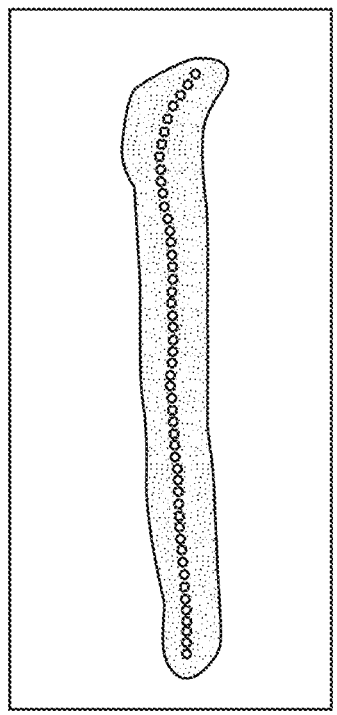
FIG. 98. Extraction of plate midline curve.
Figure 99:
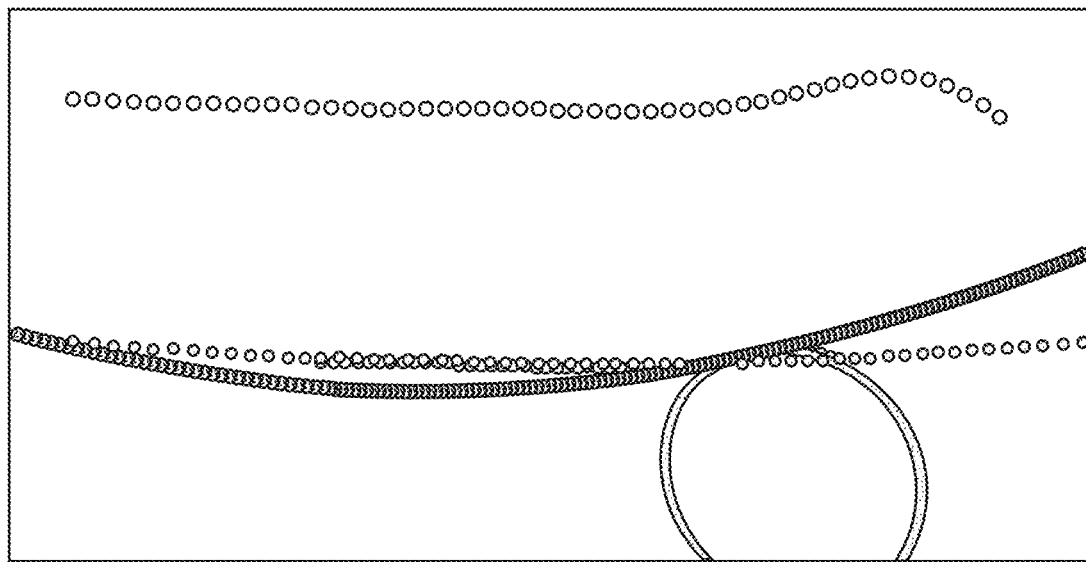
FIG. 99. Computing 3D radii of curvature for plate midline curve.
Figure 100:
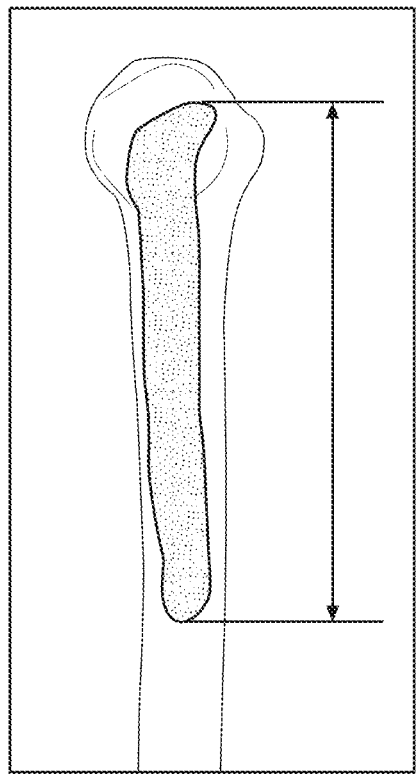
FIG. 100. Calculating plate length.
Figure 101:
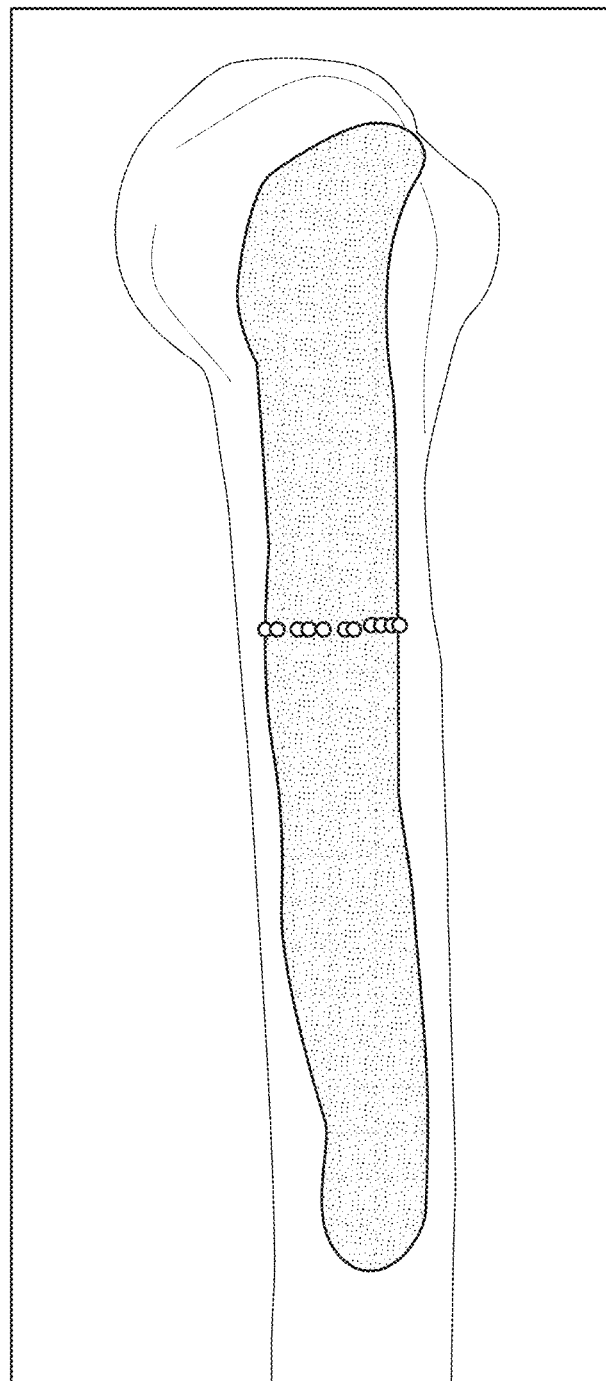
FIG. 101. Calculating mid-plate width.
Figure 102:
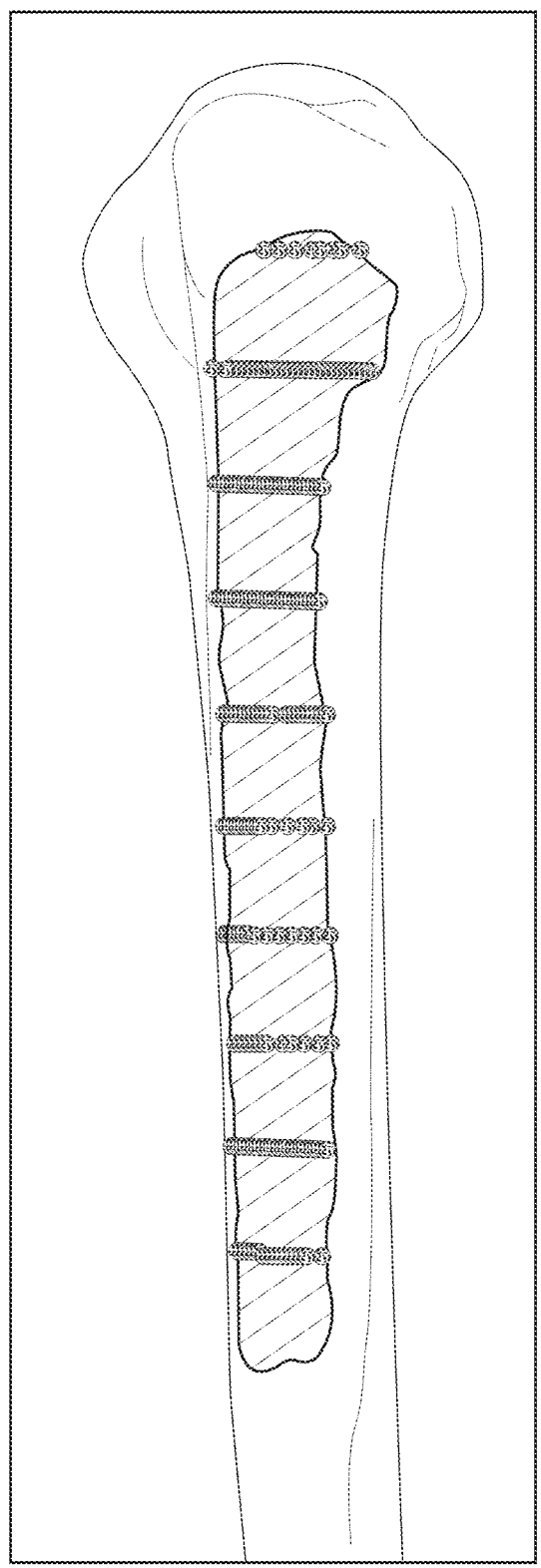
FIG. 102. Calculating plate cross sectional radii.
Figure 103:
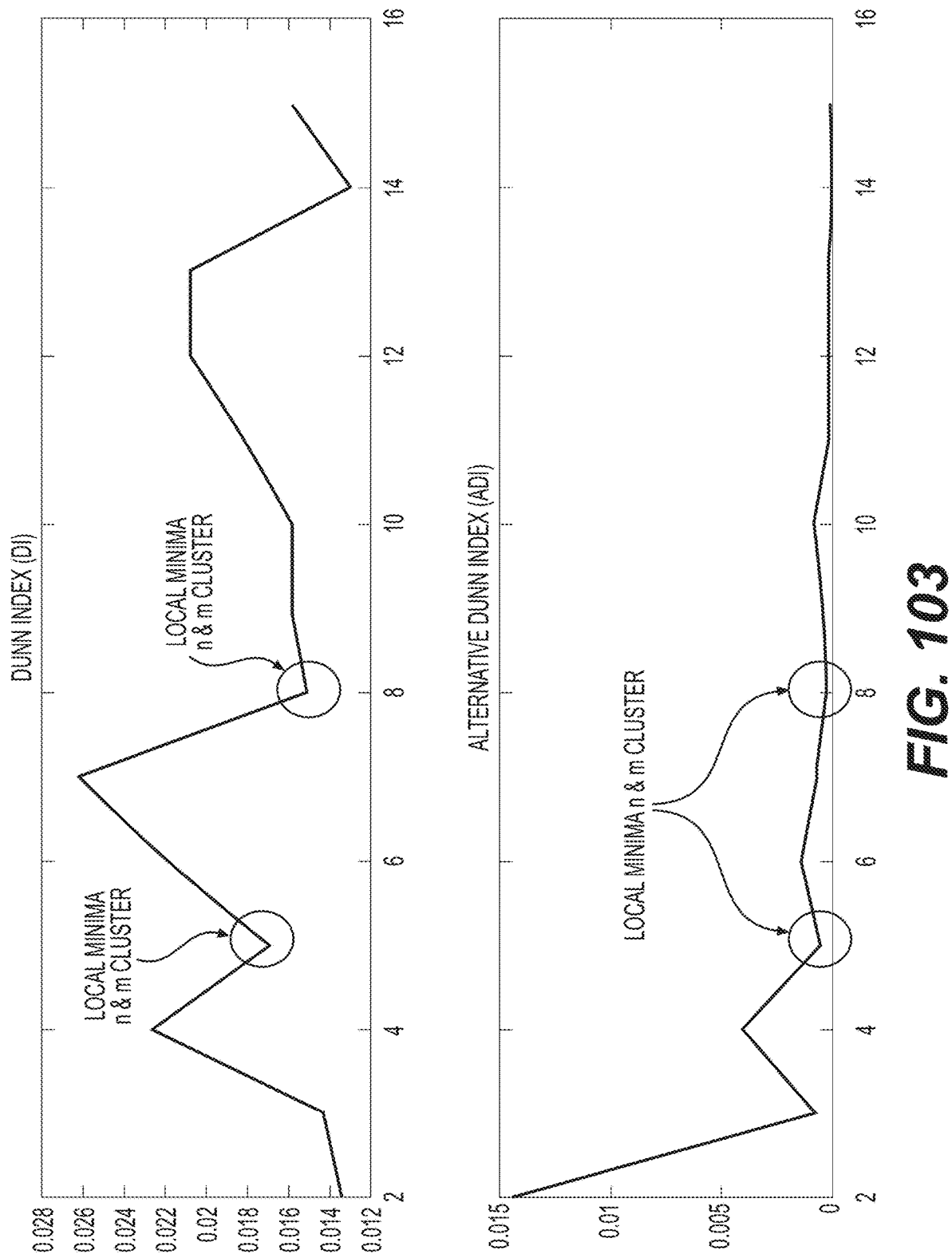
FIG. 103. Determining optimal number of clusters.
Figure 104:
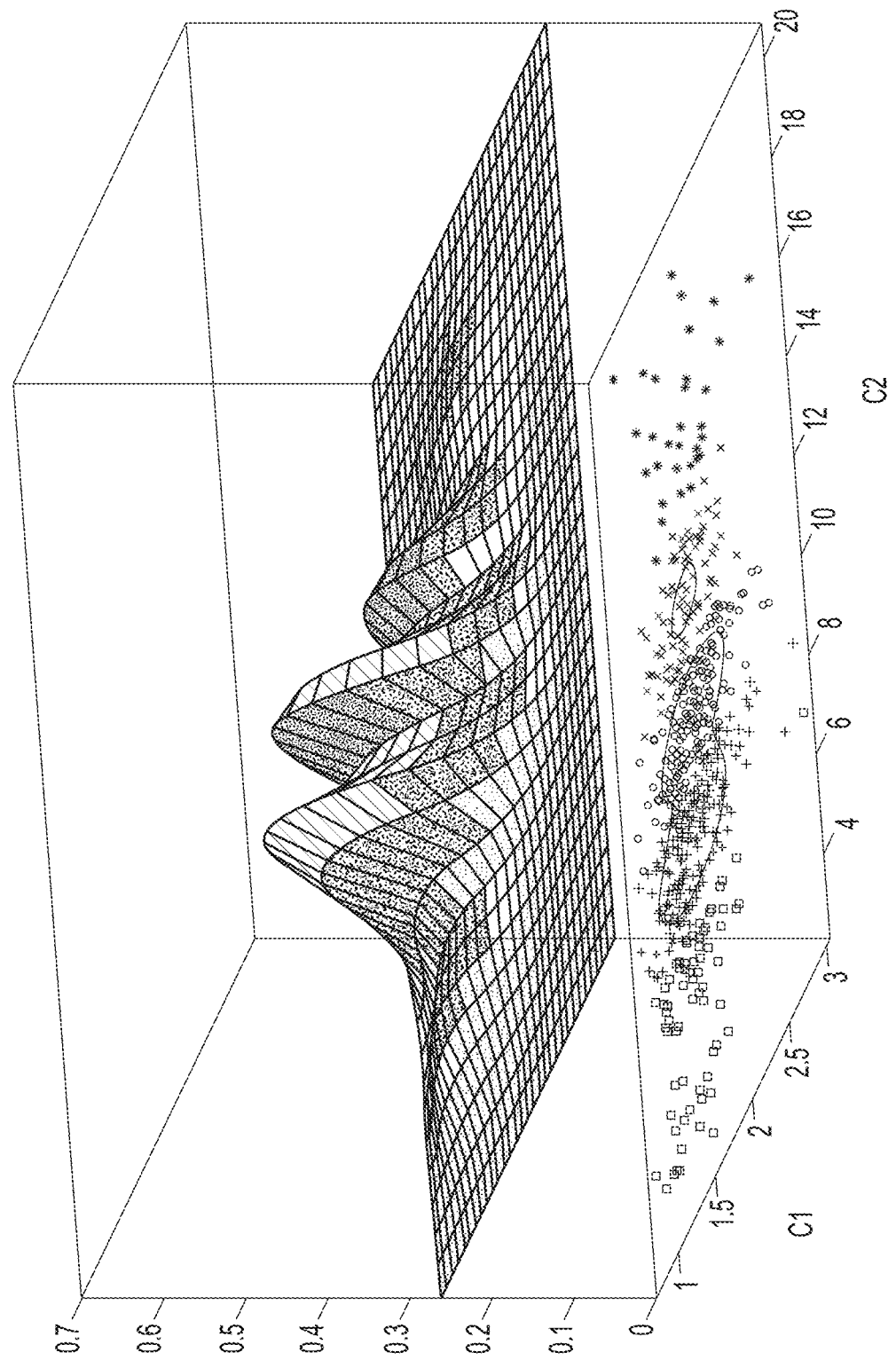
FIG. 104. Plate sizes clustering. Shown in FIG. 95 as "Clustering".
Figure 105:
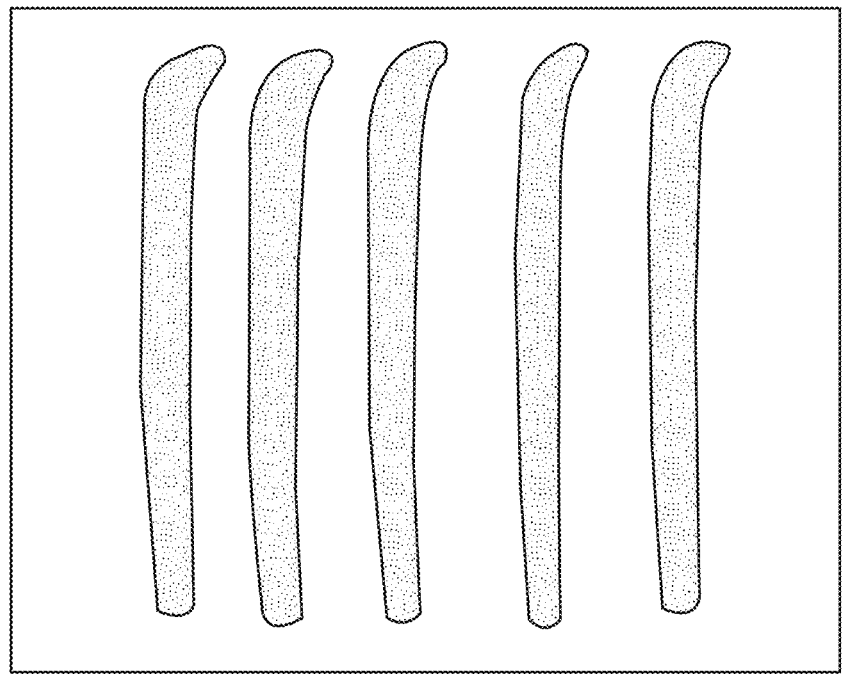
FIG. 105. Parameterization of plate sizes. Shown in FIG. 95 as "Parameterized Curves" and "Generate Models".
Figure 106:
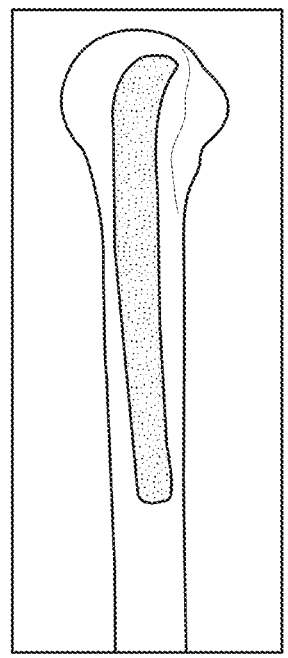
FIG. 106. Fitting generated plate on population for evaluation.
Figure 109:
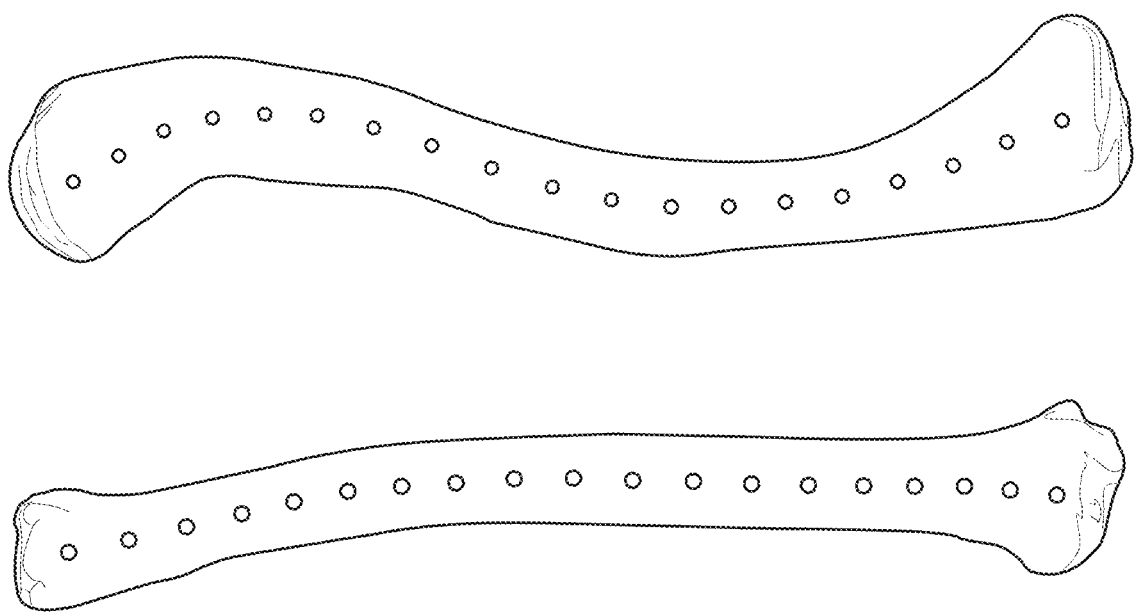
FIG. 109. Identifying Clavicle Midline Curvature. The Midline curvature is not symmetrically "S" shaped, according to a statistical analysis of the anatomical population.

As depicted in FIG. 93, in the context of the acetabulum, the jig generation module may generate instructions for fabricating reaming and acetabular implant placement guides for the acetabular cup. In particular, from the template data and associated planning parameters, the shape and placement of a patient-specific acetabular implant is known with respect to the patient's residual pelvis. Consequently, the virtual templating module, using the patient-specific 3D acetabulum model, calculates the size and position of the acetabular cup implant with respect to the patient's residual bone and, thus, provides the jig generation module with information as to how much of the patient's residual pelvis is intended to be retained and the desired implant orientation. Consistent with this bone retention data, the jig generation module utilizes the bone retention data to assign one or more bone cuts/reaming to reduce the patient's current pelvis to the residual bone necessary to accept the acetabular implant as planned. Using the intended bone cut(s), the jig generation module generates a virtual 3D model of a cutting guide/jig having a shape configured to mate with two portions of the patient's pelvis via only one orientation. In other words, the 3D model of the cutting jig is created as a "negative" of the anatomical surface of the patient's pelvis so that the tangible reaming guide precisely matches the patient anatomy. In this fashion, any guesswork associated with positioning of the reaming jig is eliminated. After the jig generation module generates the virtual 3D model of the reaming jig, the module outputs machine code necessary for a rapid prototyping machine, CNC machine, or similar device to fabricate a tangible reaming jig. By way of example, the exemplary acetabular component jig for reaming the acetabulum comprises a four-piece structure, where a first piece is configured to be received in the native acetabulum and temporarily mount to the second piece until the second piece is secured to the pelvis using the first piece as a placement guide. After the second piece is fastened to the pelvis, the first piece may be removed. Thereafter, the third piece includes a cylindrical or partially cylindrical component that uniquely interfaces with the second piece to ensure the reamer can longitudinally traverse with respect to the third piece, but its orientation is fixed using a combination of the first and third pieces. Following reaming, the reamer is removed and the third piece is removed from the first piece. The acetabular cup implant is mounted to the reamed acetabulum using a fourth piece. In particular, the fourth piece is shaped uniquely to engage the first piece in only a single orientation, while at the same time being formed to be received within the interior of the acetabular cup implant. After the implant cup is positioned, both the first and fourth pieces are removed. It should also be noted that additional jigs may be created for drilling one or more holes into the pelvis to seat the acetabular implant, where each drilling jig is mounted in succession to the first piece in order to verify the orientation of the drill bit.

Creation of Trauma Plates

Referring to FIGS. 95-108, an exemplary process and system are described for creating bone plates (i.e., trauma plates) across a predetermined population. Those skilled in the art are aware that bone is able to undergo regeneration to repair itself subsequent to a fracture. Depending on the severity and location of the fracture, prior art trauma plates were utilized that often required bending or other modifications in the operating room to conform to an irregular bone shape and achieve maximum contact between the bone fragments. However, excessive bending decreases the service life of the trauma plate, which may lead to bone plate failure and/or trauma plate-screw fixation loosening. The instant process and system provides a more accurate trauma plate shape to reduce or eliminate having to contour the plate interoperatively, thereby increasing plate service life and increasing the time until any bone plate-screw fixation loosening occurs.

The foregoing exemplary explanation for creating trauma plates is applicable to any and all bones for which trauma plates may be applied. For purposes of brevity, the exemplary explanation describes the system and process for creation of a trauma plate for use with the humerus bone. But it should be understood that the process and system is equally applicable to other bones of the body and fabrication of corresponding trauma plates and is in no way restricted to humerus trauma plates.

As part of the exemplary process and system for creating trauma plates, a statistical bone atlas is created and/or utilized for the bone(s) in question. By way of explanation, the bone in question comprises a humerus. Those skilled in the art are familiar with statistical atlases and how to construct a statistical atlas in the context of one or more bones. Consequently, a detailed discussion of constructing the statistical bone atlas has been omitted in furtherance of brevity. Nevertheless, what may be unique as to the statistical bone atlas of the exemplary system and process is categorizing humeri within the statistical bone atlas based upon gender, age, ethnicity, deformation, and/or partial construction. In this fashion, one or more trauma plates may be mass customized to one or more of the foregoing categories, where the one or more categories establish a particular bone population.

In exemplary form, the statistical bone atlas includes anatomical data that may be in various forms. By way of example, the statistical bone atlas may include two dimensional or three dimensional images, as well as information as to bone parameters from which measurements may be taken. Exemplary atlas input data may be in the form of X-ray images, CT scan images, MRI images, laser scanned images, ultrasound images, segmented bones, physical measurement data, and any other information from which bone models may be created. This input data is utilized by software accessing the statistical atlas data to construct three dimensional bone models (or access three dimensional bone models having already been created and saved as part of the statistical atlas), from which the software is operative to create a mean bone model or template bone model in three dimensions.

Using the template bone model, the software can automatically designate or allows manual designation of points upon the exterior surface of the template bone model. By way of explanation, in the context of the mean humerus model, a user of the software establishes a general boundary shape for the eventual trauma plate by generally outlining the shape of the trauma plate on the exterior surface of the humerus model. The general boundary shape of the trauma plate can also be accomplished by the user designating a series of points on the exterior surface of the humerus model that correspond to an outer boundary. Once the outer boundary or boundary points are established, the software may automatically designate or allows manual designation of points on the exterior surface of the humerus model within the established boundary. By way of example, the software provides a percent fill operation upon which the user can designate that percentage within the boundary of the trauma plate to be designated by a series of points, each corresponding to a distinct location on the exterior of the humerus model. In addition, the software provides a manual point designation feature upon which the user may designate one or more points upon the exterior surface of the humerus model within the boundary. It should be noted that in cases where manual point designation is utilized, the user need not establish a boundary as a prefatory matter to designating points upon the exterior of the humerus model. Rather, when the manual designation of points is completed, the boundary is established by the outermost points designated.

After the designation of points on the exterior surface of the template bone model, the localized points are propagated throughout the bone population in question. In particular, the localized points are automatically applied to each three dimensional bone model within the given population by the software via point correspondence of the statistical atlas. By way of example, the given bone population may be gender and ethnic specific to comprise humeri from Caucasian women. Using the propagated points for each bone model of the population, the software fills in the voids between points within the boundary using a three dimensional filling process to create a three dimensional rendering of the trauma plate for each bone. Thereafter, the software calculates the longitudinal midline of the three dimensional rendering of each trauma plate via a thinning process.

The midline of each three dimensional trauma plate rendering comprises a three dimensional midline having various curvatures along the length thereof. The software extracts the three dimensional midline and, using a least square fitting, determines the preferred number of radii of curvature that cooperatively best approximate the predominant curvature of the three dimensional midline. In the context of humeri, it has been determined that three radii of curvature accurately approximate the midline curvature. But this number may vary depending upon the bone population and the boundary of the trauma plate. Additional features can be included here as well, such as cross-sectional curvature at one or more locations along the length of the plate, location of muscles, nerves and other soft tissues to avoid, or any other feature relevant to defining plate size or shape. By way of example, the three radii of curvature for the midline represent the bend in the trauma plate in the proximal humerus, the transition between the humeral shaft and the humeral head, and the curvature of the humeral shaft. Each radii of curvature is recorded and a four dimensional feature vector was applied to the radii of curvature data to cluster the radii into groups that best fit the population. In exemplary form, the cluster data may indicate that multiple trauma plates are necessary to properly fit the population. Once the radii of curvature data is clustered, the trauma plate dimensions may be finalized.

Upon feature extraction related to the plate design, the software determines the best number of clusters that fits the population. It must be noted that there are some instances where there are two or more clusters that provide local minima as outlined in FIG. 100. In order to determine the optimum choice that provides acceptable error tolerance as well as reasonable number of plates in each family, the software generates three dimensional surface model for the plates in each clusters. Automatic evaluation is then performed by placing those plates on the population and computing the mismatch between the plate and the bone surface. Results of this analysis allow the software to pick the optimal number of plates to be used for this specific population. The final plate models are then parameterized and screw locations are placed on each plate in such a fashion as to avoid muscle and soft tissue locations as well as maximize fixation. The width of the screws are determined by the cross sectional analysis of the bone at each screw level across the population.

The instant process and method was validated for the humerus using a cadaver study. In particular, CT scans were taken of cadaver humerus bones from Caucasian white females. These CT scans were utilized by the software to create separate three dimensional models for each humeri. It should be noted that neither the CT scans nor the three dimensional models utilized during this validation study were part of the statistical atlas and relevant population utilized to create the humeral trauma plates. Consequently, the CT scans nor the three dimensional models comprised new data and models used to validate the humeral trauma plates designed. After the three dimensional validation models had been generated, each of the models was categorized to a particular cluster (the clusters resulting from designing the humeral trauma plate from the design population). Based upon which cluster the validation model was categorized to, the designed humeral trauma plate for that cluster was fitted to the appropriate validation three dimensional humeral bone model and measurements were calculated showing any spacing between the exterior surface of the validation three dimensional humeral bone model and the underside surface of the humeral trauma plate. FIG. 107 depicts a distance map of the trauma plate fitted upon to the validation three dimensional humeral bone model to show areas of maximum distance between the bone and trauma plate. It can be seen that a majority of the trauma plate is minimally spaced from the bone, while areas of less conformity only show spacing that ranges between 0.06 and 0.09 centimeters. Consequently, it was determined at the conclusion of this cadaver study that the trauma plates designed pursuant to the foregoing exemplary process using the foregoing system had extraordinary contour matching that, when applied intraoperatively, obviated the practice of surgeons having to bend or manually reshape bone plates.

In another exemplary instance of this process, trauma plates were created for the clavicle. Here, a statistical atlas was created from several clavicle bones, which sufficiently captured the variation within Caucasian population. Additionally, defined within the statistical atlas were locations relating to muscle attachment sites. Cross-sectional contours were extracted at 5% increments along the entire bone, as well as at muscle attachment sites and at the clavicle waist. Maximum and minimum dimensions of each cross-sectional contour were calculated. In addition, the entire three-dimensional surface was examined for asymmetry by analyzing the magnitude and directional differences between homologous points across all bone surfaces in the dataset. The results confirm the existing studies on clavicle asymmetry, namely that the left clavicle is longer than the right, but the right is thicker than the left. However, the patterns of asymmetry differ between males and females. Additionally, the clavicle midline does not follow a symmetrical "S" shape, as in existing plate designs. Males are significantly asymmetric in all dimensions and at muscle and ligament attachment site contours ($p<0.05$), whereas female asymmetry is more variable. We hypothesize that this has to do with the absolute and relative differences in male muscle strength compared to females. However, an area with no muscle attachments on the posterior midshaft was significantly asymmetric in both sexes. From the extracted features, clustering was performed to find the family of clavicle plates to optimally fit the population. Additionally, screw fixation locations and length can be determined to optimally avoid soft tissues (muscle attachments) and prevent additional fractures or plate loosening as a result of screws which are too long or too short. Using the process, several plates families were designed, as seen in FIGS. 110-114.

Creation of Trauma Plate Placement Guides

Figure 115:
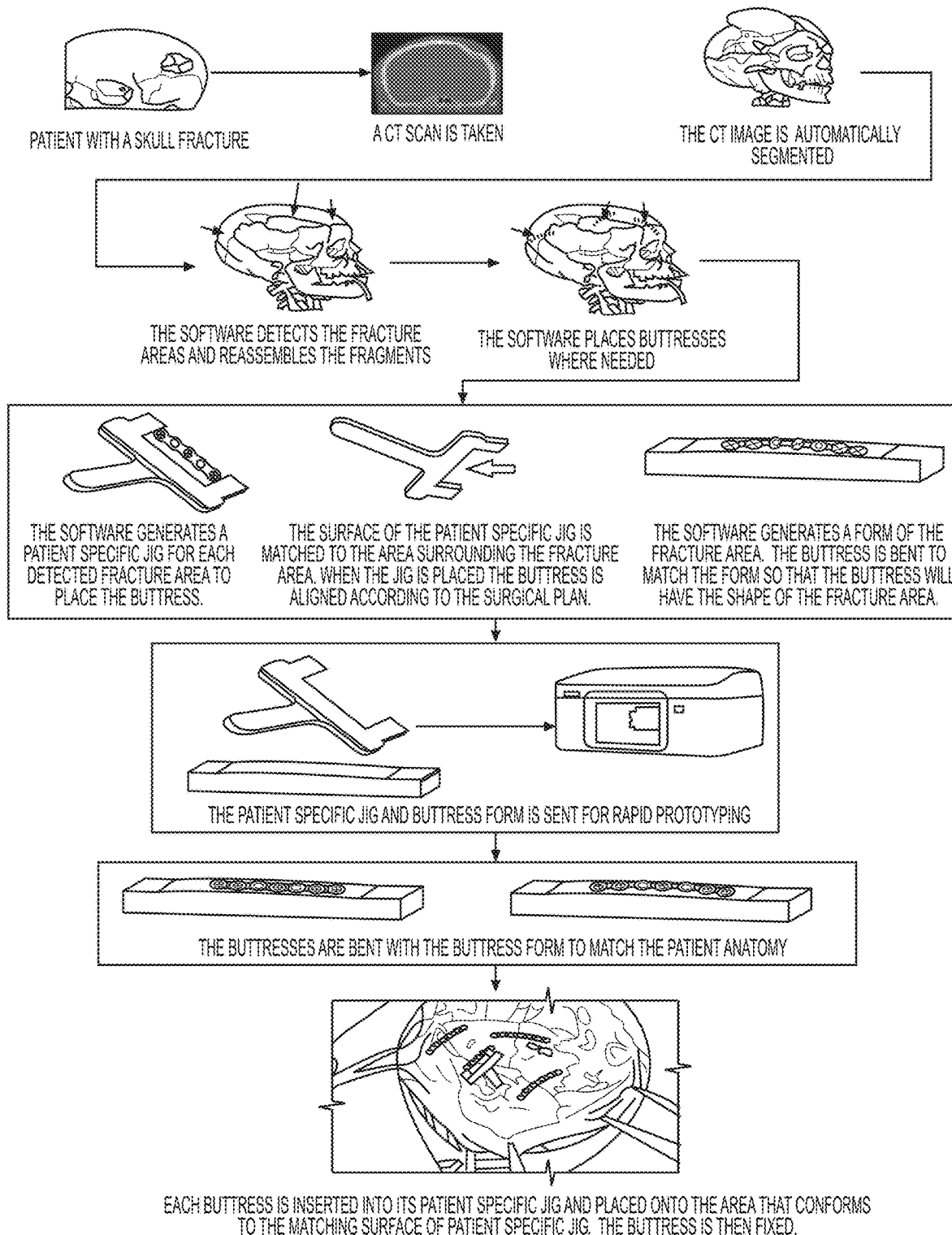
FIG. 115. Process of generating customized plate placement guides for trauma reconstructive surgeries.

Referring to FIG. 115, an exemplary process and system are described for creating trauma plate placement guides that are patient-specific. Those skilled in the art are aware that bone can fracture at one or more locations resulting in bone fragments that are separated from one another. As part of reconstructive surgery to repair the bone, these fragments are held in a fixed orientation using one or more trauma plates. Reconstructive surgeons attempted to piece the bone back together using innate knowledge rather than patient-specific anatomical fact. Consequently, to the extent patient bone anatomy varied from normal, the bone fragments were grossly distorted, or the number of bone fragments was large, surgeons would resort to using prior art trauma plates and having the bone fragments match the shape of the plate rather than vice versa. The instant process and system improves upon prior art trauma plate application by creation of trauma plate placement guides and customized trauma plates that match the trauma plates to the bone to replicate the original bone shape and orientation.

The exemplary system flow begins with receiving input data representative of a fractured anatomy. For purposes of explanation only, the fractured anatomy comprises a human skull. It should be noted that the foregoing process and system is equally applicable to other anatomies/bones including, without limitation, bones in the arms, legs, and torso. In exemplary form, anatomy data input may be in the form of X-rays, CT scans, MRIs, or any other imaging data from which bone size and shape may be represented.

The input anatomy data is utilized to construct a three dimensional virtual model of the fractured anatomy. By way of example, the input anatomy data comprises a computed tomography scan of a fractured skull that is processed by software to segment this scan and generate a three dimensional model. Those skilled in the art are familiar with how to utilize computed tomography scans to construct three dimensional virtual models. Consequently, a detailed description of this aspect of the process has been omitted in furtherance of brevity.

Subsequent to generation of the three dimensional virtual model of the fractured skull, the software compares the three dimensional virtual model of the skull with data from a statistical atlas to determine areas in the three dimensional virtual model where the skull is fractured. In particular, the software utilizes features extracted from the surface model of the input anatomy (ex: surface roughness, curvature, shape index, curvedness, neighbor connectivity) to extract areas of fracture sites. The outline contours of those fracture sites are then extracted and matched together to find the matching fracture sites. Fractured fragments are also matched with the atlas to indicate the best location to place the matched fracture sites in order to reconstruct the normal anatomy.

After the software generates a reconstructed three dimensional virtual model of the fractured skull, buttresses may be manually and/or automatically positioned on the exterior of the reconstructed three dimensional virtual skull model. The automatic placement of the buttresses is the result of programmed logic to maximize stability of the bone fragments while minimizing the number of buttresses. As used herein, the term buttress and plurals thereof refer to any support used to steady bone fragments with respect to one another. In certain instances, practical experience by a surgeon or other learned user may supplement or supplant to the logic when making use of the manual buttress placement feature. In any event, a series of buttresses are programmed into the software that allows the software or a user of the software to select differing buttresses for differing applications. At the same time, the length of the buttresses may be manually or automatically manipulated based upon the dimensions of the fracture and bone fragments.

Subsequent to buttress assignment and placement on the reconstructed three dimensional virtual skull model, the software dimensions and contour of each buttress is recorded by the software. This recordation includes information necessary for fabrication of each buttress or at the very least information helpful to allow a surgeon or other learned individual to take existing buttresses and conform each to a placement guide. In the context of molding an existing buttress, the software extracts the contours of the reconstructed three dimensional virtual skull model to generate computer-aided design (CAD) instructions for creation of one or more tangible models indicative of the reconstructed three dimensional skull model. These CAD instructions are sent to a rapid prototyping machine, which creates the one or more tangible models indicative of the reconstructed three dimensional skull model. By recreating the proper anatomical surface as a tangible model, each buttress may be applied to the tangible model at the target location and manually conformed prior to implantation and fastening to the patient's skull.

Based upon the location and length of any buttress, the software also extracts the contours of the reconstructed three dimensional virtual skull model to generate contour data for one or more patient-specific buttress placement guides. In particular, a placement guide may be generated for each buttress. In this manner, the placement guide includes a surface contour that matches the contour of the patient's skull in a single orientation. Given that the location of the buttress is known on the virtual model of the reconstructed skull, as is the contour of the adjacent exterior skull surface, the software combines the two to create a virtual patient-specific placement guide. This virtual guide is output in the form of CAD instructions to a rapid prototyping machine for fabrication.

In this exemplary embodiment, the fabricated patient-specific placement guide comprises an elongated handle configured to be gripped by a surgeon. Extending from the end of the elongated handle is a block C-shaped contour plate. The underside of the contour plate is concave to match the convex topography of the skull at the location where the buttress should be positioned. Though not required, the ends (or another portion) of the contour plate may be fastened to the buttress, or the contour plate may simple provide a working window within which the buttress is aligned and ultimately fastened to the skull. Post attachment of the buttress to the skull, the contour plate may be removed.

Customized Cutting & Placement Guides, Plates

Figure 116:
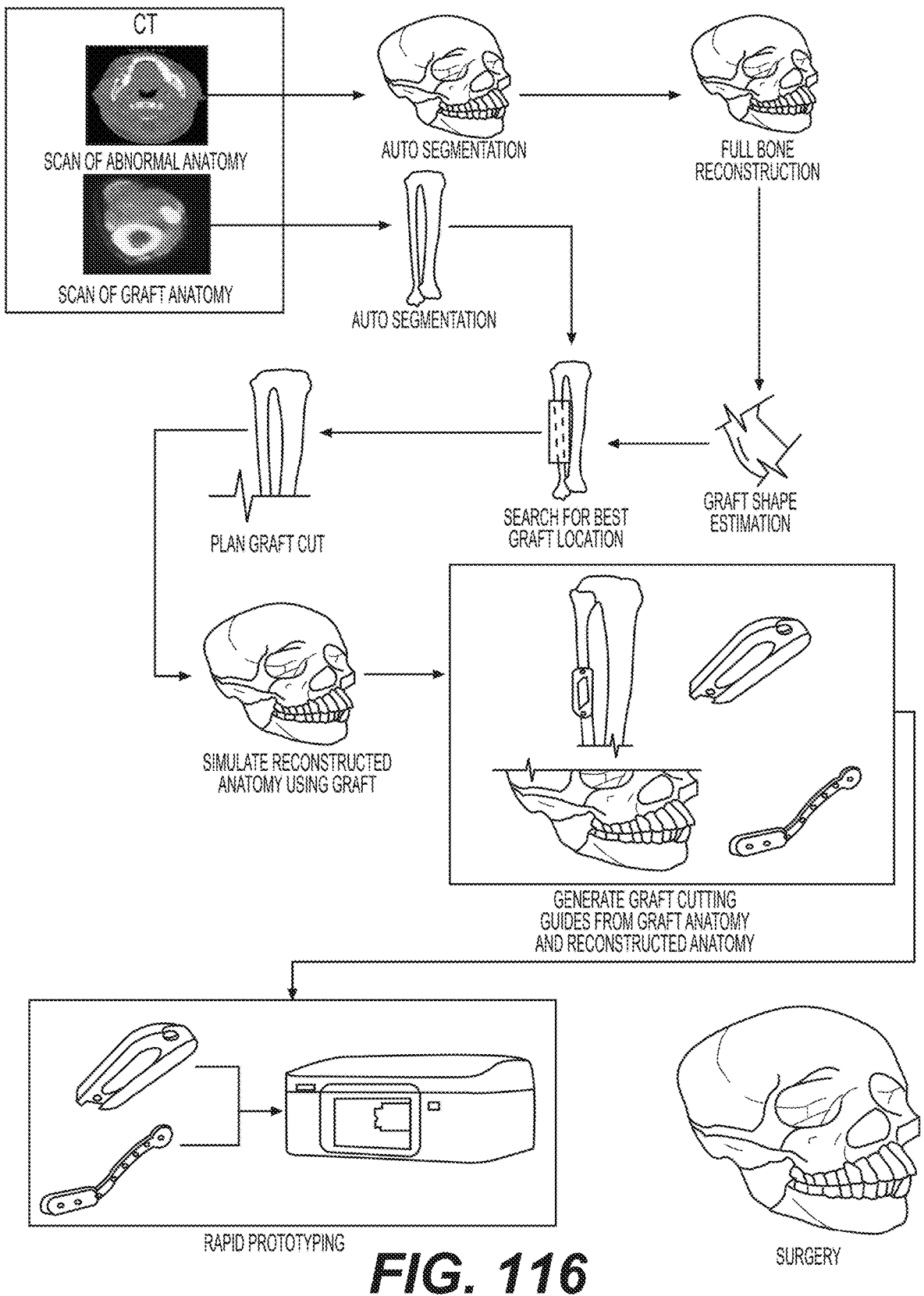
FIG. 116. A process of generating customized cutting and placement guide for reconstructive surgeries using bone grafts.

Referring to FIG. 116, reconstruction of a deformed, fractured, or partial anatomy is one of the complex problems facing healthcare providers. Abnormal anatomy may be the result of birth conditions, tumors, diseases, or personal injuries. As part of providing treatment for various ailments, healthcare providers may find it advantageous to reconstruct an anatomy or construct an anatomy to facilitate treatment for various conditions that may include, without limitation, broken/shattered bones, bone degeneration, orthopedic implant revision, orthopedic initial implantation, and disease.

The present disclosure provides a system and methods for bone and tissue reconstruction using bone grafts. In order to carry out this reconstruction, the system and associated methods utilizes current anatomy images of a patient to construct two virtual 3D models: (a) a first 3D model representative of the current abnormal anatomy; and, (2) a second 3D model representative of the reconstructed anatomy of the patient. Reference is had to the prior "Full Anatomy Reconstruction" section for a detailed explanation of using patient images (X-rays, CT scans, MRI images, etc.) to arrive at virtual models of the patient's abnormal anatomy and reconstructed anatomy. The present system and methods builds upon the system described in the "Full Anatomy Reconstruction" section to utilize the two 3D virtual models in combination with constructing a 3D virtual model of one or more bones from which a bone graft may be taken (i.e., a donor bone). As will be described in more detail hereafter, the 3D virtual models of the patient's reconstructed and abnormal anatomy are analyzed to generate a 3D virtual model of the bone graft needed for reconstruction. This 3D virtual graft model is compared to the 3D virtual model of the donor bone to access one or more sites on the donor bone from which a bone graft can be excised. After determining the excise location(s), cutting guides and graft placement guides are designed and fabricated for gathering the grafted bone and mounting the grafted bone to the site of reconstruction.

By way of exemplary explanation, the instant system and methods will be described in the context of a facial reconstruction, where the donor bone comprises the fibula. Those skilled in the art should realize that the instant system and methods are applicable to any reconstructive surgical procedure utilizing one or more bone grafts. Moreover, while discussing facial reconstruction and the fibula as the bone donor, those skilled in the art should understand that the exemplary system and methods may be used with donor bones other than the fibula.

As a prefatory step to discussing the exemplary system and methods for use with reconstructive surgical planning and surgical procedures using bone grafts, it is presumed that the patient's abnormal anatomy has been imaged and virtual 3D models of the patient's abnormal and reconstructed anatomy have been generated pursuant to those processes described in the prior "Full Anatomy Reconstruction" section. Consequently, a detailed discussion of utilizing patient images to generate both virtual 3D models of the patient's abnormal and reconstructed anatomy has been omitted in furtherance of brevity.

After virtual 3D models of the patient's abnormal and reconstructed anatomy have been created, the software compares the anatomies and highlights areas of difference. In particular, the areas in common between the virtual 3D models denotes bone that will be retained, whereas areas that differ is indicative of one or more sites for reconstruction. The software extracts from the virtual 3D model of the patient's reconstructed anatomy those areas not in common and isolates these areas as separate 3D virtual models of the intended bone graft. The surgeon or other pre-operative planner may view the virtual 3D bone graft models and use his judgment as to the bone or bones from which the bone grafts might be best excised.

Regardless as to the logic utilized to initially choose a possible bone as a graft candidate, the bone(s) in question is imaged using conventional modalities (X-ray, CT, MRI, etc.). Using the processes described in the prior "Full Anatomy Reconstruction" section, each imaged bone is segmented and a virtual 3D model of the imaged bone is created. This 3D donor bone model is compared to the virtual 3D bone graft model to isolate areas in common. In particular, the software compares the surface contours of the 3D donor bone model with the surface contours of the virtual 3D bone graft model to identify areas in common or having similar curvature. Presuming no areas are in common or similar, the process can be restarted by analyzing another possible donor bone. In contrast, if one or more areas in common or having similar curvature exist in the donor bone, these areas are highlighted on the 3D donor bone model. In particular, the highlighted areas mimic the shape of the virtual 3D bone graft model. If the area in common is judged to be appropriate for excising the bone graft, the software virtually excises the bone graft as a virtual 3D model and applies the bone graft (which has contours specific/unique as to the donor bone) to the virtual 3D model of the patient's abnormal anatomy to verify potential fit and any areas of the patient's abnormal anatomy that may need to be excised as part of the reconstruction. In circumstances where application of the virtual 3D model of the excised bone to the virtual 3D model of the patient's abnormal anatomy results less than satisfactory reconstruction, the process may be restarted at the bone selection point or restarted to excise a different area of bone. But presuming application of the virtual 3D model of the excised bone to the virtual 3D model of the patient's abnormal anatomy results in an appropriate fit, the system moves forward with designing jigs to facilitate excising the bone graft and mounting the bone graft to the patient's residual bone.

In this exemplary embodiment, the system generates and outputs machine code necessary for a rapid prototyping machine, CNC machine, or similar device to fabricate a bone graft cutting guide and a bone graft placement guide. In order to generate the outputs necessary to fabricate the bone graft cutting guide and a bone graft placement guide, the system utilizes the virtual 3D model of the excised bone to the virtual 3D model of the patient's abnormal anatomy.

In particular, the virtual 3D model of the excised bone defines the boundary of a virtual 3D cutting guide. Moreover, in this exemplary context, a portion of the fibula is intended to be excised to provide the bone graft. In order to ensure the appropriate portion of the fibula is excised, the virtual 3D cutting guide includes a window within which a cutting device (saw, cutting drill, etc.) traverses to create the appropriately outlined bone graft. Not only does the virtual 3D cutting guide need to be shaped to create the appropriate bone graft outline, but it also needs to be shaped to ensure placement of the cutting guide on the patient's donor bone is particularized. More specifically, the placement of the cutting guide on the donor bones needs to concurrently ensure the excised bone includes the correct outline shape and also exhibits the correct contours. In this fashion, the underside of the virtual 3D cutting guide is designed to be the "negative" of the surface of the donor bone where the cutting guide will be mounted. Exemplary mounting techniques for securing the cutting guide to the donor bone may include, without limitation, screws, dowels, and pins. In order to accommodate one or more of these mounting techniques or others, the virtual 3D cutting guide is also designed to include one or more through orifices besides the window within which the surgical cutter traverses. After the design of the virtual 3D cutting guide is completed, the system generates and outputs machine code necessary for a rapid prototyping machine, CNC machine, or similar device to fabricate the bone graft cutting guide, which is followed by fabrication of the actual cutting guide.

In addition to the cutting guide, the software also designs one or more bone graft placement guides. The bone graft placement guides are patient-specific and conform to the anatomy of the patient (both donor bone and residual bone to which the donor bone is mounted) to ensure correct placement of the bone graft with respect to the residual bone. In exemplary form, the bone graft placement guide is configured for a mandible bone reconstructive procedure. In order to design the bone graft placement guides, the software utilizes the virtual 3D model of the excised bone applied to the virtual 3D model of the patient's abnormal anatomy to construct a hybrid model. Using this hybrid model, joints are identified where the bone graft will interface with (and hopefully join via bone growth) the adjacent residual bone. At these joints, depending upon various factors, such as surgeon preference, the system identifies bone graft plate locations and, for each plate, one or more guides to facilitate correct placement and securing of the plates to the bone graft and residual bone.

Those skilled in the art are familiar with conventional mandible bone plates and, accordingly, a detailed discussion of general designs of mandible bone plates has been omitted in furtherance of brevity. What the present system and methods accomplish, unlike conventional systems and methods, is the formation of patient-specific bone plates and placement guides that account for the shape of both the residual bone and the bone graft. In particular, for each bone plate location identified (either automatically or manually), the system designed a virtual 3D bone plate and associated placement guide. Each virtual 3D bone plate and guide model is overlaid with respect to the hybrid 3D model (including bone graft and patient residual bone in their reconstructed location) to ensure the underside of each virtual 3D bone plate and guide model is the negative of the underlying bone, whether that comprises the bone graft or the residual bone. In this manner, the virtual 3D bone plate and guide model work together to ensure proper placement of the bone plate and corresponding engagement between the bone plate, bone graft, and residual bone. Exemplary mounting techniques for securing a bone plate to a bone graft and residual bone may include, without limitation, screws, dowels, and pins. In order to accommodate one or more of these mounting techniques or others, each virtual 3D bone plate and placement guide includes one or more through orifices. After the design of each virtual 3D bone plate and guide is completed, the system generates and outputs machine code necessary for a rapid prototyping machine, CNC machine, or similar device to fabricate each 3D bone plate and guide, which is followed by fabrication of the actual bone plate and guide.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of designing a patient-specific bone graft placement guide as part of a facial reconstruction surgery, the method comprising:
    identifying a bone graft from a donor bone that includes identifying an area of the donor bone having a surface contour suitable for a craniomaxillofacial bone graft; and
    designing the patient-specific bone graft placement guide incorporating an orifice outlining the craniomaxillofacial bone graft, the patient-specific bone graft placement guide incorporating a shape configured to correctly align the patient-specific bone graft placement guide on a craniomaxillofacial patient bone in only a single orientation and position.

2. A method of designing at least one of a patient-specific bone cutting guide, a patient-specific bone graft placement guide, a patient-specific bone plate placement guide, and a patient-specific bone plate, the method comprising:
    identifying a first abnormal aspect of a virtual, patient-specific 3D surface representation of a patient's craniomaxillofacial bone, to be replaced as part of a surgical procedure, using surface contours of the virtual, patient-specific 3D surface representation;
    comparing a virtual, patient-specific 3D surface representation of a donor bone with a virtual, patient-specific 3D surface representation of a craniomaxillofacial bone graft model to identify a virtual donor graft section of the donor bone;
    generating a tangible, patient-specific bone cutting guide using a virtual, patient-specific craniomaxillofacial bone graft placement guide that embodies surface contours matching surface contours of the virtual donor graft section.

3. The method of claim 2, further comprising:
    at least one of generating and obtaining the virtual, patient-specific 3D surface representation of the patient's craniomaxillofacial bone using patient-specific anatomical data; and,
    at least one of generating and obtaining the virtual, patient-specific 3D surface representation of the craniomaxillofacial bone graft model using a template, virtual 3D bone model.

4. The method of claim 2, wherein identifying the first abnormal aspect includes comparing surface curvatures of the virtual, patient-specific 3D surface representation of the patient's craniomaxillofacial bone and virtual, 3D surface representations of normal bones.

5. The method of claim 4, wherein comparing surface curvatures of the virtual, patient-specific 3D surface representation of the patient's craniomaxillofacial bone and virtual, 3D surface representations of normal bones is at least one of performed manually by a human or automatically by a computer.

6. The method of claim 2, wherein identifying the first abnormal aspect includes identifying virtual bone cut locations on the virtual, patient-specific 3D surface representation of the patient's craniomaxillofacial bone.

7. The method of claim 2, wherein comparing the virtual, patient-specific 3D surface representation of the donor bone with the virtual, patient-specific 3D surface representation of the craniomaxillofacial bone graft model includes comparing surface contours from both 3D surface representations to identify at least one of areas having common curvature and areas having similar curvature.

8. The method of claim 2, further comprising applying the virtual donor graft section to a virtual, resected patient-specific 3D surface representation of the patient's craniomaxillofacial bone to verify fit of the virtual donor graft section.

9. The method of claim 2, further comprising generating the virtual, patient-specific bone cutting guide embodying surface contours matching surface contours of the virtual, patient-specific 3D surface representation of the donor bone.

10. The method of claim 9, wherein the virtual, patient-specific bone cutting guide defines a window outlining an intended shape of the virtual donor graft section.

11. The method of claim 9, wherein the surface contours matching the surface contours of the virtual, patient-specific 3D surface representation of the donor bone are negatives of the surface of the virtual, patient-specific 3D surface representation where the virtual, patient-specific bone cutting guide is mounted.

12. The method of claim 9, wherein the virtual, patient-specific bone cutting guide defines at least one mounting orifice configured to receive at least one of a virtual screw, a virtual dowel, and a virtual pin.

13. The method of claim 2, wherein the tangible, patient-specific bone cutting guide defines a window outlining an intended shape of the donor graft section.

14. The method of claim 2, wherein the tangible, patient-specific bone cutting guide includes surface contours matching surface contours of the donor bone.

15. The method of claim 2, wherein an underside of the tangible, patient-specific bone cutting guide includes a surface that is the negative of a surface of the donor bone.

16. The method of claim 2, wherein the tangible, patient-specific bone cutting guide defines at least one mounting orifice configured to receive at least one of a screw, a dowel, and a pin.

17. The method of claim 2, wherein the tangible, patient-specific bone cutting guide is generated from machine code output in the form of at least one of computer numerical control machine instructions and rapid prototyping machine instructions.

18. The method of claim 2, further comprising generating a virtual, patient-specific craniomaxillofacial bone graft placement guide embodying surface contours matching surface contours of the virtual donor graft section and the virtual, patient-specific 3D surface representation of the patient's craniomaxillofacial bone.

19. The method of claim 18, wherein the surface contours matching the surface contours of the virtual donor graft section and the virtual, patient-specific 3D surface representation of the patient's craniomaxillofacial bone are negatives of the surfaces of the virtual donor graft section and the virtual, patient-specific 3D surface representation of the patient's craniomaxillofacial bone.

20. The method of claim 18, wherein the virtual, patient-specific craniomaxillofacial bone graft placement guide defines at least one mounting orifice configured to receive at least one of a virtual screw, a virtual dowel, and a virtual pin.

21. The method of claim 18, further comprising generating a tangible, patient-specific craniomaxillofacial bone graft placement guide using the virtual, patient-specific craniomaxillofacial bone graft placement guide.

22. The method of claim 21, wherein the tangible, patient-specific craniomaxillofacial bone graft placement guide includes surface contours matching the surface contours of the donor graft section and the patient's craniomaxillofacial bone.

23. The method of claim 21, wherein an underside of the tangible, patient-specific craniomaxillofacial bone graft placement guide includes a surface that is the negative of surfaces of the donor graft section and the patient's craniomaxillofacial bone.

24. The method of claim 21, wherein the tangible, patient-specific craniomaxillofacial bone graft placement guide defines at least one mounting orifice configured to receive at least one of a screw, a dowel, and a pin.

25. The method of claim 21, wherein the tangible, patient-specific craniomaxillofacial bone graft placement guide is generated from machine code output in the form of at least one of computer numerical control machine instructions and rapid prototyping machine instructions.

26. The method of claim 2, further comprising generating a virtual, patient-specific bone plate placement guide embodying surface contours matching surface contours of at least one of the virtual donor graft section and the virtual, patient-specific 3D surface representation of the patient's craniomaxillofacial bone.

27. The method of claim 26, wherein the surface contours matching at least one of the surface contours of the virtual donor graft section and the virtual, patient-specific 3D surface representation of the patient's craniomaxillofacial bone are negatives of at least one of the surfaces of the virtual donor graft section and the virtual, patient-specific 3D surface representation of the patient's craniomaxillofacial bone.

28. The method of claim 26, wherein the virtual, patient-specific bone plate placement guide defines at least one mounting orifice configured to receive at least one of a virtual screw, a virtual dowel, and a virtual pin.

29. The method of claim 26, further comprising generating a tangible, patient-specific bone plate placement guide using the virtual, patient-specific bone plate placement guide.

30. The method of claim 29, wherein the tangible, patient-specific bone plate placement guide includes surface contours matching at least one of the surface contours of the donor graft section and the patient's craniomaxillofacial bone.

31. The method of claim 29, wherein an underside of the tangible, patient-specific bone plate placement guide includes a surface that is the negative of at least one of the donor graft section and the patient's craniomaxillofacial bone.

32. The method of claim 29, wherein the tangible, patient-specific bone plate placement guide defines at least one mounting orifice configured to receive at least one of a screw, a dowel, and a pin.

33. The method of claim 29, wherein the tangible, patient-specific bone plate placement guide is generated from machine code output in the form of at least one of computer numerical control machine instructions and rapid prototyping machine instructions.

34. The method of claim 2, further comprising generating a virtual, patient-specific bone plate embodying surface contours matching surface contours of at least one of the virtual donor graft section and the virtual, patient-specific 3D surface representation of the patient's craniomaxillofacial bone.

35. The method of claim 34, wherein the surface contours matching at least one of the surface contours of the virtual donor graft section and the virtual, patient-specific 3D surface representation of the patient's craniomaxillofacial bone are negatives of at least one of the surfaces of the virtual donor graft section and the virtual, patient-specific 3D surface representation of the patient's craniomaxillofacial bone.

36. The method of claim 34, wherein the virtual, patient-specific bone plate defines at least one mounting orifice configured to receive at least one of a virtual screw, a virtual dowel, and a virtual pin.

37. The method of claim 34, further comprising generating a tangible, patient-specific bone plate using the virtual, patient-specific bone plate.

38. The method of claim 37, wherein the tangible, patient-specific bone plate includes surface contours matching at least one of the surface contours of the donor graft section and the patient's craniomaxillofacial bone.

39. The method of claim 37, wherein an underside of the tangible, patient-specific bone plate includes a surface that is the negative of at least one of the donor graft section and the patient's craniomaxillofacial bone.

40. The method of claim 37, wherein the tangible, patient-specific bone plate defines at least one mounting orifice configured to receive at least one of a screw, a dowel, and a pin.

41. The method of claim 2, further comprising establishing at least one virtual resection plane with respect to the virtual, patient-specific 3D surface representation of the patient's craniomaxillofacial bone.

42. A method of designing at least one of a patient-specific bone cutting guide, a patient-specific graft placement guide, and a patient-specific bone plate placement guide, the method comprising:
- identifying a first abnormal aspect of a virtual, patient-specific 3D surface representation of a patient's craniomaxillofacial bone, to be replaced as part of a surgical procedure, using surface contours of the virtual, patient-specific 3D surface representation;
- comparing a virtual, patient-specific 3D surface representation of a donor bone with a virtual, patient-specific 3D surface representation of a craniomaxillofacial bone graft model to identify a virtual donor graft section of the donor bone;
- generating a tangible, patient-specific craniomaxillofacial bone plate using a virtual, patient-specific craniomaxillofacial bone plate that embodies surface contours matching surface contours of the virtual donor graft section and the virtual, patient-specific 3D surface representation of the patient's craniomaxillofacial bone.

* * * * *